(12) United States Patent
Milne et al.

(10) Patent No.: US 9,084,826 B2
(45) Date of Patent: Jul. 21, 2015

(54) FATTY ACID CONJUGATES OF STATIN AND FXR AGONISTS; COMPOSITIONS AND METHOD OF USES

(71) Applicant: Catabasis Pharmaceuticals, Inc., Cambridge, MA (US)

(72) Inventors: Jill C. Milne, Brookline, MA (US); Michael R. Jirousek, Cambridge, MA (US); Amal Ting, Newton, MA (US); Chi B. Vu, Arlington, MA (US); Allison Wensley, Cambridge, MA (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/874,993

(22) Filed: May 1, 2013

(65) Prior Publication Data

US 2013/0316995 A1 Nov. 28, 2013

Related U.S. Application Data

(60) Provisional application No. 61/641,033, filed on May 1, 2012.

(51) Int. Cl.
| | | |
|---|---|---|
| *A61K 31/58* | (2006.01) | |
| *A61K 47/48* | (2006.01) | |
| *A61K 31/505* | (2006.01) | |
| *A61K 31/366* | (2006.01) | |
| *A61K 31/40* | (2006.01) | |

(52) U.S. Cl.
CPC ............. *A61K 47/481* (2013.01); *A61K 31/366* (2013.01); *A61K 31/40* (2013.01); *A61K 31/505* (2013.01); *A61K 47/48038* (2013.01); *A61K 47/48123* (2013.01)

(58) Field of Classification Search
USPC .................. 514/176, 423, 275, 215; 544/332; 546/329
See application file for complete search history.

(56) References Cited

U.S. PATENT DOCUMENTS

| | | | |
|---|---|---|---|
| 7,501,403 | B2 | 3/2009 | Gilat |
| 2004/0106589 | A1 | 6/2004 | Webb et al. |
| 2006/0046967 | A1 | 3/2006 | Satyam |
| 2006/0211762 | A1 | 9/2006 | Rongen et al. |
| 2009/0131384 | A1 | 5/2009 | Uysal et al. |
| 2010/0174075 | A1* | 7/2010 | Wharton et al. .............. 544/297 |

FOREIGN PATENT DOCUMENTS

WO WO-2011/109681 A1 9/2011

OTHER PUBLICATIONS

Doggrell "New targets in and potential treatments for cholesterol gallstone disease" Curr Opin Investig Drugs. Apr. 2006;7(4):344-8.
Hageman "A role of the bile salt receptor FXR in atherosclerosis" Arterioscler Thromb Vasc Biol. Aug. 2010;30(8):1519-28.
International Search Report for International Application No. PCT/US2013/039103, mailed Oct. 4, 2013, 1 page.
Written Opinion for International Application No. PCT/US2013/039103, mailed Oct. 4, 2013, 6 pages.

* cited by examiner

*Primary Examiner* — Rei-Tsang Shiao
(74) *Attorney, Agent, or Firm* — Goodwin Procter LLP

(57) ABSTRACT

The invention relates to fatty acid statin conjugates and fatty acid FXR agonist conjugates; compositions comprising an effective amount of a fatty acid statin conjugate or a fatty acid FXR agonist conjugate; and methods for treating or preventing a metabolic disease comprising the administration of an effective amount of a fatty acid statin conjugate or a fatty acid FXR agonist conjugate.

15 Claims, 2 Drawing Sheets

FATTY ACID CONJUGATES OF STATIN AND FXR AGONISTS; COMPOSITIONS AND METHOD OF USES

PRIORITY CLAIM

This application claims priority to U.S. Provisional Application 61/641,033 filed May 1, 2012, which is hereby incorporated by reference in its entirety.

FIELD OF THE INVENTION

The invention relates to fatty acid statin conjugates and fatty acid FXR agonist conjugates; compositions comprising an effective amount of a fatty acid statin conjugate or a fatty acid FXR agonist conjugate; and methods for treating or preventing a metabolic disease comprising the administration of an effective amount of a fatty acid statin conjugate or a fatty acid FXR agonist conjugate. All patents, patent applications, and publications cited herein are hereby incorporated by reference in their entireties.

BACKGROUND OF THE INVENTION

Oily cold water fish, such as salmon, trout, herring, and tuna are the source of dietary marine omega-3 fatty acids, with eicosapentaenoic acid (EPA) and docosahexaenoic acid (DHA) being the key marine derived omega-3 fatty acids. Omega-3 fatty acids have previously been shown to improve insulin sensitivity and glucose tolerance in normoglycemic men and in obese individuals. Omega-3 fatty acids have also been shown to improve insulin resistance in obese and non-obese patients with an inflammatory phenotype. Lipid, glucose, and insulin metabolism have been shown to improve in overweight hypertensive subjects through treatment with omega-3 fatty acids. Omega-3 fatty acids (EPA/DHA) have also been shown to decrease triglycerides and to reduce the risk for sudden death caused by cardiac arrhythmias in addition to improve mortality in patients at risk of a cardiovascular event. Omega-3 fatty acids have also been taken as dietary supplements part of therapy used to treat dyslipidemia, and anti-inflammatory properties. A higher intake of omega-3 fatty acids lower levels of circulating TNF-α and IL-6, two of the cytokines that are markedly increased during inflammation processes (Chapkin et al, *Prostaglandins, Leukot Essent Fatty Acids* 2009, 81, p. 187-191; Duda et al, *Cardiovasc Res* 2009, 84, p. 33-41). In addition, a higher intake of omega-3 fatty acids has also been shown to increase levels of the well-characterized anti-inflammatory cytokine IL-10 (Bradley et al, *Obesity (Silver Spring)* 2008, 16, p. 938-944).

Both DHA and EPA are characterized as long chain fatty acids (aliphatic portion between 12-22 carbons). Medium chain fatty acids are characterized as those having the aliphatic portion between 6-12 carbons. Lipoic acid is a medium chain fatty acid found naturally in the body. It plays many important roles such as free radical scavenger, chelator to heavy metals and signal transduction mediator in various inflammatory and metabolic pathways, including the NF-κB pathway (Shay, K. P. et al. *Biochim. Biophys. Acta* 2009, 1790, 1149-1160). Lipoic acid has been found to be useful in a number of chronic diseases that are associated with oxidative stress (for a review see Smith, A. R. et al *Curr. Med. Chem.* 2004, 11, p. 1135-46). Lipoic acid has now been evaluated in the clinic for the treatment of diabetes (Morcos, M. et al *Diabetes Res. Clin. Pract.* 2001, 52, p. 175-183) and diabetic neuropathy (Mijnhout, G. S. et al *Neth. J. Med.* 2010, 110, p. 158-162). Lipoic acid has also been found to be potentially useful in treating cardiovascular diseases (Ghibu, S. et al, *J. Cardiovasc. Pharmacol.* 2009, 54, p. 391-8), Alzheimer's disease (Maczurek, A. et al, *Adv. Drug Deliv. Rev.* 2008, 60, p. 1463-70) and multiple sclerosis (Yadav, V. *Multiple Sclerosis* 2005, 11, p. 159-65; Salinthone, S. et al, *Endocr. Metab. Immune Disord. Drug Targets* 2008, 8, p. 132-42).

Statins have been used widely to lower low-density cholesterol (LDL-C), a key risk factor in cardiovascular disease. Because of their ability to inhibit 3-hydroxy-3-methylglutaryl CoA (HMG-CoA) reductase, these agents can essentially block the rate-limiting step in the cholesterol biosynthesis in the liver. After extended clinical use, statins have been shown to be safe and effective for both primary prevention of coronary heart disease and secondary prevention of coronary events. More recently, there is increasing evidence that indicates that statins can exert beneficial effects on inflammatory processes. For instance, after treatment with atorvastatin, a DNA microarray analysis of human peripheral blood lymphocytes showed a significant decrease in the gene expression of six cytokines (IL-6, IL-8, IL-1, PAI-1, TGF-b1, TGF-b2) and five chemokines (CCL2, CCL7, CCL13, CCL18, CXCL1) (Wang et al, *Biomedicine & Pharmacotherapy* 2011, 65, p. 118-122). The high mobility group box-1 (HMGB1) has recently been implicated as a potential pro-inflammatory cytokine that could play a critical role in endothelial dysfunction and atherosclerosis. Treatment of endothelial cells with atorvastatin has been shown to markedly suppress HMGB1-induced Toll like receptor 4 (TLR4) expression, NF-κB nuclear translocation and DNA binding (Yang et al, *Molecular & Cellular Biochemistry* 2010, 345, p. 189-195).

Because of the ability of statins and omega-3 fatty acid to act on the NF-κB axis, a synergistic activity would provide a great benefit in treating a number of metabolic diseases. Synergistic activity can be achieved through a fatty acid statin conjugates which are comprised of a statin covalently linked to a fatty acid to form a plasma stable molecular entity. However, once delivered inside cells, intracellular enzymes hydrolyze the fatty acid statin conjugate into the individual components. In addition, a fatty acid statin conjugate can also display synergistic activity on the various lipid synthesis pathways that cannot be replicated by administering the individual components (i.e. omega-3 fatty acid alone and statin alone) or a combination of the individual components not covalently linked. For instance, the statin drug class has been used extensively in the clinic to lower cholesterol. However, statin treatment has been shown to significantly increase the expression of proprotein convertase subtilisin/kexin type 9 (PCSK9) (Dubuc et al *Arterioscler. Thromb. Vasc.* 2004, p. 1453-1459). The increased level of PCSK9 could essentially counteract some of the beneficial effects of statins since PCSK9 could enhance the degradation of LDL receptors, leading to higher plasma levels of LDC-C. As demonstrated herein, a fatty acid statin conjugate shows a different activity profile toward PCSK9 that cannot be replicated by administering a statin and an omega-3 fatty acid. Selective targeting to certain tissue types can enhance the overall efficacy, as well as reduce the side effects. Selective targeting of fatty acid statin conjugates to certain tissue types (such as the liver) can be carried out using omega-3 fatty acids as well as non-omega-3 fatty acids. Examples of non-omega-3 fatty acids that can be used to form covalent conjugates with statins include saturated fatty acids, omega-6 fatty acids, omega-9 fatty acids, omega-1 fatty acids, omega-7 fatty acids, omega-12 fatty acids, omega-15 fatty acids, sapienic acid, linoelaidic acid, pinolenic acid, and podocarpic acid.

The farnesoid X receptor (FXR) is a nuclear hormone receptor expressed in the liver, gall bladder, kidney, adrenal glands and intestine. Upon activation by bile acids, FXR binds to DNA as a heterodimer with the retinoid X receptor (RXR) and this binding, in turn, regulates the expression of a number of genes and proteins involved in bile acid and cholesterol homeostasis, triglyceride synthesis and lipogenesis (For reviews on FXR see: Kalaany et al *Annu. Rev. Physiol.*

2006, 68, p. 159-191; Zhang et al *FEBS Lett.* 2008, 582, p. 10-18). In addition, FXR can help maintain glucose homeostasis, possibly because of its effects on gluconeogenesis, insulin sensitization and glycogen synthesis (Zhang et al *Proc. Natl. Acad. Sci. USA* 2006, 103, p. 1006; Cariou et al *FEBS Lett.* 2005, 579, p. 4076). Activation of FXR has been shown to result in increased hepatic expression of receptors that are involved in lipoprotein clearance (VLDL receptor and syndecan-1) and increased apoC-II that coactivates lipoprotein lipase (LPL). In addition FXR activation results in decreased expression of proteins such as apoC-III and ANGPTL3 that could function as inhibitors of LPL (Lee et al *Trends Biochem. Sci.* 2006, 31, p. 572-580). Thus, agonists of FXR can potentially be useful in treating a number of metabolic diseases because of its ability to lower plasma triglycerides, repress hepatic lipogenesis and triglyceride synthesis, as well as increase the clearance of triglyceride-rich lipoproteins from the blood. The fatty acid FXR agonist conjugates are comprised of an FXR agonist covalently linked to a fatty acid. This fatty acid FXR agonist conjugate is stable in the plasma. However, once delivered inside cells, intracellular enzymes would hydrolyze the conjugate into the individual components. Because of the ability of FXR agonists and omega-3 fatty acids to impact the different lipid synthesis pathway, a fatty acid FXR agonist conjugate will display synergistic activity that cannot be replicated by administering the individual components or a combination of the individual components. Selective targeting to certain tissue types can enhance the overall efficacy, as well as reduce the side effects. Selective targeting of fatty acid FXR agonist conjugates to certain tissue types (such as the liver) can be carried out using omega-3 fatty acids as well as non-omega-3 fatty acids.

SUMMARY OF THE INVENTION

The invention is based in part on the discovery of fatty acid statin conjugates and fatty acid FXR agonist conjugates and their demonstrated effects in achieving improved treatment that cannot be achieved by administering the individual components alone or in combination. These novel conjugates are useful in the treatment or prevention of metabolic disorders including atherosclerosis, dyslipidemia, coronary heart disease, hypercholesterolemia, Type 2 diabetes, elevated cholesterol, metabolic syndrome, diabetic nephropathy, IgA nephropathy, chronic kidney disease (CKD) and cardiovascular disease.

Accordingly in one aspect, a molecular conjugate is described which comprises a statin covalently linked to a fatty acid, wherein the fatty acid is selected from the group consisting of lipoic acid, omega-3 fatty acids and fatty acids that are metabolized in vivo to omega-3 fatty acids, saturated fatty acids, omega-6 fatty acids, omega-9 fatty acids and the conjugate is capable of hydrolysis to produce free statin and free fatty acid.

In another aspect, compounds of the Formula I are described:

Formula I

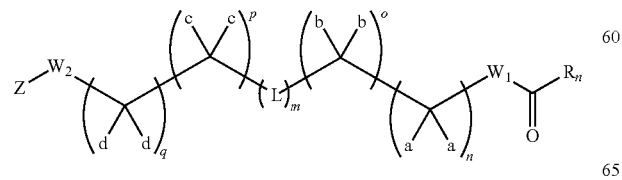

and pharmaceutically acceptable salts, hydrates, solvates, prodrugs, enantiomers and stereoisomers thereof;

wherein $R_n$ is

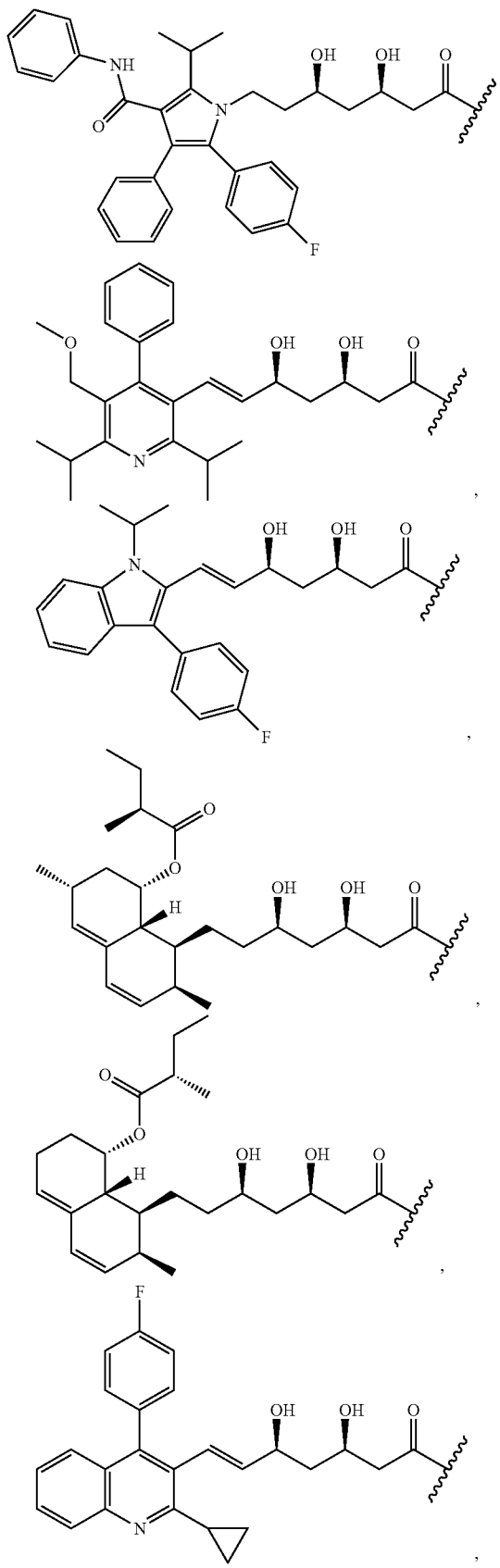

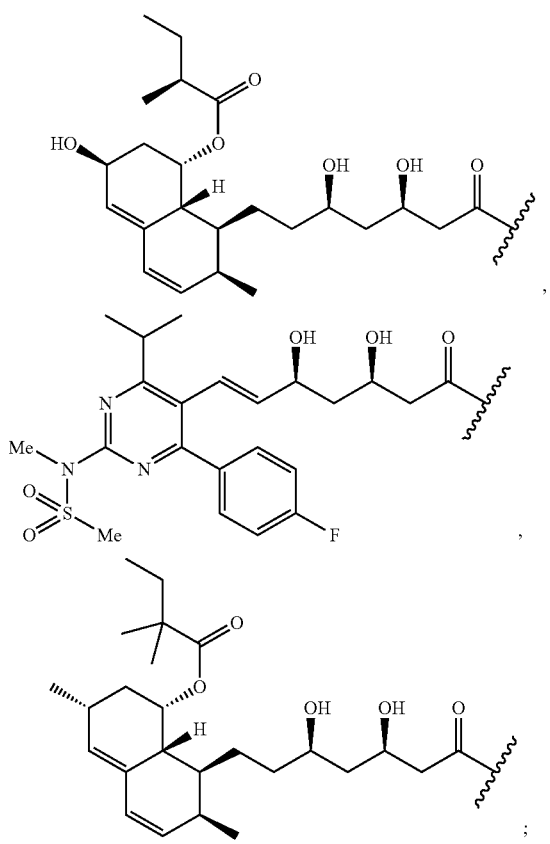

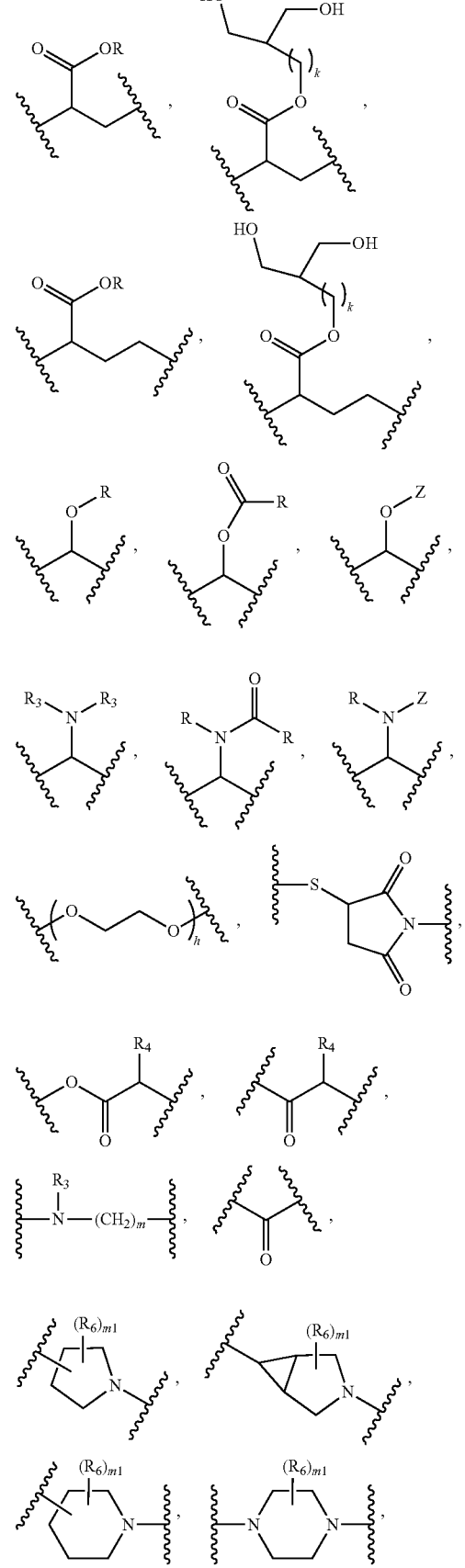

$W_1$ and $W_2$ are each independently null, O, S, NH, NR, or $W_1$ and $W_2$ can be taken together can form an imidazolidine or piperazine group;

each a, b, c, and d is independently —H, -D, —CH$_3$, —OCH$_3$, —OCH$_2$CH$_3$, —C(O)OR, —O—Z, or benzyl, or two of a, b, c, and d can be taken together, along with the single carbon to which they are bound, to form a cycloalkyl or heterocycle;

each n, o, p, and q is independently 0, 1, or 2;

each L is independently —O—, —S—, —S(O)—, —S(O)$_2$—, —S—S—, —(C$_1$-C$_6$alkyl)-, —(C$_3$-C$_6$cycloalkyl)-, a heterocycle, a heteroaryl,

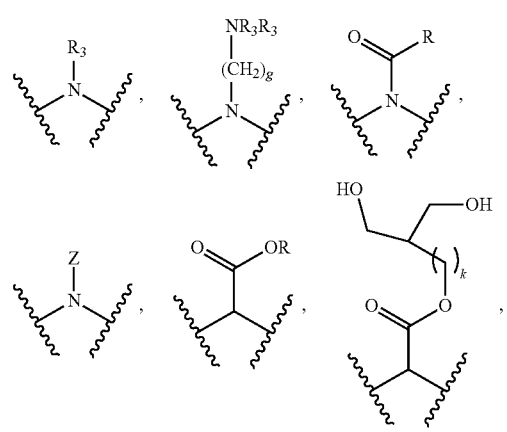

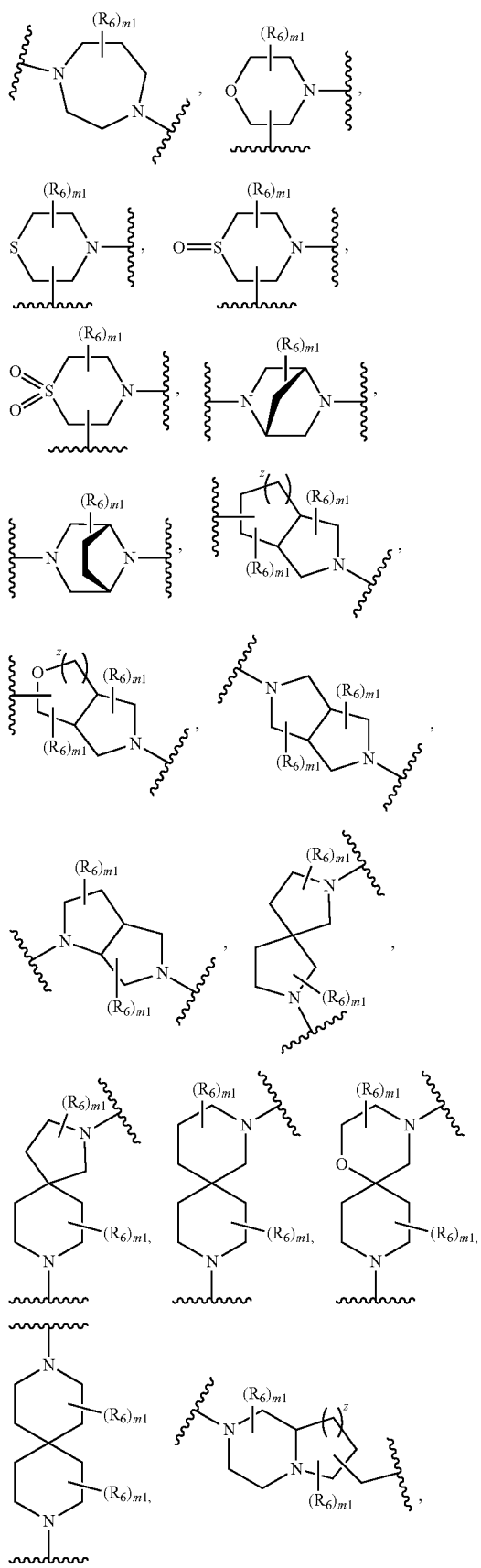

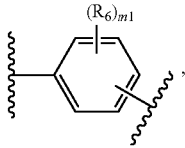

wherein the representation of L is not limited directionally left to right as is depicted, rather either the left side or the right side of L can be bound to the $W_1$ side of the compound of Formula I;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl;

each g is independently 2, 3 or 4;
each h is independently 1, 2, 3 or 4;
m is 0, 1, 2, or 3; if m is more than 1, then L can be the same or different;
m1 is 0, 1, 2 or 3;
k is 0, 1, 2, or 3;
z is 1, 2, or 3;
each $R_3$ is independently H or $C_1$-$C_6$ alkyl, or both $R_3$ groups, when taken together with the nitrogen to which they are attached, can form a heterocycle;
each $R_4$ is independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;
each e is independently H or any one of the side chains of the naturally occurring amino acids;
each Z is independently —H, or

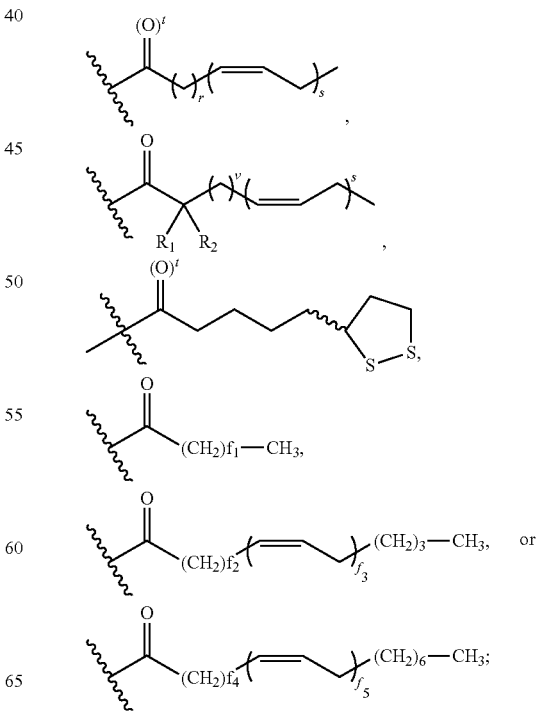

with the proviso that there is at least one

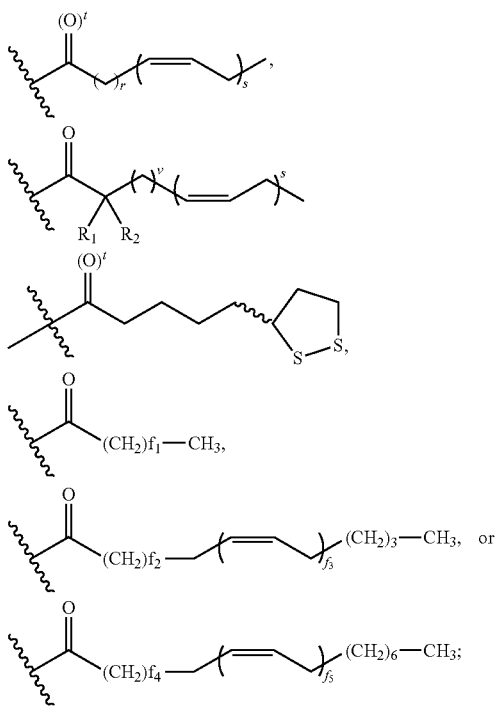

in the compound;
each r is independently 2, 3, or 7;
each s is independently 3, 5, or 6;
each t is independently 0 or 1;
each v is independently 1, 2, or 6;
each $f_1$ is independently 4, 5, 6, 7, 8, 9, 10, 11, 12, 13, 14, 15, 16, 17, 18, 19, 20, 21, 22, 23, 24, 25 or 26;
each $f_2$ is independently 3, 4, 5, 6, 7, 8, 9, 10 or 11;
each $f_3$ is independently 2, 3, 4 or 5;
each $f_4$ is independently 3, 7, 8, 9, 11 or 13;
each $f_5$ is independently 1 or 3;
$R_1$ and $R_2$ are each independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl; and
each R is independently —H, or straight or branched $C_1$-$C_4$ alkyl optionally substituted with OH, or halogen;
provided that
when each of m, n, o, p, and q, is 0, $W_1$ and $W_2$ are each null, and Z is

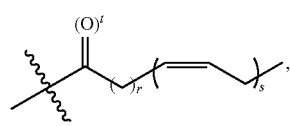

then t must be 0; and
when each of m, n, o, p, and q is 0, and $W_1$ and $W_2$ are each null, then Z must not be

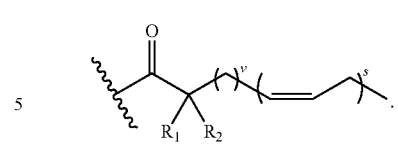

In another aspect, compounds of the Formula II are described:

Formula II

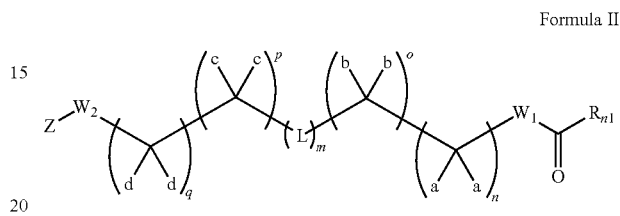

and pharmaceutically acceptable salts, hydrates, solvates, prodrugs, enantiomers and stereoisomers thereof;
wherein $R_{n1}$ is

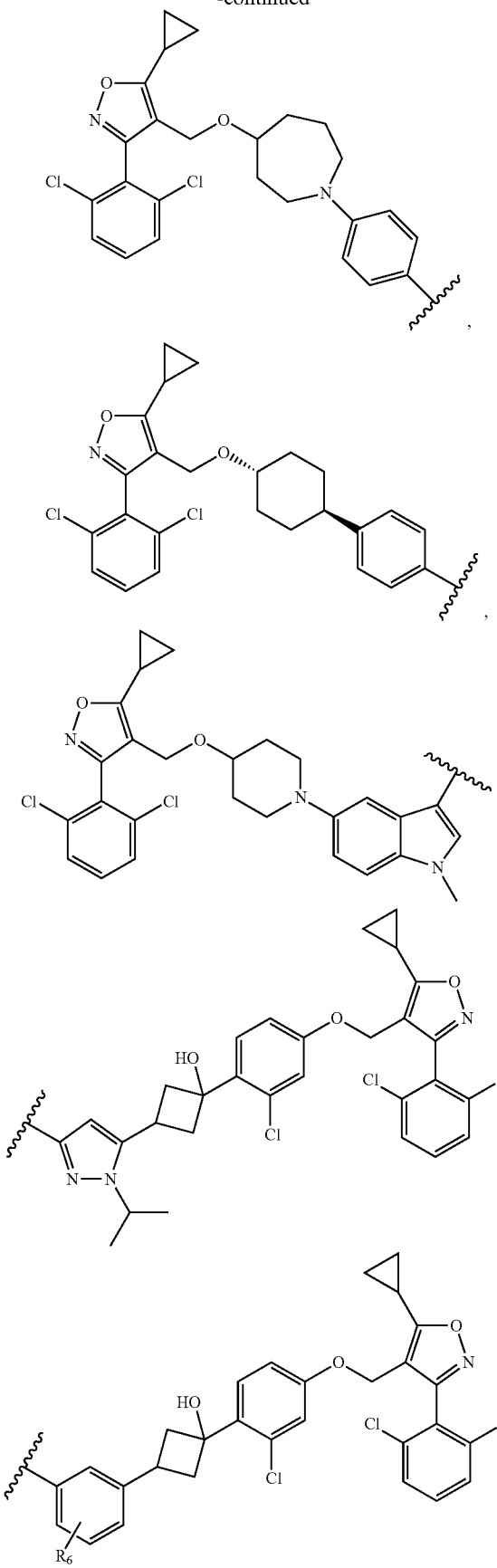

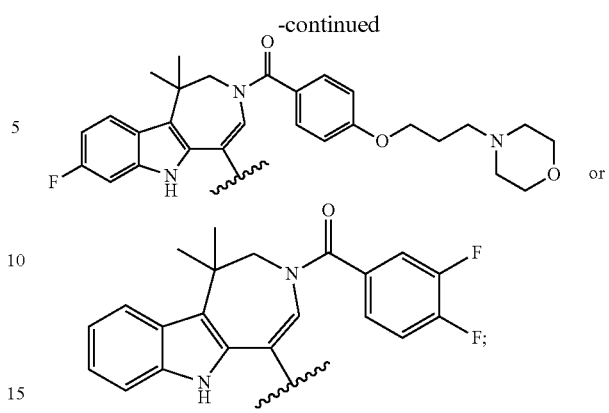

$W_1$ and $W_2$ are each independently null, O, S, NH, NR, or $W_1$ and $W_2$ can be taken together can form an imidazolidine or piperazine group;

each a, b, c, and d is independently —H, -D, —CH$_3$, —OCH$_3$, —OCH$_2$CH$_3$, —C(O)OR, —O—Z, or benzyl, or two of a, b, c, and d can be taken together, along with the single carbon to which they are bound, to form a cycloalkyl or heterocycle;

each n, o, p, and q is independently 0, 1, or 2;

each L is independently —O—, —S—, —S(O)—, —S(O)$_2$—, —S—S—, —(C$_1$-C$_6$alkyl)-, —(C$_3$-C$_6$cycloalkyl)-, a heterocycle, a heteroaryl,

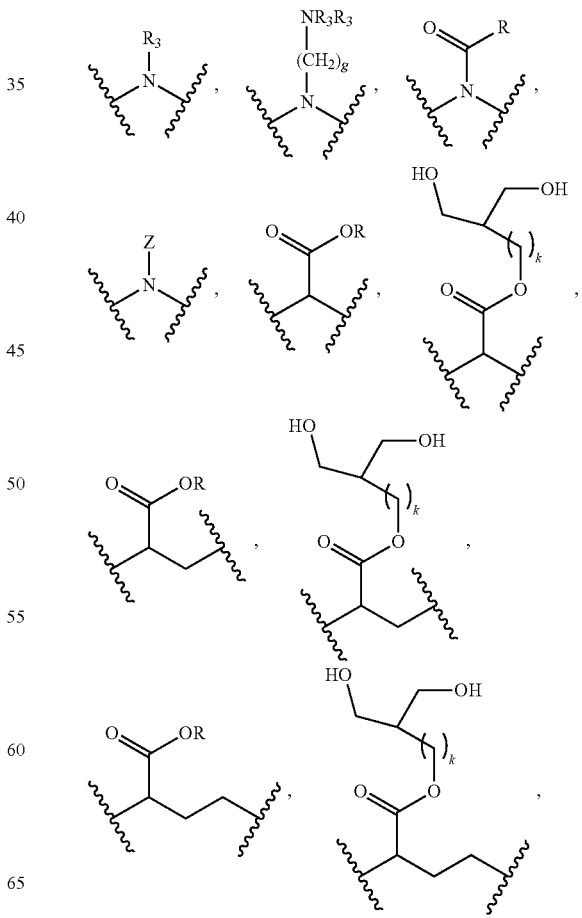

-continued

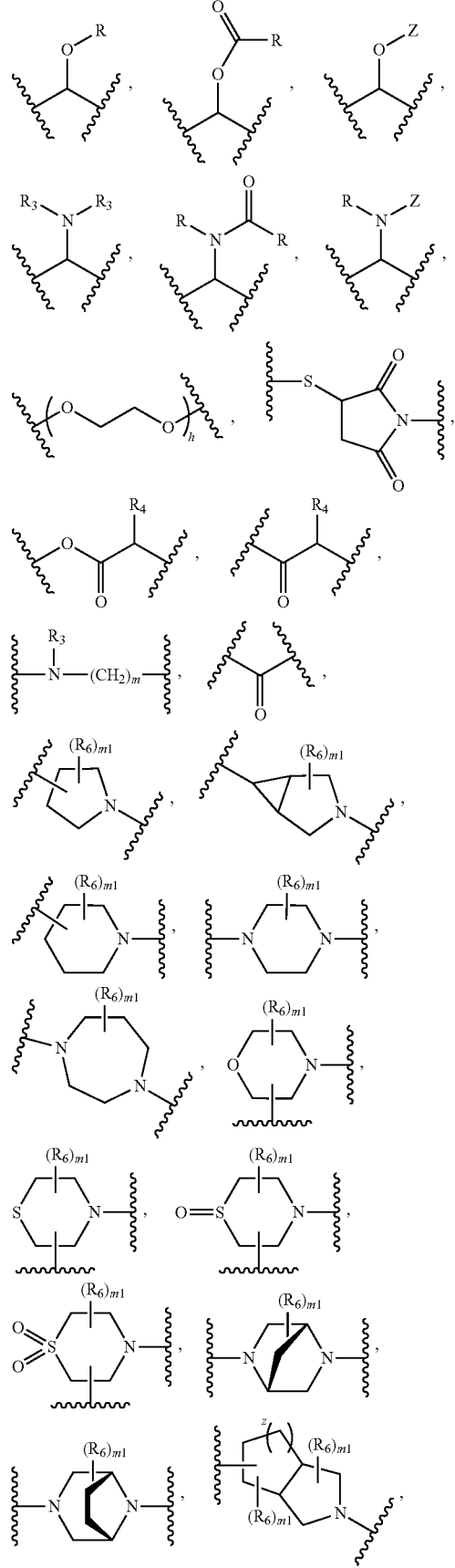

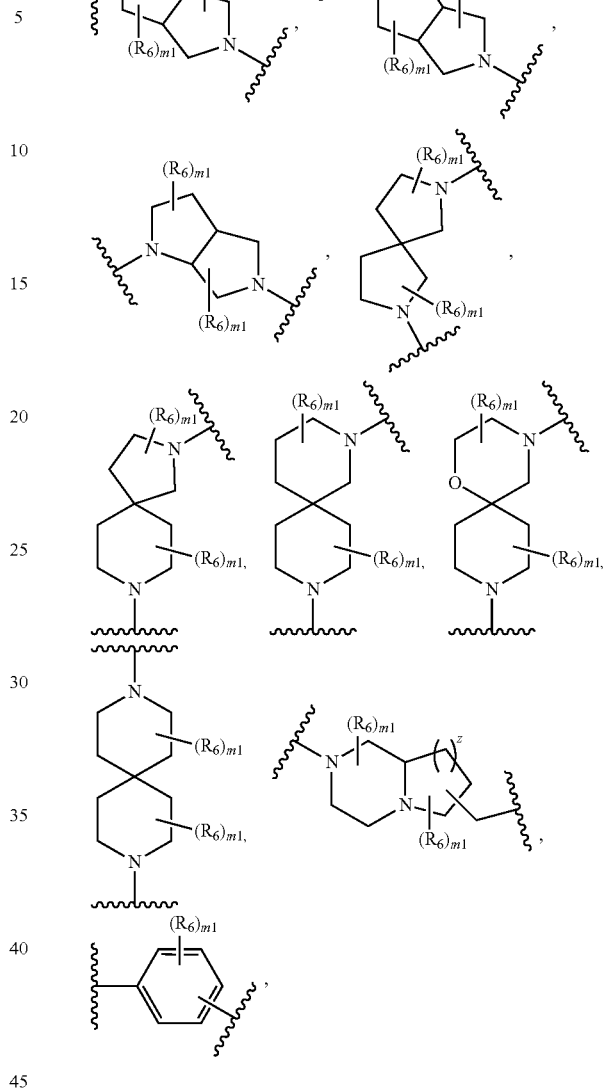

wherein the representation of L is not limited directionally left to right as is depicted, rather either the left side or the right side of L can be bound to the $W_1$ side of the compound of Formula II;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each g is independently 2, 3 or 4;
each h is independently 1, 2, 3 or 4;
m is 0, 1, 2, or 3; if m is more than 1, then L can be the same or different;
m1 is 0, 1, 2 or 3;
k is 0, 1, 2, or 3;
z is 1, 2, or 3;
each $R_3$ is independently H or $C_1$-$C_6$ alkyl, or both $R_3$ groups, when taken together with the nitrogen to which they are attached, can form a heterocycle;

each $R_4$ is independently e, H or straight or branched $C_1$-$C_{10}$ alkyl which can be optionally substituted with OH, $NH_2$, $CO_2R$, $CONH_2$, phenyl, $C_6H_4OH$, imidazole or arginine;

each e is independently H or any one of the side chains of the naturally occurring amino acids;

each Z is independently —H, or

[chemical structure: $(O)^t$, with $( )_r$ and $( )_s$ groups]

[chemical structure with $R_1$, $R_2$, $(O)^t$, $( )_v$, $( )_s$]

[chemical structure with dithiolane ring (S-S)]

[chemical structure: $(CH_2)f_1$—$CH_3$]

[chemical structure: $(CH_2)f_2$, $( )_{f_3}$, $(CH_2)_3$—$CH_3$], or

[chemical structure: $(CH_2)f_4$, $( )_{f_5}$, $(CH_2)_6$—$CH_3$];

with the proviso that there is at least one

[chemical structure: $(O)^t$, $( )_r$, $( )_s$]

[chemical structure with $R_1$, $R_2$, $(O)^t$, $( )_v$, $( )_s$]

[chemical structure with dithiolane (S-S), $(O)^t$]

[chemical structure: $(CH_2)f_1$—$CH_3$]

[chemical structure: $(CH_2)f_2$, $( )_{f_3}$, $(CH_2)_3$—$CH_3$], or

[chemical structure: $(CH_2)f_4$, $( )_{f_5}$, $(CH_2)_6$—$CH_3$];

in the compound;

each r is independently 2, 3, or 7;
each s is independently 3, 5, or 6;
each t is independently 0 or 1;
each v is independently 1, 2, or 6;
each $f_1$ is independently 4, 5, 6, 7, 8, 9, 10, 11, 12, 13, 14, 15, 16, 17, 18, 19, 20, 21, 22, 23, 24, 25 or 26;
each $f_2$ is independently 3, 4, 5, 6, 7, 8, 9, 10 or 11;
each $f_3$ is independently 2, 3, 4 or 5;
each $f_4$ is independently 3, 7, 8, 9, 11 or 13;
each $f_5$ is independently 1 or 3;
$R_1$ and $R_2$ are each independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_1$-$C_3$ alkene, —$C_1$-$C_3$ alkyne, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2C_1$-$C_3$ alkyl; and each R is independently —H, or straight or branched $C_1$-$C_4$ alkyl optionally substituted with OH, or halogen;

provided that when each of m, n, o, p, and q, is 0, $W_1$ and $W_2$ are each null, and Z is

[chemical structure: $(O)^t$, $( )_r$, $( )_s$], then t must be 0; and when each of m, n, o, p, and q is 0, and $W_1$ and $W_2$ are each null, then Z must not be

[chemical structure with $R_1$, $R_2$, $(O)^t$, $( )_v$, $( )_s$].

In Formula I, and II any one or more of H may be substituted with a deuterium. It is also understood in Formula I and II that a methyl substituent can be substituted with a $C_1$-$C_6$ alkyl.

Also described are pharmaceutical formulations comprising at least one fatty acid statin conjugate.

Also described herein are methods of treating a disease susceptible to treatment with a fatty acid statin conjugate in a patient in need thereof by administering to the patient an effective amount of a fatty acid statin conjugate.

Also described herein are methods of treating metabolic diseases by administering to a patient in need thereof an effective amount of a fatty acid statin conjugate.

The invention also includes pharmaceutical compositions that comprise an effective amount of a fatty acid statin conjugate and a pharmaceutically acceptable carrier. The compositions are useful for treatment or prevention of metabolic disorders including atherosclerosis, dyslipidemia, coronary heart disease, hypercholesterolemia, Type 2 diabetes, elevated cholesterol, metabolic syndrome, diabetic nephropathy, IgA nephropathy, chronic kidney disease (CKD) and cardiovascular disease.

Also described are pharmaceutical formulations comprising at least one fatty acid FXR agonist conjugate.

Also described herein are methods of treating a disease susceptible to treatment with a fatty acid FXR agonist conjugate in a patient in need thereof by administering to the patient an effective amount of a fatty acid FXR agonist conjugate.

Also described herein are methods of treating metabolic diseases by administering to a patient in need thereof an effective amount of a fatty acid FXR agonist conjugate.

The invention also includes pharmaceutical compositions that comprise an effective amount of a fatty acid FXR agonist conjugate and a pharmaceutically acceptable carrier. The compositions are useful for treatment or prevention of metabolic disorders including atherosclerosis, dyslipidemia, coronary heart disease, hypercholesterolemia, Type 2 diabetes, elevated cholesterol, metabolic syndrome, diabetic nephropathy, IgA nephropathy, chronic kidney disease (CKD) and cardiovascular disease.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DETAILED DESCRIPTION OF THE INVENTION

Figure 1:
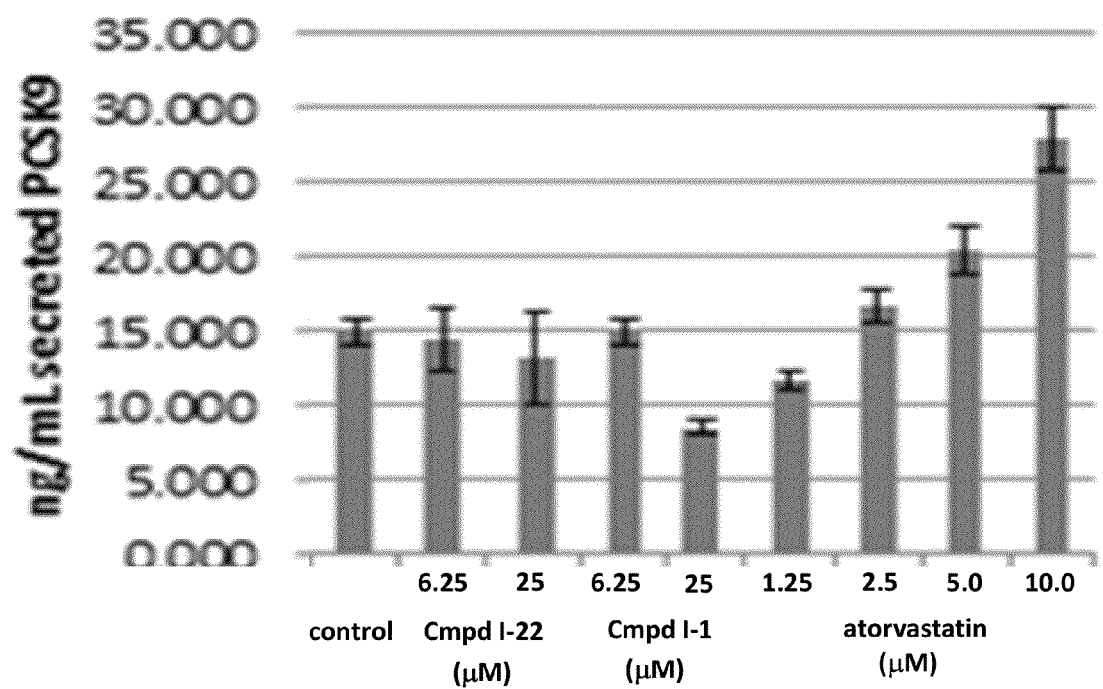
FIG. 1 illustrates PCSK9 secretion levels in HepG2 assay using compounds I-1, compound 1-22, and atorvastatin.

The fatty acid statin conjugates have been designed to bring together statin analogs and fatty acids into a single molecular conjugate. The activity of the fatty acid statin conjugates is substantially greater than the sum of the individual components of the molecular conjugate, suggesting that the activity induced by the fatty acid statin conjugates is synergistic.

The fatty acid FXR agonist conjugates have been designed to bring together FXR agonists and fatty acids into a single molecular conjugate. The activity of the fatty acid FXR agonist conjugates is substantially greater than the sum of the individual components of the molecular conjugate, suggesting that the activity induced by the fatty acid FXR agonist conjugates is synergistic.

DEFINITIONS

The following definitions are used in connection with the fatty acid statin conjugates and fatty acid FXR agonist conjugates:

The term "fatty acid statin conjugates" and "fatty acid FXR agonist conjugates" includes any and all possible isomers, stereoisomers, enantiomers, diastereomers, tautomers, pharmaceutically acceptable salts, hydrates, solvates, and prodrugs of the fatty acid statin conjugates and fatty acid FXR agonist conjugates described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl.

It is understood that any of the substitutable hydrogens on an alkyl or cycloalkyl can be substituted with halogen, $C_1$-$C_3$ alkyl, hydroxyl, alkoxy and cyano groups.

The term "heterocycle" as used herein refers to a cyclic hydrocarbon containing 3-6 atoms wherein at least one of the atoms is an O, N, or S. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a monocyclic or bicyclic ring structure having 5 to 12 ring atoms wherein one or more of the ring atoms is a heteroatom, e.g. N, O or S and wherein one or more rings of the bicyclic ring structure is aromatic. Some examples of heteroaryl are pyridyl, furyl, pyrrolyl, thienyl, thiazolyl, oxazolyl, imidazolyl, indolyl, tetrazolyl, benzofuryl, xanthenes and dihydroindole. It is understood that any of the substitutable hydrogens on a heteroaryl can be substituted with halogen, $C_1$-$C_3$ alkyl, hydroxyl, alkoxy and cyano groups.

The term "any one of the side chains of the naturally occurring amino acids" as used herein means a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine and Tyrosine.

The term "fatty acid" as used herein means an omega-3 fatty acid and fatty acids that are metabolized in vivo to omega-3 fatty acids. Non-limiting examples of fatty acids are all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), tetracosahexaenoic acid (nisinic acid or all-cis-6,9,12,15,18,21-tetracosenoic acid). In addition, the term "fatty acid" can also refer to medium chain fatty acids such as lipoic acid. The term "fatty acid" can also refers to the group consisting of saturated fatty acids. The saturated fatty acids can have the alkyl side chain ranging from 6 linear carbons (hexanoic acid) up to 26 linear carbons (cerotic acid). Other commonly used saturated fatty acids include caprylic acid, capric acid, undecanoic acid, lauric acid, tridecanoic acid, myristic acid, pentadecanoic acid, palmitic acid, margaric acid, stearic acid, 12-hydroxy stearic, nonadecanoic acid, arachidic acid, heneicosanoic acid, behenic acid, tricosanoic acid and lignoceric acid. The term "fatty acid" can also refers to the group consisting of omega-6 fatty acids. Commonly used omega-6 fatty acids include linoleic acid, linoelaidic acid, gamma-linolenic acid, calendic acid, 10,13-nonadecadienoic acid, eicosadienoic acid, di-homo-gamma-linolenic acid, arachidonic acid, heneicosadienoic acid, docosadienoic aid, adrenic acid, docosapentaenoic acid, and tetracosapentaenoic acid. The term "fatty acid" is selected from the group consisting of omega-9 fatty acids. Commonly used omega-9 fatty acids include oleic acid, elaidic acid, gondoic acid, gadoleic acid, mead acid, 12-heneicosenoic acid, nervonic acid, and Z-tetracos-15-enoic acid. The term "fatty acid" can also refers to the group consisting of omega-1 fatty acids that include hendecenoic acid, 11-dodecenoic acid, 12-tridecenoic acid, and 14-pentadecenoic acid. The term "fatty acid" is selected from the group consisting of omega-5 fatty acids that include myristoleic acid, 9-transtetradecenoic acid, 10-pentadecenoic acid and 10-transpentadecenoic acid. The term "fatty acid" is selected from the group consisting of omega-7 fatty acids that include palmitoleic acid, 9-trans-hexadecenoic acid, 10-heptadecenoic acid, 10-trans-heptadecenoic acid, vaccenic acid and trans-vaccenic acid. The term "fatty acid" can also refers to the group consisting of omega-12 fatty acids that include petroselinic acid, petroselaidic acid, 7-nonadenoic acid, 7-trans-nonadenoic acid, and 8-eicosenoic acid. The term "fatty acid" can also refers to sapienica acid, linoelaidic acid, pinolenic acid and podocarpic acid.

The term "statin" as used herein refers to any of the class of compounds known as 3-hydroxy-3-methylglutaryl CoA (HMG-CoA) reductase inhibitors, and any derivatives thereof, including but not limited to atorvastatin, cerivastatin, fluvastatin, lovastatin, mevastatin, pitavastatin, pravastatin, rosuvastatin, and simvastatin.

The term "FXR agonist" as used herein refers to the following acid or ester derivatives (R=H or $C_1$-$C_4$ alkyl, straight or branched):

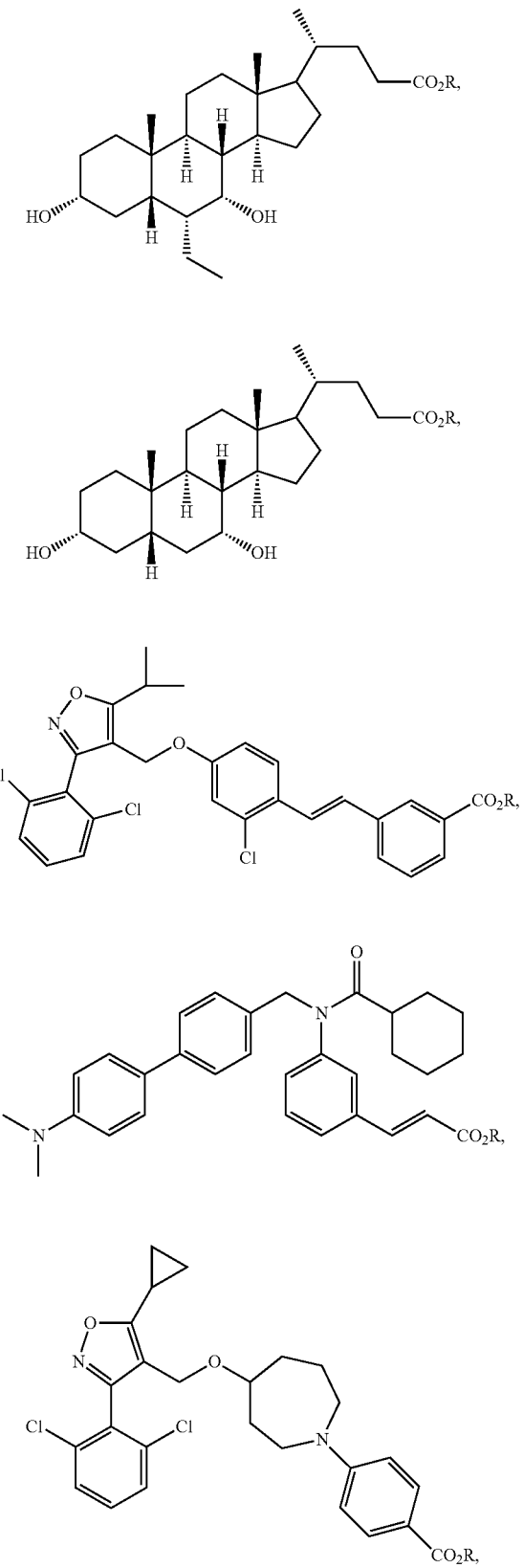

-continued

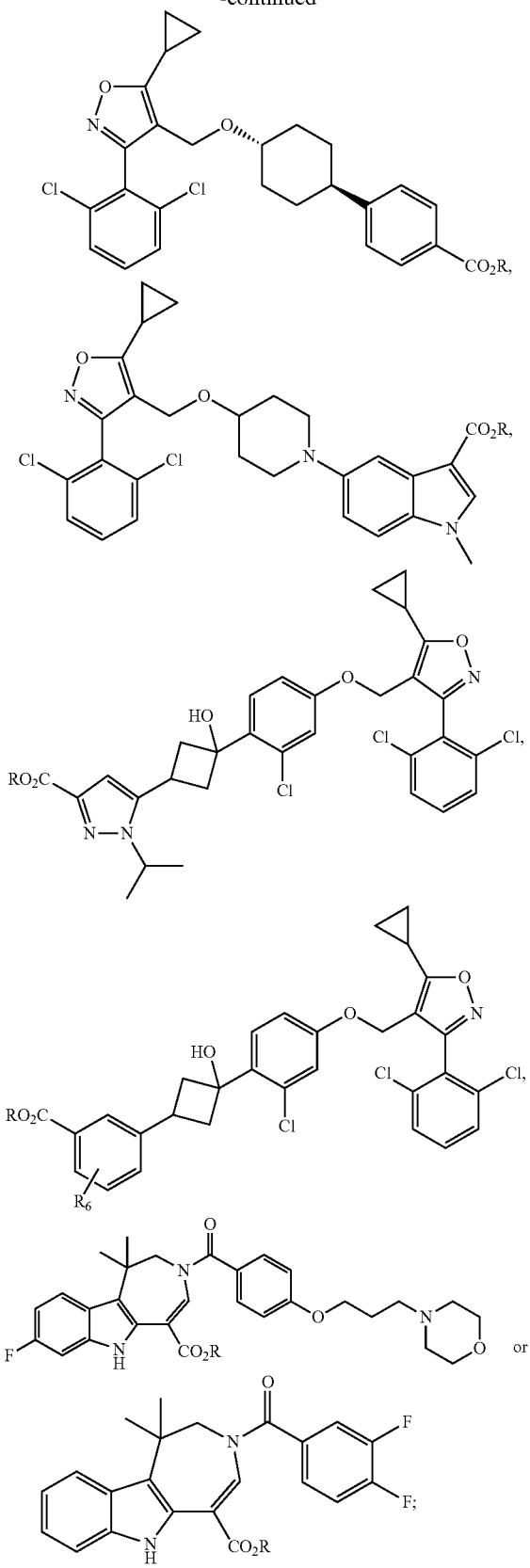

Additional non-limiting examples of FXR agonists are shown in US 2010/0093818, WO 2009/012125, WO 2013/007387, WO 2013/008164, WO 2003/007387, WO 2007/140174, WO 2008/157270, U.S. Pat. No. 8,309,581, U.S. Pat. No. 7,816,540, U.S. Pat. No. 7,825,258, U.S. Pat. No. 7,790,904, and U.S. Pat. No. 8,193,192. Still, non-additional examples of FXR agonists are shown in Grienke et al *Bioog. Med. Chem.* 2011, p. 6779-6791; Lundquist et al *J. Med. Chem.* 2010, 53, p. 1774-1787; Mehlmann et al *Bioorg. Med. Chem. Lett.* 2009, 19, p. 5289-5292; Abel et al *Bioorg. Med. Chem. Lett.* 2010, 20, p. 4911-4917; Richter et al *Bioorg. Med. Chem. Lett.* 2011, 21, p. 191-194.

A "subject" is a mammal, e.g., a human, mouse, rat, guinea pig, dog, cat, horse, cow, pig, or non-human primate, such as a monkey, chimpanzee, baboon or rhesus, and the terms "subject" and "patient" are used interchangeably herein.

The invention also includes pharmaceutical compositions comprising an effective amount of a fatty acid statin conjugate or a fatty acid FXR agonist conjugate and a pharmaceutically acceptable carrier. The invention includes a fatty acid statin conjugate or a fatty acid FXR agonist conjugate provided as a pharmaceutically acceptable prodrug, hydrate, salt, such as a pharmaceutically acceptable salt, enantiomers, stereoisomers, or mixtures thereof.

Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide and valerate salts.

The term "metabolic disease" as used herein refers to disorders, diseases and syndromes involving dyslipidemia, and the terms metabolic disorder, metabolic disease, and metabolic syndrome are used interchangeably herein.

An "effective amount" when used in connection with a fatty acid statin conjugate or a fatty acid FXR agonist conjugate is an amount effective for treating or preventing a metabolic disease.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug conjugate or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a fatty acid statin conjugate or a fatty acid FXR agonist conjugate.

The following abbreviations are used herein and have the indicated definitions: Boc and BOC are tert-butoxycarbonyl, $Boc_2O$ is di-tert-butyl dicarbonate, BSA is bovine serum albumin, CDI is 1,1'-carbonyldiimidazole, DCC is N,N'-dicyclohexylcarbodiimide, DIEA is N,N-diisopropylethylamine, DMAP is 4-dimethylaminopyridine, DMEM is Dulbecco's Modified Eagle Medium, DMF is N,N-dimethylformamide, DOSS is sodium dioctyl sulfosuccinate, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, h is hour, HATU is 2-(7-aza-1H-benzotriazole-1-yl)-1,1,3,3-tetramethyluronium hexafluorophosphate, HIV is human immunodeficiency virus, HPMC is hydroxypropyl methylcellulose, oxone is potassium peroxymonosulfate, Pd/C is palladium on carbon, TFA is trifluoroacetic acid, TGPS is tocopherol propylene glycol succinate, and THF is tetrahydrofuran.

Compounds

Accordingly in one aspect, the present invention provides a molecular conjugate which comprises a statin and a fatty acid covalently linked, wherein the fatty acid is selected from the group consisting of lipoic acid, omega-3 fatty acids and fatty acids that are metabolized in vivo to omega-3 fatty acids, saturated fatty acids, omega-6 fatty acids and omega-9 fatty acids. In some embodiments, the conjugate comprises at least one amide and the conjugate is capable of hydrolysis to produce free statin and free fatty acid.

In another aspect, the present invention provides a molecular conjugate which comprises an FXR agonist and a fatty acid covalently linked, wherein the fatty acid is selected from the group consisting of lipoic acid, omega-3 fatty acids and fatty acids that are metabolized in vivo to omega-3 fatty acids, saturated fatty acids, omega-6 fatty acids and omega-9 fatty acids. In some embodiments, the conjugate comprises at least one amide and the conjugate is capable of hydrolysis to produce free FXR agonist and free fatty acid.

In some embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid, tetracosahexaenoic acid and lipoic acid. In other embodiments, the fatty acid is selected from eicosapentaenoic acid, docosahexaenoic acid and lipoic acid. In other embodiments, the fatty acid is selected from linoleic acid and oleic acid. In other embodiments, the fatty acid is selected from a saturated fatty acid containing a 14, 15 or 16 carbon chain. In some embodiments, the hydrolysis is enzymatic.

In another aspect, the present invention provides fatty acid statin conjugates according to Formula I and fatty acid FXR agonist conjugates according to Formula II:

Formula I

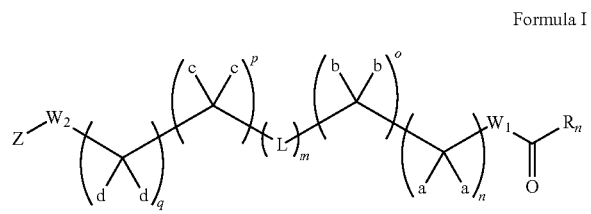

Formula II

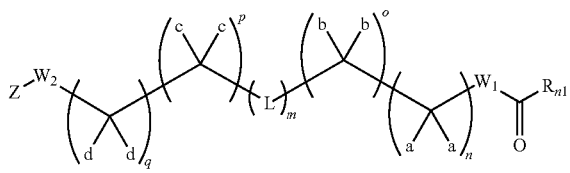

and pharmaceutically acceptable salts, hydrates, solvates, prodrugs, enantiomers and stereoisomers thereof;

wherein $R_1$, $R_2$, $R_3$, $W_1$, $W_2$, L, a, c, b, d, e, g, h, m, ml, n, o, p, q, Z, r, s, t, v, $f_1$, $f_2$, $f_3$, $f_4$, $f_5$, $R_6$, $R_n$ and $R_{n1}$ are as defined above for Formula I and Formula II, with the proviso that there is at least one

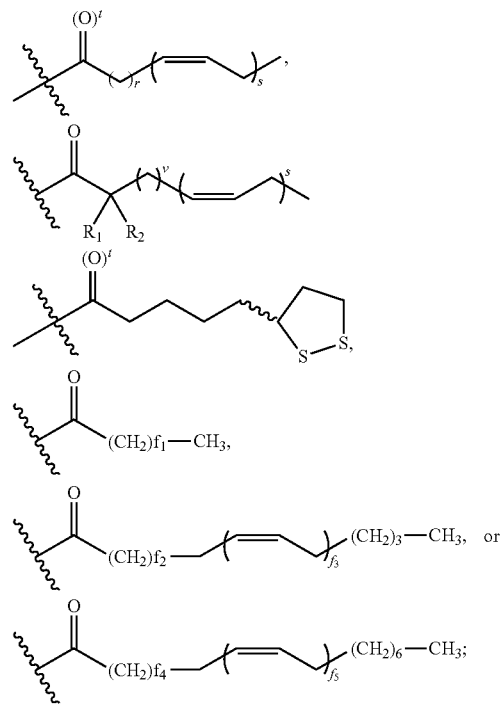

in the conjugate.

In some embodiments, one Z is

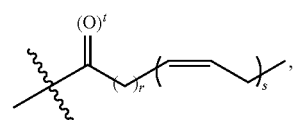

and r is 2.

In some embodiments, one Z is

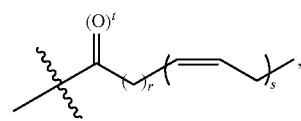

and r is 3.

In some embodiments, one Z is

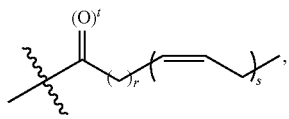

and r is 7.

In other embodiments, one Z is

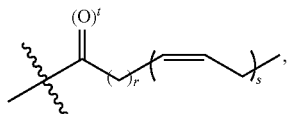

and s is 3.

In some embodiments, one Z is

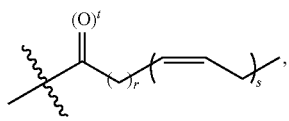

and s is 5.

In some embodiments, one Z is

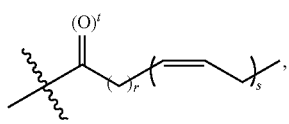

and s is 6.

In some embodiments, one Z is

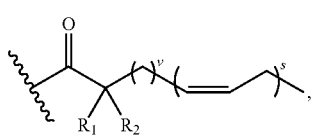

and v is 1.

In other embodiments, one Z is

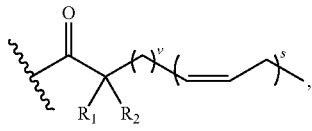

and v is 2.

In some embodiments, one Z is

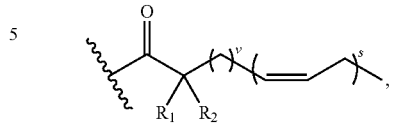

and v is 6.

In some embodiments, one Z is

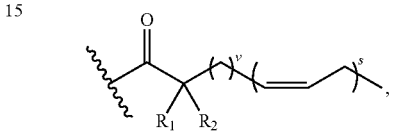

and s is 3.

In some embodiments, one Z is

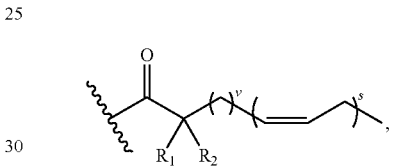

and s is 5.

In other embodiments, one Z is

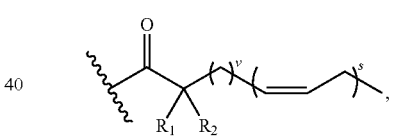

and s is 6.

In other embodiments, Z is

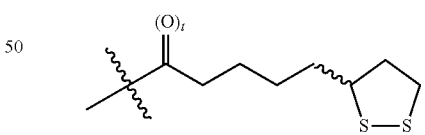

and t is 1.

In some embodiments, Z is

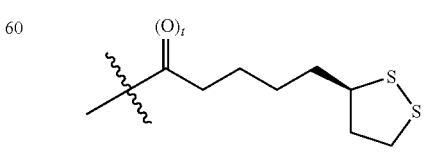

and t is 1.

In some embodiments, Z is

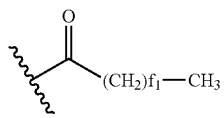

wherein $f_1$ is 14.

In some embodiments, Z is

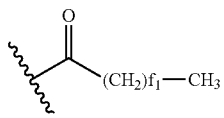

wherein $f_1$ is 15.

In some embodiments, Z is

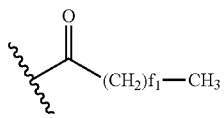

wherein $f_1$ is 16.

In some embodiments, Z is

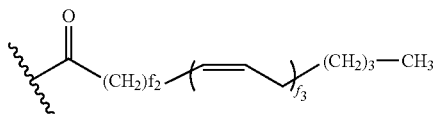

wherein $f_2=3$ and $f_3=4$.

In some embodiments, Z is

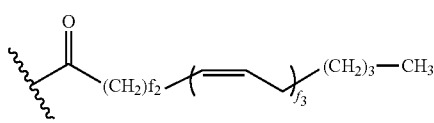

wherein $f_2=7$ and $f_3=2$.

In some embodiments, Z is

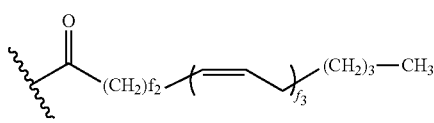

wherein $f_2=2$ and $f_3=5$.

In some embodiments, Z is

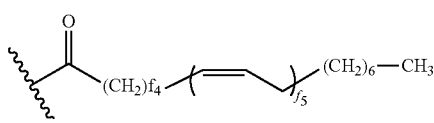

wherein $f_4=7$ and $f_5=1$.

In some embodiments, $R_n$ is

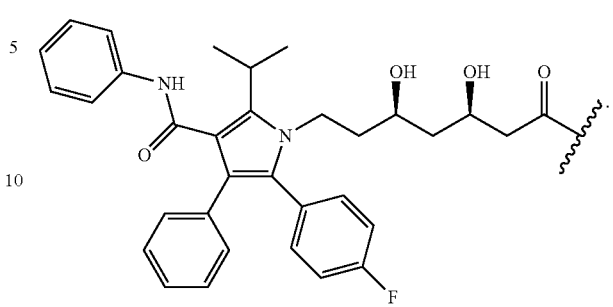

In some embodiments, $R_n$ is

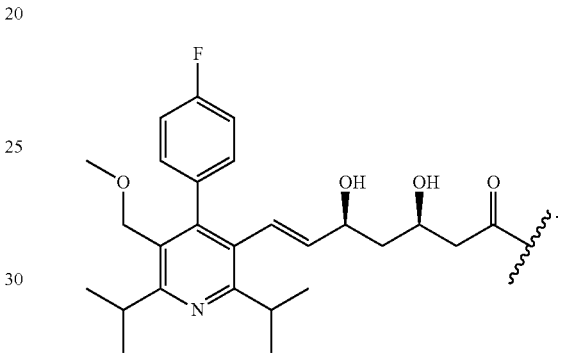

In some embodiments, $R_n$ is

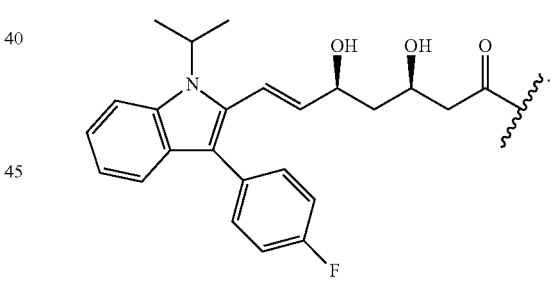

In some embodiments, $R_n$ is

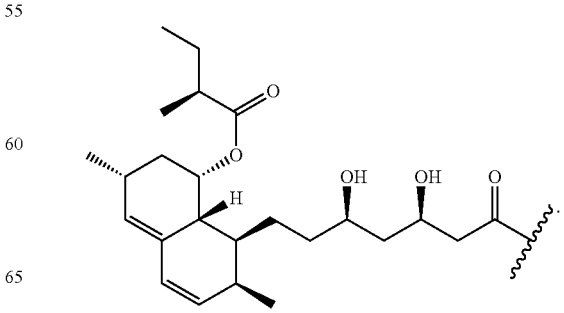

In some embodiments, $R_n$ is
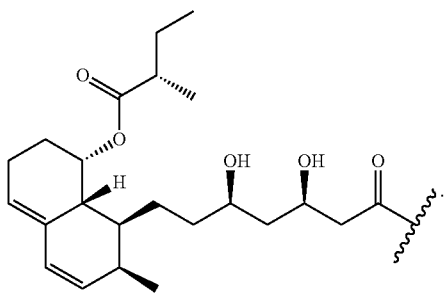 [SMILES: *C(=O)C[C@H](O)C[C@H](O)CC[C@@H]1[C@@H]2C(=CCC[C@@H]2OC(=O)[C@@H](C)CC)C=C[C@@H]1C]
In some embodiments, $R_n$ is
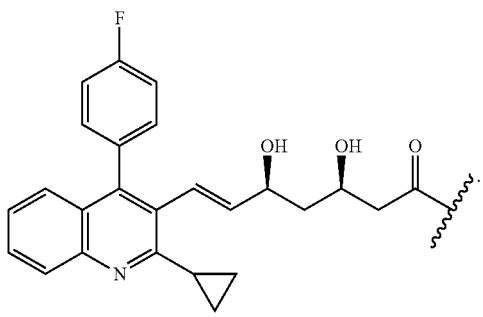 [SMILES: *C(=O)C[C@H](O)C[C@H](O)/C=C/c1c(C2CC2)nc2ccccc2c1-c1ccc(F)cc1]
In some embodiments, $R_n$ is
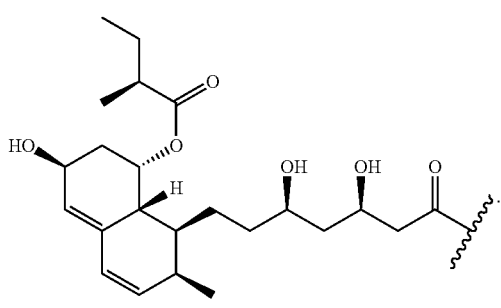 [SMILES: *C(=O)C[C@H](O)C[C@H](O)CC[C@@H]1[C@@H]2C(=C[C@@H](O)C[C@@H]2OC(=O)[C@@H](C)CC)C=C[C@@H]1C]
In some embodiments, $R_n$ is
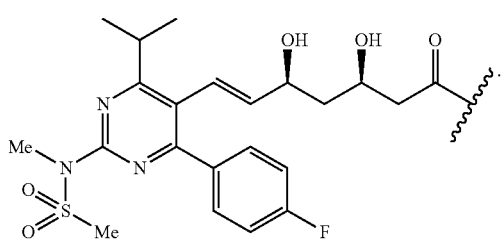 [SMILES: *C(=O)C[C@H](O)C[C@H](O)/C=C/c1c(-c2ccc(F)cc2)nc(N(C)S(C)(=O)=O)nc1C(C)C]
In some embodiments, $R_n$ is
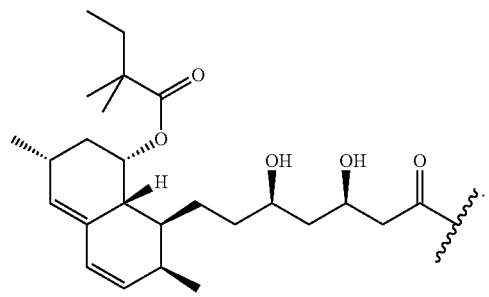 [SMILES: *C(=O)C[C@H](O)C[C@H](O)CC[C@@H]1[C@@H]2C(=C[C@H](C)C[C@@H]2OC(=O)C(C)(C)CC)C=C[C@@H]1C]
In some embodiments, $R_{n1}$ is
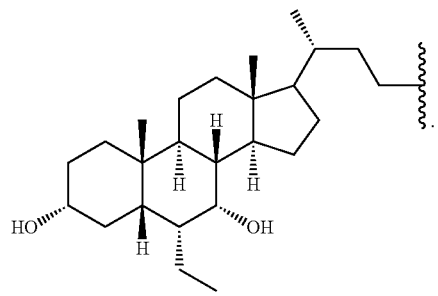
In some embodiments, $R_{n1}$ is
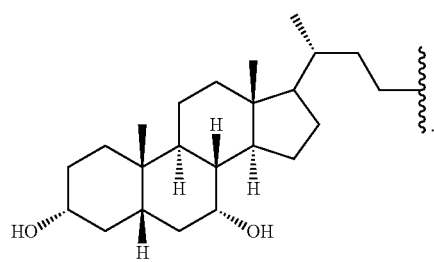
In some embodiments, $R_{n1}$ is
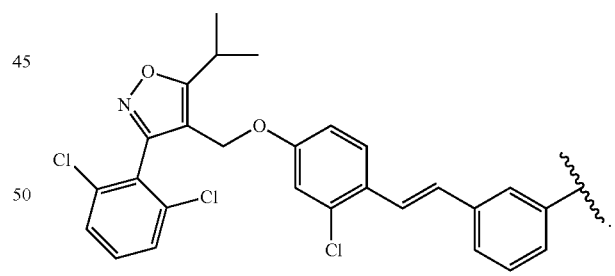
In some embodiments, $R_{n1}$ is
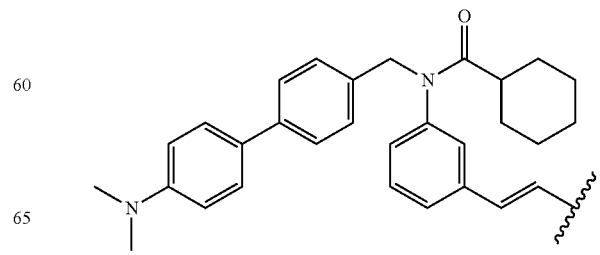

In some embodiments, $R_{n1}$ is

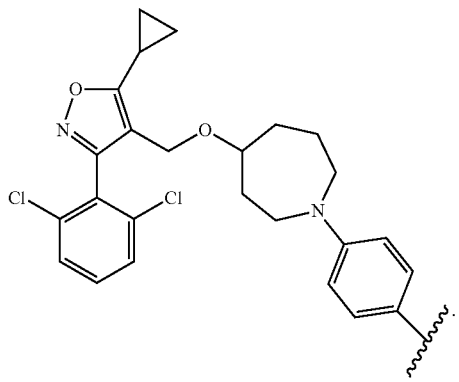 [SMILES: *c1ccc(N2CCCC(OCc3c(-c4c(Cl)cccc4Cl)noc3C3CC3)CC2)cc1]

In some embodiments, $R_{n1}$ is

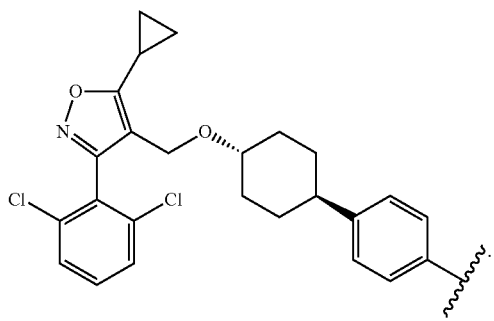 [SMILES: *c1ccc([C@H]2CC[C@H](OCc3c(-c4c(Cl)cccc4Cl)noc3C3CC3)CC2)cc1]

In some embodiments, $R_{n1}$ is

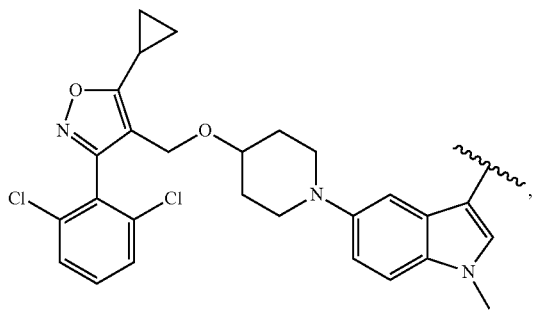 [SMILES: *c1cn(C)c2ccc(N3CCC(OCc4c(-c5c(Cl)cccc5Cl)noc4C4CC4)CC3)cc12]

In some embodiments, $R_{n1}$ is

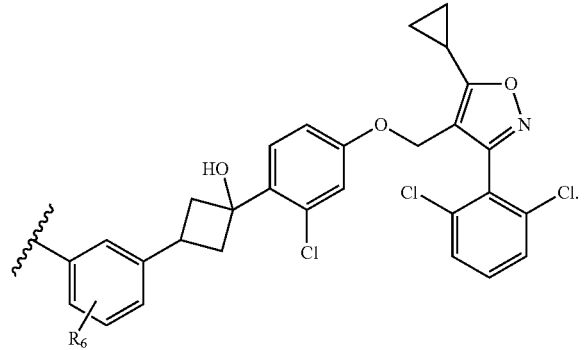

In some embodiments, $R_{n1}$ is

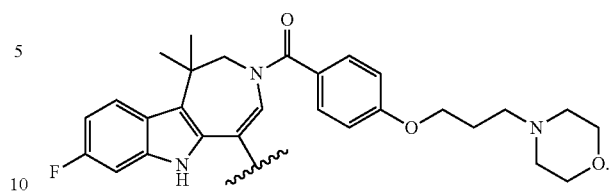

In some embodiments, $R_{n1}$ is

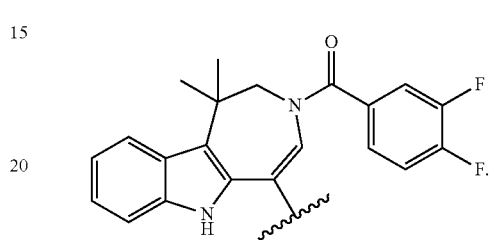

In some embodiments, $W_1$ is NH.
In some embodiments, $W_2$ is NH.
In some embodiments, $W_1$ is O.
In some embodiments, $W_2$ is O.
In some embodiments, $W_1$ is null.
In some embodiments, $W_2$ is null.
In some embodiments, $W_1$ and $W_2$ are each NH.
In some embodiments, $W_1$ and $W_2$ are each null.
In some embodiments, $W_1$ is O and $W_2$ is NH.
In some embodiments, $W_1$ and $W_2$ are each NR, and R is $CH_3$.
In some embodiments, m is 0.
In other embodiments, m is 1.
In other embodiments, m is 2.
In some embodiments, L is —S— or —S—S—.
In some embodiments, L is —O—.
In some embodiments, L is —C(O)—.
In some embodiments, L is heteroaryl.
In some embodiments, L is heterocycle.
In some embodiments, L is

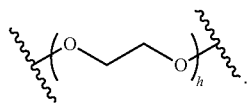

In some embodiments, L is

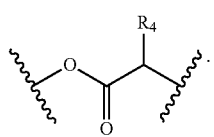

In some embodiments, L is
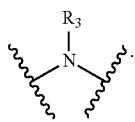
In some embodiments, L is
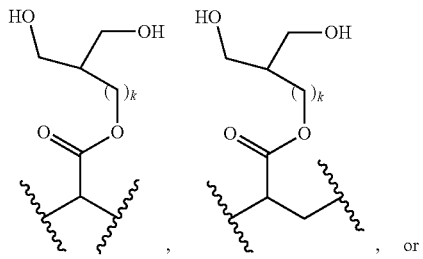
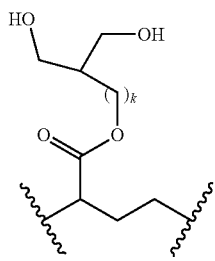
In some embodiments, L is
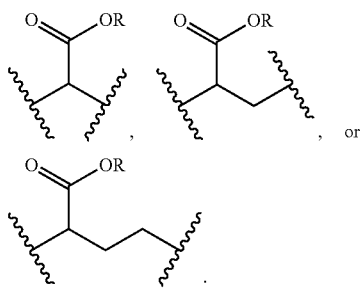
In some embodiments, L is
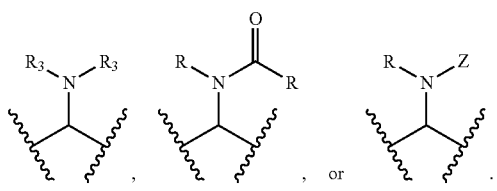
In some embodiments, L is
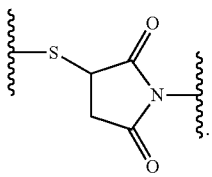 [SMILES: *SC1CC(=O)N(*)C1=O]
In some embodiments, L is
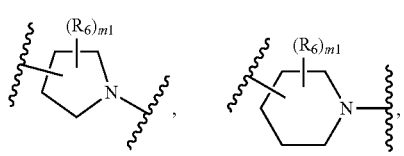
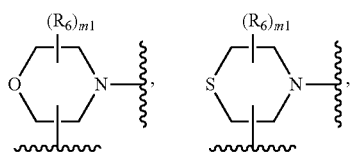
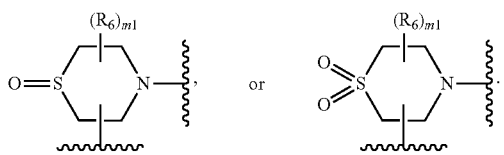
In some embodiments, L is
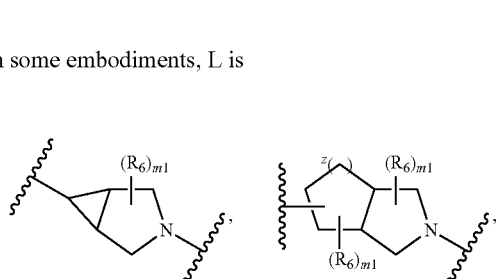
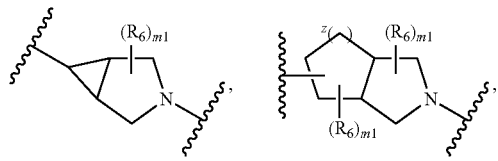
In some embodiments, L is
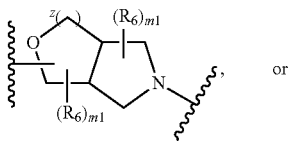  or  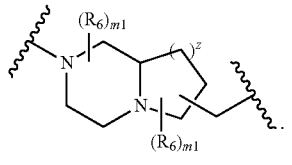
In some embodiments, L is
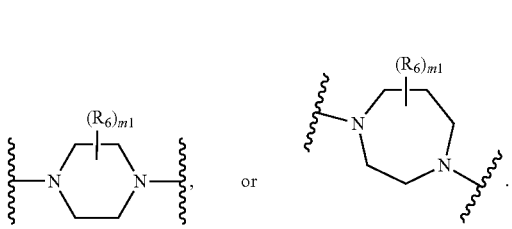

-continued

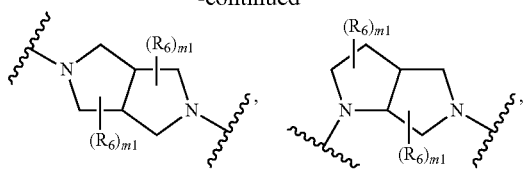

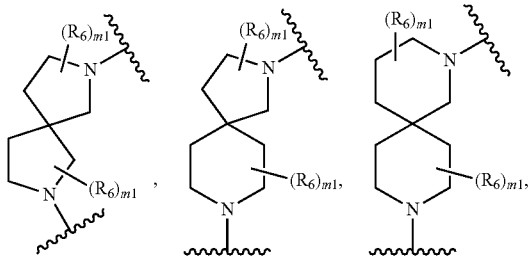

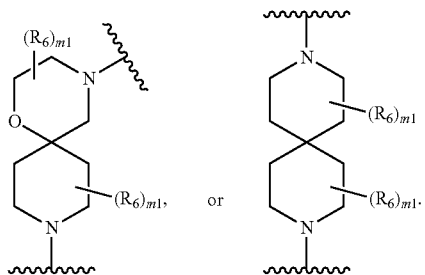

In other embodiments, one of n, o, p, and q is 1.
In some embodiments, two of n, o, p, and q are each 1.
In other embodiments, three of n, o, p, and q are each 1.
In some embodiments n, o, p, and q are each 1.
In some embodiments, one d is C(O)OR.
In some embodiments, r is 2 and s is 6.
In some embodiments, r is 3 and s is 5.
In some embodiments, t is 1.
In some embodiments, $W_1$ and $W_2$ are each NH, m is 0, n, and o are each 1, and p and q are each 0.
In some embodiments, $W_1$ and $W_2$ are each NH, m is 1, n, o, p, and q are each 1, and L is O.
In some embodiments, $W_1$ and $W_2$ are each NH, m is 1, n, o, p, and q are each 1, and L is

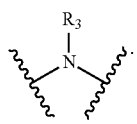

In some embodiments, $W_1$ and $W_2$ are each NH, m is 1, n, o, p, and q are each 1, and L is —S—S—.
In some embodiments, $W_1$ and $W_2$ are each NH, m is 1, n and o are each 0, p and q are each 1, and L is

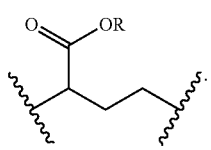

In some embodiments, $W_1$ and $W_2$ are each NH, m is 1, k is 0, n and o are each 0, p and q are each 1, and L is

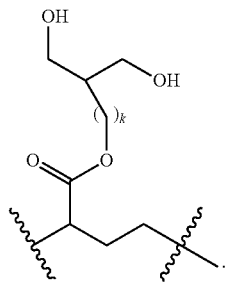

In some embodiments, $W_1$ and $W_2$ are each NH, m is 1, n and o are each 1, p and q are each 0, and L is

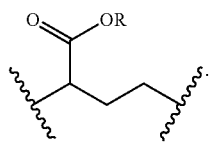

In some embodiments, $W_1$ and $W_2$ are each NH, m is 1, k is 0, n is 1, o, p and q are each 0, and L is

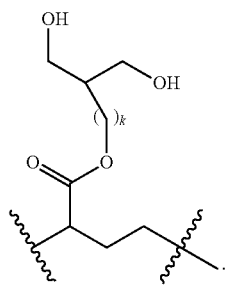

In some embodiments, $W_1$ and $W_2$ are each NH, m is 1, n, o, and p are each 0, and q is 1, and L is

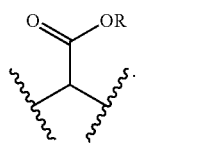

In some embodiments, $W_1$ and $W_2$ are each NH, m is 1, k is 1, n, o, and p are each 0, and
q is 1, and L is

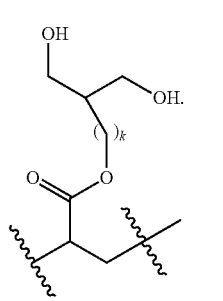

In some embodiments, $W_1$ and $W_2$ are each NH, m is 1, n is 1, and o, p, and q are each 0, and L is

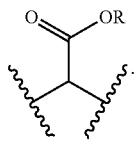

In some embodiments, $W_1$ and $W_2$ are each NH, m is 1, k is 1, o, p, and q are each 0, and L is

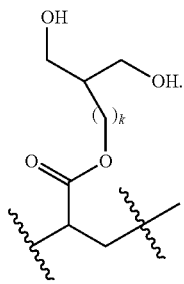

In some embodiments, $W_1$ and $W_2$ are each NH, m is 1, n, o, p, and q are each 1, and L is

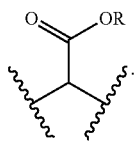

In some embodiments, $W_1$ and $W_2$ are each NH, m is 1, n, o, p, and q are each 1, and L is

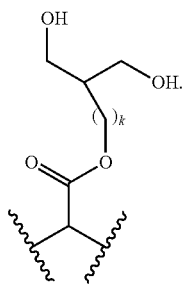

In some embodiments, $W_1$ and $W_2$ are each NH, m is 0, k is 1, o and p are each 1, and q is 0.

In some embodiments, $W_1$ and $W_2$ are each NH, m is 0, n, o, p, and q are each 1.

In some embodiments, $W_1$ and $W_2$ are each NH, m is 0, n and o are each 1, p and q are each 0, and each a is $CH_3$.

In some embodiments, $W_1$ and $W_2$ are each NH, m is 0, n and o are each 1, p and q are each 0, and each b is $CH_3$.

In some embodiments, $W_1$ and $W_2$ are each NH, m is 1, n, o, p, and q are each 1, $R_3$ is H, and L is

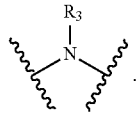

In some embodiments, $W_1$ and $W_2$ are each NH, m is 1, n, p and q are each 1, and o is 2, $R_3$ is H, and L is

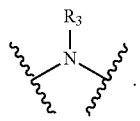

In some embodiments, $W_1$ and $W_2$ are each NH, m is 1, n, o, p are each 1, and q is 2, and L is

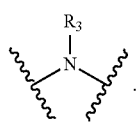

In some embodiments, $W_1$ and $W_2$ are each NH, m is 1, n, o, p, and q are each 1, and L is

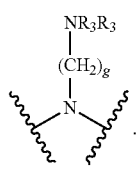

In some embodiments, $W_1$ and $W_2$ are each NH, m is 1, n and p are each 1, and o and q are each 0, and L is —C(O)—.

In some embodiments, $W_1$ and $W_2$ are each NH, m is 1, n and p are each 1, and o, and q are each 0, and L is

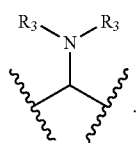

In some embodiments, $W_1$ and $W_2$ are each NH, m is 1, n, o, p, q are each 1, and L is

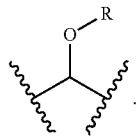

In some embodiments, $W_1$ and $W_2$ are each NH, m is 1, n, o, p, and q are each 1, h is 1, and L is

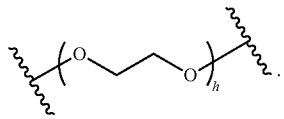

In some embodiments, $W_1$ and $W_2$ are each NH, m is 1, n, o, p, and q are each 1, and L is —S—.

In some embodiments, $W_1$ and $W_2$ are each NH, m is 1, n, o, p are each 0, q is 1, one d is —CH$_3$, and L is

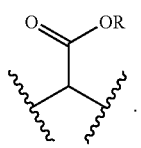

In some embodiments, $W_1$ and $W_2$ are each NH, m is 2, n, o, p, and q are each 0, one L is

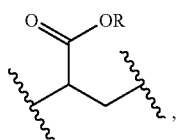

and
one L is

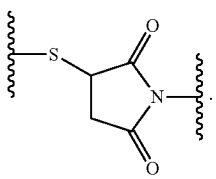 [SMILES: *SC1CC(=O)N(*)C1=O]

In some embodiments, m is 0, n, o, p, and q are each 0, and $W_1$ and $W_2$ are taken together to form an optionally substituted piperazine group.

In some embodiments, m is 1, n, o, p, and q are each 0, $W_1$ and $W_2$ are each null, and L is

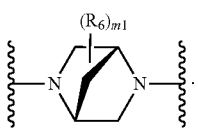

In some embodiments, m is 1, n and p are each 1, o and q are each 0, $W_1$ and $W_2$ are each NH, and L is $C_3$-$C_6$ cycloalkyl.

In some embodiments, m is 1, n is 1, o, p, and q are each 0, $W_1$ and $W_2$ are each NH, and L is $C_3$-$C_6$ cycloalkyl.

In some embodiments, m is 1, n, o, p, are each 0, q is 1, $W_1$ and $W_2$ are each NH, and L is $C_3$-$C_6$ cycloalkyl.

In some embodiments, m is 1, n, o, p, and q are each 0, $W_1$ is NH, $W_2$ is null, and L is

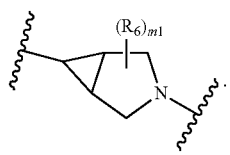

In some embodiments, m is 1, n o, p, and q are each 0, $W_1$ is null, $W_2$ is NH, and L is

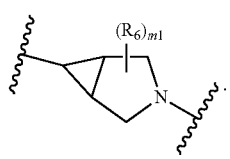

In some embodiments, m is 1, n o, p, and q are each 0, $W_1$ is NH, $W_2$ is null, and L is

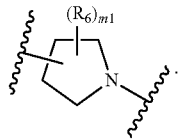

In some embodiments, m is 1, n o, p, and q are each 0, $W_1$ is null, $W_2$ is NH, and L is

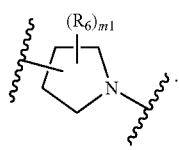

In some embodiments, m is 1, n is 1, o, p, and q are each 0, $W_1$ is NH, $W_2$ is null, and L is

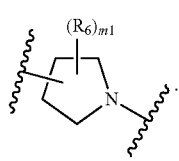

In some embodiments, m is 1, n, o, p, are each 0, q is 1, $W_1$ is null, $W_2$ is NH, and L is

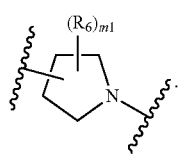

In some embodiments, m is 1, n, o, p, and q are each 0, $W_1$ is NH, $W_2$ is null, and L is

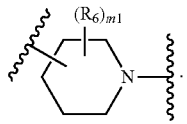

In some embodiments, m is 1, n, o, p, and q are each 0, $W_1$ is null, $W_2$ is NH, and L is

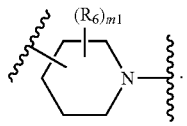

In some embodiments, m is 1, n is 1, o, p, and q are each 0, $W_1$ is NH, $W_2$ is null, and L is

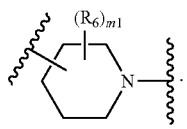

In some embodiments, m is 1, n, o, p, are each 0, q is 1, $W_1$ is null, $W_2$ is NH, and L is

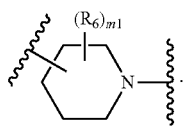

In some embodiments, m is 1, n is 1, o, p, and q are each 0, $W_1$ is NH, $W_2$ is null, and L is

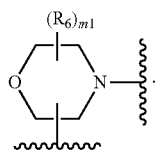

In some embodiments, m is 1, n, o, p, are each 0, q is 1, $W_1$ is null, $W_2$ is NH, and L is

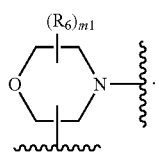

In some embodiments, m is 1, n, o, p, q are each 0, $W_1$ and $W_2$ is null, and L is

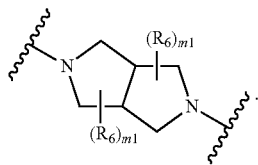

In some embodiments, m is 1, n, o, p, q are each 0, $W_1$ and $W_2$ is null, and L is

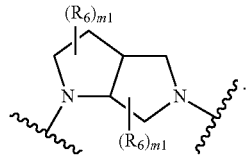

In some embodiments, m is 1, n, o, p, q are each 0, $W_1$ is NH, $W_2$ is null, and L is

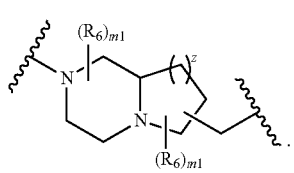

In some embodiments, m is 1, n, o, p, q are each 0, $W_1$ is null, $W_2$ is NH, and L is

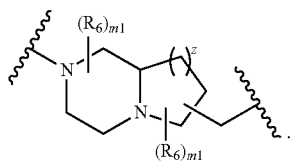

In some embodiments, m is 1, n, o, p, are each 0, q is 1, $W_1$ and $W_2$ are each and NH, is null, L is

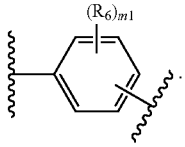

In some embodiments, m is 1, n, o, p, are each 0, q is 1, $W_1$ and $W_2$ are each NH, is null, and L is a heteroaryl.

In some of the foregoing embodiments, r is 2, s is 6 and t is 1.

In some of the foregoing embodiments, r is 3, s is 5 and t is 1.

In some of the foregoing embodiments, Z is

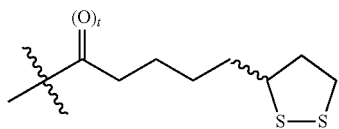

and
t is 1.

In Formula I and Formula II, any one or more of H may be substituted with a deuterium. It is also understood in Formula I and Formula II that a methyl substituent can be substituted with a $C_1$-$C_6$ alkyl.

In other illustrative embodiments, compounds of Formula I and Formula II are as set forth below:

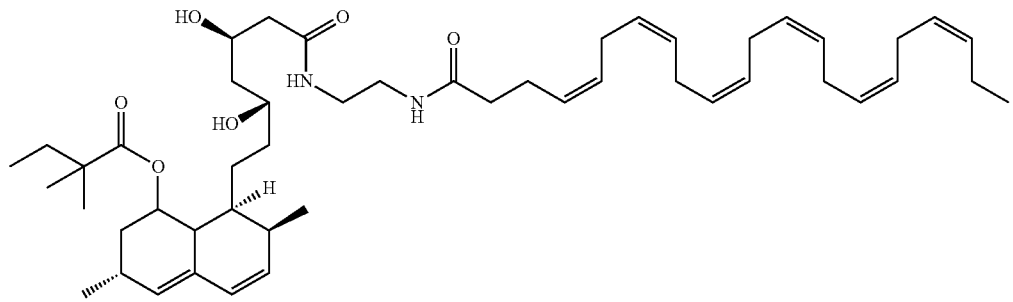 [SMILES: CC/C=C\C/C=C\C/C=C\C/C=C\C/C=C\C/C=C\CCC(=O)NCCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-7-((2-((4Z,7Z,10Z,13Z,16Z,19Z)-docosa-4,7,10,13,16,19-hexaenamido)ethyl)amino)-3,5-dihydroxy-7-oxoheptyl)-3,7-dimethyl-1,2,3,7,8,8a-hexahydronaphthalen-1-yl 2,2-dimethylbutanoate (I-1)

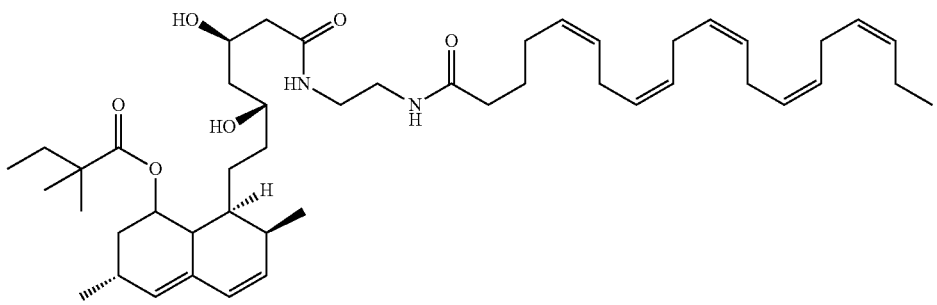 [SMILES: CC/C=C\C/C=C\C/C=C\C/C=C\C/C=C\CCCC(=O)NCCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7-((2-((5Z,8Z,11Z,14Z,17Z)-icosa-5,8,11,14,17-pentaenamido)ethyl)amino)-7-oxoheptyl)-3,7-dimethyl-1,2,3,7,8,8a-hexahydronaphthalen-1-yl 2,2-dimethylbutanoate (I-2)

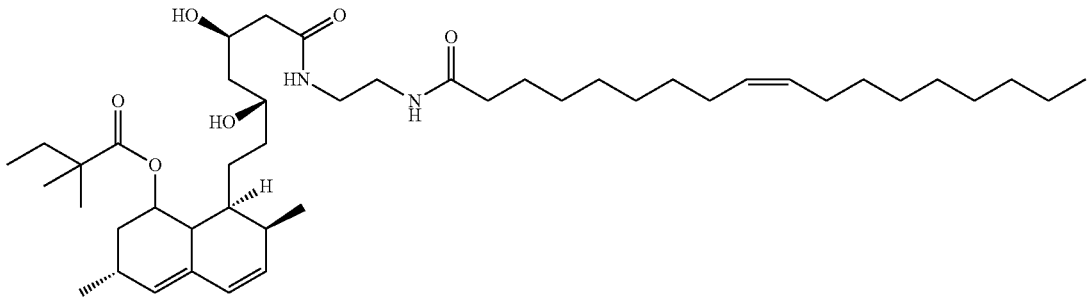 [SMILES: CCCCCCCC/C=C\CCCCCCCC(=O)NCCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7-(2-oleamidoethyl)amino)-7-oxoheptyl)-3,7-dimethyl-1,2,3,7,8,8a-hexahydronaphthalen-1-yl 2,2-dimethylbutanoate (I-3)

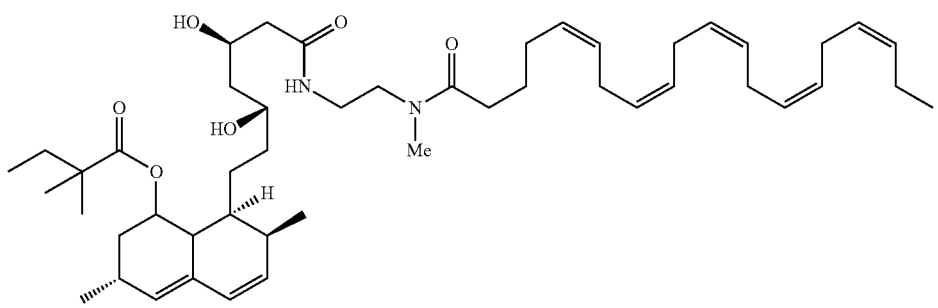 [SMILES: CC/C=C\C/C=C\C/C=C\C/C=C\C/C=C\CCCC(=O)N(C)CCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7-((2-((5Z,8Z,11Z,14Z,17Z)—N-methylicosa-5,8,11,14,17-pentaenamido)ethyl)amino)-7-oxoheptyl)-3,7-dimethyl-1,2,3,7,8,8a-hexahydronaphthalen-1-yl 2,2-dimethylbutanoate (I-4)

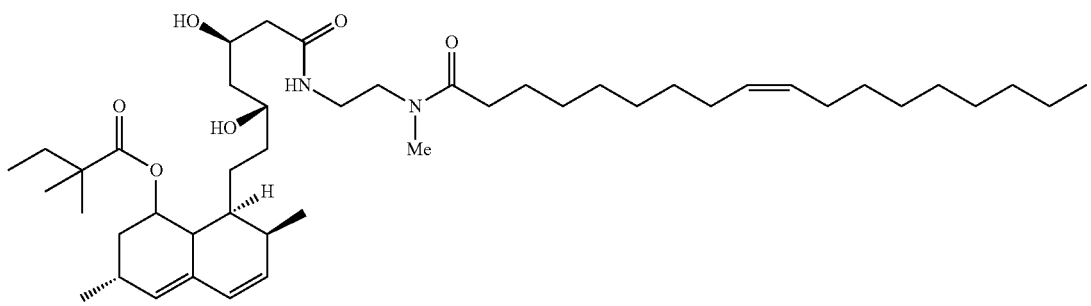 [SMILES: CCCCCCCC/C=C\CCCCCCCC(=O)N(C)CCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7((2-(N-methyloleamido)ethyl)amino)-7-oxoheptyl)-3,7-dimethyl-1,2,3,7,8,8a-hexahydronaphthalen-1-yl 2,2-dimethylbutanoate (I-5)

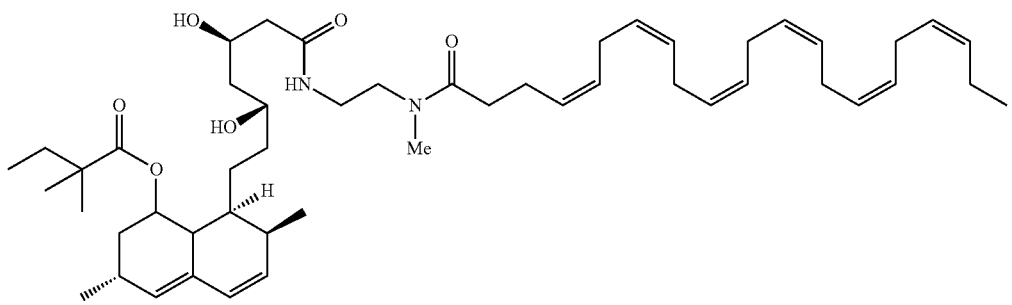 [SMILES: CC/C=C\C/C=C\C/C=C\C/C=C\C/C=C\C/C=C\CCC(=O)N(C)CCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7-((2-((4Z,7Z,10Z,13Z,16Z,19Z)—N-methyldocosa-4,7,10,13,16,19-hexaenamido)ethyl)amino)-7-oxoheptyl)-3,7-dimethyl-1,2,3,7,8,8a-hexahydronaphthalen-1-yl 2,2-dimethylbutanoate (I-6)

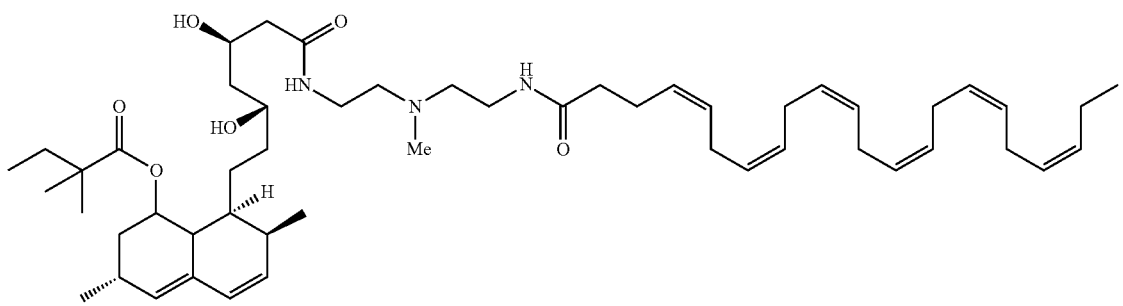 [SMILES: CC/C=C\C/C=C\C/C=C\C/C=C\C/C=C\C/C=C\CCC(=O)NCCN(C)CCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-7-((2-((2-((4Z,7Z,10Z,13Z,16Z,19Z)-docosa-4,7,10,13,16,19-hexaenamido)ethyl)(methyl)amino)ethyl)amino)-3,5-dihydroxy-7-oxoheptyl)-3,7-dimethyl-1,2,3,7,8,8a-hexahydronaphthalen-1-yl 2,2-dimethylbutanoate (I-7)

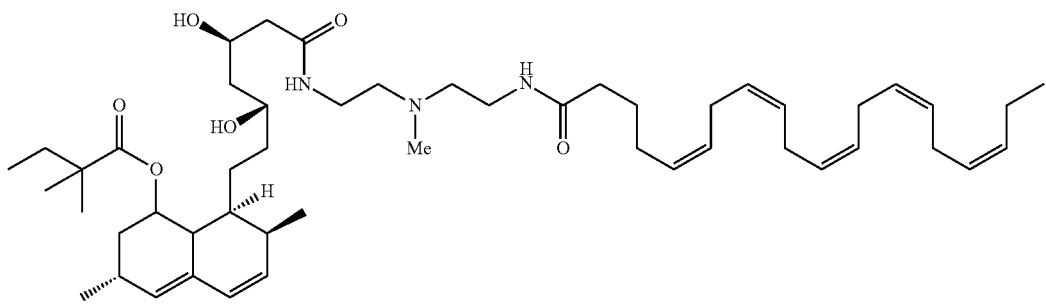 [SMILES: CC/C=C\C/C=C\C/C=C\C/C=C\C/C=C\CCCC(=O)NCCN(C)CCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7-((2-((2-((5Z,8Z,11Z,14Z,17Z)-icosa-5,8,11,14,17-pentaenamido)ethyl)(methyl)amino)ethyl)amino)-7-oxoheptyl)-3,7-dimethyl-1,2,3,7,8,8a-hexahydronaphthalen-1-yl 2,2-dimethylbutanoate (I-8)

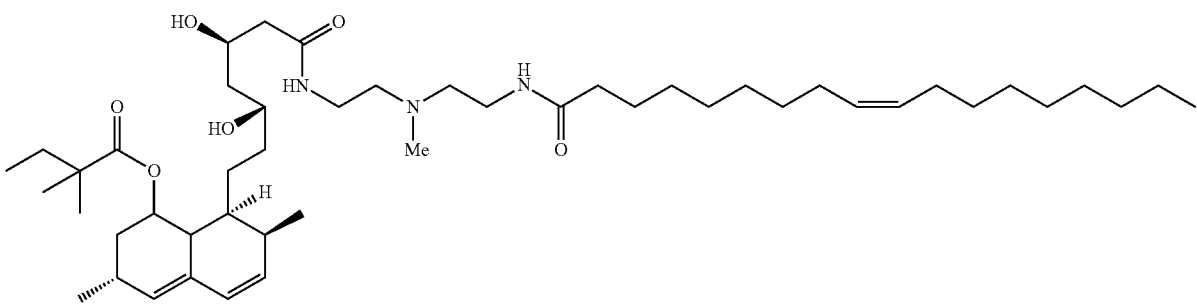 [SMILES: CCCCCCCC/C=C\CCCCCCCC(=O)NCCN(C)CCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7-((2-(methyl(2-oleamidoethyl)amino)ethyl)amino)-7-oxoheptyl)-3,7-dimethyl-1,2,3,7,8,8a-hexahydronaphthalen-1-yl 2,2-dimethylbutanoate (I-9)

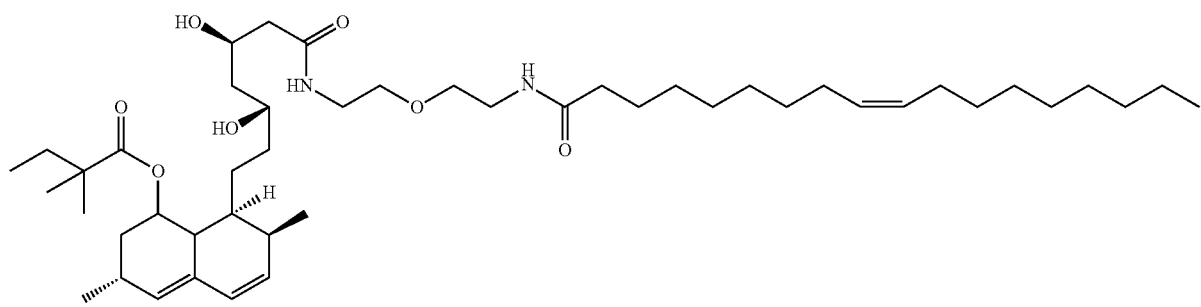 [SMILES: CCCCCCCC/C=C\CCCCCCCC(=O)NCCOCCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7-((2-(2-oleamidoethoxyl)ethyl)amino)-7-oxoheptyl)-3,7-dimethyl-1,2,3,7,8,8a-hexahydronaphthalen-1-yl 2,2-dimethylbutanoate (I-10)

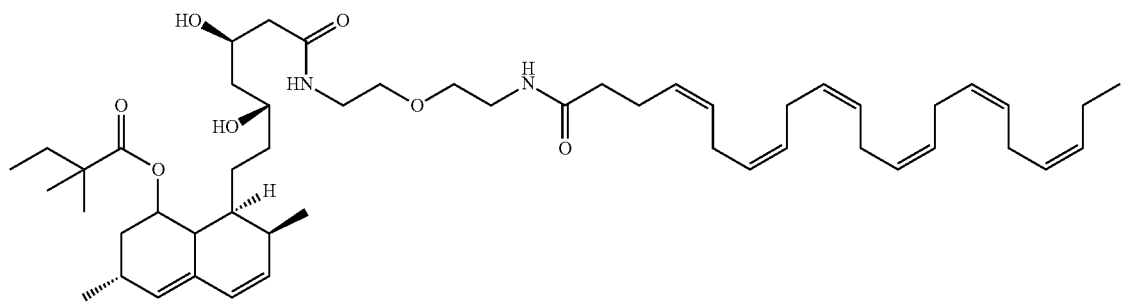 [SMILES: CC/C=C\C/C=C\C/C=C\C/C=C\C/C=C\C/C=C\CCC(=O)NCCOCCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-7-((2-(2-((4Z,7Z,10Z,13Z,16Z,19Z)-docosa-4,7,10,13,16,19-hexaenamido)ethoxy)ethyl)amino)-3,5-dihydroxy-7-oxoheptyl)-3,7-dimethyl-1,2,3,7,8,8a-hexahydronaphthalen-1-yl 2,2-dimethylbutanoate (I-11)

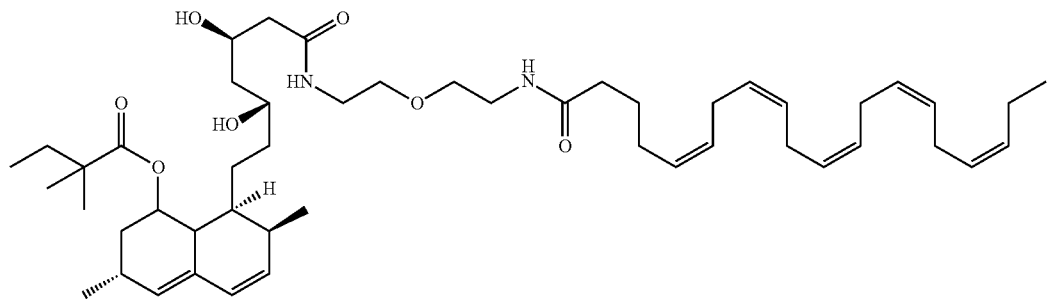 [SMILES: CC/C=C\C/C=C\C/C=C\C/C=C\C/C=C\CCCC(=O)NCCOCCNC(=O)C[C@H](O)C[C@@H](O)CC[C@@H]1C2C(=C[C@H](C)CC2OC(=O)C(C)(C)CC)C=C[C@@H]1C]

(3R,7S,8S)-8-((3S,5R)-3,5-dihydroxy-7-((2-(2-((5Z,8Z,11Z,14Z,17Z)-icosa-5,8,11,14,17-pentaenamido)ethoxy)ethyl)amino)-7-oxoheptyl)-3,7-dimethyl-1,2,3,7,8,8a-hexahydronaphthalen-1-yl 2,2-dimethylbutanoate (I-12)

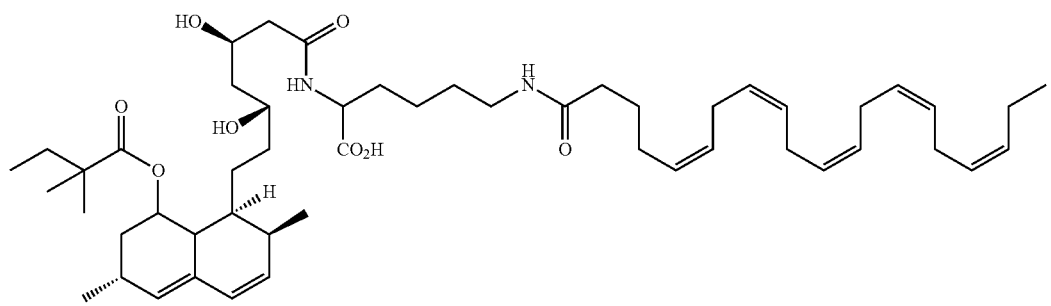 [SMILES: CC/C=C\C/C=C\C/C=C\C/C=C\C/C=C\CCCC(=O)NCCCCC(NC(=O)C[C@H](O)C[C@@H](O)CC[C@@H]1C2C(=C[C@H](C)CC2OC(=O)C(C)(C)CC)C=C[C@@H]1C)C(=O)O]

2-((3R,5S)-7-((1 S,2S,6R)-8-((2,2-dimethylbutanoyl)oxy)-
2,6-dimethyl-1,2,6,7,8,8a-hexahydronaphthalen-1-yl)-3,
5-dihydroxyheptanamido)-6-((5Z,8Z,11Z,14Z,17Z)-
icosa-5,8,11,14,17-pentaenamido)hexanoic acid (I-13)

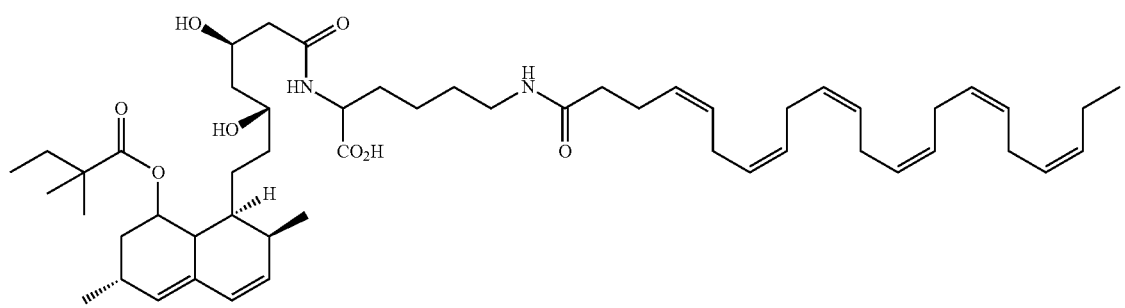 [SMILES: CC/C=C\C/C=C\C/C=C\C/C=C\C/C=C\C/C=C\CCC(=O)NCCCCC(NC(=O)C[C@H](O)C[C@@H](O)CC[C@@H]1C2C(=C[C@H](C)CC2OC(=O)C(C)(C)CC)C=C[C@@H]1C)C(=O)O]

2-((3R,5S)-7-((1S,2S,6R)-8-((2,2-dimethylbutanoyl)
oxy)-2,6-dimethyl-1,2,6,7,8,8a-hexahydronaphthalen-1-yl)-
3,5-dihydroxyheptanamido)-6-((4Z,7Z,10Z,13Z,16Z,19Z)-
docosa-4,7,10,13,16,19-hexaenamido)hexanoic acid (I-14)

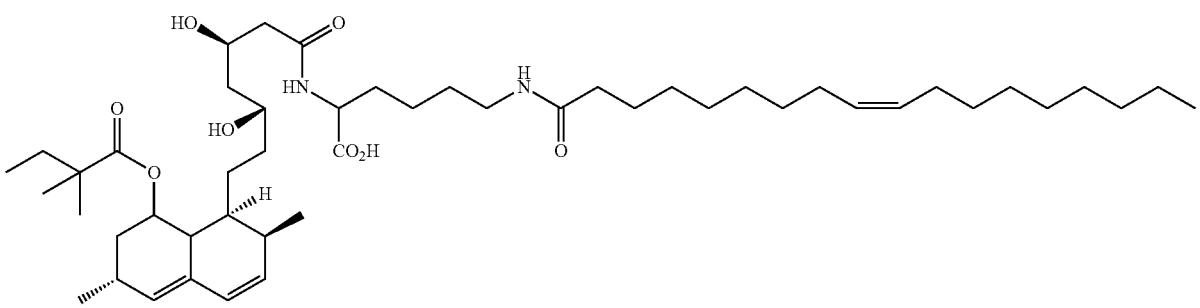 [SMILES: CCCCCCCC/C=C\CCCCCCCC(=O)NCCCCC(NC(=O)C[C@H](O)C[C@@H](O)CC[C@@H]1C2C(=C[C@H](C)CC2OC(=O)C(C)(C)CC)C=C[C@@H]1C)C(=O)O]

2-((3R,5S)-7-((1 S,2S,6R)-8-((2,2-dimethylbutanoyl)oxy)-
2,6-dimethyl-1,2,6,7,8,8a-hexahydronaphthalen-1-yl)-3,
5-dihydroxyheptanamido)-6-oleamidohexanoic acid
(I-15)

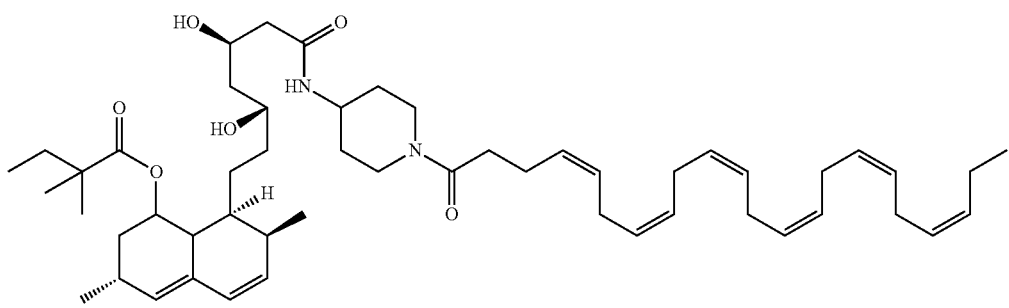 [SMILES: CC/C=C\C/C=C\C/C=C\C/C=C\C/C=C\C/C=C\CCC(=O)N1CCC(NC(=O)C[C@H](O)C[C@@H](O)CC[C@@H]2C3C(=C[C@H](C)CC3OC(=O)C(C)(C)CC)C=C[C@@H]2C)CC1]

(3R,7S,8S)-8-((3S,5R)-7-((1-((4Z,7Z,10Z,13Z,16Z,19Z)-docosa-4,7,10,13,16,19-hexaenoyl)piperidin-4-yl)amino)-3,5-dihydroxy-7-oxoheptyl)-3,7-dimethyl-1,2,3,7,8,8a-hexahydronaphthalen-1-yl 2,2-dimethylbutanoate (I-16)

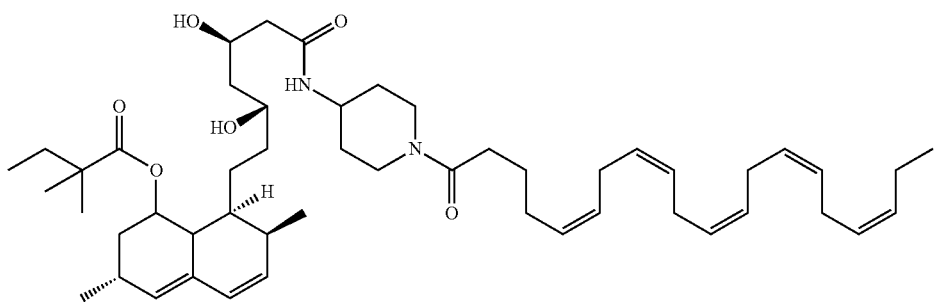 [SMILES: CC/C=C\C/C=C\C/C=C\C/C=C\C/C=C\CCCC(=O)N1CCC(NC(=O)C[C@H](O)C[C@@H](O)CC[C@@H]2C3C(=C[C@H](C)CC3OC(=O)C(C)(C)CC)C=C[C@@H]2C)CC1]

(3R,7S,8S)-8-((3S,5R)-3,5-dihydroxy-7-((1-((5Z,8Z,11Z,14Z,17Z)-icosa-5,8,11,14,17-pentaenoyl)piperidin-4-yl)amino)-7-oxoheptyl)-3,7-dimethyl-1,2,3,7,8,8a-hexahydronaphthalen-1-yl 2,2-dimethylbutanoate (I-17)

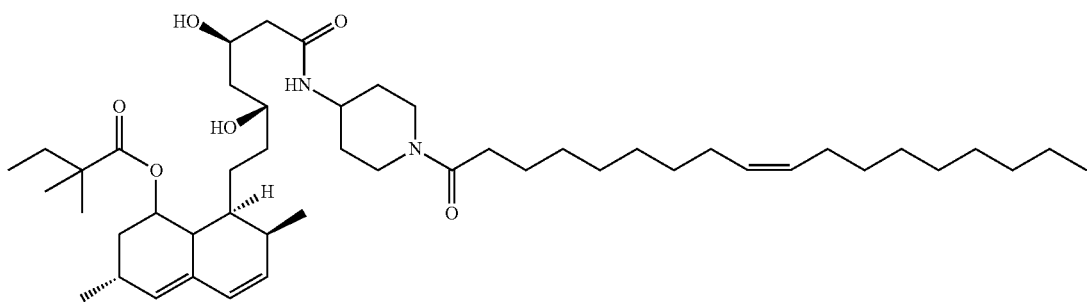 [SMILES: CCCCCCCC/C=C\CCCCCCCC(=O)N1CCC(NC(=O)C[C@H](O)C[C@@H](O)CC[C@@H]2C3C(=C[C@H](C)CC3OC(=O)C(C)(C)CC)C=C[C@@H]2C)CC1]

(3R,7S,8S)-8-((3S,5R)-3,5-dihydroxy-7-((1-oleoylpiperidin-4-yl)amino)-7-oxoheptyl)-3,7-dimethyl-1,2,3,7,8,8a-hexahydronaphthalen-1-yl 2,2-dimethylbutanoate (I-18)

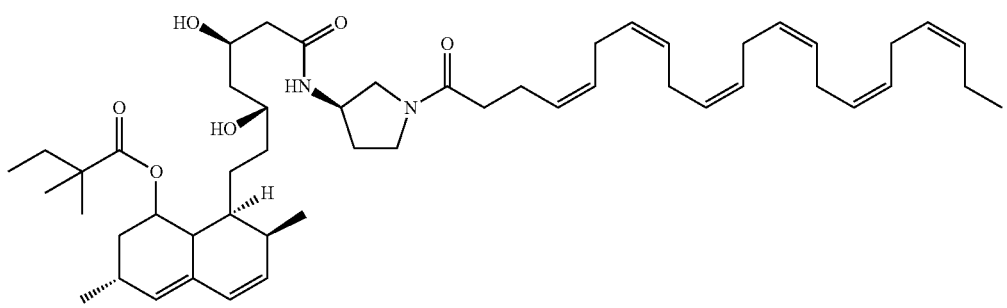 [SMILES: CC/C=C\C/C=C\C/C=C\C/C=C\C/C=C\C/C=C\CCC(=O)N1CC[C@@H](NC(=O)C[C@H](O)C[C@@H](O)CC[C@@H]2C3C(=C[C@H](C)CC3OC(=O)C(C)(C)CC)C=C[C@@H]2C)C1]

(3R,7S,8S)-8-((3S,5R)-7-(((S)-1-((4Z,7Z,10Z,13Z,16Z,
19Z)-docosa-4,7,10,13,16,19-hexaenoyl)pyrrolidin-3-yl)
amino)-3,5-dihydroxy-7-oxoheptyl)-3,7-dimethyl-1,2,3,7,8,
8a-hexahydronaphthalen-1-yl 2,2-dimethylbutanoate (I-19)

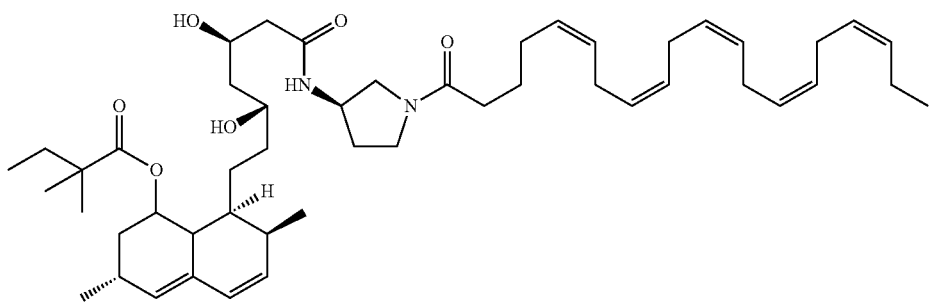 [SMILES: CC/C=C\C/C=C\C/C=C\C/C=C\C/C=C\CCCC(=O)N1CC[C@@H](NC(=O)C[C@H](O)C[C@@H](O)CC[C@@H]2C3C(=C[C@H](C)CC3OC(=O)C(C)(C)CC)C=C[C@@H]2C)C1]

(3R,7S,8S)-8-((3S,5R)-3,5-dihydroxy-7-(((S)-1-((5Z,8Z,
11Z,14Z,17Z)-icosa-5,8,11,14,17-pentaenoyl)pyrrolidin-
3-yl)amino)-7-oxoheptyl)-3,7-dimethyl-1,2,3,7,8,8a-
hexahydronaphthalen-1-yl 2,2-dimethylbutanoate (I-20)

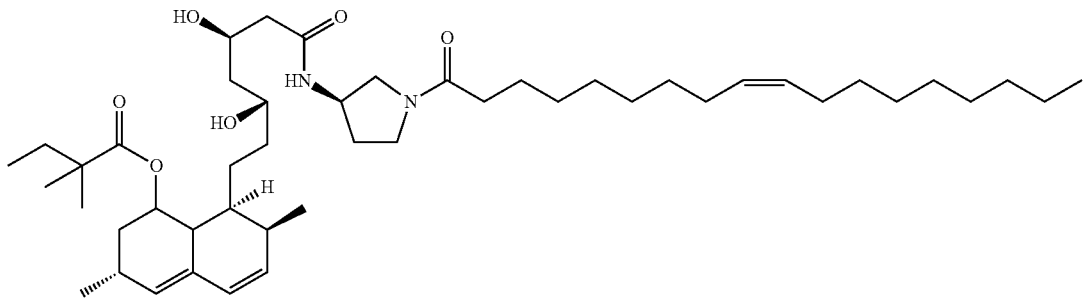 [SMILES: CCCCCCCC/C=C\CCCCCCCC(=O)N1CC[C@@H](NC(=O)C[C@H](O)C[C@@H](O)CC[C@@H]2C3C(=C[C@H](C)CC3OC(=O)C(C)(C)CC)C=C[C@@H]2C)C1]

(3R,7S,8S)-8-((3S,5R)-3,5-dihydroxy-7-(((S)-1-oleoylpyr-
rolidin-3-yl)amino)-7-oxoheptyl)-3,7-dimethyl-1,2,3,7,8,
8a-hexahydronaphthalen-1-yl 2,2-dimethylbutanoate
(I-21)

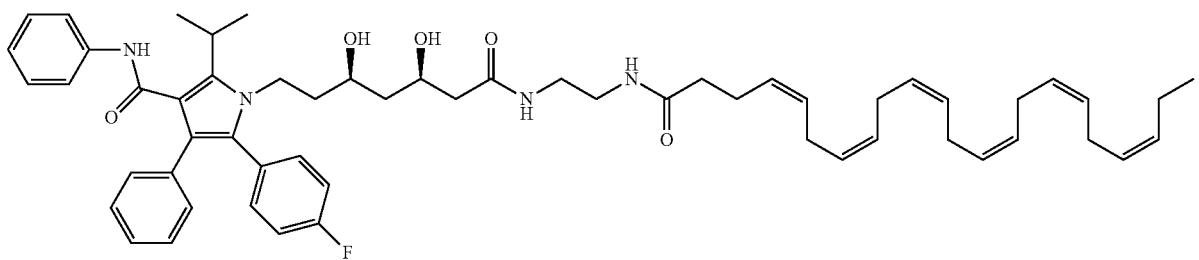 [SMILES: CC/C=C\C/C=C\C/C=C\C/C=C\C/C=C\C/C=C\CCC(=O)NCCNC(=O)C[C@H](O)C[C@H](O)CCn1c(-c2ccc(F)cc2)c(-c2ccccc2)c(C(=O)Nc2ccccc2)c1C(C)C]

1-((3R,5R)-7-((2-((4Z,7Z,10Z,13Z,16Z,19Z)-docosa-4,7,10,13,16,19-hexaenamido)ethyl)amino)-3,5-dihydroxy-7-oxoheptyl)-5-(4-fluorophenyl)-2-isopropyl-N,4-diphenyl-1H-pyrrole-3-carboxamide (I-22)

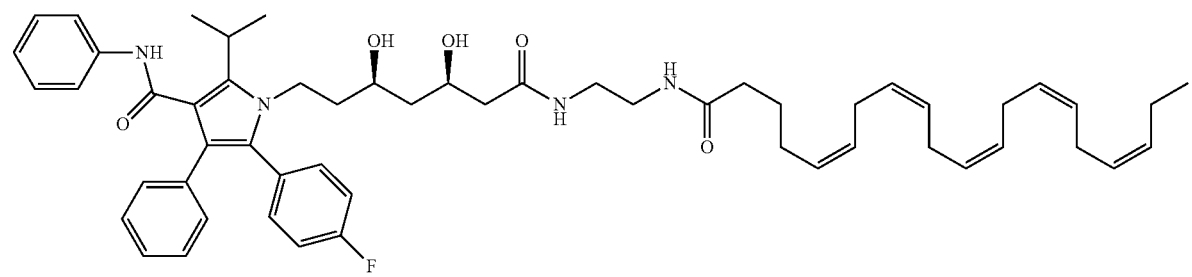 [SMILES: CC/C=C\C/C=C\C/C=C\C/C=C\C/C=C\CCCC(=O)NCCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-((5Z,8Z,11Z,14Z,17Z)-icosa-5,8,11,14,17-pentaenamido)ethyl)amino)-7-oxoheptyl)-5-(4-fluorophenyl)-2-isopropyl-N,4-diphenyl-1H-pyrrole-3-carboxamide (I-23)

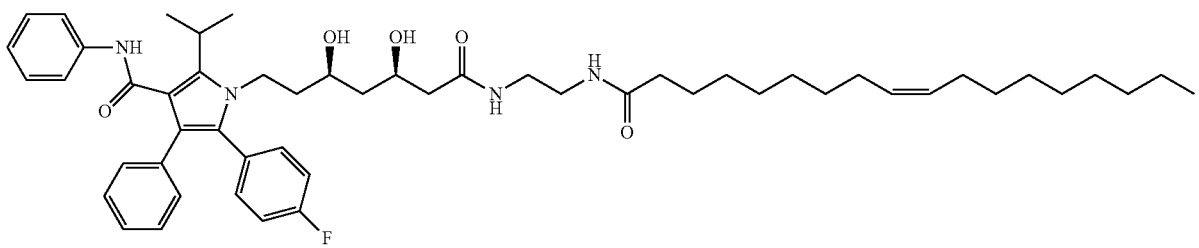 [SMILES: CCCCCCCC/C=C\CCCCCCCC(=O)NCCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-oleamidoethyl)amino)-7-oxoheptyl)-5-(4-fluorophenyl)-2-isopropyl-N,4-diphenyl-1H-pyrrole-3-carboxamide (I-24)

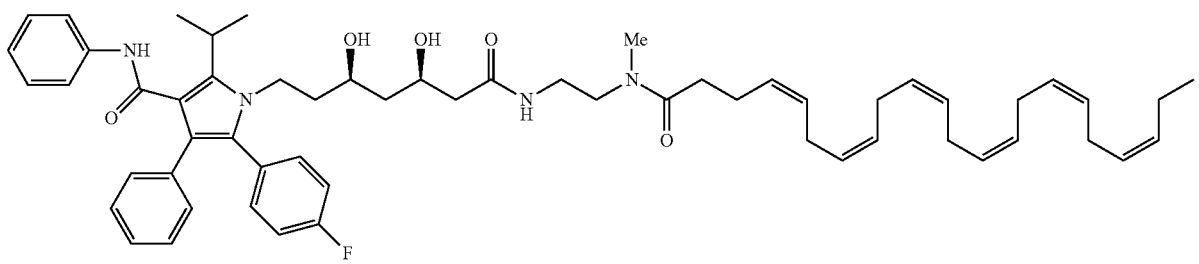 [SMILES: CC/C=C\C/C=C\C/C=C\C/C=C\C/C=C\C/C=C\CCC(=O)N(C)CCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-((4Z,7Z,10Z,13Z,16Z,19Z)—N-methyldocosa-4,7,10,13,16,19-hexaenamido)ethyl)amino)-7-oxoheptyl)-5-(4-fluorophenyl)-2-isopropyl-N,4-diphenyl-1H-pyrrole-3-carboxamide (I-25)

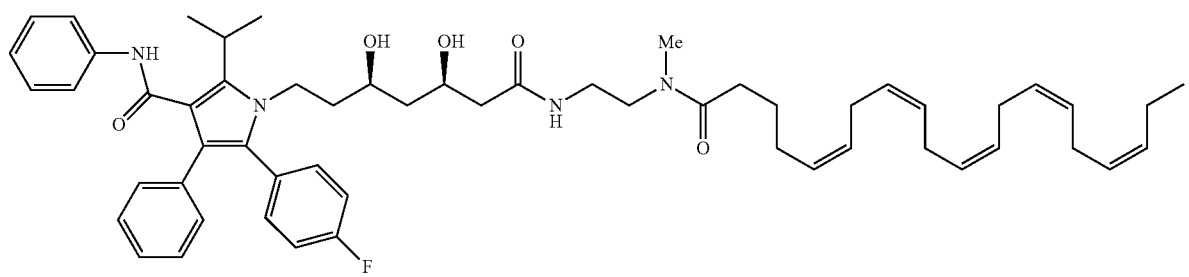 [SMILES: CC/C=C\C/C=C\C/C=C\C/C=C\C/C=C\CCCC(=O)N(C)CCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-((5Z,8Z,11Z,14Z,17Z)—N-methylicosa-5,8,11,14,17-pentaenamido)ethyl)amino)-7-oxoheptyl)-5-(4-fluorophenyl)-2-isopropyl-N,4-diphenyl-1H-pyrrole-3-carboxamide (I-26)

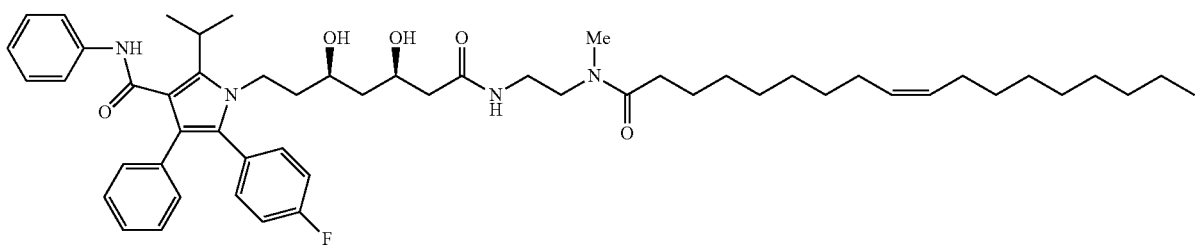 [SMILES: CCCCCCCC/C=C\CCCCCCCC(=O)N(C)CCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-(N-methyloleamido)ethyl)amino)-7-oxoheptyl)-5-(4-fluorophenyl)-2-isopropyl-N,4-diphenyl-1H-pyrrole-3-carboxamide (I-27)

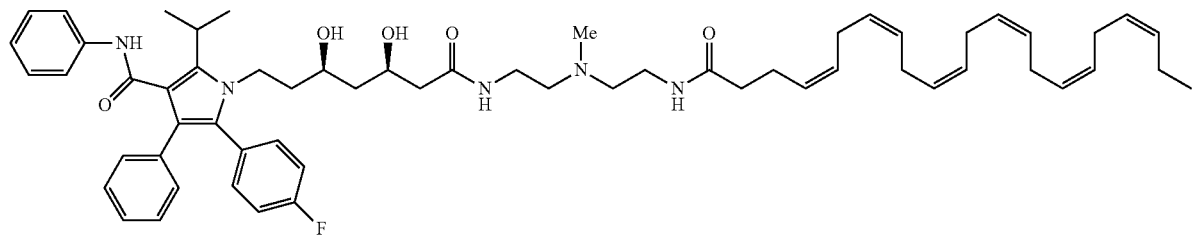 [SMILES: CC/C=C\C/C=C\C/C=C\C/C=C\C/C=C\C/C=C\CCC(=O)NCCN(C)CCNC(=O)C[C@H](O)C[C@H](O)CCn1c(-c2ccc(F)cc2)c(-c2ccccc2)c(C(=O)Nc2ccccc2)c1C(C)C]

1-((3R,5R)-7-((2-((2-((4Z,7Z,10Z,13Z,16Z,19Z)-docosa-4,7,10,13,16,19-hexaenamido)ethyl)(methyl)amino)ethyl)amino)-3,5-dihydroxy-7-oxoheptyl)-5-(4-fluorophenyl)-2-isopropyl-N,4-diphenyl-1H-pyrrole-3-carboxamide (I-28)

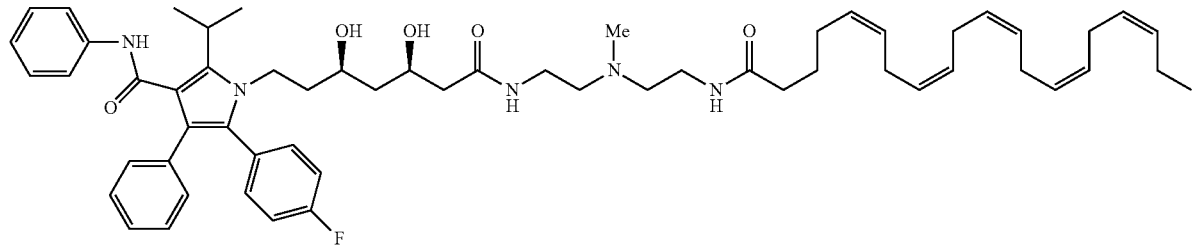 [SMILES: CC/C=C\C/C=C\C/C=C\C/C=C\C/C=C\CCCC(=O)NCCN(C)CCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-((2-((5Z,8Z,11Z,14Z,17Z)-icosa-5,8,11,14,17-pentaenamido)ethyl)(methyl)amino)ethyl)amino)-7-oxoheptyl)-5-(4-fluorophenyl)-2-isopropyl-N,4-diphenyl-1H-pyrrole-3-carboxamide (I-29)

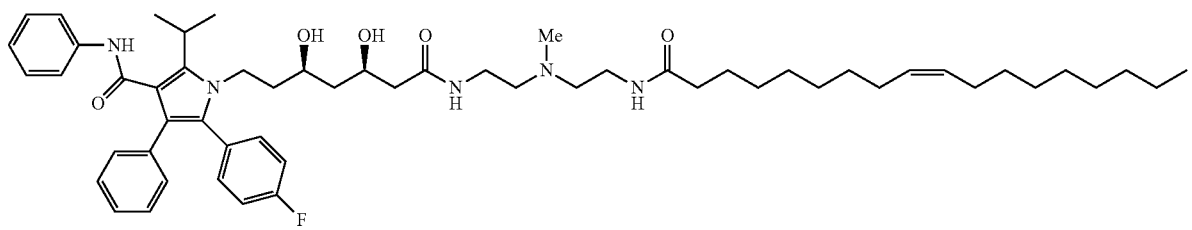 [SMILES: CCCCCCCC/C=C\CCCCCCCC(=O)NCCN(C)CCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-(methyl(2-oleamidoethyl)
amino)ethyl)amino)-7-oxoheptyl)-5-(4-fluorophenyl)-2-
isopropyl-N,4-diphenyl-1H-pyrrole-3-carboxamide (I-30)

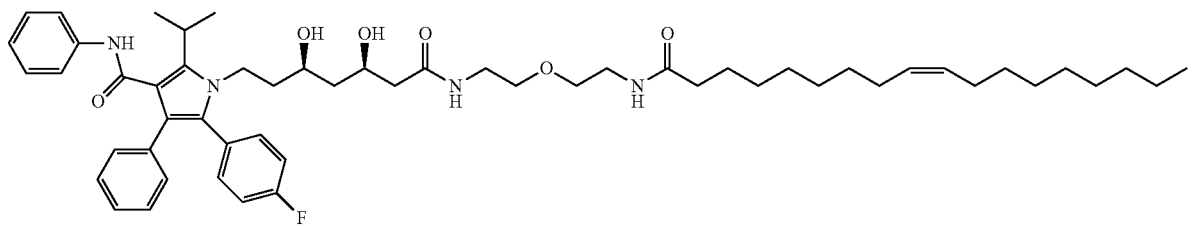 [SMILES: CCCCCCCC/C=C\CCCCCCCC(=O)NCCOCCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-(2-oleamidoethoxy)ethyl)
amino)-7-oxoheptyl)-5-(4-fluorophenyl)-2-isopropyl-N,
4-diphenyl-1H-pyrrole-3-carboxamide (I-31)

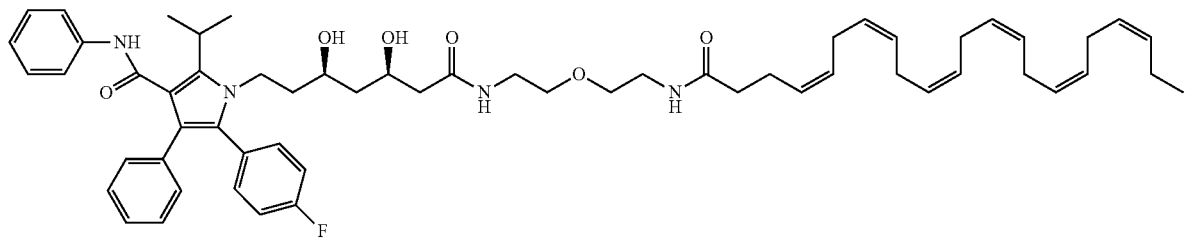 [SMILES: CC/C=C\C/C=C\C/C=C\C/C=C\C/C=C\C/C=C\CCC(=O)NCCOCCNC(=O)C[C@H](O)C[C@H](O)CCn1c(-c2ccc(F)cc2)c(-c2ccccc2)c(C(=O)Nc2ccccc2)c1C(C)C]

1-((3R,5R)-7-((2-(2-((4Z,7Z,10Z,13Z,16Z,19Z)-docosa-4,7,
10,13,16,19-hexaenamido)ethoxy)ethyl)amino)-3,5-dihy-
droxy-7-oxoheptyl)-5-(4-fluorophenyl)-2-isopropyl-N,4-
diphenyl-1H-pyrrole-3-carboxamide (I-32)

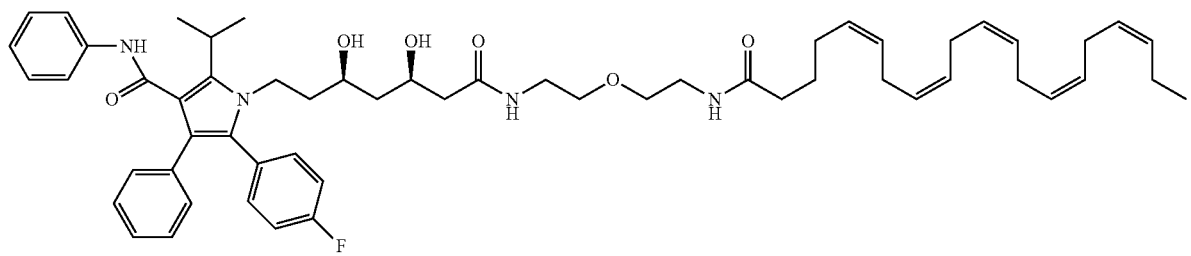 [SMILES: CC/C=C\C/C=C\C/C=C\C/C=C\C/C=C\CCCC(=O)NCCOCCNC(=O)C[C@H](O)C[C@H](O)CCn1c(-c2ccc(F)cc2)c(-c2ccccc2)c(C(=O)Nc2ccccc2)c1C(C)C]

1-((3R,5R)-3,5-dihydroxy-7-((2-(2-((5Z,8Z,11Z,14Z,17Z)-
icosa-5,8,11,14,17-pentaenamido)ethoxy)ethyl)amino)-
7-oxoheptyl)-5-(4-fluorophenyl)-2-isopropyl-N,4-diphe-
nyl-1H-pyrrole-3-carboxamide (I-33)

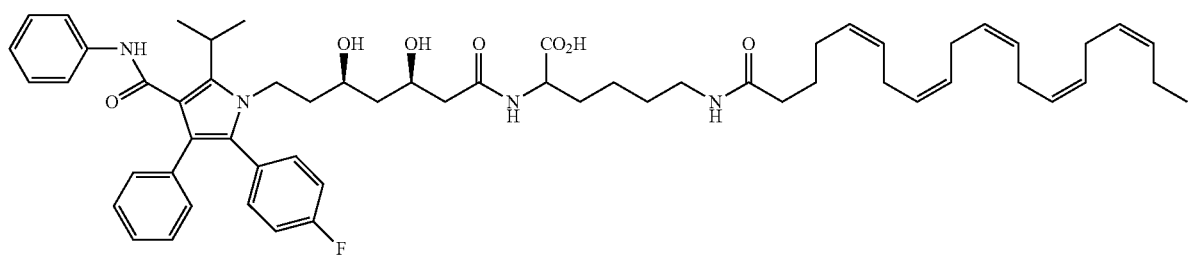 [SMILES: CC/C=C\C/C=C\C/C=C\C/C=C\C/C=C\CCCC(=O)NCCCCC(NC(=O)C[C@H](O)C[C@H](O)CCn1c(-c2ccc(F)cc2)c(-c2ccccc2)c(C(=O)Nc2ccccc2)c1C(C)C)C(=O)O]

2-((3R,5R)-7-(2-(4-fluorophenyl)-5-isopropyl-3-phenyl-4-(phenylcarbamoyl)-1H-pyrrol-1-yl)-3,5-dihydroxyheptanamido)-6-((5Z,8Z,11Z,14Z,17Z)-icosa-5,8,11,14,17-pentaenamido)hexanoic acid (I-34)

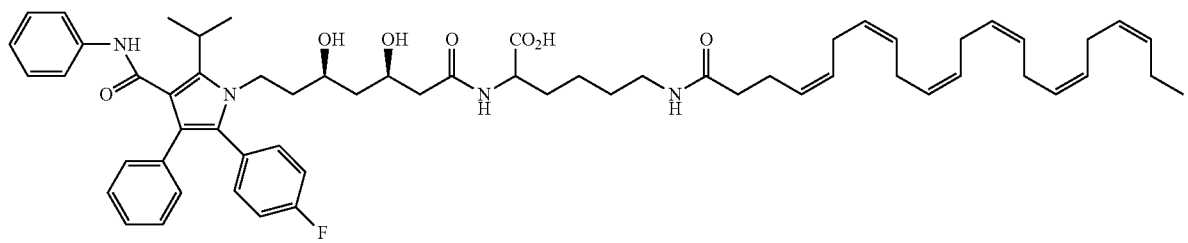 [SMILES: CC/C=C\C/C=C\C/C=C\C/C=C\C/C=C\C/C=C\CCC(=O)NCCCCC(NC(=O)C[C@H](O)C[C@H](O)CCn1c(-c2ccc(F)cc2)c(-c2ccccc2)c(C(=O)Nc2ccccc2)c1C(C)C)C(=O)O]

6-((4Z,7Z,10Z,13Z,16Z,19Z)-docosa-4,7,10,13,16,19-hexaenamido)-2-((3R,5R)-7-(2-(4-fluorophenyl)-5-isopropyl-3-phenyl-4-(phenylcarbamoyl)-1H-pyrrol-1-yl)-3,5-dihydroxyheptanamido)hexanoic acid (I-35)

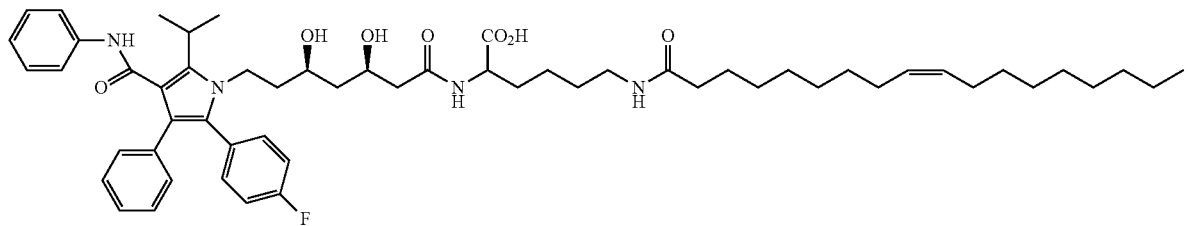 [SMILES: CCCCCCCC/C=C\CCCCCCCC(=O)NCCCCC(NC(=O)C[C@H](O)C[C@H](O)CCn1c(-c2ccc(F)cc2)c(-c2ccccc2)c(C(=O)Nc2ccccc2)c1C(C)C)C(=O)O]

2-((3R,5R)-7-(2-(4-fluorophenyl)-5-isopropyl-3-phenyl-4-(phenylcarbamoyl)-1H-pyrrol-1-yl)-3,5-dihydroxyheptanamido)-6-oleamidohexanoic acid (I-36)

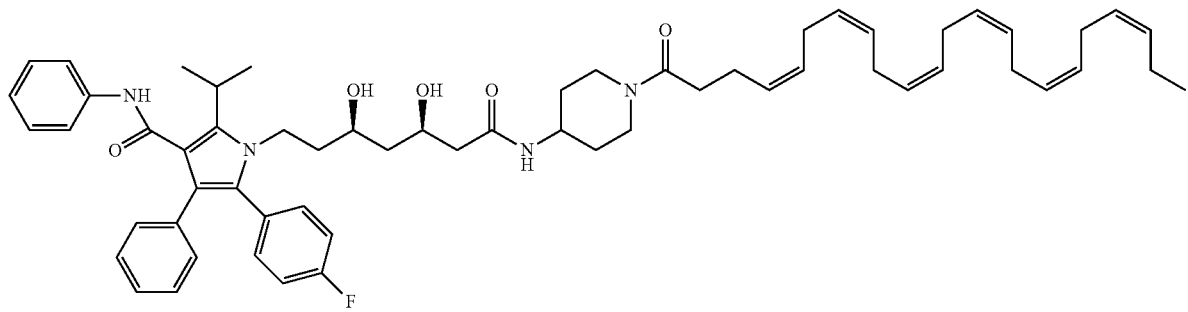 [SMILES: CC/C=C\C/C=C\C/C=C\C/C=C\C/C=C\C/C=C\CCC(=O)N1CCC(NC(=O)C[C@H](O)C[C@H](O)CCn2c(-c3ccc(F)cc3)c(-c3ccccc3)c(C(=O)Nc3ccccc3)c2C(C)C)CC1]

1-((3R,5R)-7-((1-((4Z,7Z,10Z,13Z,16Z,19Z)-docosa-4,7,10,13,16,19-hexaenoyl)piperidin-4-yl)amino)-3,5-dihydroxy-7-oxoheptyl)-5-(4-fluorophenyl)-2-isopropyl-N,4-diphenyl-1H-pyrrole-3-carboxamide (I-37)

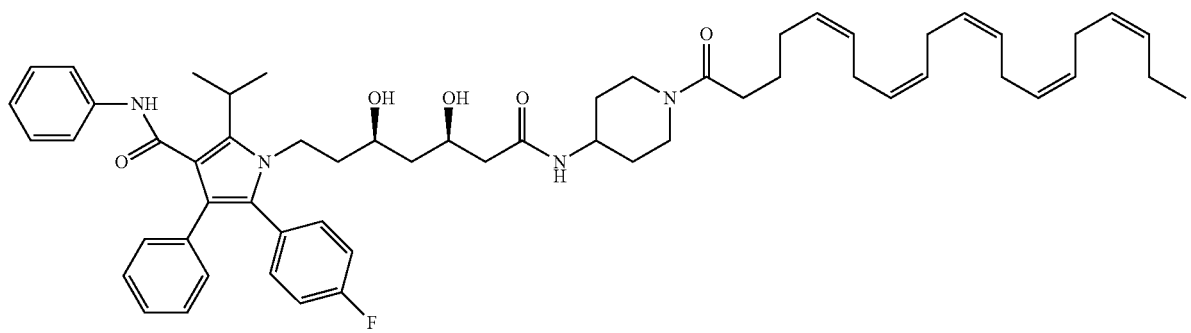 [SMILES: CC/C=C\C/C=C\C/C=C\C/C=C\C/C=C\CCCC(=O)N1CCC(NC(=O)C[C@H](O)C[C@H](O)CCn2c(-c3ccc(F)cc3)c(-c3ccccc3)c(C(=O)Nc3ccccc3)c2C(C)C)CC1]

1-((3R,5R)-3,5-dihydroxy-7-((1-((5Z,8Z,11Z,14Z,17Z)-icosa-5,8,11,14,17-pentaenoyl)piperidin-4-yl)amino)-7-oxoheptyl)-5-(4-fluorophenyl)-2-isopropyl-N,4-diphenyl-1H-pyrrole-3-carboxamide (I-38)

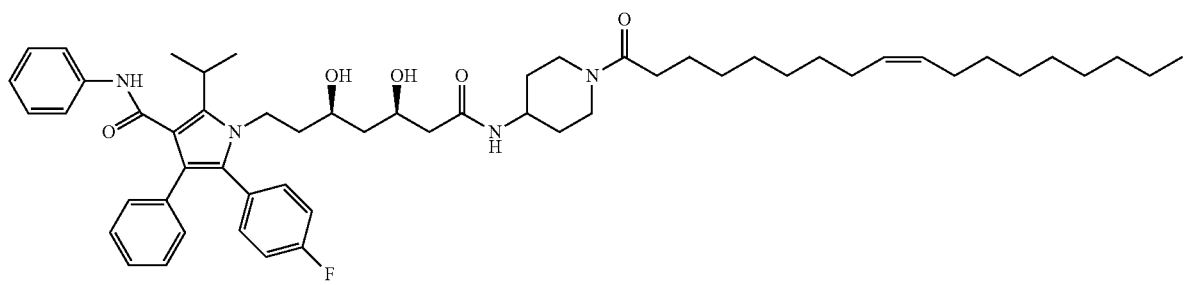 [SMILES: CCCCCCCC/C=C\CCCCCCCC(=O)N1CCC(NC(=O)C[C@H](O)C[C@H](O)CCn2c(-c3ccc(F)cc3)c(-c3ccccc3)c(C(=O)Nc3ccccc3)c2C(C)C)CC1]

1-((3R,5R)-3,5-dihydroxy-7-((1-oleoylpiperidin-4-yl)amino)-7-oxoheptyl)-5-(4-fluorophenyl)-2-isopropyl-N,4-diphenyl-1H-pyrrole-3-carboxamide (I-39)

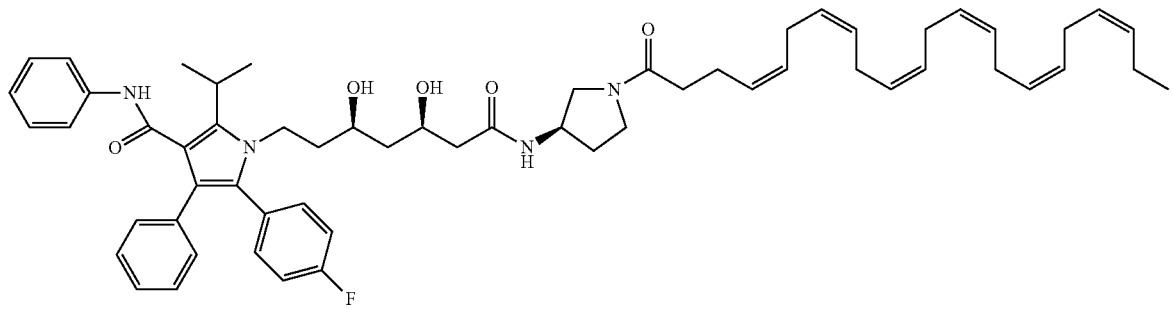 [SMILES: CC/C=C\C/C=C\C/C=C\C/C=C\C/C=C\C/C=C\CCC(=O)N1CC[C@@H](NC(=O)C[C@H](O)C[C@H](O)CCn2c(-c3ccc(F)cc3)c(-c3ccccc3)c(C(=O)Nc3ccccc3)c2C(C)C)C1]

1-((3R,5R)-7-(((R)-1-((4Z,7Z,10Z,13Z,16Z,19Z)-docosa-4,7,10,13,16,19-hexaenoyl)pyrrolidin-3-yl)amino)-3,5-dihydroxy-7-oxoheptyl)-5-(4-fluorophenyl)-2-isopropyl-N,4-diphenyl-1H-pyrrole-3-carboxamide (I-40)

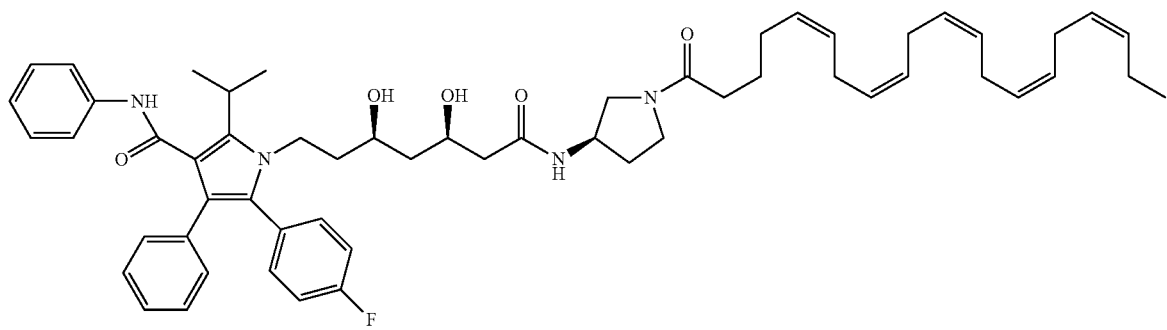 [SMILES: CC/C=C\C/C=C\C/C=C\C/C=C\C/C=C\CCCC(=O)N1CC[C@@H](NC(=O)C[C@H](O)C[C@H](O)CCn2c(-c3ccc(F)cc3)c(-c3ccccc3)c(C(=O)Nc3ccccc3)c2C(C)C)C1]

1-((3R,5R)-3,5-dihydroxy-7-(((R)-1-((5Z,8Z,11Z,14Z, 17Z)-icosa-5,8,11,14,17-pentaenoyl)pyrrolidin-3-yl) amino)-7-oxoheptyl)-5-(4-fluorophenyl)-2-isopropyl-N, 4-diphenyl-1H-pyrrole-3-carboxamide (I-41)

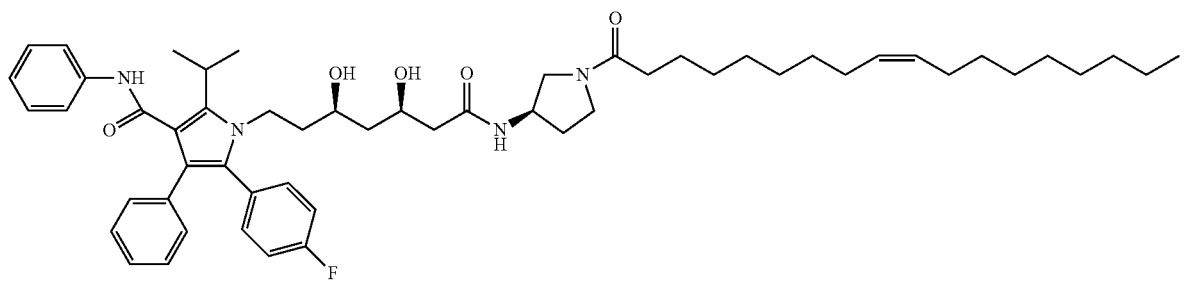 [SMILES: CCCCCCCC/C=C\CCCCCCCC(=O)N1CC[C@@H](NC(=O)C[C@H](O)C[C@H](O)CCn2c(-c3ccc(F)cc3)c(-c3ccccc3)c(C(=O)Nc3ccccc3)c2C(C)C)C1]

1-((3R,5R)-3,5-dihydroxy-7-(((R)-1-oleoylpyrrolidin-3-yl) amino)-7-oxoheptyl)-5-(4-fluorophenyl)-2-isopropyl-N, 4-diphenyl-1H-pyrrole-3-carboxamide (I-42)

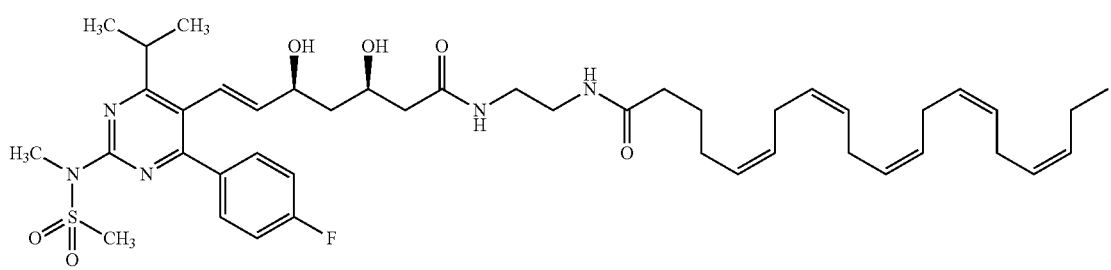 [SMILES: CC/C=C\C/C=C\C/C=C\C/C=C\C/C=C\CCCC(=O)NCCNC(=O)C[C@H](O)C[C@H](O)/C=C/c1c(-c2ccc(F)cc2)nc(N(C)S(C)(=O)=O)nc1C(C)C]

(5Z,8Z,11Z,14Z,17Z)—N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)icosa-5,8, 11,14,17-pentaenamide (I-43)

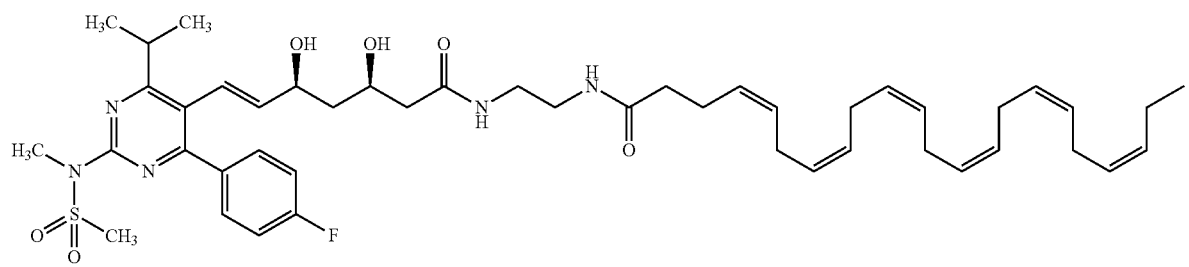 [SMILES: CC/C=C\C/C=C\C/C=C\C/C=C\C/C=C\C/C=C\CCC(=O)NCCNC(=O)C[C@H](O)C[C@H](O)/C=C/c1c(-c2ccc(F)cc2)nc(N(C)S(C)(=O)=O)nc1C(C)C]

(4Z,7Z,10Z,13Z,16Z,19Z)—N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)docosa-4,7,10,13,16,19-hexaenamide (I-44)

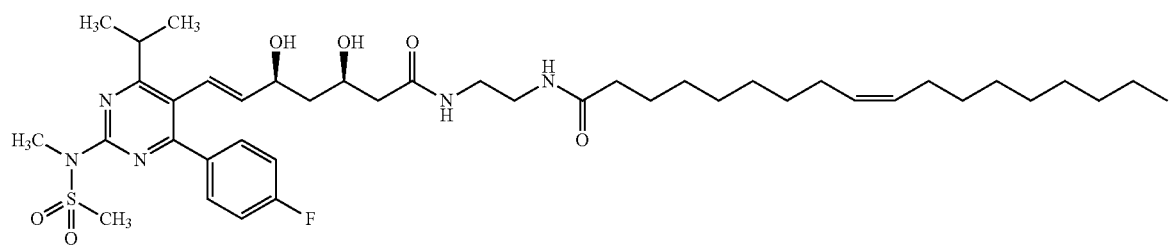 [SMILES: CCCCCCCC/C=C\CCCCCCCC(=O)NCCNC(=O)C[C@H](O)C[C@H](O)/C=C/c1c(-c2ccc(F)cc2)nc(N(C)S(C)(=O)=O)nc1C(C)C]

N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)oleamide (I-45)

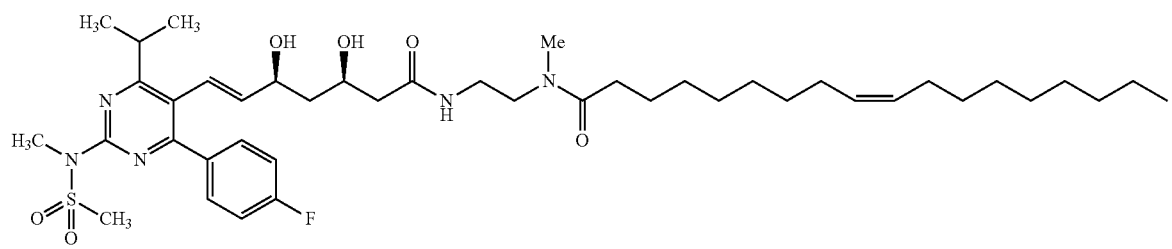 [SMILES: CCCCCCCC/C=C\CCCCCCCC(=O)N(C)CCNC(=O)C[C@H](O)C[C@H](O)/C=C/c1c(-c2ccc(F)cc2)nc(N(C)S(C)(=O)=O)nc1C(C)C]

N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)-N-methyloleamide (I-46)

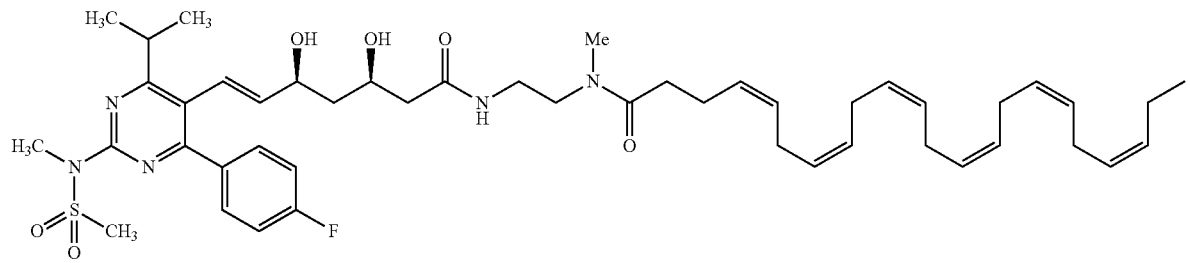 [SMILES: CC/C=C\C/C=C\C/C=C\C/C=C\C/C=C\C/C=C\CCC(=O)N(C)CCNC(=O)C[C@H](O)C[C@H](O)/C=C/c1c(-c2ccc(F)cc2)nc(N(C)S(C)(=O)=O)nc1C(C)C]

(4Z,7Z,10Z,13Z,16Z,19Z)—N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)-N-methyldocosa-4,7,10,13,16,19-hexaenamide (I-47)

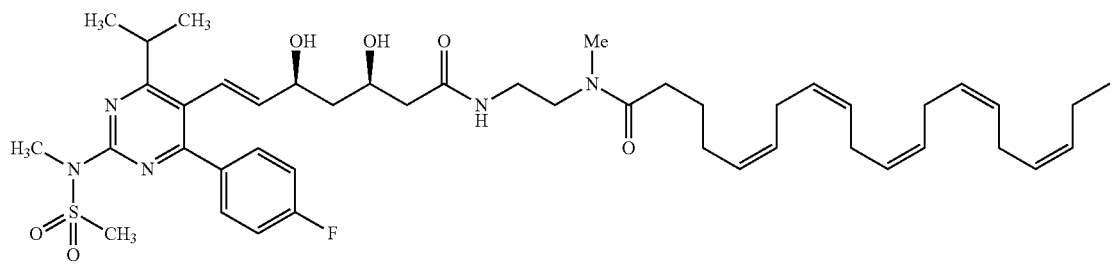 [SMILES: CC/C=C\C/C=C\C/C=C\C/C=C\C/C=C\CCCC(=O)N(C)CCNC(=O)C[C@H](O)C[C@H](O)/C=C/c1c(-c2ccc(F)cc2)nc(N(C)S(C)(=O)=O)nc1C(C)C]

(5Z,8Z,11Z,14Z,17Z)—N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)-N-methylicosa-5,8,11,14,17-pentaenamide (I-48)

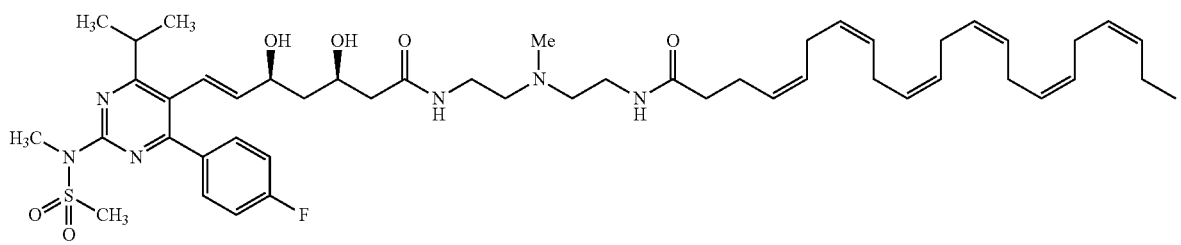 [SMILES: CC/C=C\C/C=C\C/C=C\C/C=C\C/C=C\C/C=C\CCC(=O)NCCN(C)CCNC(=O)C[C@H](O)C[C@H](O)/C=C/c1c(-c2ccc(F)cc2)nc(N(C)S(C)(=O)=O)nc1C(C)C]

(4Z,7Z,10Z,13Z,16Z,19Z)—N-(2-((2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)(methyl)amino)ethyl)docosa-4,7,10,13,16,19-hexaenamide (I-49)

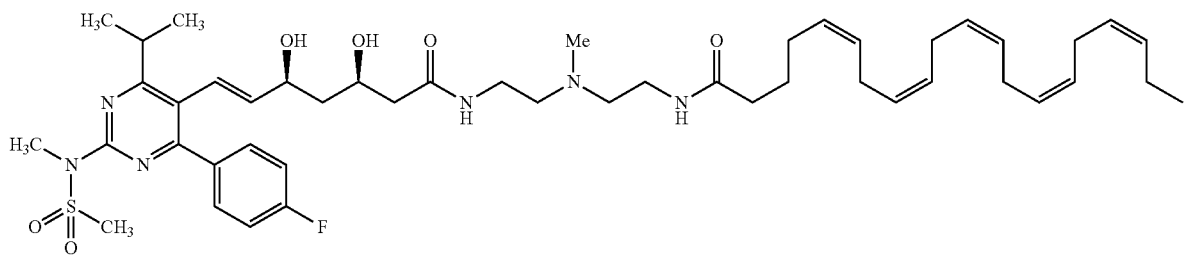 [SMILES: CC/C=C\C/C=C\C/C=C\C/C=C\C/C=C\CCCC(=O)NCCN(C)CCNC(=O)C[C@H](O)C[C@H](O)/C=C/c1c(-c2ccc(F)cc2)nc(N(C)S(C)(=O)=O)nc1C(C)C]

(5Z,8Z,11Z,14Z,17Z)—N-(2-((2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)(methyl)amino)ethyl)icosa-5,8,11,14,17-pentaenamide (I-50)

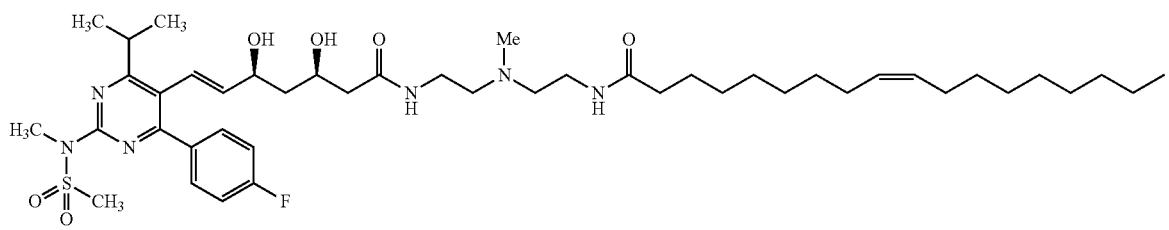 [SMILES: CCCCCCCC/C=C\CCCCCCCC(=O)NCCN(C)CCNC(=O)C[C@H](O)C[C@H](O)/C=C/c1c(-c2ccc(F)cc2)nc(N(C)S(C)(=O)=O)nc1C(C)C]

N-(2-((2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)(methyl)amino)ethyl)oleamide (I-51)

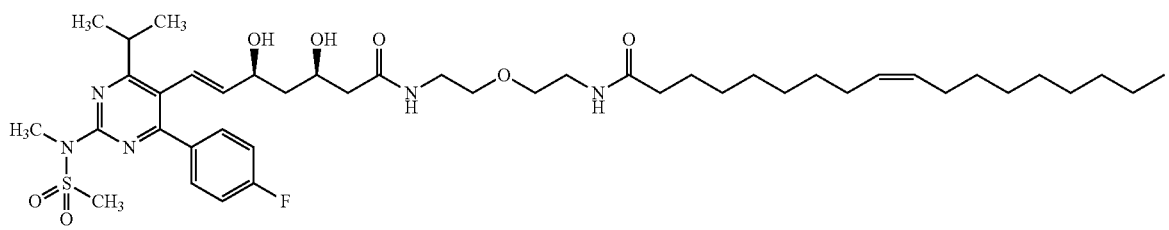 [SMILES: CCCCCCCC/C=C\CCCCCCCC(=O)NCCOCCNC(=O)C[C@H](O)C[C@H](O)/C=C/c1c(-c2ccc(F)cc2)nc(N(C)S(C)(=O)=O)nc1C(C)C]

N-(2-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethoxy)ethyl)oleamide (I-52)

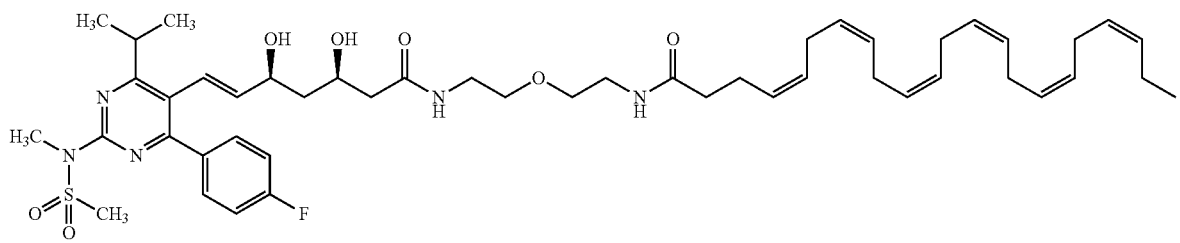 [SMILES: CC/C=C\C/C=C\C/C=C\C/C=C\C/C=C\C/C=C\CCC(=O)NCCOCCNC(=O)C[C@H](O)C[C@H](O)/C=C/c1c(-c2ccc(F)cc2)nc(N(C)S(C)(=O)=O)nc1C(C)C]

(4Z,7Z,10Z,13Z,16Z,19Z)—N-(2-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethoxy)ethyl)docosa-4,7,10,13,16,19-hexaenamide (I-53)

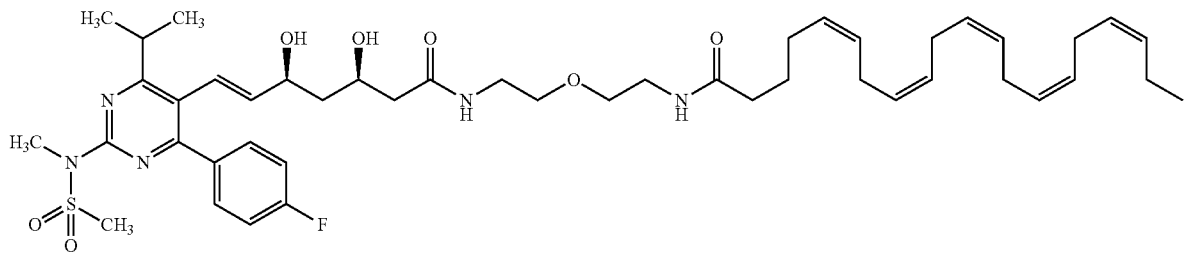 [SMILES: CC/C=C\C/C=C\C/C=C\C/C=C\C/C=C\CCCC(=O)NCCOCCNC(=O)C[C@H](O)C[C@H](O)/C=C/c1c(-c2ccc(F)cc2)nc(N(C)S(C)(=O)=O)nc1C(C)C]

(5Z,8Z,11Z,14Z,17Z)—N-(2-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethoxy)ethyl)icosa-5,8,11,14,17-pentaenamide (I-54)

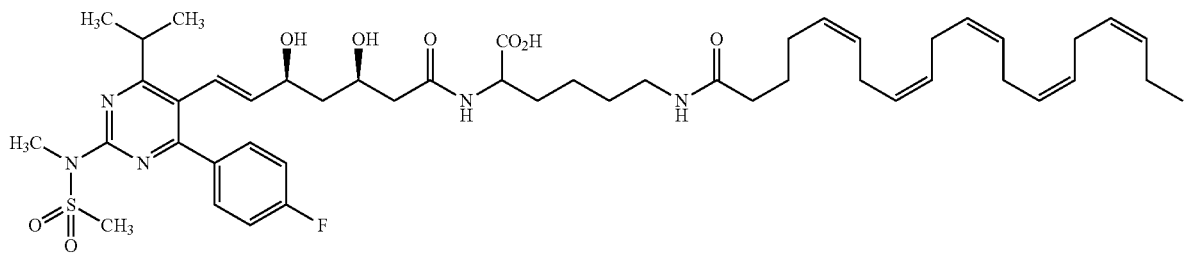 [SMILES: CC/C=C\C/C=C\C/C=C\C/C=C\C/C=C\CCCC(=O)NCCCCC(NC(=O)C[C@H](O)C[C@H](O)/C=C/c1c(-c2ccc(F)cc2)nc(N(C)S(C)(=O)=O)nc1C(C)C)C(=O)O]

2-((3R,5S,E)-7-(4-(4-fluorophenyl)-6-isopropyl-2-(N-methylmethylsulfonamido)pyrimidin-5-yl)-3,5-dihydroxyhept-6-enamido)-6-((5Z,8Z,11Z,14Z,17Z)-icosa-5,8,11,14,17-pentaenamido)hexanoic acid (I-55)

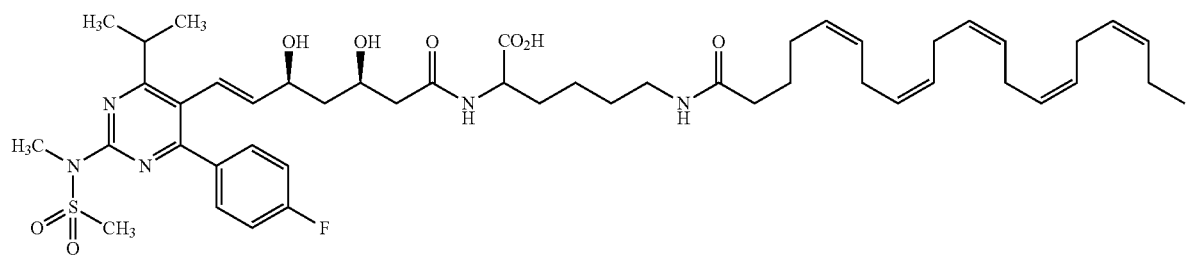 [SMILES: CC/C=C\C/C=C\C/C=C\C/C=C\C/C=C\CCCC(=O)NCCCCC(NC(=O)C[C@H](O)C[C@H](O)/C=C/c1c(-c2ccc(F)cc2)nc(N(C)S(C)(=O)=O)nc1C(C)C)C(=O)O]

6-((4Z,7Z,10Z,13Z,16Z,19Z)-docosa-4,7,10,13,16,19-
hexaenamido)-2-((3R,5S,E)-7-(4-(4-fluorophenyl)-6-iso-
propyl-2-(N-methylmethylsulfonamido)pyrimidin-5-yl)-
3,5-dihydroxyhept-6-enamido)hexanoic acid (I-56)

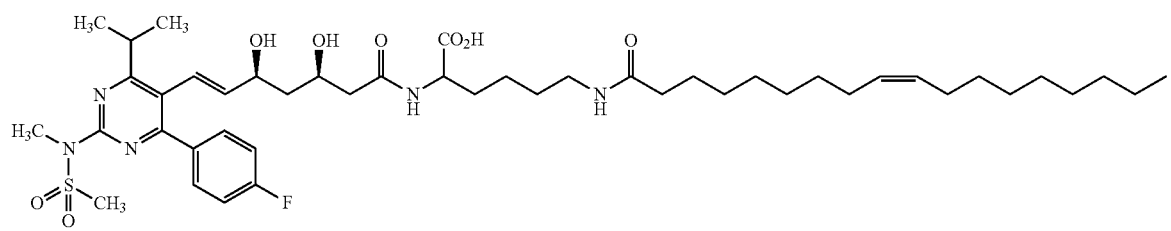 [SMILES: CCCCCCCC/C=C\CCCCCCCC(=O)NCCCCC(NC(=O)C[C@H](O)C[C@H](O)/C=C/c1c(-c2ccc(F)cc2)nc(N(C)S(C)(=O)=O)nc1C(C)C)C(=O)O]

2-((3R,5S,E)-7-(4-(4-fluorophenyl)-6-isopropyl-2-(N-meth-
ylmethylsulfonamido)pyrimidin-5-yl)-3,5-dihydroxy-
hept-6-enamido)-6-oleamidohexanoic acid (I-57)

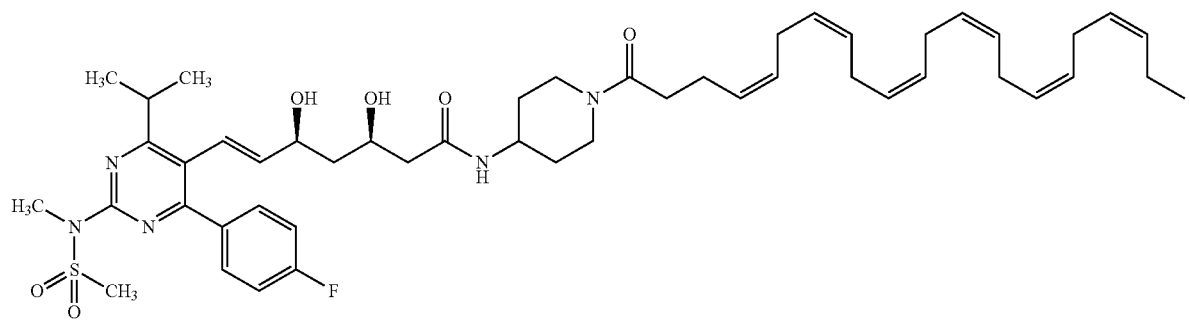 [SMILES: CC/C=C\C/C=C\C/C=C\C/C=C\C/C=C\C/C=C\CCC(=O)N1CCC(NC(=O)C[C@H](O)C[C@H](O)/C=C/c2c(-c3ccc(F)cc3)nc(N(C)S(C)(=O)=O)nc2C(C)C)CC1]

(3R,5S,E)-N-(1-((4Z,7Z,10Z,13Z,16Z,19Z)-docosa-4,7,10,
13,16,19-hexaenoyl)piperidin-4-yl)-7-(4-(4-fluorophe-
nyl)-6-isopropyl-2-(N-methylmethylsulfonamido)pyrimi-
din-5-yl)-3,5-dihydroxyhept-6-enamide (I-58)

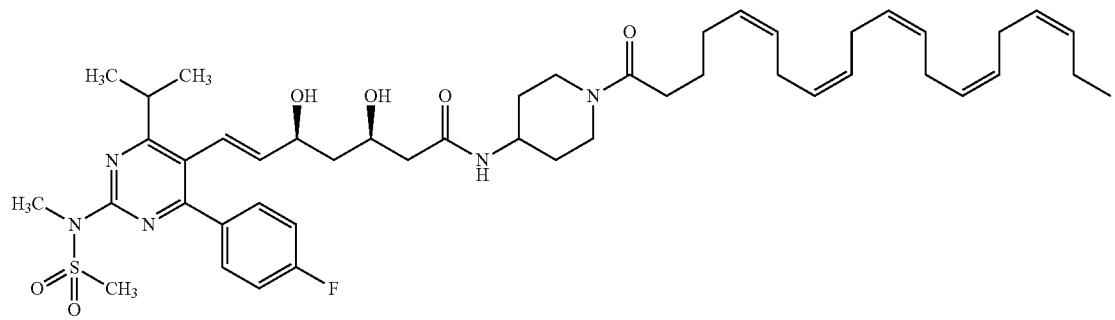 [SMILES: CC/C=C\C/C=C\C/C=C\C/C=C\C/C=C\CCCC(=O)N1CCC(NC(=O)C[C@H](O)C[C@H](O)/C=C/c2c(-c3ccc(F)cc3)nc(N(C)S(C)(=O)=O)nc2C(C)C)CC1]

(3R,5S,E)-7-(4-(4-fluorophenyl)-6-isopropyl-2-(N-methyl-
methylsulfonamido)pyrimidin-5-yl)-3,5-dihydroxy-N-(1-
((5Z,8Z,11Z,14Z,17Z)-icosa-5,8,11,14,17-pentaenoyl)pi-
peridin-4-yl)hept-6-enamide (I-59)

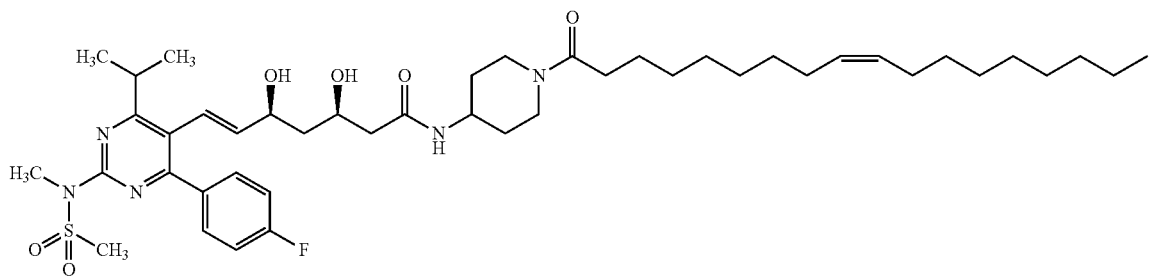 [SMILES: CCCCCCCC/C=C\CCCCCCCC(=O)N1CCC(NC(=O)C[C@H](O)C[C@H](O)/C=C/c2c(-c3ccc(F)cc3)nc(N(C)S(C)(=O)=O)nc2C(C)C)CC1]

(3R,5S,E)-7-(4-(4-fluorophenyl)-6-isopropyl-2-(N-methyl-methylsulfonamido)pyrimidin-5-yl)-3,5-dihydroxy-N-(1-oleoylpiperidin-4-yl)hept-6-enamide (I-60)

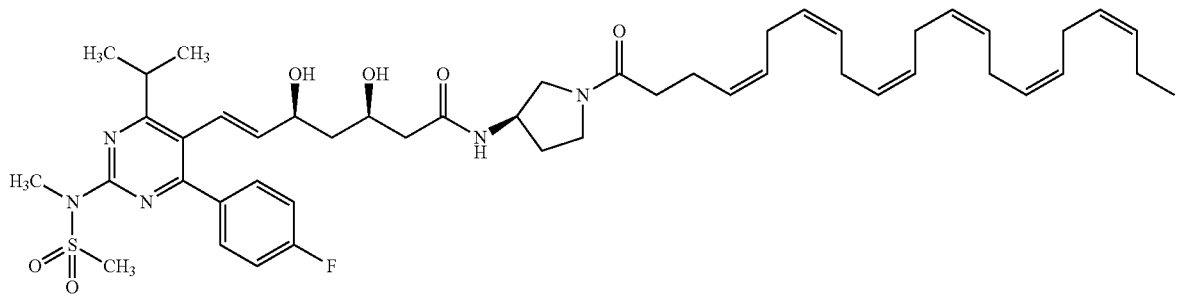 [SMILES: CC/C=C\C/C=C\C/C=C\C/C=C\C/C=C\C/C=C\CCC(=O)N1CC[C@@H](NC(=O)C[C@H](O)C[C@H](O)/C=C/c2c(-c3ccc(F)cc3)nc(N(C)S(C)(=O)=O)nc2C(C)C)C1]

(3R,5S,E)-N—((R)-1-((4Z,7Z,10Z,13Z,16Z,19Z)-docosa-4,7,10,13,16,19-hexaenoyl)pyrrolidin-3-yl)-7-(4-(4-fluorophenyl)-6-isopropyl-2-(N-methylmethylsulfonamido)pyrimidin-5-yl)-3,5-dihydroxyhept-6-enamide (I-61)

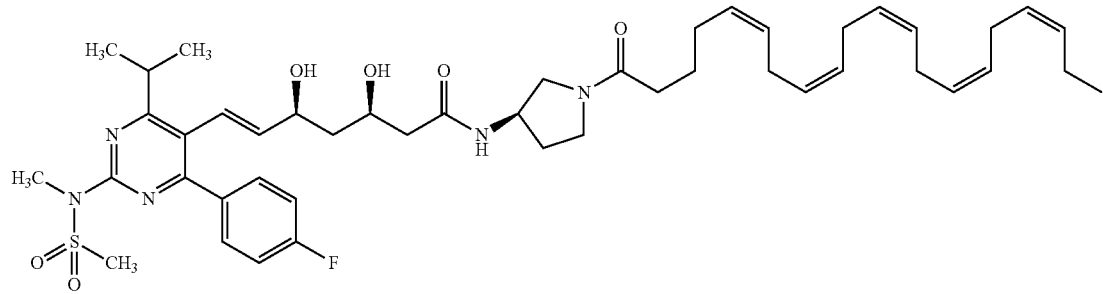 [SMILES: CC/C=C\C/C=C\C/C=C\C/C=C\C/C=C\CCCC(=O)N1CC[C@@H](NC(=O)C[C@H](O)C[C@H](O)/C=C/c2c(-c3ccc(F)cc3)nc(N(C)S(C)(=O)=O)nc2C(C)C)C1]

(3R,5S,E)-7-(4-(4-fluorophenyl)-6-isopropyl-2-(N-methyl-methylsulfonamido)pyrimidin-5-yl)-3,5-dihydroxy-N—((R)-1-((5Z,8Z,11Z,14Z,17Z)-icosa-5,8,11,14,17-pentaenoyl)pyrrolidin-3-yl)hept-6-enamide (I-62)

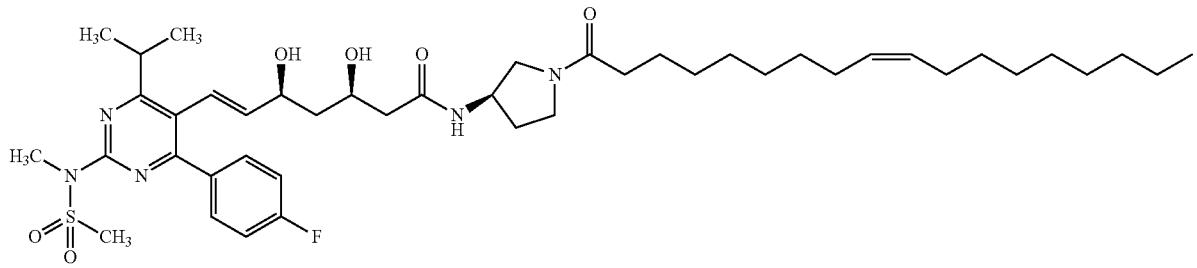 [SMILES: CCCCCCCC/C=C\CCCCCCCC(=O)N1CC[C@@H](NC(=O)C[C@H](O)C[C@H](O)/C=C/c2c(-c3ccc(F)cc3)nc(N(C)S(C)(=O)=O)nc2C(C)C)C1]

(3R,5S,E)-7-(4-(4-fluorophenyl)-6-isopropyl-2-(N-methyl-methylsulfonamido)pyrimidin-5-yl)-3,5-dihydroxy-N—((R)-1-oleoylpyrrolidin-3-yl)hept-6-enamide (I-63)

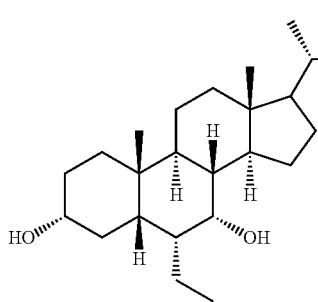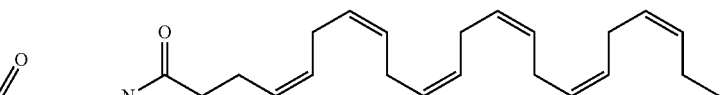

(4Z,7Z,10Z,13Z,16Z,19Z)—N-(2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)docosa-4,7,10,13,16,19-hexaenamide (II-1)

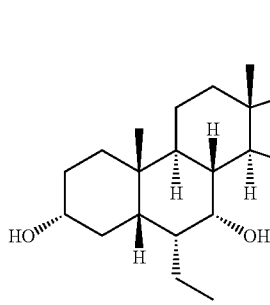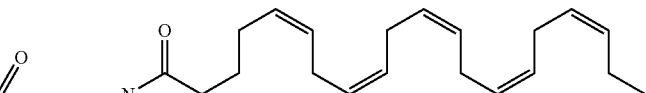

(5Z,8Z,11Z,14Z,17Z)—N-(2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)icosa-5,8,11,14,17-pentaenamide (II-2)

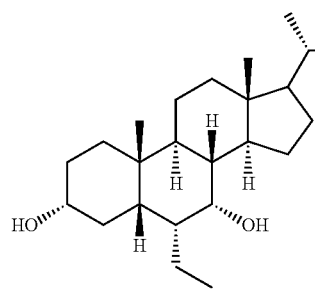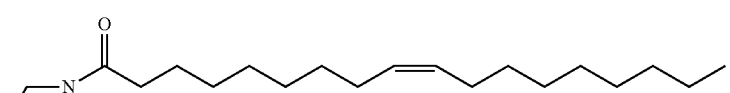

N-(2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)oleamide (II-3)

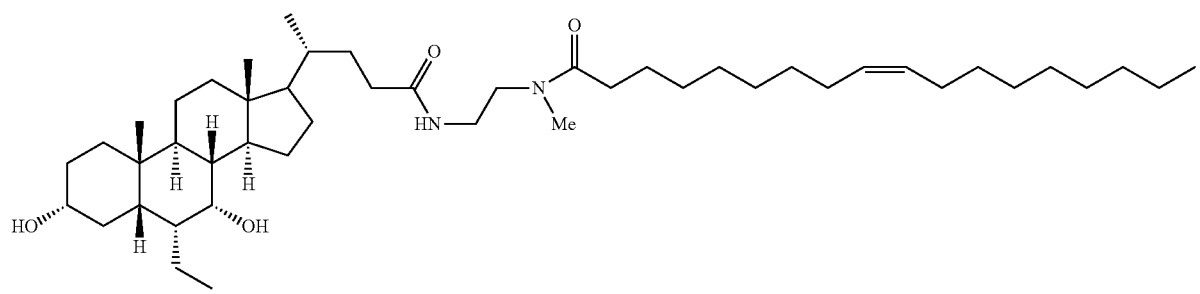

N-(2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)-N-methyloleamide (II-4)

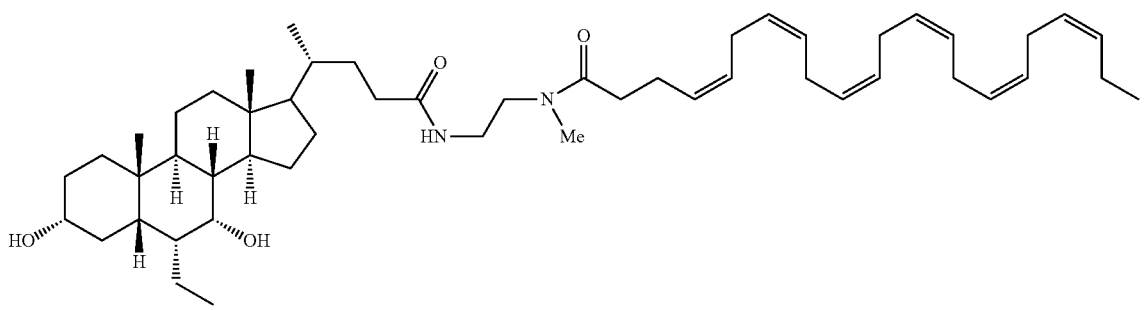

(4Z,7Z,10Z,13Z,16Z,19Z)—N-(2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)-N-methyldocosa-4,7,10,13,16,19-hexaenamide (II-5)

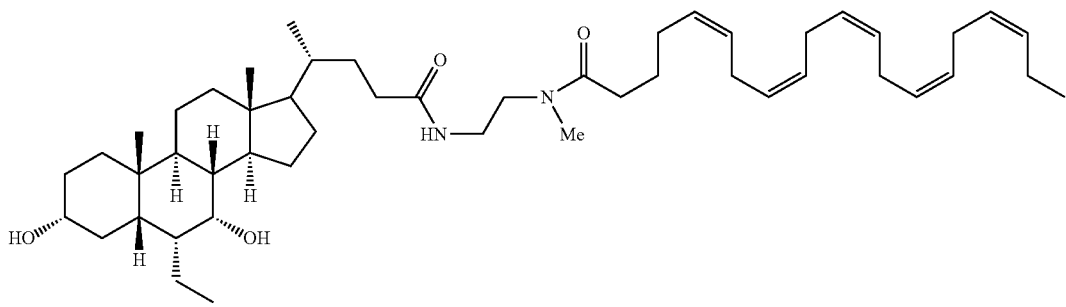

(5Z,8Z,11Z,14Z,17Z)—N-(2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)-N-methylicosa-5,8,11,14,17-pentaenamide (II-6)

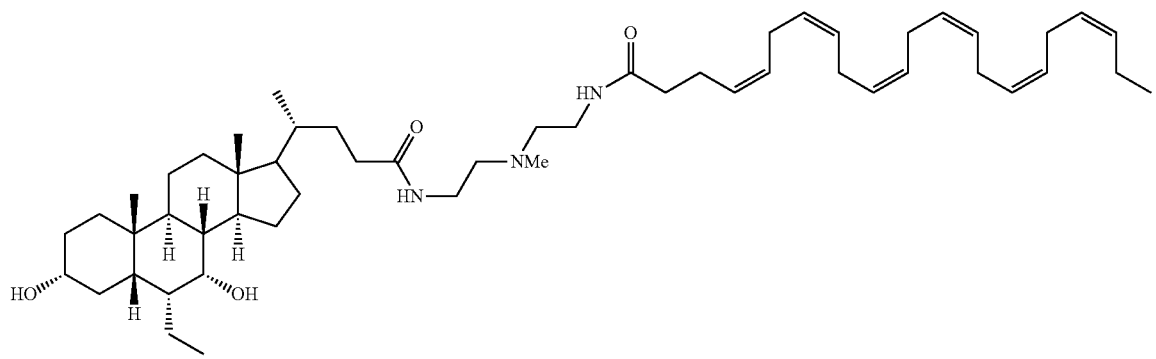

(4Z,7Z,10Z,13Z,16Z,19Z)—N-(2-((2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)(methyl)amino)ethyl)docosa-4,7,10,13,16,19-hexaenamide (II-7)

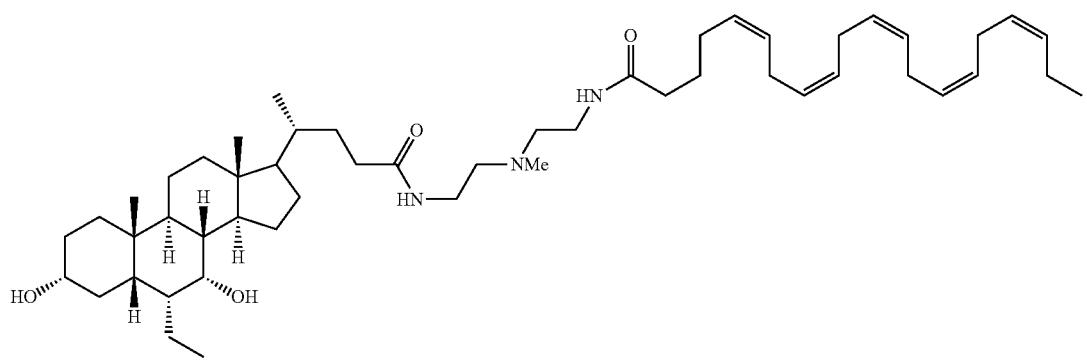

(5Z,8Z,11Z,14Z,17Z)—N-(2-((2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)(methyl)amino)ethyl)icosa-5,8,11,14,17-pentaenamide (II-8)

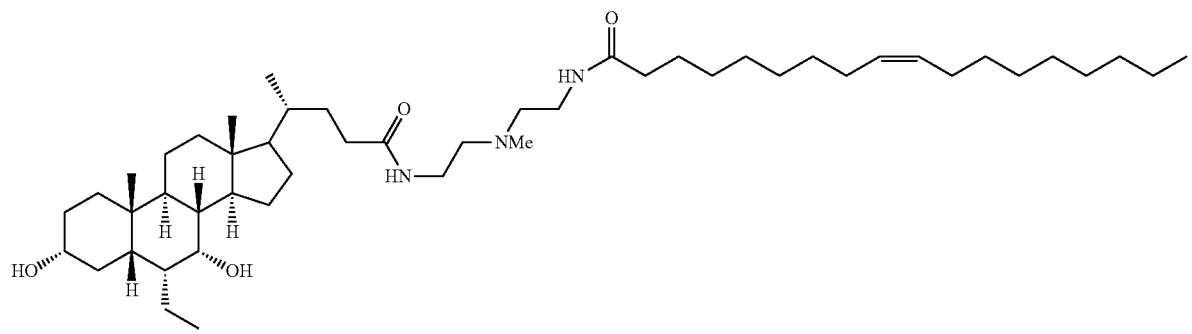

N-(2-((2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)(methyl)amino)ethyl)oleamide (II-9)

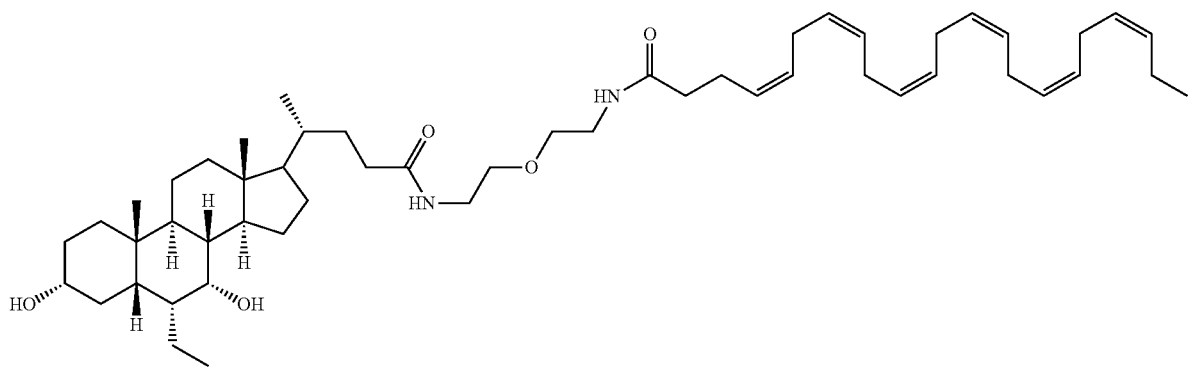

(4Z,7Z,10Z,13Z,16Z,19Z)—N-(2-(2-((4R)-4-((3R,5S,6R, 7R,8S,9S,10S,13R,14S)-6-ethyl-3,7-dihydroxy-10,13-dimethylhexadecahydro-1H-cyclopenta[a]phenanthren-17-yl)pentanamido)ethoxy)ethyl)docosa-4,7,10,13,16, 19-hexaenamide (II-10)

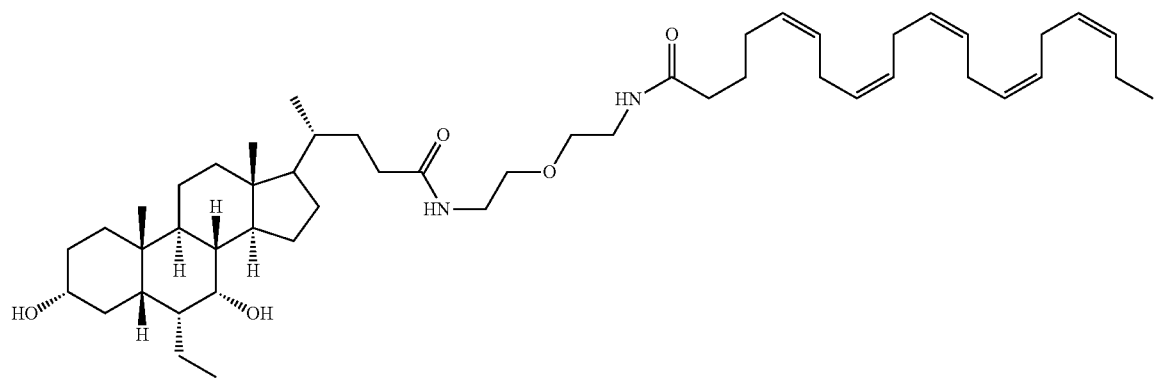

(5Z,8Z,11Z,14Z,17Z)—N-(2-(2-((4R)-4-((3R,5S,6R,7R,8S, 9S,10S,13R,14S)-6-ethyl-3,7-dihydroxy-10,13-dimethyl-hexadecahydro-1H-cyclopenta[a]phenanthren-17-yl)pentanamido)ethoxy)ethyl)icosa-5,8,11,14,17-pentaenamide (II-11)

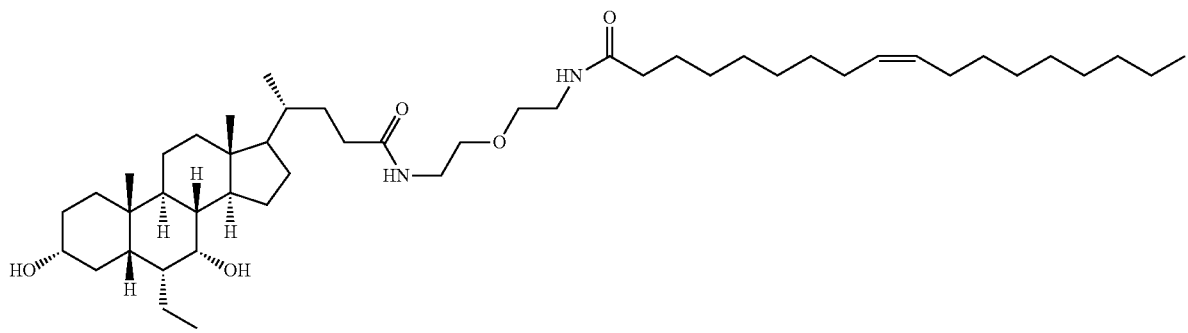

N-(2-(2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethoxy) ethyl)oleamide (II-12)

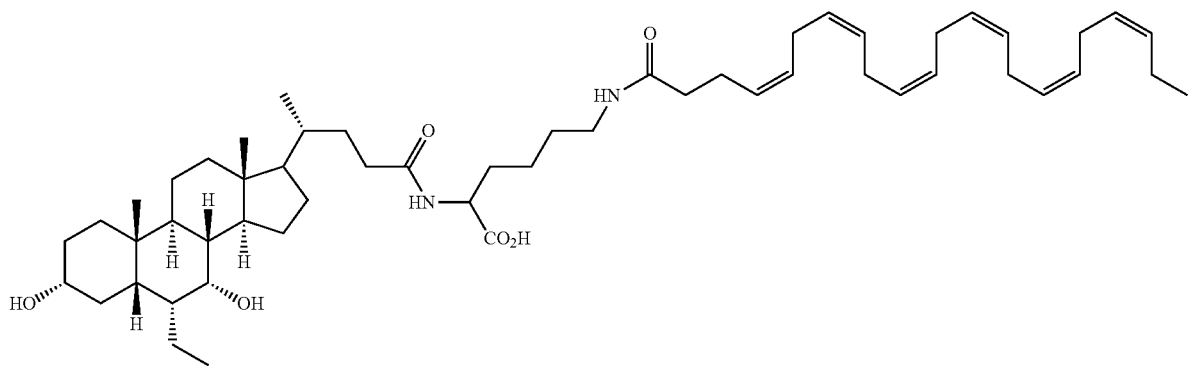

6-((4Z,7Z,10Z,13Z,16Z,19Z)-docosa-4,7,10,13,16,19-hexaenamido)-2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)hexanoic acid (II-13)

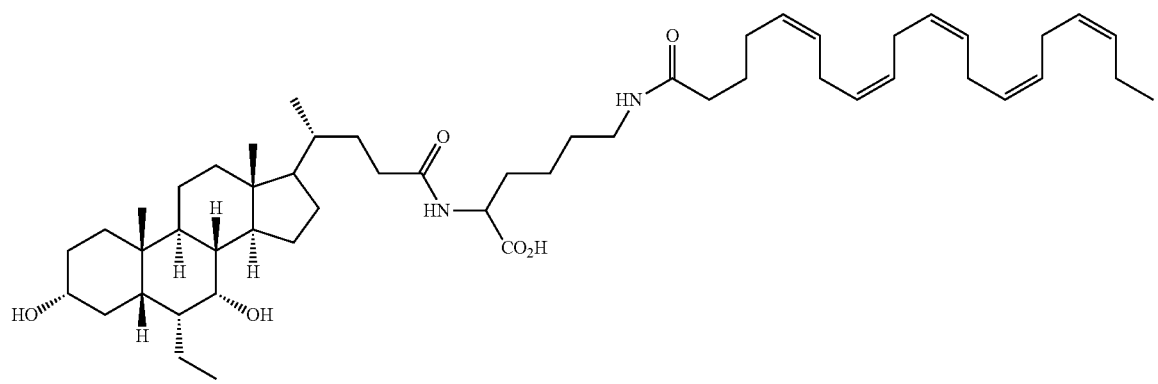

2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)-6-((5Z,8Z,11Z,14Z,17Z)-icosa-5,8,11,14,17-pentaenamido)hexanoic acid (II-14)

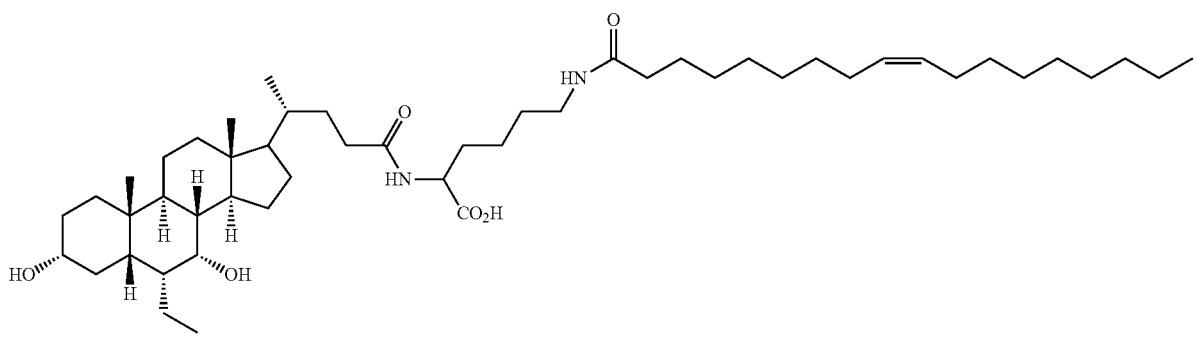

2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)-6-oleamidohexanoic acid (II-15)

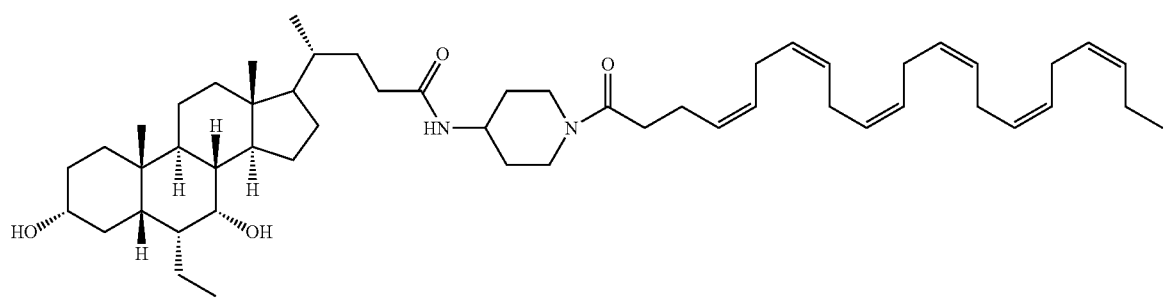

(4R)—N-(1-((4Z,7Z,10Z,13Z,16Z,19Z)-docosa-4,7,10,13,
16,19-hexaenoyl)piperidin-4-yl)-4-((3R,5S,6R,7R,8S,9S,
10S,13R,14S)-6-ethyl-3,7-dihydroxy-10,13-dimethyl-
hexadecahydro-1H-cyclopenta[a]phenanthren-17-yl)
pentanamide (II-16)

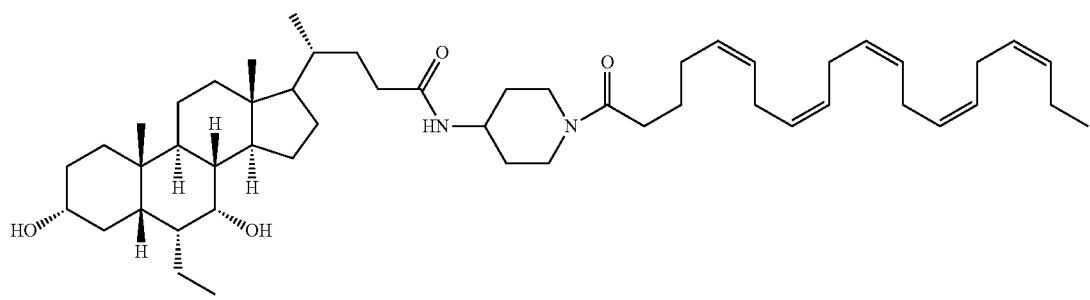

(4R)-4-((3R,5S,6R,7R,8S,9S,10S,13R,14S)-6-ethyl-3,7-di-
hydroxy-10,13-dimethylhexadecahydro-1H-cyclopenta
[a]phenanthren-17-yl)-N-(1-((5Z,8Z,11Z,14Z,17Z)-
icosa-5,8,11,14,17-pentaenoyl)piperidin-4-yl)
pentanamide (II-17)

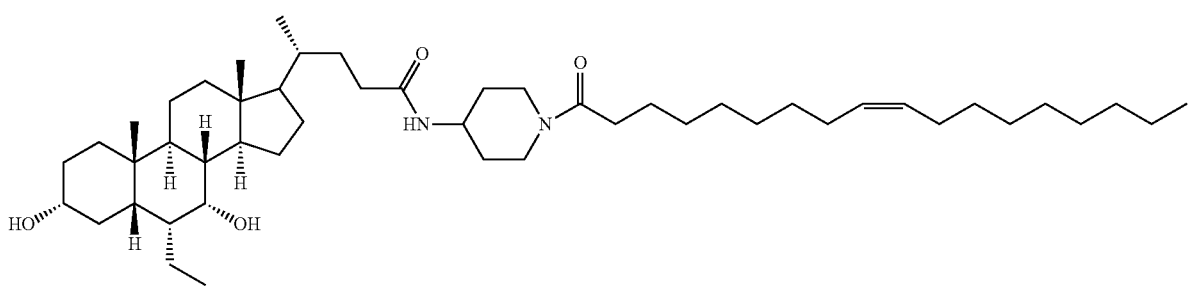

(4R)-4-((3R,5S,6R,7R,8S,9S,10S,13R,14S)-6-ethyl-3,7-di-
hydroxy-10,13-dimethylhexadecahydro-1H-cyclopenta
[a]phenanthren-17-yl)-N-(1-oleoylpiperidin-4-yl)pen-
tanamide (II-18)

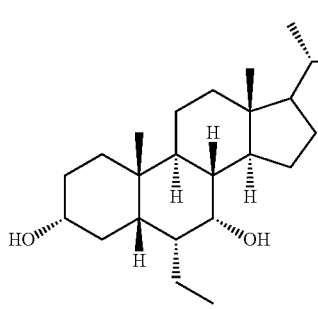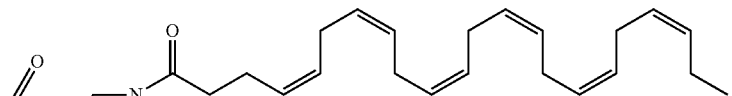

(4R)—N—((R)-1-((4Z,7Z,10Z,13Z,16Z,19Z)-docosa-4,7,
10,13,16,19-hexaenoyl)pyrrolidin-3-yl)-4-((3R,5S,6R,
7R,8S,9S,10S,13R,14S)-6-ethyl-3,7-dihydroxy-10,13-
dimethylhexadecahydro-1H-cyclopenta[a]phenanthren-
17-yl)pentanamide (II-19)

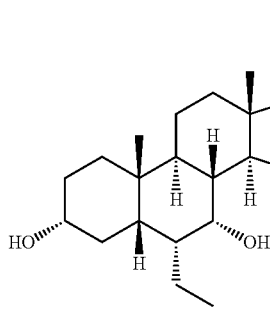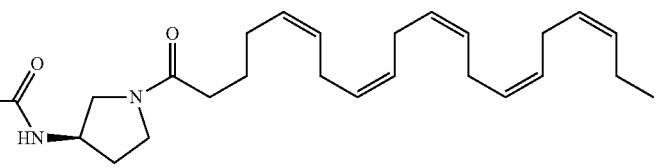

(4R)-4-((3R,5S,6R,7R,8S,9S,10S,13R,14S)-6-ethyl-3,7-di-
hydroxy-10,13-dimethylhexadecahydro-1H-cyclopenta
[a]phenanthren-17-yl)-N—((R)-1-((5Z,8Z,11Z,14Z,
17Z)-icosa-5,8,11,14,17-pentaenoyl)pyrrolidin-3-yl)
pentanamide (II-20)

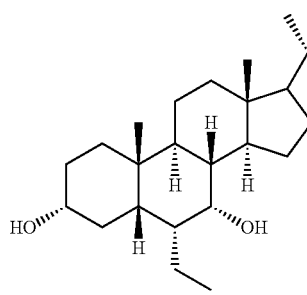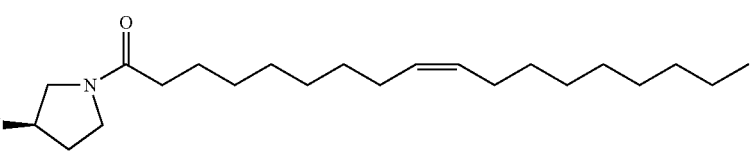

(4R)-4-((3R,5S,6R,7R,8S,9S,10S,13R,14S)-6-ethyl-3,7-di-
hydroxy-10,13-dimethylhexadecahydro-1H-cyclopenta
[a]phenanthren-17-yl)-N—((R)-1-oleoylpyrrolidin-3-yl)
pentanamide (II-21)

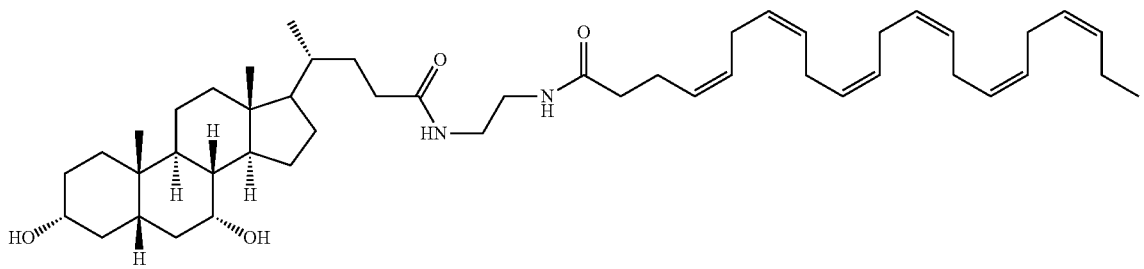

(4Z,7Z,10Z,13Z,16Z,19Z)—N-(2-((4R)-4-((3R,5S,7R,8R,
9S,10S,13R,14S)-3,7-dihydroxy-10,13-dimethylhexa-
decahydro-1H-cyclopenta[a]phenanthren-17-yl)pentana-
mido)ethyl)docosa-4,7,10,13,16,19-hexaenamide (II-22)

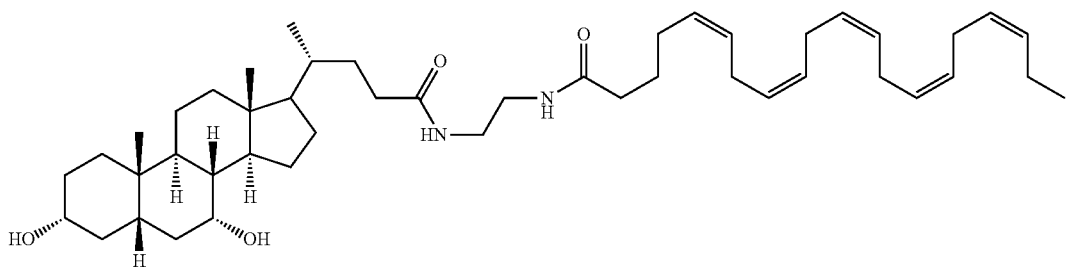

(5Z,8Z,11Z,14Z,17Z)—N-(2-((4R)-4-((3R,5S,7R,8R,9S,
10S,13R,14S)-3,7-dihydroxy-10,13-dimethylhexa-
decahydro-1H-cyclopenta[a]phenanthren-17-yl)pentana-
mido)ethyl)icosa-5,8,11,14,17-pentaenamide (II-23)

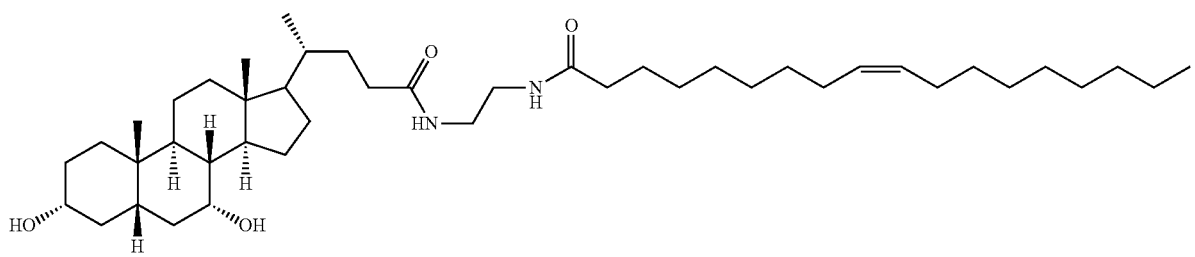

N-(2-((4R)-4-((3R,5S,7R,8R,9S,10S,13R,14S)-3,7-dihy-
droxy-10,13-dimethylhexadecahydro-1H-cyclopenta[a]
phenanthren-17-yl)pentanamido)ethyl)oleamide (II-24)

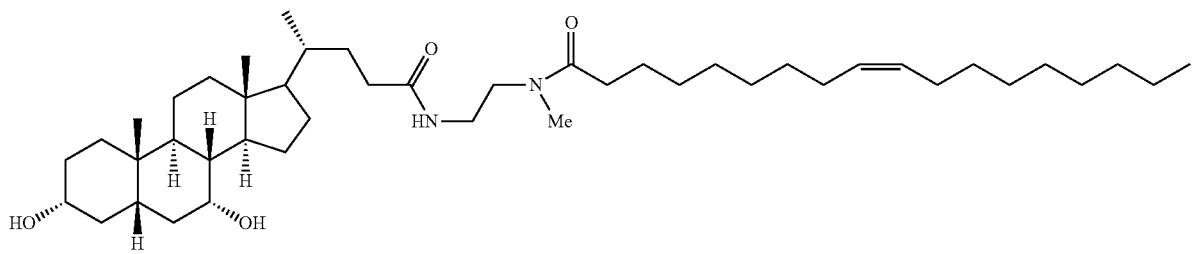

N-(2-((4R)-4-((3R,5S,7R,8R,9S,10S,13R,14S)-3,7-dihy-
droxy-10,13-dimethylhexadecahydro-1H-cyclopenta[a]
phenanthren-17-yl)pentanamido)ethyl)-N-methyloleam-
ide (II-25)

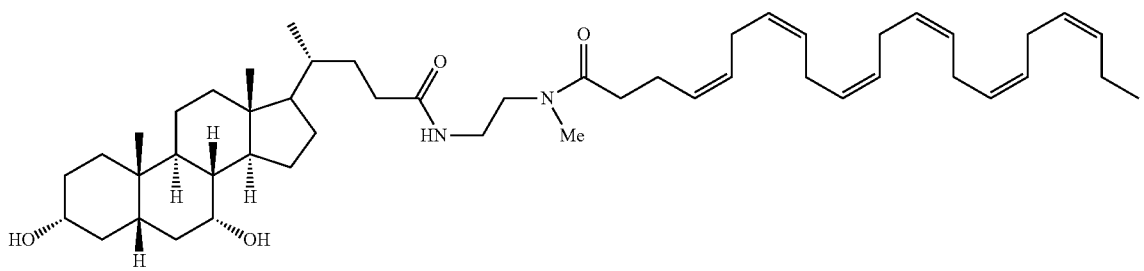

(4Z,7Z,10Z,13Z,16Z,19Z)—N-(2-((4R)-4-((3R,5S,7R,8R,
9S,10S,13R,14S)-3,7-dihydroxy-10,13-dimethylhexa-
decahydro-1H-cyclopenta[a]phenanthren-17-yl)pentana-
mido)ethyl)-N-methyldocosa-4,7,10,13,16,19-
hexaenamide (II-26)

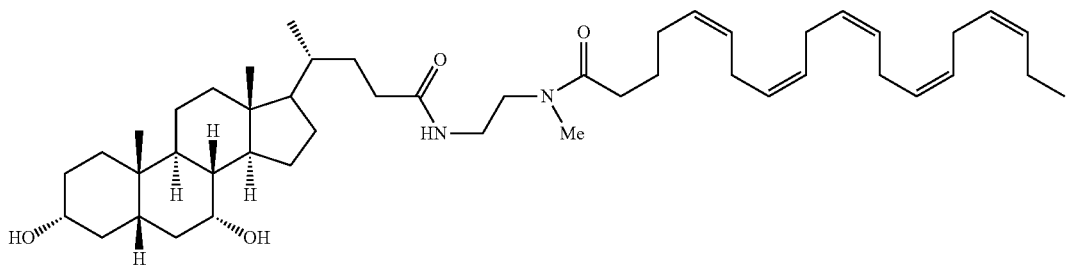

(5Z,8Z,11Z,14Z,17Z)—N-(2-((4R)-4-((3R,5S,7R,8R,9S,
10S,13R,14S)-3,7-dihydroxy-10,13-dimethylhexa-
decahydro-1H-cyclopenta[a]phenanthren-17-yl)pentana-
mido)ethyl)-N-methylicosa-5,8,11,14,17-pentaenamide
(II-27)

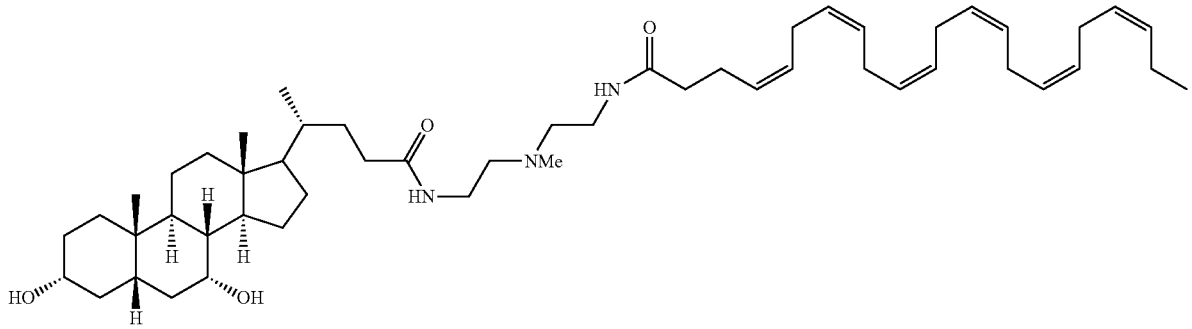

(4Z,7Z,10Z,13Z,16Z,19Z)—N-(2-((2-((4R)-4-((3R,5S,7R,
8R,9S,10S,13R,14S)-3,7-dihydroxy-10,13-dimethyl-
hexadecahydro-1H-cyclopenta[a]phenanthren-17-yl)pen-
tanamido)ethyl)(methyl)amino)ethyl)docosa-4,7,10,13,
16,19-hexaenamide (II-28)

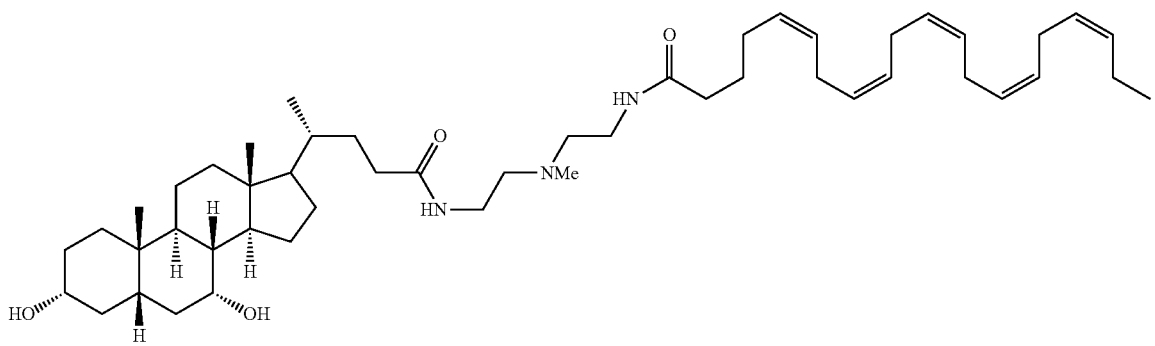

(5Z,8Z,11Z,14Z,17Z)—N-(2-((2-((4R)-4-((3R,5S,7R,8R,
9S,10S,13R,14S)-3,7-dihydroxy-10,13-dimethylhexa-
decahydro-1H-cyclopenta[a]phenanthren-17-yl)pentana-
mido)ethyl)(methyl)amino)ethyl)icosa-5,8,11,14,17-
pentaenamide (II-29)

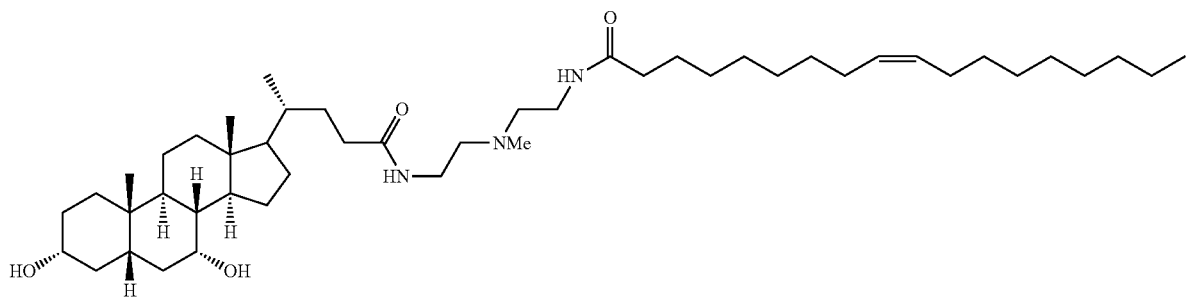

N-(2-((2-((4R)-4-((3R,5S,7R,8R,9S,10S,13R,14S)-3,7-di-
hydroxy-10,13-dimethylhexadecahydro-1H-cyclopenta
[a]phenanthren-17-yl)pentanamido)ethyl)(methyl)amino)
ethyl)oleamide (II-30)

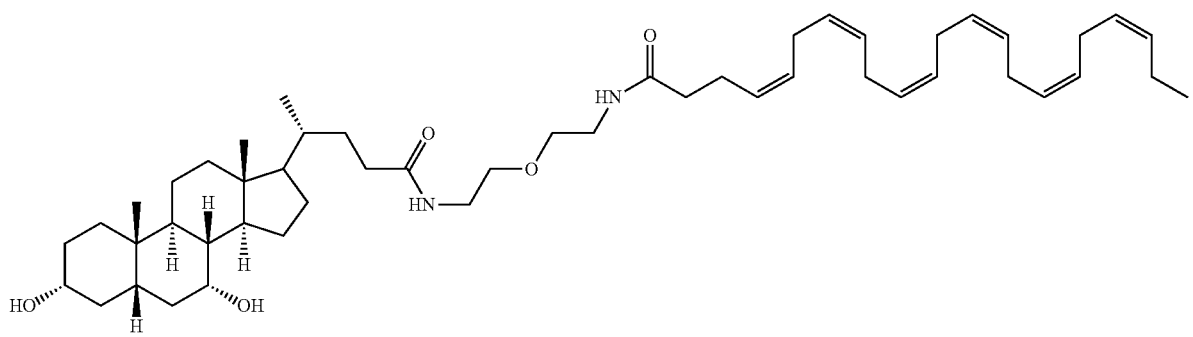

(4Z,7Z,10Z,13Z,16Z,19Z)—N-(2-(2-((4R)-4-((3R,5S,7R,
8R,9S,10S,13R,14S)-3,7-dihydroxy-10,13-dimethyl-
hexadecahydro-1H-cyclopenta[a]phenanthren-17-yl)pen-
tanamido)ethoxy)ethyl)docosa-4,7,10,13,16,19-
hexaenamide (II-31)

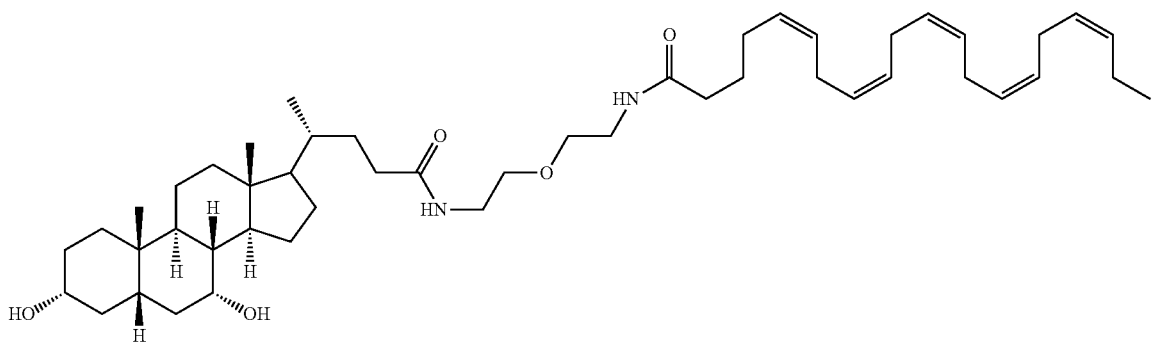

(5Z,8Z,11Z,14Z,17Z)—N-(2-(2-((4R)-4-((3R,5S,7R,8R,9S,10S,13R,14S)-3,7-dihydroxy-10,13-dimethylhexadecahydro-1H-cyclopenta[a]phenanthren-17-yl)pentanamido)ethoxy)ethyl)icosa-5,8,11,14,17-pentaenamide (II-32)

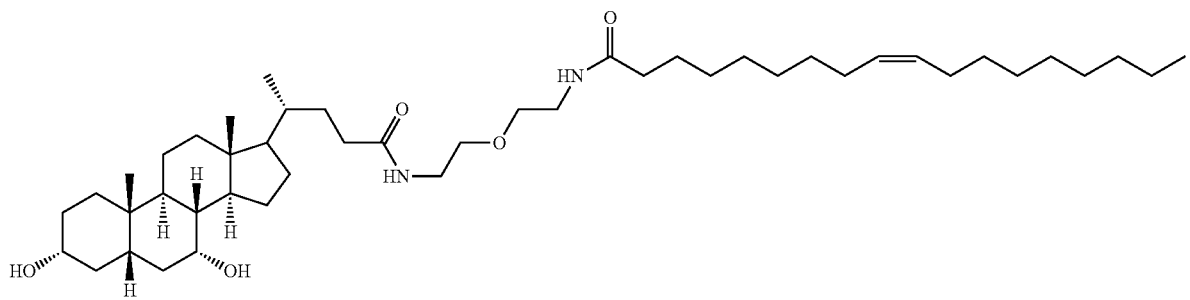

N-(2-(2-((4R)-4-((3R,5S,7R,8R,9S,10S,13R,14S)-3,7-dihydroxy-10,13-dimethylhexadecahydro-1H-cyclopenta[a]phenanthren-17-yl)pentanamido)ethoxy)ethyl)oleamide (II-33)

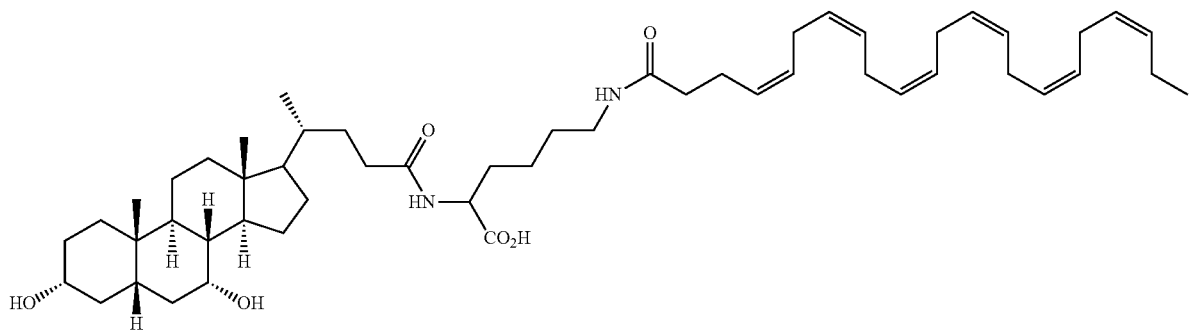

2-((4R)-4-((3R,5S,7R,8R,9S,10S,13R,14S)-3,7-dihydroxy-10,13-dimethylhexadecahydro-1H-cyclopenta[a]phenanthren-17-yl)pentanamido)-6-((4Z,7Z,10Z,13Z,16Z,19Z)-docosa-4,7,10,13,16,19-hexaenamido)hexanoic acid (II-34)

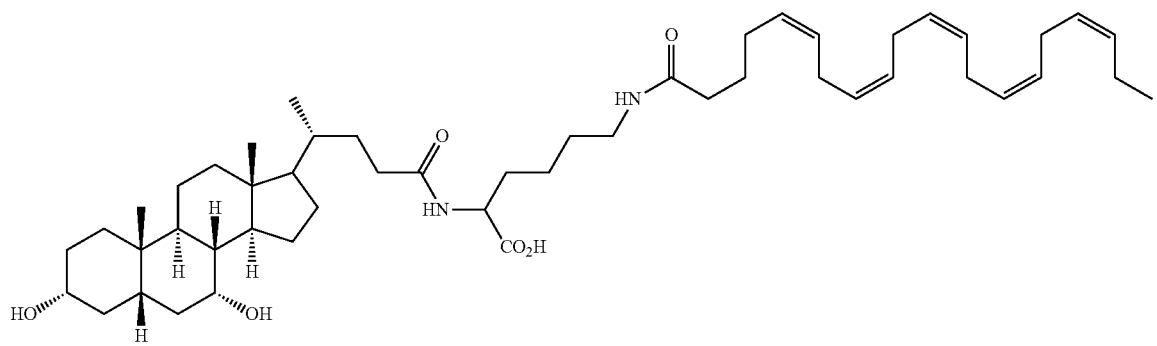

2-((4R)-4-((3R,5S,7R,8R,9S,10S,13R,14S)-3,7-dihydroxy-10,13-dimethylhexadecahydro-1H-cyclopenta[a]phenanthren-17-yl)pentanamido)-6-((5Z,8Z,11Z,14Z,17Z)-icosa-5,8,11,14,17-pentaenamido)hexanoic acid (II-35)

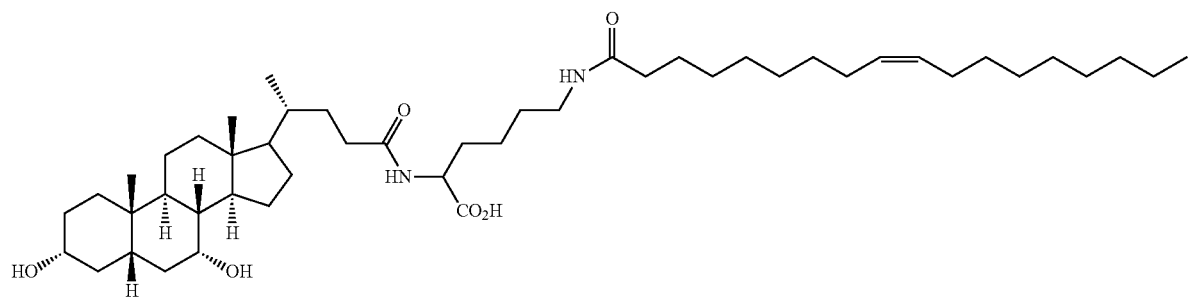

2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)-6-oleamidohexanoic acid (II-36)

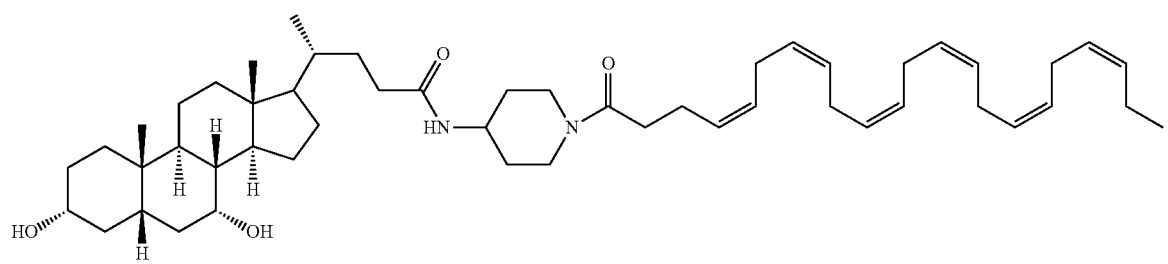

(4R)-4-((3R,5S,7R,8R,9S,10S,13R,14S)-3,7-dihydroxy-10,13-dimethylhexadecahydro-1H-cyclopenta[a]phenanthren-17-yl)-N-(1-((4Z,7Z,10Z,13Z,16Z,19Z)-docosa-4,7,10,13,16,19-hexaenoyl)piperidin-4-yl)pentanamide (II-37)

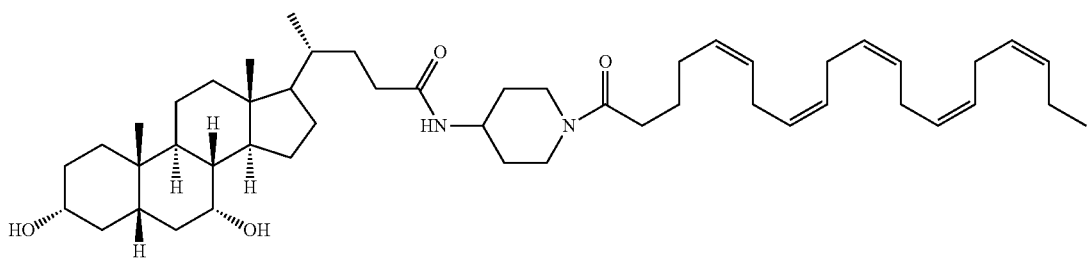

(4R)-4-((3R,5S,7R,8R,9S,10S,13R,14S)-3,7-dihydroxy-10,
13-dimethylhexadecahydro-1H-cyclopenta[a]phenan-
thren-17-yl)-N-(1-((5Z,8Z,11Z,14Z,17Z)-icosa-5,8,11,
14,17-pentaenoyl)piperidin-4-yl)pentanamide (II-38)

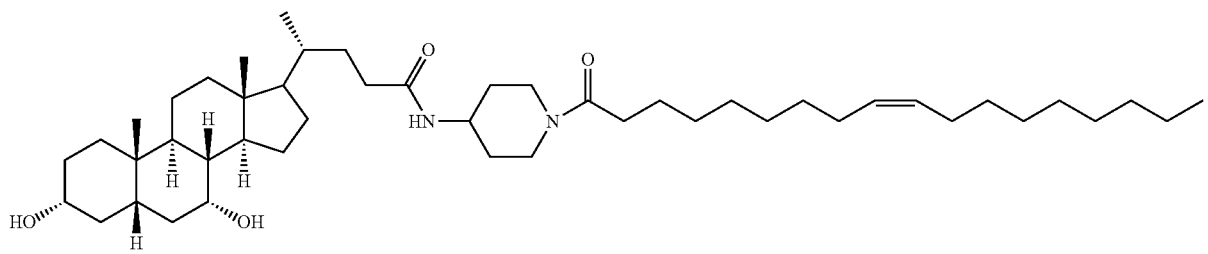

(4R)-4-((3R,5S,7R,8R,9S,10S,13R,14S)-3,7-dihydroxy-10,
13-dimethylhexadecahydro-1H-cyclopenta[a]phenan-
thren-17-yl)-N-(1-oleoylpiperidin-4-yl)pentanamide (II-39)

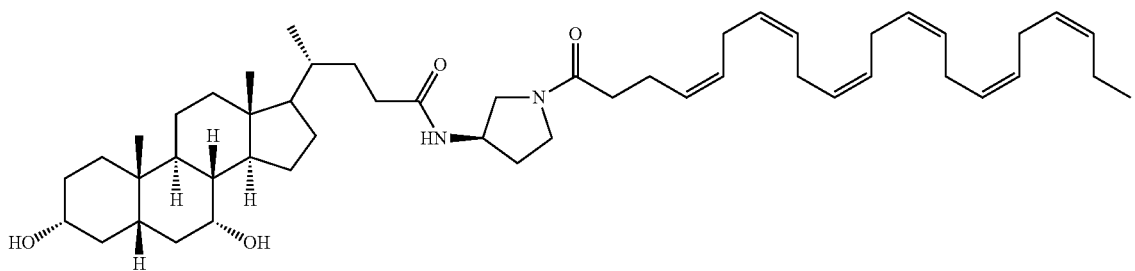

(4R)-4-((3R,5S,7R,8R,9S,10S,13R,14S)-3,7-dihydroxy-10,
13-dimethylhexadecahydro-1H-cyclopenta[a]phenan-
thren-17-yl)-N—(R)-1-((4Z,7Z,10Z,13Z,16Z,19Z)-
docosa-4,7,10,13,16,19-hexaenoyl)pyrrolidin-3-yl)
pentanamide (II-40)

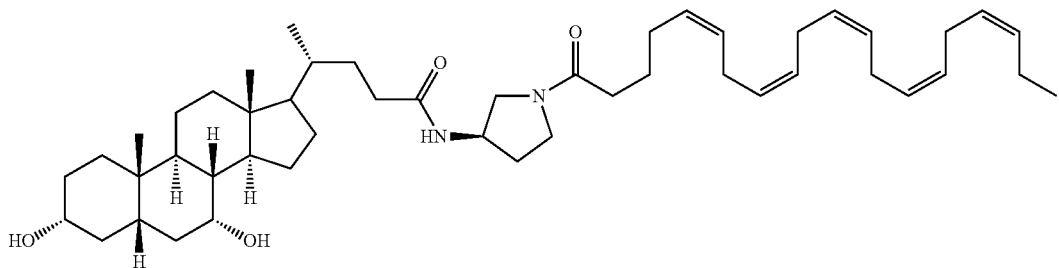

(4R)-4-((3R,5S,7R,8R,9S,10S,13R,14S)-3,7-dihydroxy-10,
13-dimethylhexadecahydro-1H-cyclopenta[a]phenan-
thren-17-yl)-N—(R)-1-((5Z,8Z,11Z,14Z,17Z)-icosa-5,8,
11,14,17-pentaenoyl)pyrrolidin-3-yl)pentanamide (II-41)

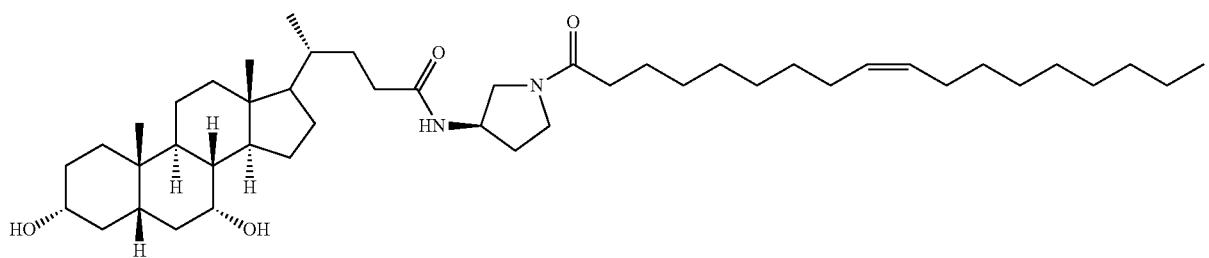

(4R)-4-((3R,5S,7R,8R,9S,10S,13R,14S)-3,7-dihydroxy-10,13-dimethylhexadecahydro-1H-cyclopenta[a]phenanthren-17-yl)-N—((R)-1-oleoylpyrrolidin-3-yl)pentanamide (II-42)

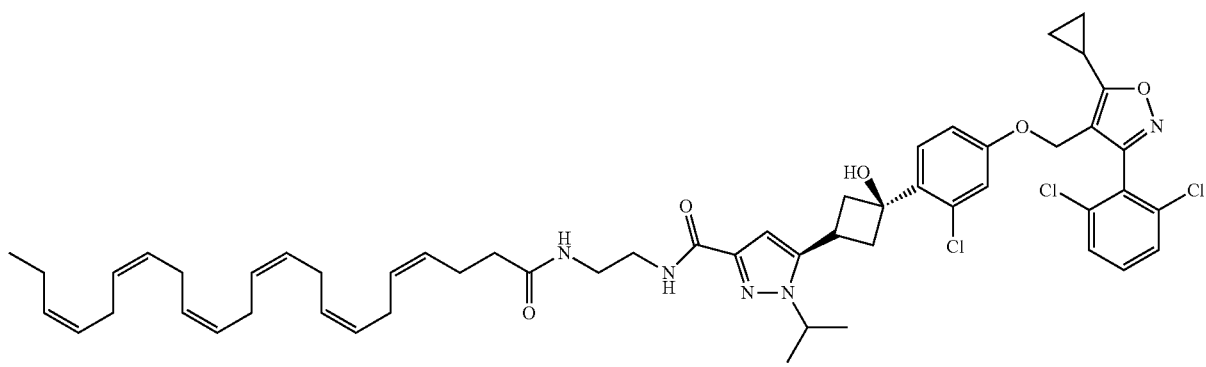

5-((1r,3r)-3-(2-chloro-4-((5-cyclopropyl-3-(2,6-dichlorophenyl)isoxazol-4-yl)methoxy)phenyl)-3-hydroxycyclobutyl)-N-(244Z,7Z,10Z,13Z,16Z,19Z)-docosa-4,7,10,13,16,19-hexaenamido)ethyl)-1-isopropyl-1H-pyrazole-3-carboxamide (II-43)

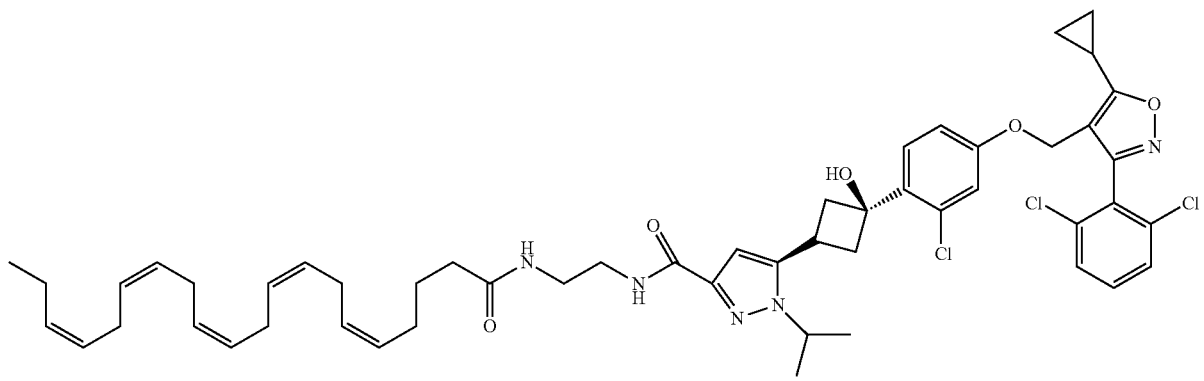

5-((1r,3r)-3-(2-chloro-4-((5-cyclopropyl-3-(2,6-dichlorophenyl)isoxazol-4-yl)methoxy)phenyl)-3-hydroxycyclobutyl)-N-(2-((5Z,8Z,11Z,14Z,17Z)-icosa-5,8,11,14,17-pentaenamido)ethyl)-1-isopropyl-1H-pyrazole-3-carboxamide (II-44)

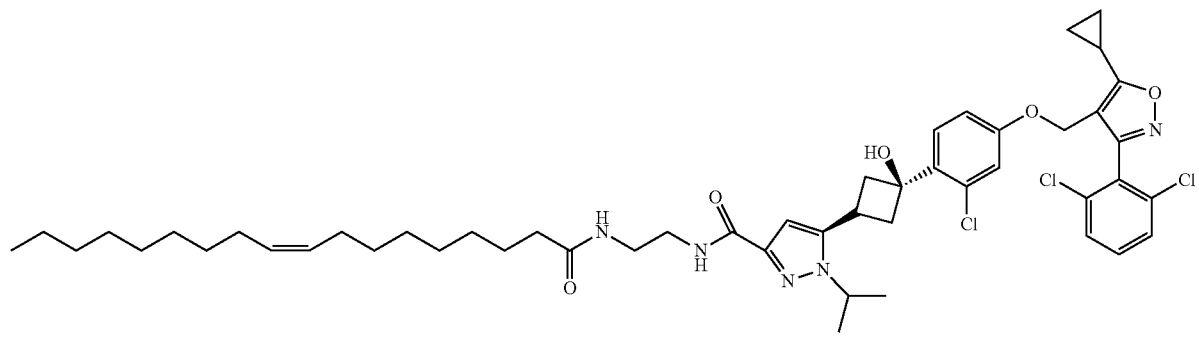

5-((1r,3r)-3-(2-chloro-4-((5-cyclopropyl-3-(2,6-dichlorophenyl)isoxazol-4-yl)methoxy)phenyl)-3-hydroxycyclobutyl)-1-isopropyl-N-(2-oleamidoethyl)-1H-pyrazole-3-carboxamide (II-45)

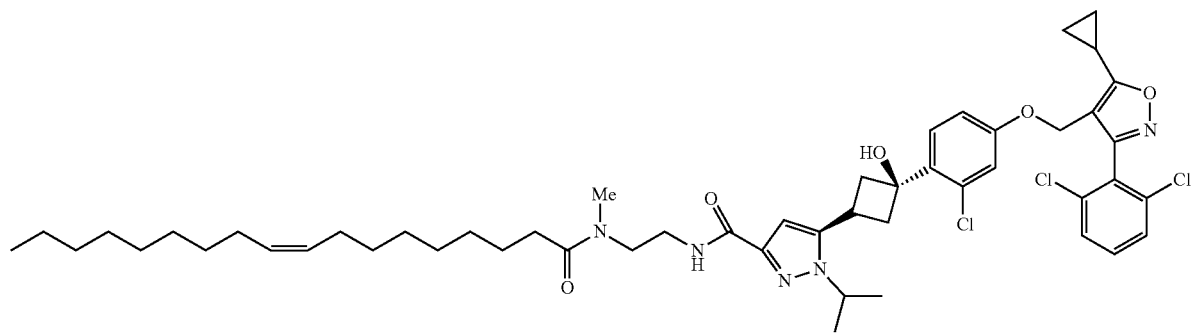

5-((1r,3r)-3-(2-chloro-4-((5-cyclopropyl-3-(2,6-dichlorophenyl)isoxazol-4-yl)methoxy)phenyl)-3-hydroxycyclobutyl)-1-isopropyl-N-(2-(N-methyloleamido)ethyl)-1H-pyrazole-3-carboxamide (II-46)

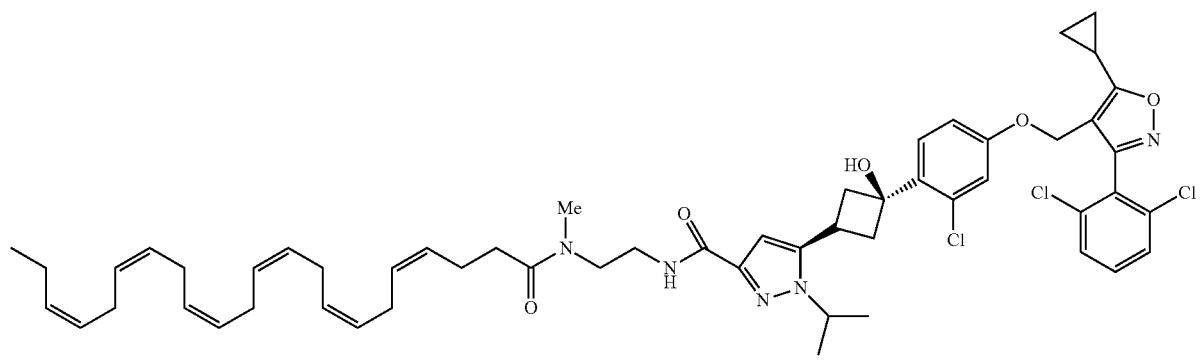

5-((1r,3r)-3-(2-chloro-4-((5-cyclopropyl-3-(2,6-dichlorophenyl)isoxazol-4-yl)methoxy)phenyl)-3-hydroxycyclobutyl)-1-isopropyl-N-(2-((4Z,7Z,10Z,13Z,16Z,19Z)-N-methyldocosa-4,7,10,13,16,19-hexaenamido)ethyl)-1H-pyrazole-3-carboxamide (II-47)

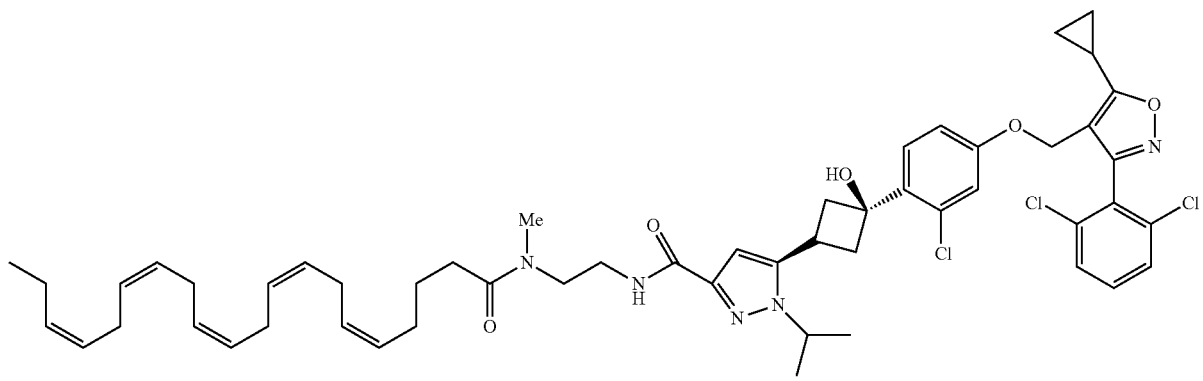

5-((1r,3r)-3-(2-chloro-4-((5-cyclopropyl-3-(2,6-dichlorophenyl)isoxazol-4-yl)methoxy)phenyl)-3-hydroxycyclobutyl)-1-isopropyl-N-(2-((5Z,8Z,11Z,14Z,17Z)—N-methylicosa-5,8,11,14,17-pentaenamido)ethyl)-1H-pyrazole-3-carboxamide (II-48)

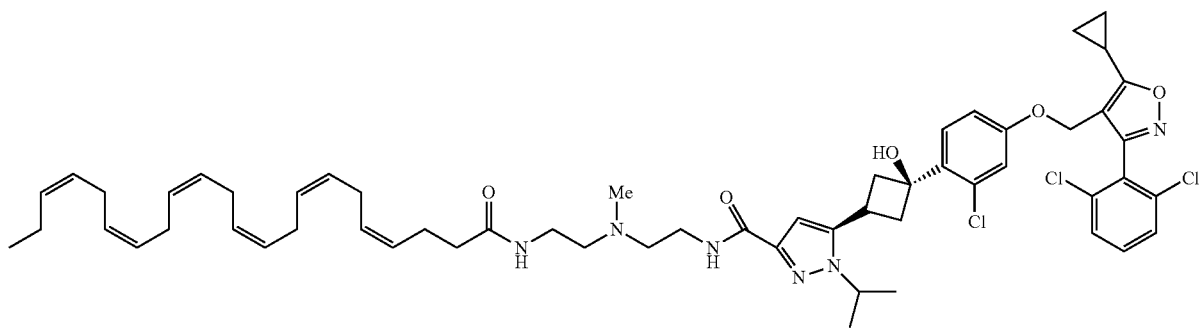

5-((1r,3r)-3-(2-chloro-4-((5-cyclopropyl-3-(2,6-dichlorophenyl)isoxazol-4-yl)methoxy)phenyl)-3-hydroxycyclobutyl)-N-(2-((2-((4Z,7Z,10Z,13Z,16Z,19Z)-docosa-4,7,10,13,16,19-hexaenamido)ethyl)(methyl)amino)ethyl)-1-isopropyl-1H-pyrazole-3-carboxamide (II-49)

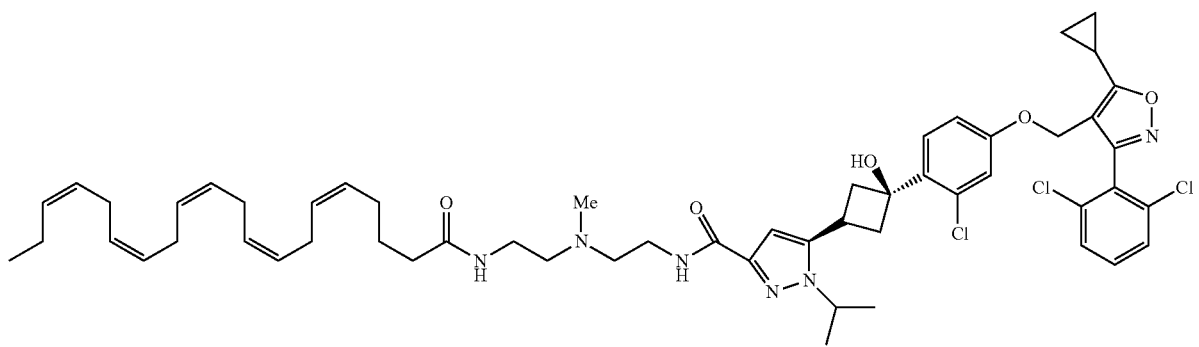

5-((1r,3r)-3-(2-chloro-4-((5-cyclopropyl-3-(2,6-dichlorophenyl)isoxazol-4-yl)methoxy)phenyl)-3-hydroxycyclobutyl)-N-(2-((2-((5Z,8Z,11Z,14Z,17Z)-icosa-5,8,11,14,17-pentaenamido)ethyl)(methyl)amino)ethyl)-1-isopropyl-1H-pyrazole-3-carboxamide (II-50)

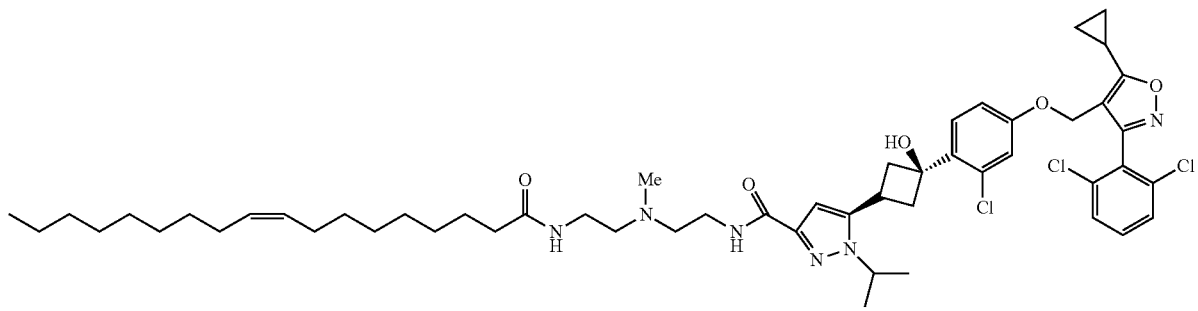

5-((1r,3r)-3-(2-chloro-4-((5-cyclopropyl-3-(2,6-dichlorophenyl)isoxazol-4-yl)methoxy)phenyl)-3-hydroxycyclobutyl)-1-isopropyl-N-(2-(methyl(2-oleamidoethyl)amino)ethyl)-1H-pyrazole-3-carboxamide (II-51)

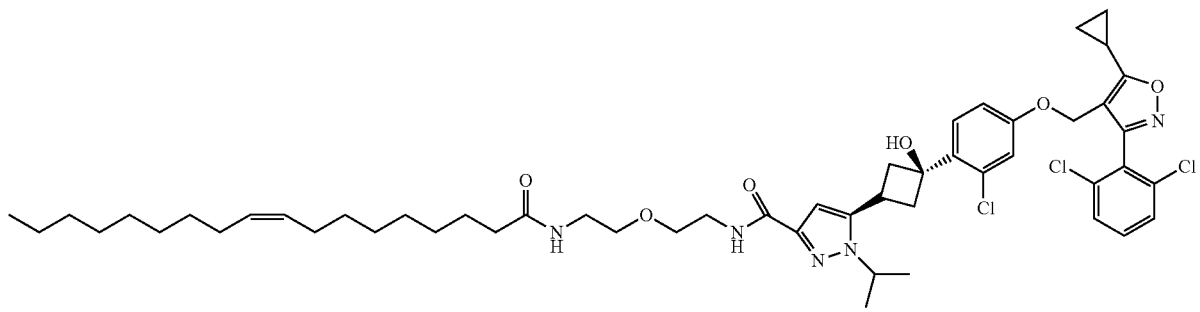

5-((1r,3r)-3-(2-chloro-4-((5-cyclopropyl-3-(2,6-dichlorophenyl)isoxazol-4-yl)methoxy)phenyl)-3-hydroxycyclobutyl)-1-isopropyl-N-(2-(2-oleamidoethoxy)ethyl)-1H-pyrazole-3-carboxamide (II-52)

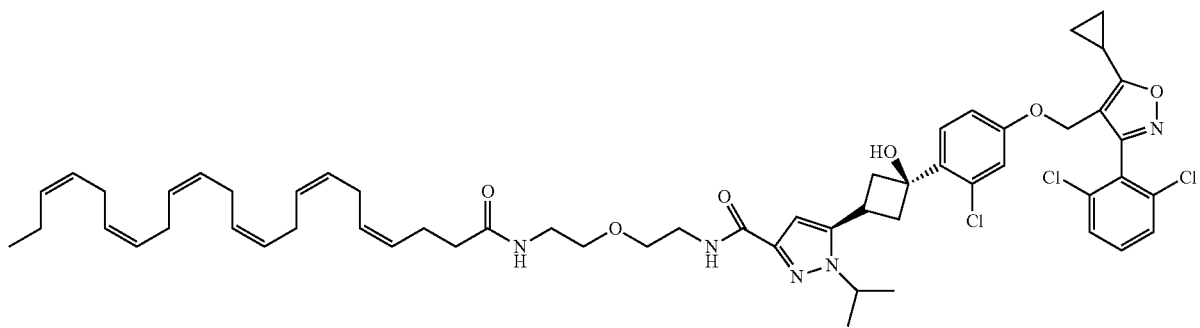

5-((1r,3r)-3-(2-chloro-4-((5-cyclopropyl-3-(2,6-dichlorophenyl)isoxazol-4-yl)methoxy)phenyl)-3-hydroxycyclobutyl)-N-(2-(2-((4Z,7Z,10Z,13Z,16Z,19Z)-docosa-4,7,10,13,16,19-hexaenamido)ethoxy)ethyl)-1-isopropyl-1H-pyrazole-3-carboxamide (II-53)

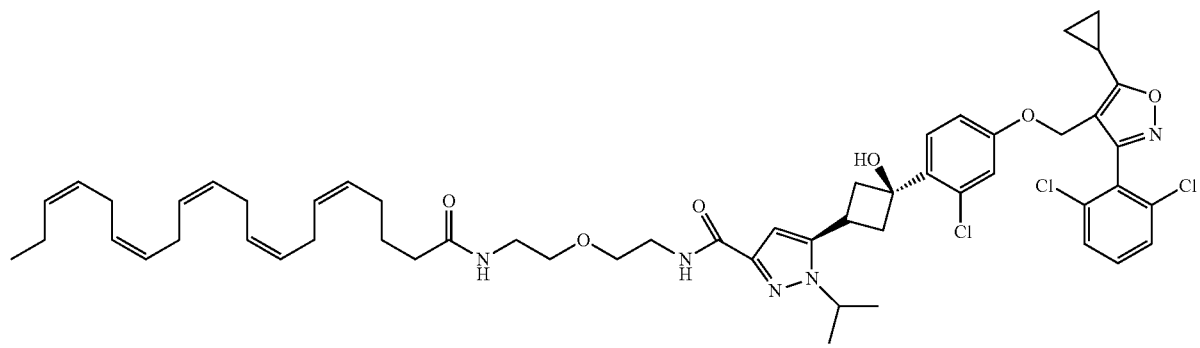

5-((1r,3r)-3-(2-chloro-4-((5-cyclopropyl-3-(2,6-dichlorophenyl)isoxazol-4-yl)methoxy)phenyl)-3-hydroxycyclobutyl)-N-(2-(2-((5Z,8Z,11Z,14Z,17Z)-icosa-5,8,11,14,17-pentaenamido)ethoxy)ethyl)-1-isopropyl-1H-pyrazole-3-carboxamide (II-54)

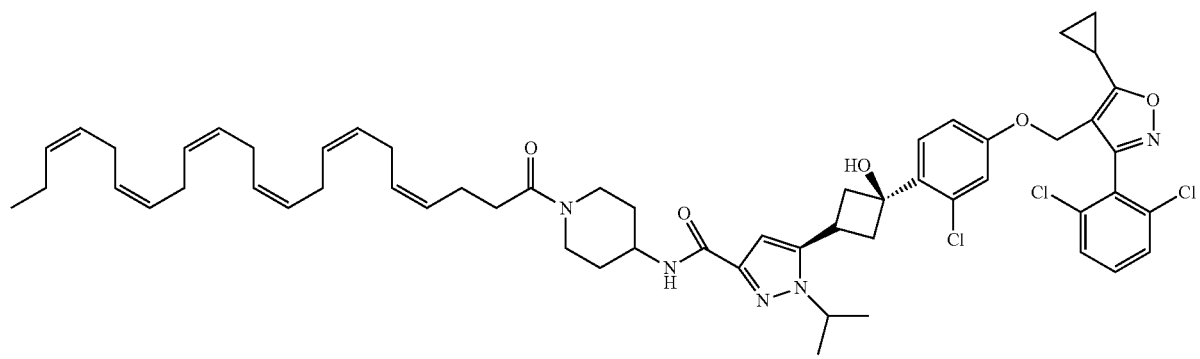

5-((1r,3r)-3-(2-chloro-4-((5-cyclopropyl-3-(2,6-dichlorophenyl)isoxazol-4-yl)methoxy)phenyl)-3-hydroxycyclobutyl)-N-(1-((4Z,7Z,10Z,13Z,16Z,19Z)-docosa-4,7,10,13,16,19-hexaenoyl)piperidin-4-yl)-1-isopropyl-1H-pyrazole-3-carboxamide (II-55)

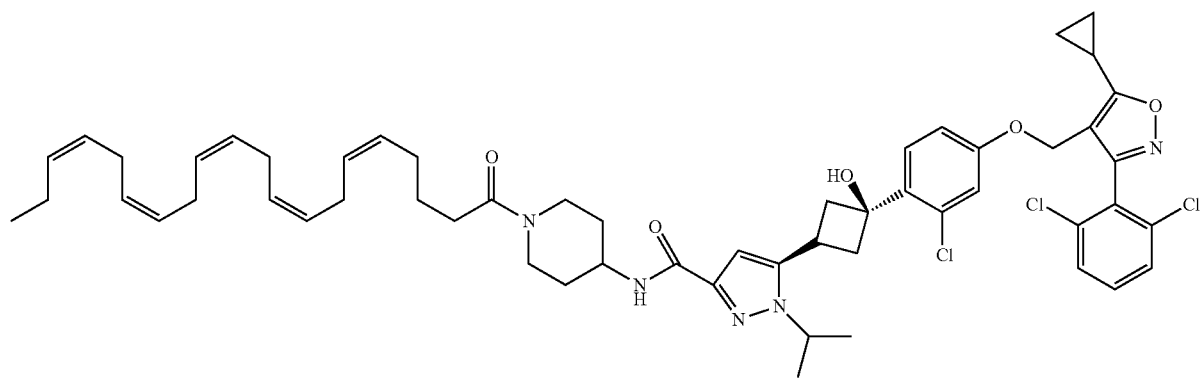

5-((1r,3r)-3-(2-chloro-4-((5-cyclopropyl-3-(2,6-dichlorophenyl)isoxazol-4-yl)methoxy)phenyl)-3-hydroxycyclobutyl)-N-(1-((5Z,8Z,11Z,14Z,17Z)-icosa-5,8,11,14,17-pentaenoyl)piperidin-4-yl)-1-isopropyl-1H-pyrazole-3-carboxamide (II-56)

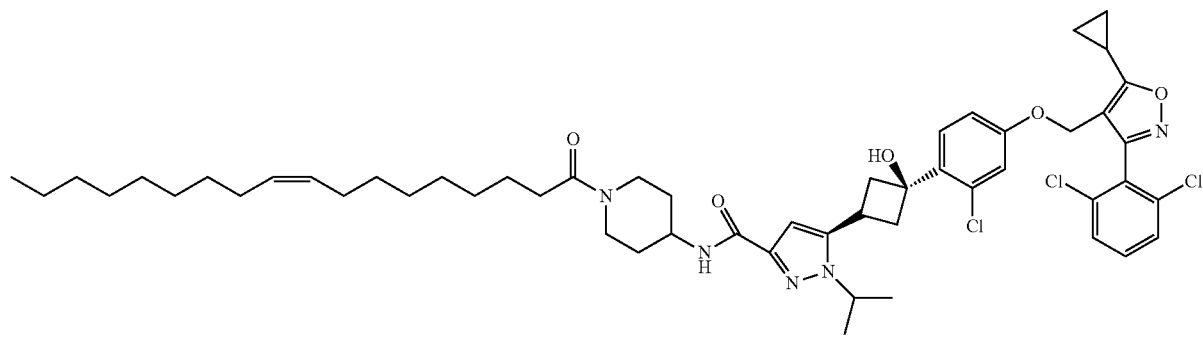

5-((1r,3r)-3-(2-chloro-4-((5-cyclopropyl-3-(2,6-dichlorophenyl)isoxazol-4-yl)methoxy)phenyl)-3-hydroxycyclobutyl)-1-isopropyl-N-(1-oleoylpiperidin-4-yl)-1H-pyrazole-3-carboxamide (II-57)

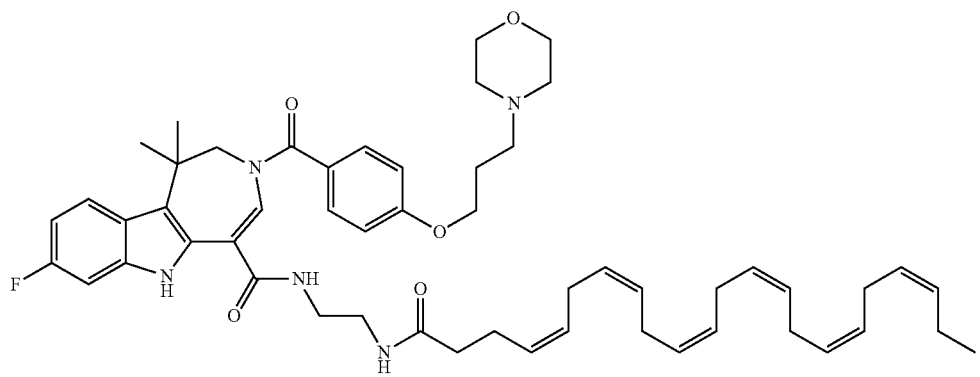 [SMILES: CC/C=C\C/C=C\C/C=C\C/C=C\C/C=C\C/C=C\CCC(=O)NCCNC(=O)C1=CN(C(=O)c2ccc(OCCCN3CCOCC3)cc2)CC(C)(C)c2c1[nH]c1cc(F)ccc21]

N-(2-((4Z,7Z,10Z,13Z,16Z,19Z)-docosa-4,7,10,13,16,19-hexaenamido)ethyl)-8-fluoro-1,1-dimethyl-3-(4-((3-morpholinopropoxy)benzoyl)-1,2,3,6-tetrahydroazepino[4,5-b]indole-5-carboxamide (II-58)

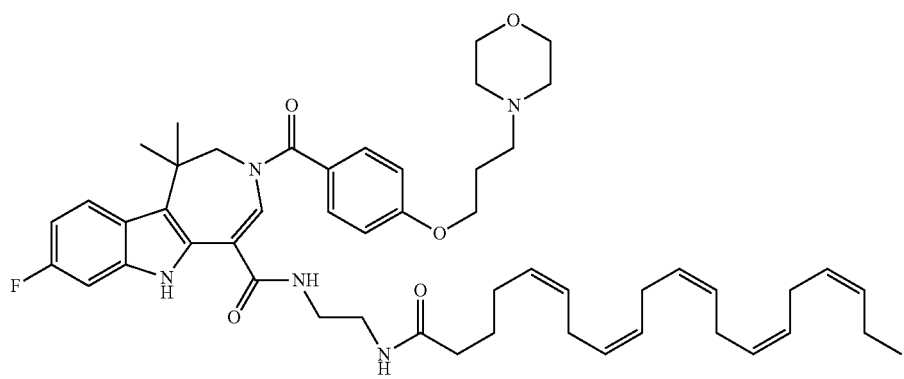 [SMILES: CC/C=C\C/C=C\C/C=C\C/C=C\C/C=C\CCCC(=O)NCCNC(=O)C1=CN(C(=O)c2ccc(OCCCN3CCOCC3)cc2)CC(C)(C)c2c1[nH]c1cc(F)ccc21]

8-fluoro-N-(2-((5Z,8Z,11Z,14Z,17Z)-icosa-5,8,11,14,17-pentaenamido)ethyl)-1,1-dimethyl-3-(4-(3-morpholinopropoxy)benzoyl)-1,2,3,6-tetrahydroazepino[4,5-b]indole-5-carboxamide (II-59)

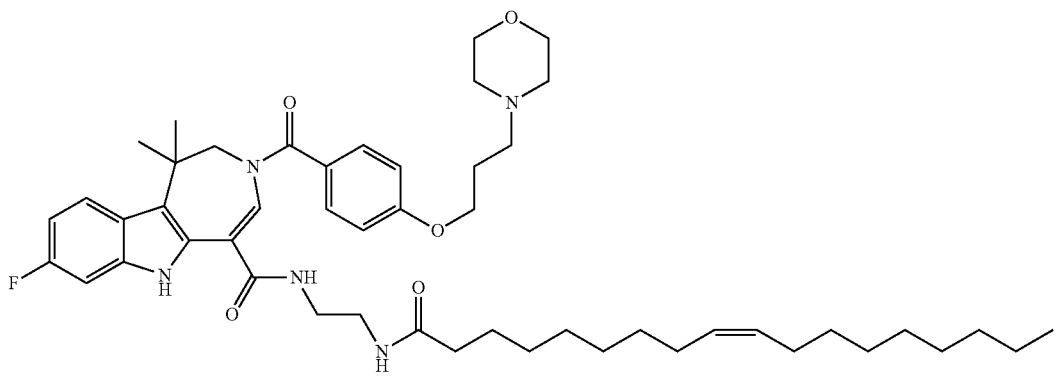 [SMILES: CCCCCCCC/C=C\CCCCCCCC(=O)NCCNC(=O)C1=CN(C(=O)c2ccc(OCCCN3CCOCC3)cc2)CC(C)(C)c2c1[nH]c1cc(F)ccc21]

(Z)-8-fluoro-1,1-dimethyl-3-(4-(3-morpholinopropoxyl)
benzoyl)-N-(2-oleamidoethyl)-1,2,3,6-tetrahydroazepino
[4,5-b]indole-5-carboxamide (II-60)

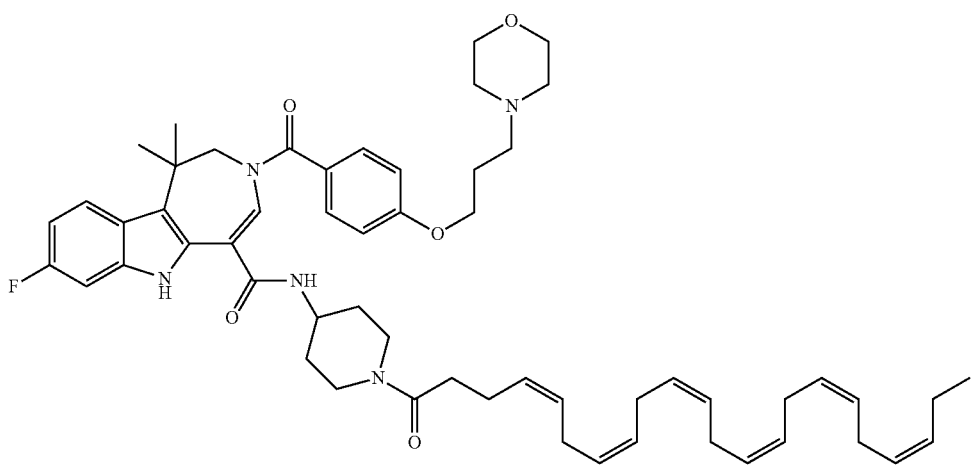 [SMILES: CC/C=C\C/C=C\C/C=C\C/C=C\C/C=C\C/C=C\CCC(=O)N1CCC(NC(=O)C2=CN(C(=O)c3ccc(OCCCN4CCOCC4)cc3)CC(C)(C)c3c2[nH]c2cc(F)ccc32)CC1]

N-(1-((4Z,7Z,10Z,13Z,16Z,19Z)-docosa-4,7,10,13,16,19-
hexaenoyl)piperidin-4-yl)-8-fluoro-1,1-dimethyl-3-(4-(3-
morpholinopropoxy)benzoyl)-1,2,3,6-tetrahydroazepino
[4,5-b]indole-5-carboxamide (II-61)

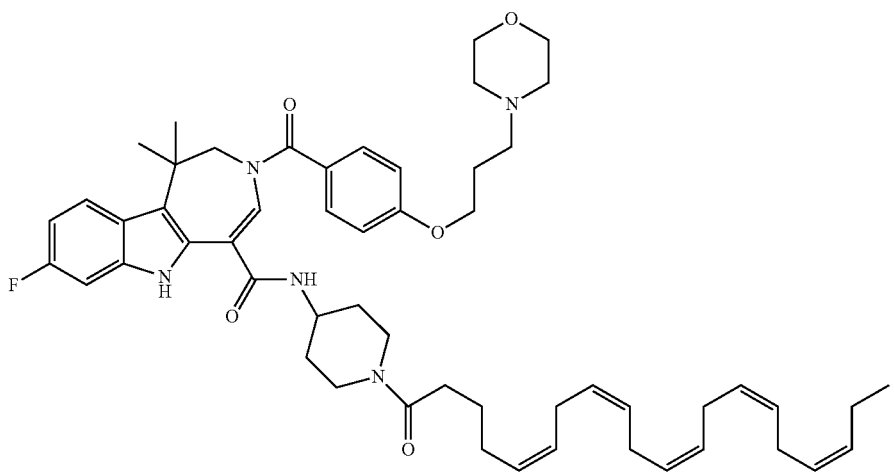 [SMILES: CC/C=C\C/C=C\C/C=C\C/C=C\C/C=C\CCCC(=O)N1CCC(NC(=O)C2=CN(C(=O)c3ccc(OCCCN4CCOCC4)cc3)CC(C)(C)c3c2[nH]c2cc(F)ccc32)CC1]

8-fluoro-N-(1-((5Z,8Z,11Z,14Z,17Z)-icosa-5,8,11,14,17-
pentaenoyl)piperidin-4-yl)-1,1-dimethyl-3-(4-(3-mor-
pholinopropoxy)benzoyl)-1,2,3,6-tetrahydroazepino[4,5-
b]indole-5-carboxamide (II-62)

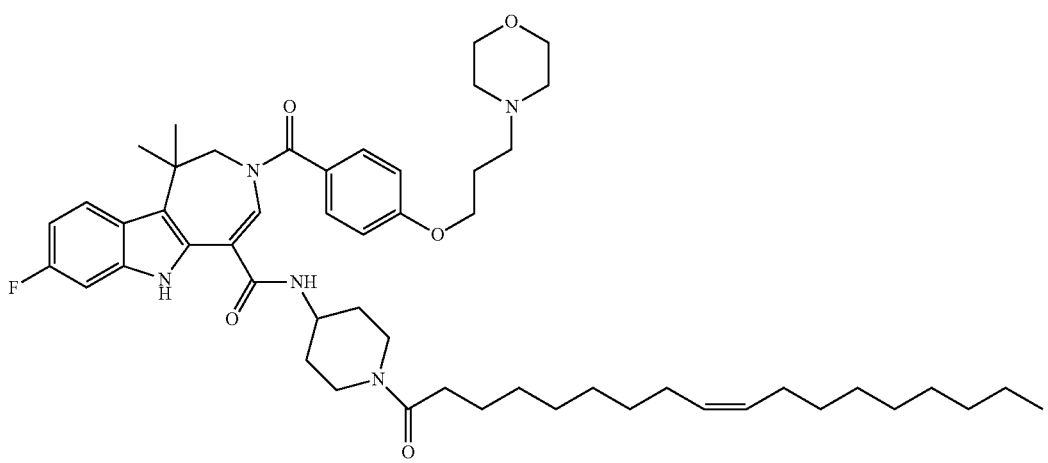 [SMILES: CCCCCCCC/C=C\CCCCCCCC(=O)N1CCC(NC(=O)C2=CN(C(=O)c3ccc(OCCCN4CCOCC4)cc3)CC(C)(C)c3c2[nH]c2cc(F)ccc32)CC1]

(Z)-8-fluoro-1,1-dimethyl-3-(4-(3-morpholinopropoxy)benzoyl)-N-(1-oleoylpiperidin-4-yl)-1,2,3,6-tetrahydroazepino[4,5-b]indole-5-carboxamide (II-63)

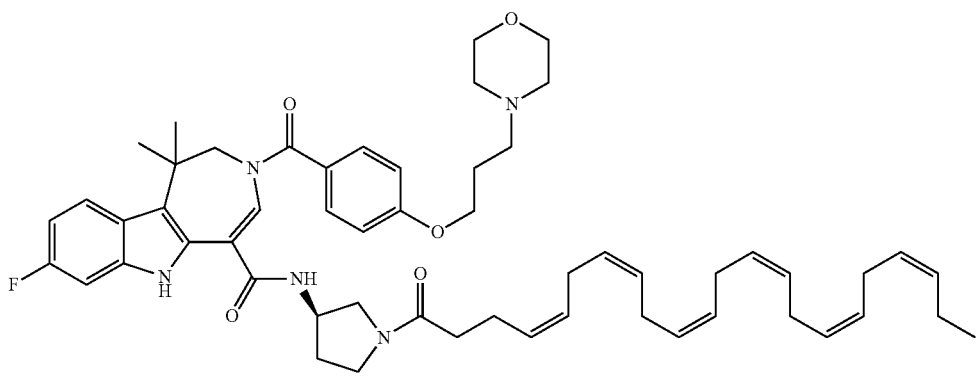 [SMILES: CC/C=C\C/C=C\C/C=C\C/C=C\C/C=C\C/C=C\CCC(=O)N1CC[C@@H](NC(=O)C2=CN(C(=O)c3ccc(OCCCN4CCOCC4)cc3)CC(C)(C)c3c2[nH]c2cc(F)ccc32)C1]

N—((R)-1-((4Z,7Z,10Z,13Z,16Z,19Z)-docosa-4,7,10,13,16,19-hexaenoyl)pyrrolidin-3-yl)-8-fluoro-1,1-dimethyl-3-(4-(3-morpholinopropoxy)benzoyl)-1,2,3,6-tetrahydroazepino[4,5-b]indole-5-carboxamide (II-64)

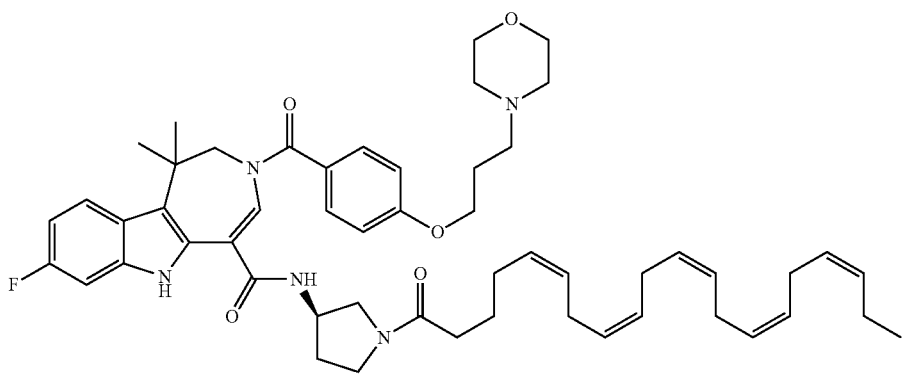 [SMILES: CC/C=C\C/C=C\C/C=C\C/C=C\C/C=C\CCCC(=O)N1CC[C@@H](NC(=O)C2=CN(C(=O)c3ccc(OCCCN4CCOCC4)cc3)CC(C)(C)c3c2[nH]c2cc(F)ccc32)C1]

8-fluoro-N—((R)-1-((5Z,8Z,11Z,14Z,17Z)-icosa-5,8,11,14,17-pentaenoyl)pyrrolidin-3-yl)-1,1-dimethyl-3-(4-(3-morpholinopropoxy)benzoyl)-1,2,3,6-tetrahydroazepino[4,5-b]indole-5-carboxamide (II-65)

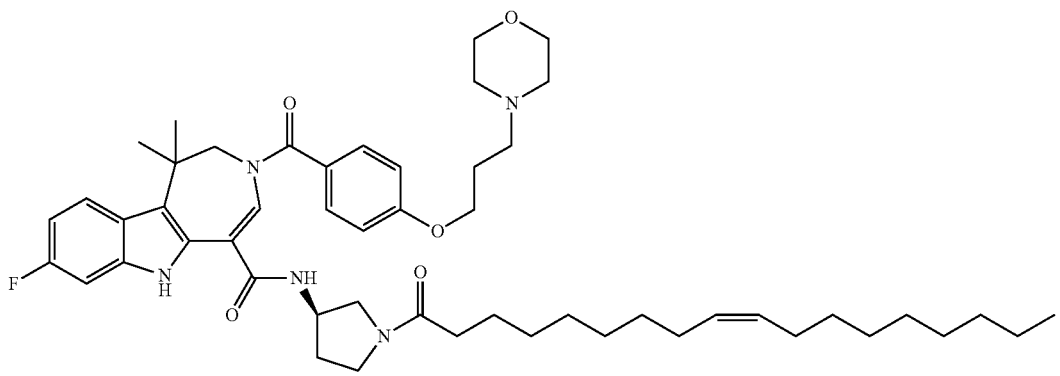 [SMILES: CCCCCCCC/C=C\CCCCCCCC(=O)N1CC[C@@H](NC(=O)C2=CN(C(=O)c3ccc(OCCCN4CCOCC4)cc3)CC(C)(C)c3c2[nH]c2cc(F)ccc32)C1]

(R,Z)-8-fluoro-1,1-dimethyl-3-(4-(3-morpholinopropoxy)
benzoyl)-N-(1-oleoylpyrrolidin-3-yl)-1,2,3,6-tetrahy-
droazepino[4,5-b]indole-5-carboxamide (II-66)

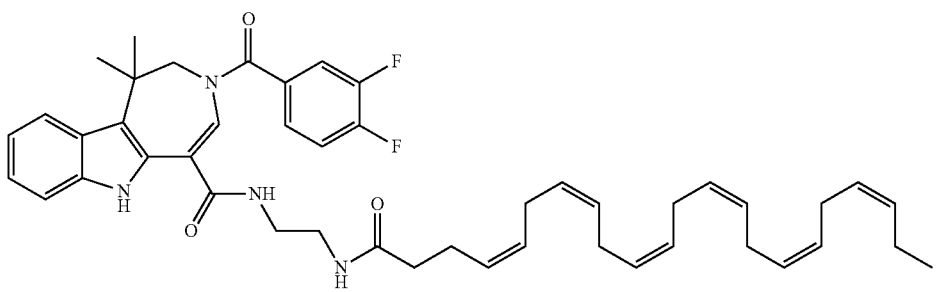 [SMILES: CC/C=C\C/C=C\C/C=C\C/C=C\C/C=C\C/C=C\CCC(=O)NCCNC(=O)C1=CN(C(=O)c2ccc(F)c(F)c2)CC(C)(C)c2c1[nH]c1ccccc21]

3-(3,4-difluorobenzoyl)-N-(2-((4Z,7Z,10Z,13Z,16Z,19Z)-
docosa-4,7,10,13,16,19-hexaenamido)ethyl)-1,1-dim-
ethyl-1,2,3,6-tetrahydroazepino[4,5-b]indole-5-carboxa-
mide (II-67)

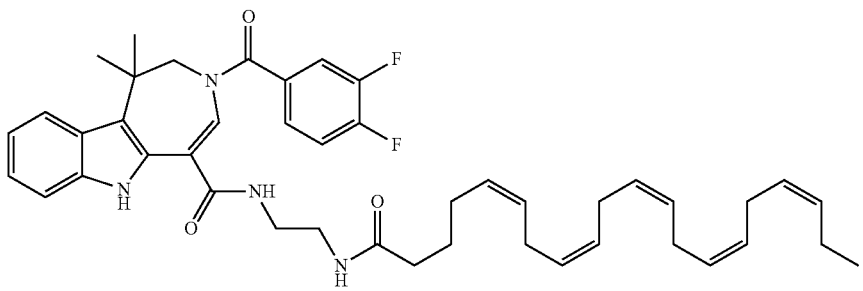 [SMILES: CC/C=C\C/C=C\C/C=C\C/C=C\C/C=C\CCCC(=O)NCCNC(=O)C1=CN(C(=O)c2ccc(F)c(F)c2)CC(C)(C)c2c1[nH]c1ccccc21]

3-(3,4-difluorobenzoyl)-N-(2-((5Z,8Z,11Z,14Z,17Z)-icosa-
5,8,11,14,17-pentaenamido)ethyl)-1,1-dimethyl-1,2,3,6-
tetrahydroazepino[4,5-b]indole-5-carboxamide (II-68)

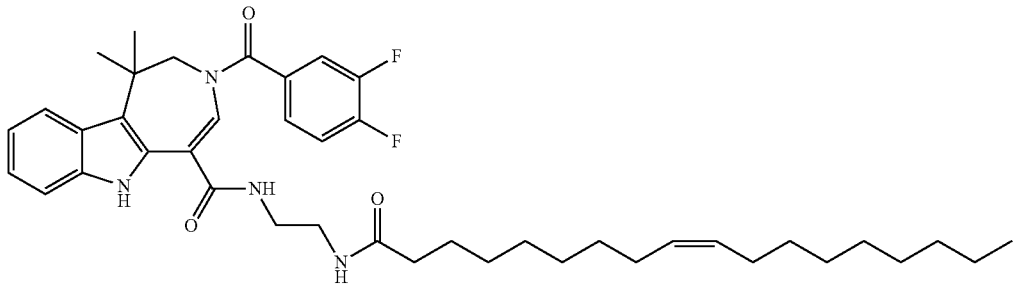 [SMILES: CCCCCCCC/C=C\CCCCCCCC(=O)NCCNC(=O)C1=CN(C(=O)c2ccc(F)c(F)c2)CC(C)(C)c2c1[nH]c1ccccc21]

(Z)-3-(3,4-difluorobenzoyl)-1,1-dimethyl-N-(2-oleamidoet-
hyl)-1,2,3,6-tetrahydroazepino[4,5-n]indole-5-carboxam-
ide (II-69)

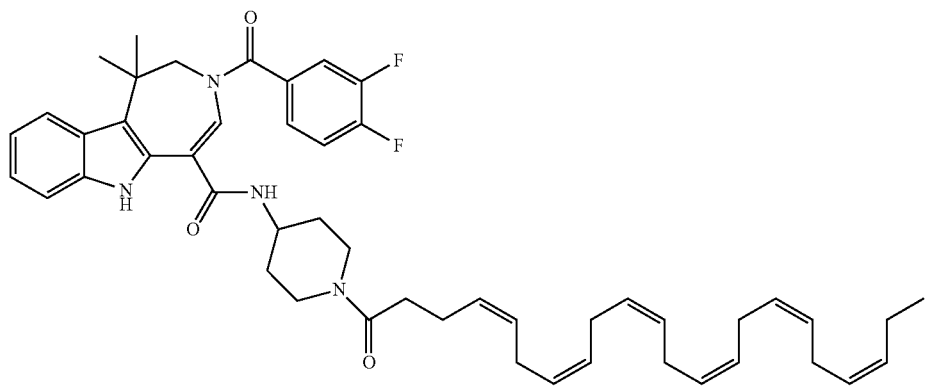 [SMILES: CC/C=C\C/C=C\C/C=C\C/C=C\C/C=C\C/C=C\CCC(=O)N1CCC(NC(=O)C2=CN(C(=O)c3ccc(F)c(F)c3)CC(C)(C)c3c2[nH]c2ccccc32)CC1]
3-(3,4-difluorobenzoyl)-N-(1-((4Z,7Z,10Z,13Z,16Z,19Z)-docosa-4,7,10,13,16,19-hexaenoyl)piperidin-4-yl)-1,1-dimethyl-1,2,3,6-tetrahydroazepino[4,5-b]indole-5-carboxamide (II-70)
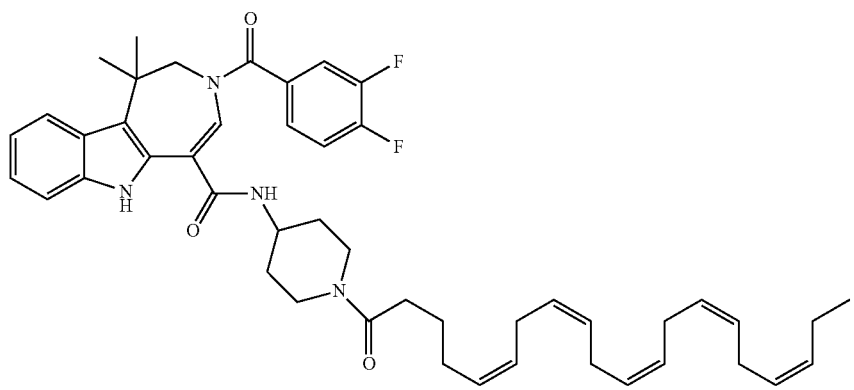 [SMILES: CC/C=C\C/C=C\C/C=C\C/C=C\C/C=C\CCCC(=O)N1CCC(NC(=O)C2=CN(C(=O)c3ccc(F)c(F)c3)CC(C)(C)c3c2[nH]c2ccccc32)CC1]
3-(3,4-difluorobenzoyl)-N-(1-((5Z,8Z,11Z,14Z,17Z)-icosa-5,8,11,14,17-pentaenoyl)piperidin-4-yl)-1,1-dimethyl-1,2,3,6-tetrahydroazepino[4,5-B]indole-5-carboxamide (II-71)
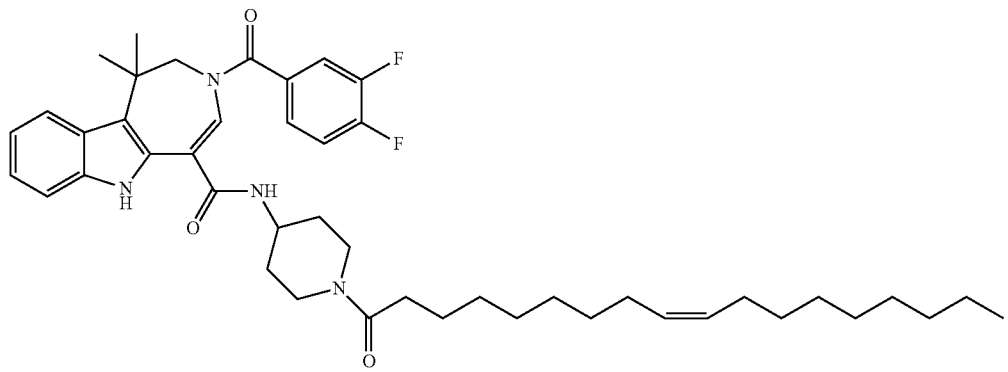 [SMILES: CCCCCCCC/C=C\CCCCCCCC(=O)N1CCC(NC(=O)C2=CN(C(=O)c3ccc(F)c(F)c3)CC(C)(C)c3c2[nH]c2ccccc32)CC1]
(Z)-3-(3,4-difluorobenzoyl)-1,1-dimethyl-N-(1-oleoylpiperidin-4-yl)-1,2,3,6-tetrahydroazepino[4,5-b]indole-5-carboxamide (II-72)

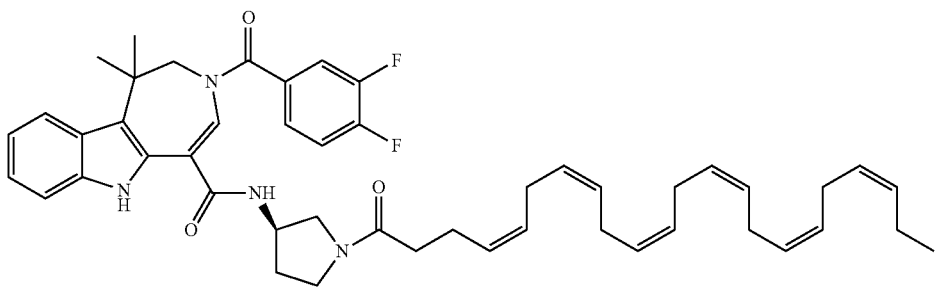 [SMILES: CC/C=C\C/C=C\C/C=C\C/C=C\C/C=C\C/C=C\CCC(=O)N1CC[C@@H](NC(=O)C2=CN(C(=O)c3ccc(F)c(F)c3)CC(C)(C)c3c2[nH]c2ccccc32)C1]

3-(3,4-difluorobenzoyl)-N—((R)-1-((4Z,7Z,10Z,13Z,16Z,19Z)-docosa-4,7,10,13,16,19-hexaenoyl)pyrrolidin-3-yl)-1,1-dimethyl-1,2,3,6-tetrahydroazepino[4,5-b]indole-5-carboxamide (II-73)

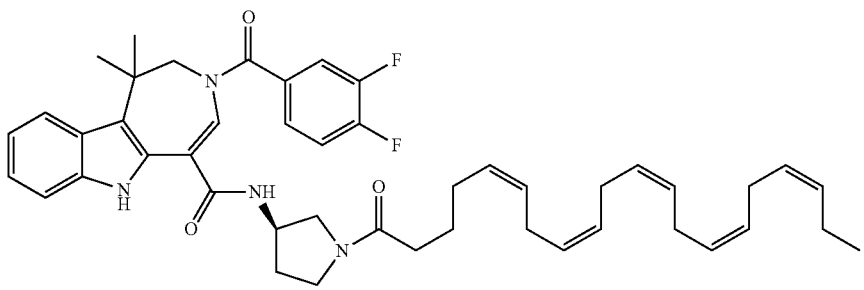 [SMILES: CC/C=C\C/C=C\C/C=C\C/C=C\C/C=C\CCCC(=O)N1CC[C@@H](NC(=O)C2=CN(C(=O)c3ccc(F)c(F)c3)CC(C)(C)c3c2[nH]c2ccccc32)C1]

3-(3,4-difluorobenzoyl)-N—((R)-1-((5Z,8Z,11Z,14Z,17Z)-icosa-5,8,11,14,17-pentaenoyl)pyrrolidin-3-yl)-1,1-dimethyl-1,2,3,6-tetrahydroazepino[4,5-b]indole-5-carboxamide (II-74)

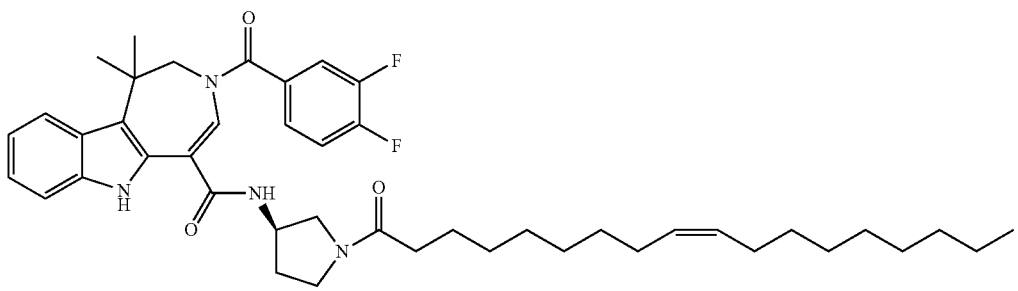 [SMILES: CCCCCCCC/C=C\CCCCCCCC(=O)N1CC[C@@H](NC(=O)C2=CN(C(=O)c3ccc(F)c(F)c3)CC(C)(C)c3c2[nH]c2ccccc32)C1]

(R,Z)-3-(3,4-difluorobenzoyl)-1,1-dimethyl-N-(1-oleoylpyrrolidin-3-yl)-1,2,3,6-tetrahydroazepino[4,5-b]indole-5-carboxamide (II-75)

Methods for Using Fatty Acid Statin Conjugates and Fatty Acid FXR Agonist Conjugates The invention includes methods for the treatment or prevention of metabolic disorders including atherosclerosis, dyslipidemia, coronary heart disease, hypercholesterolemia, familial hypercholesterolemia (including either heterozygous or homozygous familial hypercholesterolemia), Type 2 diabetes, elevated cholesterol, metabolic syndrome, diabetic nephropathy, IgA nephropathy, chronic kidney disease (CKD), abdominal aortic aneurysm and cardiovascular disease. Hyperlipidemia are classified according to which types of lipids are elevated, that is hypercholesterolemia, hypertriglyceridemia, or both in combined hyperlipidemia. Elevated levels of lipoprotein may also be classified as a form of hyperlipidemia. There are five types of hyperlipoproteinemia (types I through V) and these are further classified according to the Fredrikson classification, based on the pattern of lipoproteins on electrophoresis or ultracentrifugation. Type I hyperlipoproteinemia has three subtypes: Type Ia (also called Buerger-Gruetz syndrome or familial hyperchylomicronemia), Type Ib (also called familial apoprotein CII deficiency) and Type Ic. Due to defects in either decreased in lipoprotein lipase (LPL), altered ApoC2 or LPL inhibitor in blood, all three subtypes of Type I hyperlipoproteinemia share the same characteristic increase in chylomicrons. The frequency of occurrence for Type I hyperlipoproteinemia is 1 in 1,000,000 and thus far no drug therapy is available and treatment has consisted only of diet. Type II hyperlipoproteinemia has two subtypes: Type IIa (also called familial hypercholesterolemia) is characterized by an elevated level of low-density lipoprotein (LDL); and Type IIb (also called familial combined hyperlipidemia) is characterized by an elevated level of LDL and very-low density lipoprotein (VLDL). Type III hyperlipoproteinemia (also called familial dysbetalipoproteinemia) is characterized by an elevated level of intermediate-density lipoprotein (IDL). Type IV hyperlipoproteinemia (also called familial hypertriglyceridemia) is characterized by an elevated level of VLDL. Type V hyperlipoproteinemia is characterized by an elevated level of VLDL and chylomicrons. Treatment for Type V hyperlipoproteinemia thus far has not been adequate with using just niacin or fibrate. Also provided in the invention is a method for inhibiting, preventing, or treating a metabolic disease, or symptoms of a metabolic disease, in a subject. Examples of such disorders include, but are not limited to hypertriglyceridemia, hypertension, heart failure, cardiac arrhythmias, cardric dysthythmias, myocarditis, low HDL levels, high LDL levels, sudden death, stable angina, acute myocardial infarction, secondary prevention of myocardial infarction, cardiomyopathy, endocarditis, insulin resistance, impaired glucose tolerance, stroke, intermittent claudication, hyperphosphatemia, carotid atherosclerosis, peripheral arterial disease, diabetic nephropathy, hypercholesterolemia in HIV infection, acute coronary syndrome (ACS), fatty liver disease, arterial occlusive diseases, cerebral arteriosclerosis, cerebrovascular disorders, myocardial ischemia, diabetic autonomic neuropathy, nonalcoholic fatty liver disease (NFLD), and nonalcoholic steatohepatitis (NASH).

Compounds of this invention can also be used to potentially treat or prevent cholestasis, an impairment in the flow of bile acids, and a component of many liver diseases. These liver diseases include cholelithiasis, cholestasis of pregnancy, primary biliary cirrhosis (PBC), primary sclerosing cholangitis, progressive familial intrahepatic cholestasis type 1 (PFIC 1 or Byler disease), PFIC2 and PFIC3. Other rare diseases that can be treated with compounds of this invention include neutral lipid storage disease (Chanarin-Dorfman syndrome), beta-sitosterolemia, dys betalipoproteinemia, Wolman's disease, cerebrotendinous xanthomatosis, sitosterolemia, and Niemann-Pick disease.

In some embodiments, the subject is administered an effective amount of a fatty acid statin conjugate or a fatty acid FXR agonist conjugate.

The invention also includes pharmaceutical compositions useful for treating or preventing a metabolic disease, or for inhibiting a metabolic disease, or more than one of these activities. The compositions can be suitable for internal use and comprise an effective amount of a fatty acid statin conjugate and a pharmaceutically acceptable carrier or a fatty acid FXR agonist conjugate and a pharmaceutically acceptable carrier. The fatty acid statin conjugates or fatty acid FXR agonist conjugates are especially useful in that they demonstrate very low peripheral toxicity or no peripheral toxicity.

The fatty acid statin conjugates or fatty acid FXR agonist conjugates can each be administered in amounts that are sufficient to treat or prevent a metabolic disease or prevent the development thereof in subjects.

Administration of the fatty acid statin conjugates or fatty acid FXR agonist conjugates can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a fatty acid statin or FXR agonist conjugate and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the fatty acid statin conjugate is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the fatty acid statin conjugates.

The fatty acid statin conjugates and fatty acid FXR agonist conjugates can be also formulated as a suppository that can be prepared from fatty emulsions or suspensions; using polyalkylene glycols such as propylene glycol, as the carrier.

The fatty acid statin conjugates or fatty acid FXR agonist conjugates can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

Fatty acid statin conjugates or fatty acid FXR agonist conjugates can also be delivered by the use of monoclonal antibodies as individual carriers to which the fatty acid statin conjugates are coupled. The fatty acid statin conjugates can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the fatty acid statin conjugates or the fatty acid FXR agonist conjugates can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, fatty acid statin conjugates are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 90%, from about 10% to about 90%, or from about 30% to about 90% of the fatty acid statin conjugate or fatty acid FXR agonist conjugate by weight or volume.

The dosage regimen utilizing the fatty acid statin conjugate or the fatty acid FXR agonist conjugate is selected in accordance with a variety of factors including type, species, age, weight, sex and medical condition of the patient; the severity of the condition to be treated; the route of administration; the renal or hepatic function of the patient; and the particular fatty acid statin conjugate employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 5,000 mg of the fatty acid statin conjugate or the fatty acid FXR agonist conjugate per day. Compositions for in vivo or in vitro use can contain about 20, 50, 75, 100, 150, 250, 500, 750, 1,000, 1,250, 2,500, 3,500, or 5,000 mg of the fatty acid statin conjugate or the fatty acid FXR agonist conjugate. In one embodiment, the compositions are in the form of a tablet that can be scored. Effective plasma levels of the fatty acid statin conjugate or the fatty acid FXR agonist conjugate can range from about 5 ng/mL to about 5,000 ng/mL. Appropriate dosages of the fatty acid statin conjugates or the fatty acid FXR agonist conjugates can be determined as set forth in Goodman, L. S.; Gilman, A. *The Pharmacological Basis of Therapeutics,* 5th ed.; MacMillan: New York, 1975, pp. 201-226.

Fatty acid statin conjugates or fatty acid FXR agonist conjugates can be administered in a single daily dose, or the total daily dosage can be administered in divided doses of two, three or four times daily. Furthermore, fatty acid statin conjugates or fatty acid FXR agonist conjugates can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the fatty acid statin conjugate ranges from about 0.1% to about 15%, w/w or w/v.

Methods of Making

Methods for Making the Fatty Acid Statin Conjugates or Fatty Acid FXR Agonist Conjugates Examples of synthetic pathways useful for making fatty acid statin conjugates of Formula I are set forth in the Examples below and generalized in Schemes 1-10. Fatty acid FXR agonist conjugates of Formula II can also be prepared using the generalized Schemes 1-10 using the appropriate FXR agonists as the carboxylic acid components.

Scheme 1

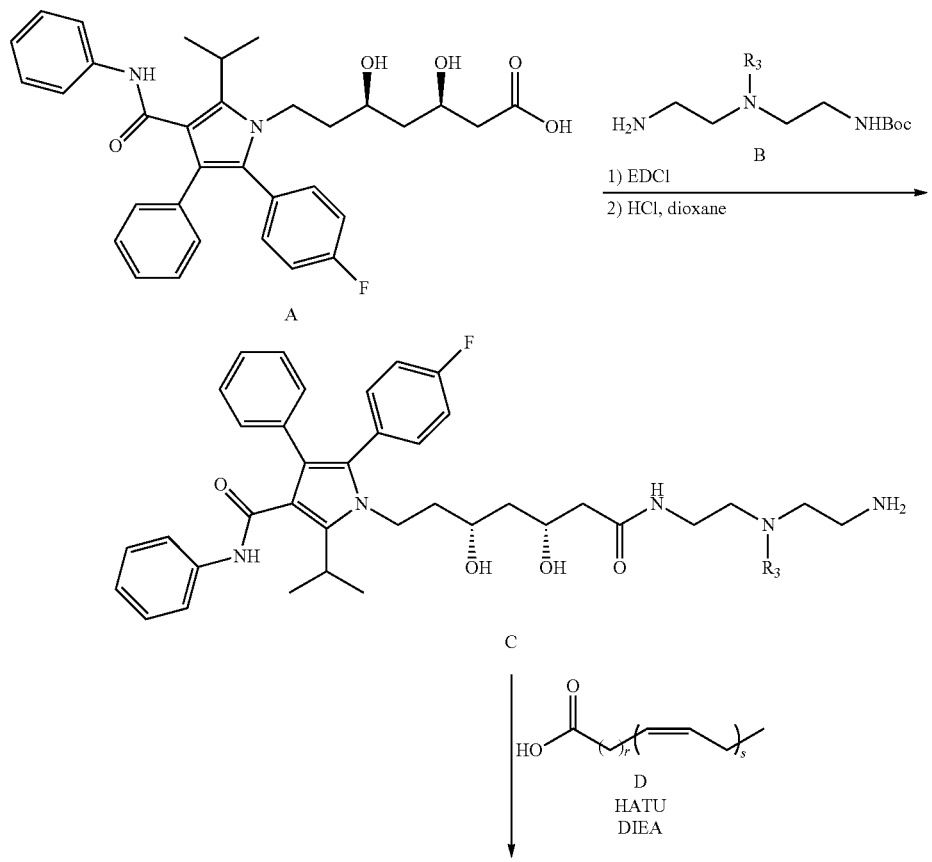

wherein R$_3$, r, and s are as defined above.

The mono-BOC protected amine of the formula B can be obtained from commercial sources or prepared according to the procedures outlined in Krapcho et al. *Synthetic Commun.* 1990, 20, 2559-2564. The commercially available compound A (or its corresponding sodium salt) can be amidated with the amine B using a coupling reagent such as DCC, CDI, EDC, or optionally with a tertiary amine base and/or catalyst, e.g., DMAP, followed by deprotection of the BOC group with acids such as TFA or HCl in a solvent such as CH$_2$Cl$_2$ or dioxane to produce the coupled compound C. Activation of compound C with a coupling agent such as HATU in the presence of an amine such as DIEA followed by addition of a fatty acid of formula D affords compounds of the formula E. To those familiar in the art, the fatty acid D can also be substituted with lipoic acid in this scheme and in the subsequent schemes. Also, to those familiar in the art, compound A, as shown above, represents atorvastatin. The chemistry shown in this scheme and in subsequent schemes can also be employed using other statins. In addition, compound A can also be substituted with an appropriate FXR agonist. Examples of FXR agonists that can be used instead of compound A are shown below:

Scheme 2

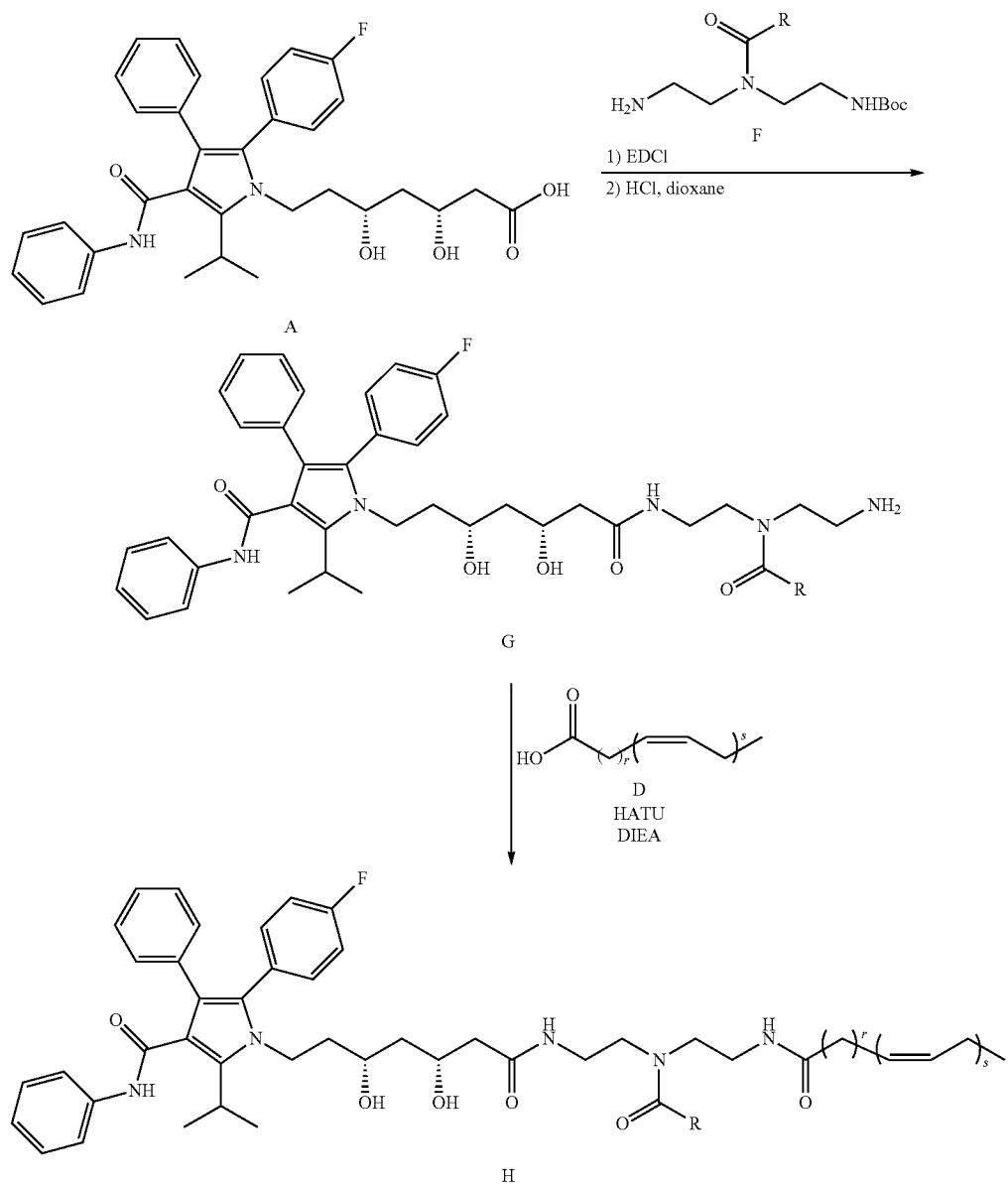

wherein R, r, and s are as defined above.

The acylated amine of the formula F can be prepared using the procedures outlined in Andruszkiewicz et al. *Synthetic Commun.* 2008, 38, 905-913. Compound A can be amidated with the amine F using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound G. Activation of compound G with a coupling agent such as HATU in the presence of an amine such as DIEA followed by addition of a fatty acid of formula D affords compounds of the formula H.

Scheme 3
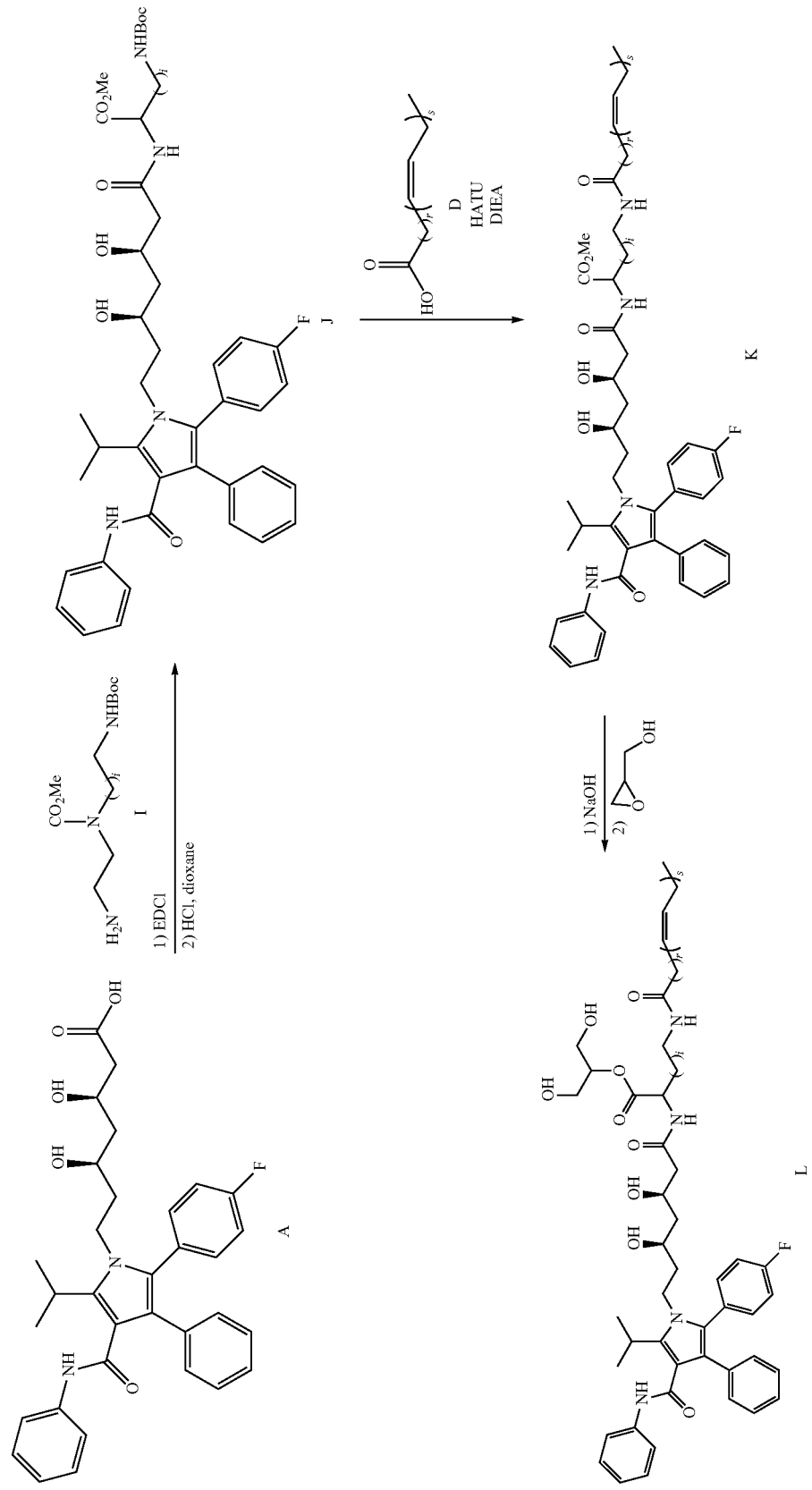

wherein r and s are as defined above.

Compound A can be amidated with the corresponding amine I (where i=0, 1, 2 or 3) using a coupling reagent such as DCC, CDI, EDC, or optionally with a tertiary amine base and/or catalyst, e.g., DMAP, followed by deprotection of the BOC group with acids such as TFA or HCl in a solvent such as CH$_2$Cl$_2$ or dioxane to produce the coupled compound J.

Activation of compound J with a coupling agent such as HATU in the presence of an amine such as DIEA followed by addition of a fatty acid of formula D affords compounds of the formula K. Hydrolysis of the ester under basic conditions such as NaOH or LiOH produces the corresponding acid, which can be coupled with glycidol to afford compounds of the formula L.

Scheme 4

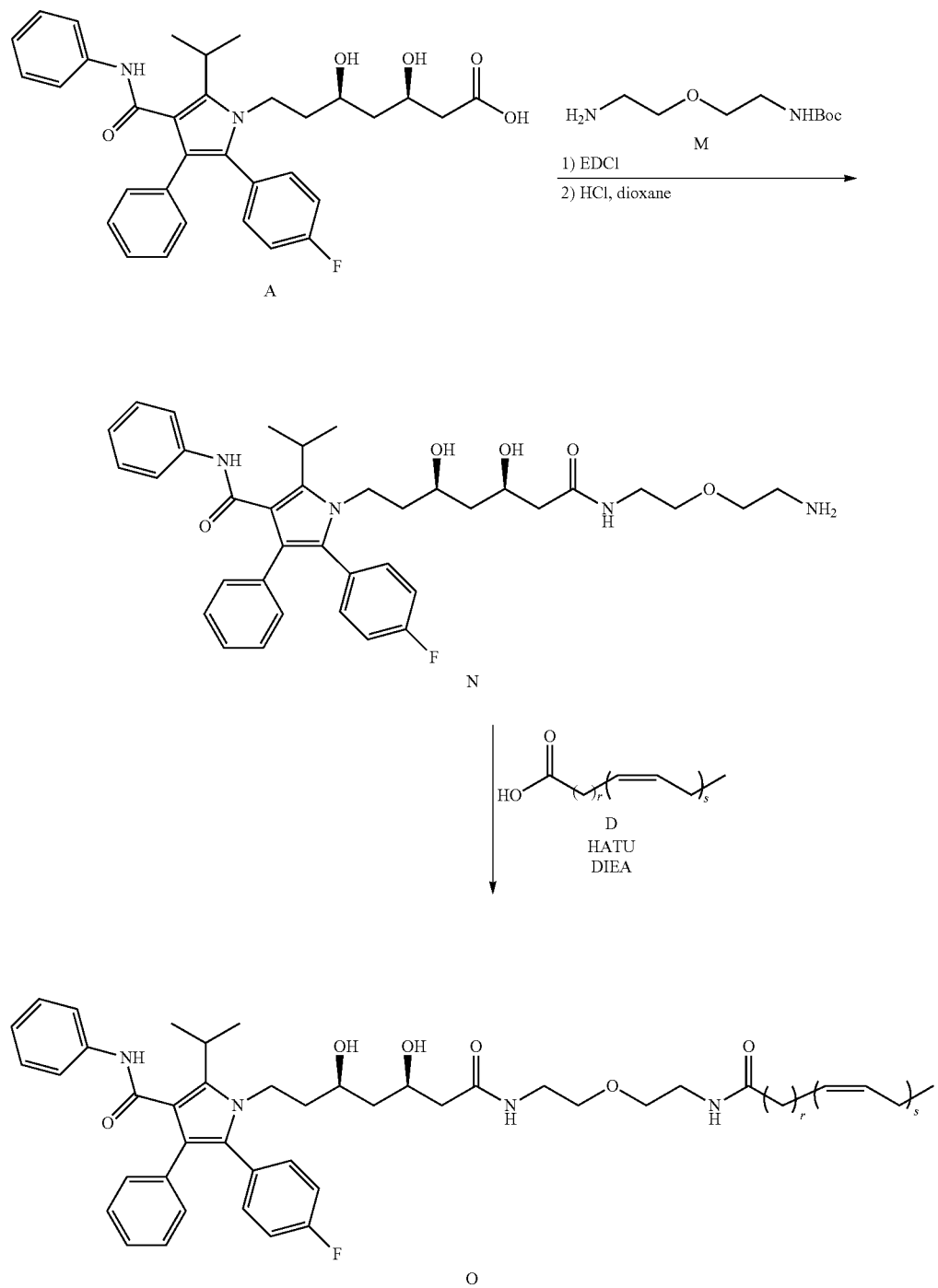

wherein r and s are as defined above.

The amine M can be prepared according to the procedures outlined in Dahan et al. *J. Org. Chem.* 2007, 72, 2289-2296. Compound A can be coupled with the amine M using a coupling reagent such as DCC, CDI, EDC, or optionally with a tertiary amine base and/or catalyst, e.g., DMAP, followed by deprotection of the BOC group with acids such as TFA or HCl in a solvent such as $CH_2Cl_2$ or dioxane to produce the coupled compound N. Activation of compound N with a coupling agent such as HATU in the presence of an amine such as DIEA followed by addition of a fatty acid of formula D affords compounds of the formula O.

Scheme 5

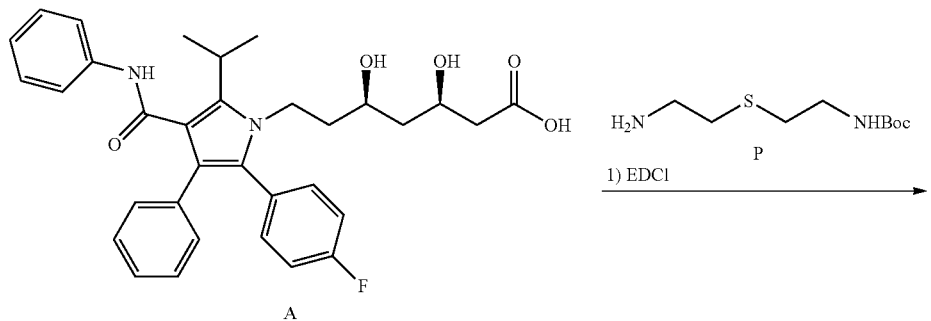

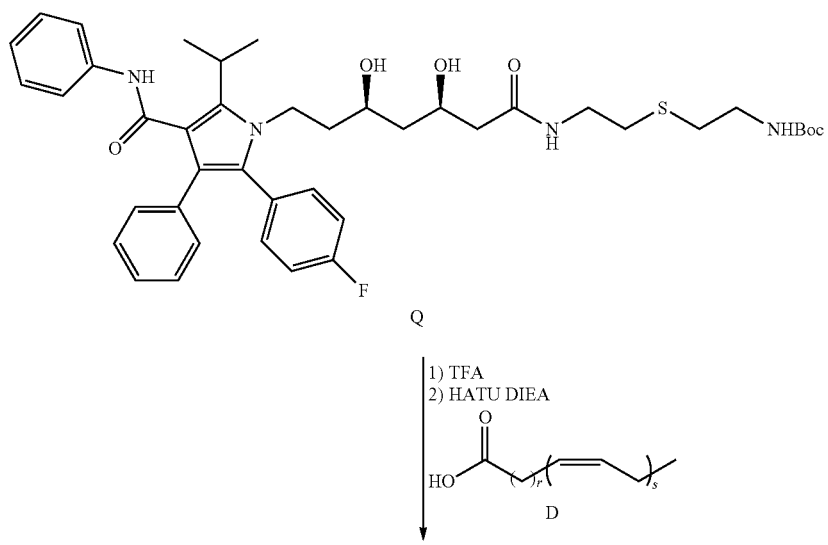

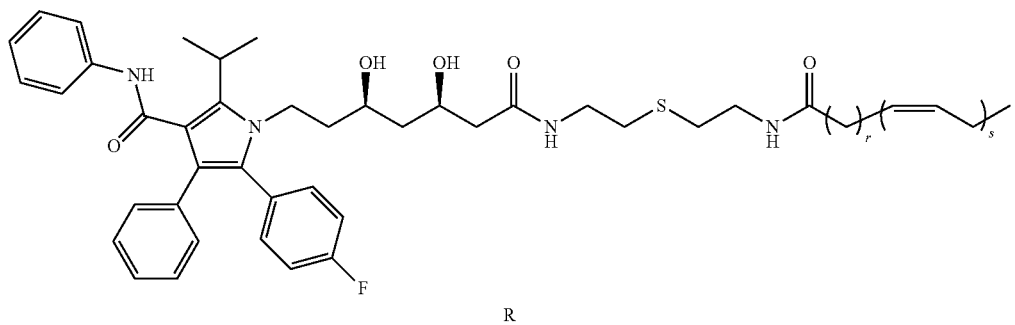

wherein r and s are as defined above.

Compound A can be amidated with the commercially available amine P using a coupling reagent such as DCC, CDI, EDC, or optionally with a tertiary amine base and/or catalyst, e.g., DMAP, to afford compound Q. The BOC group in compound Q can be removed with acids such as TFA or HCl in a solvent such as CH$_2$Cl$_2$ or dioxane and the resulting amine can be coupled with a fatty acid of formula D using a coupling agent such as HATU in the presence of an amine such as DIEA to afford compounds of the formula R. To those skilled in the art, the sulfur group in formula Q can be oxidized to the corresponding sulfoxide or sulfone using an oxidizing agent such as H$_2$O$_2$ or oxone.

Scheme 6

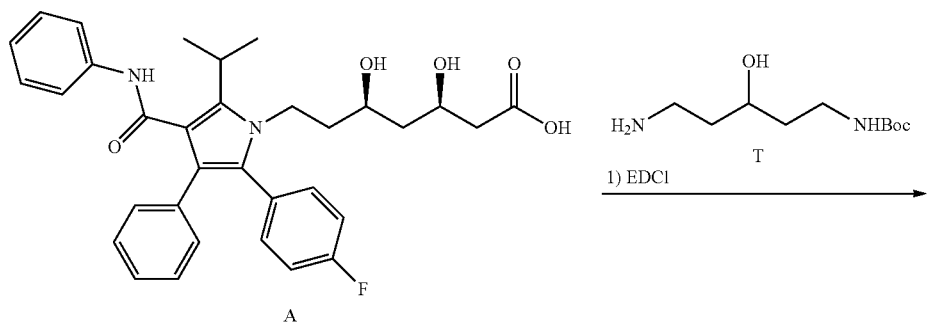

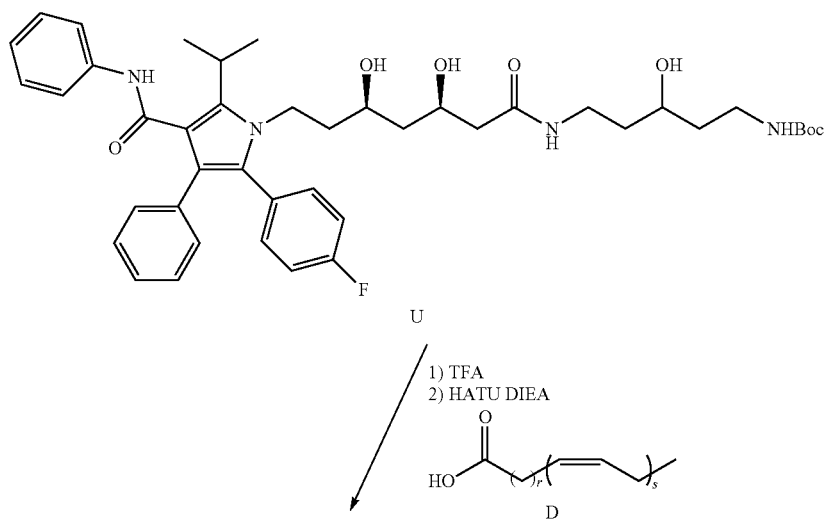

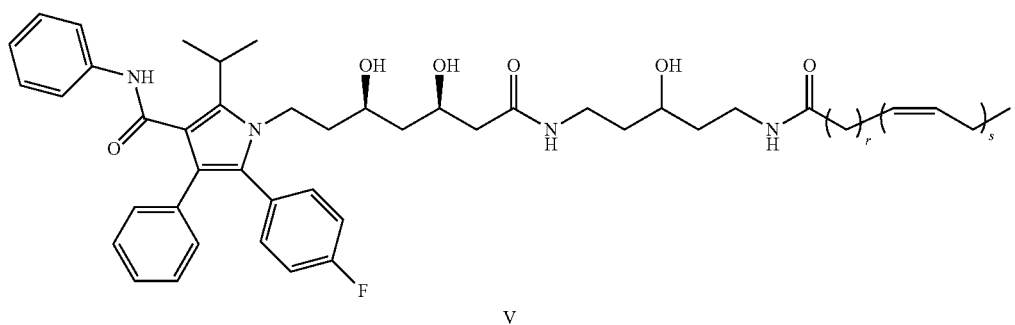

wherein R$_3$, r, and s are as defined above.

The amine T can be prepared from the commercially available diamine according to the procedures outlined in Dahan et al. *J. Org. Chem.* 2007, 72, 2289-2296. Compound A can be amidated with the amine T using a coupling reagent such as DCC, CDI, EDC, or optionally with a tertiary amine base and/or catalyst, e.g., DMAP, to afford compound U. The BOC group of compound U can be removed with acids such as TFA or HCl in a solvent such as $CH_2Cl_2$ or dioxane and the resulting amine can be coupled with a fatty acid of formula D using HATU in the presence of an amine such as DIEA to afford compounds of the formula V.

Scheme 7

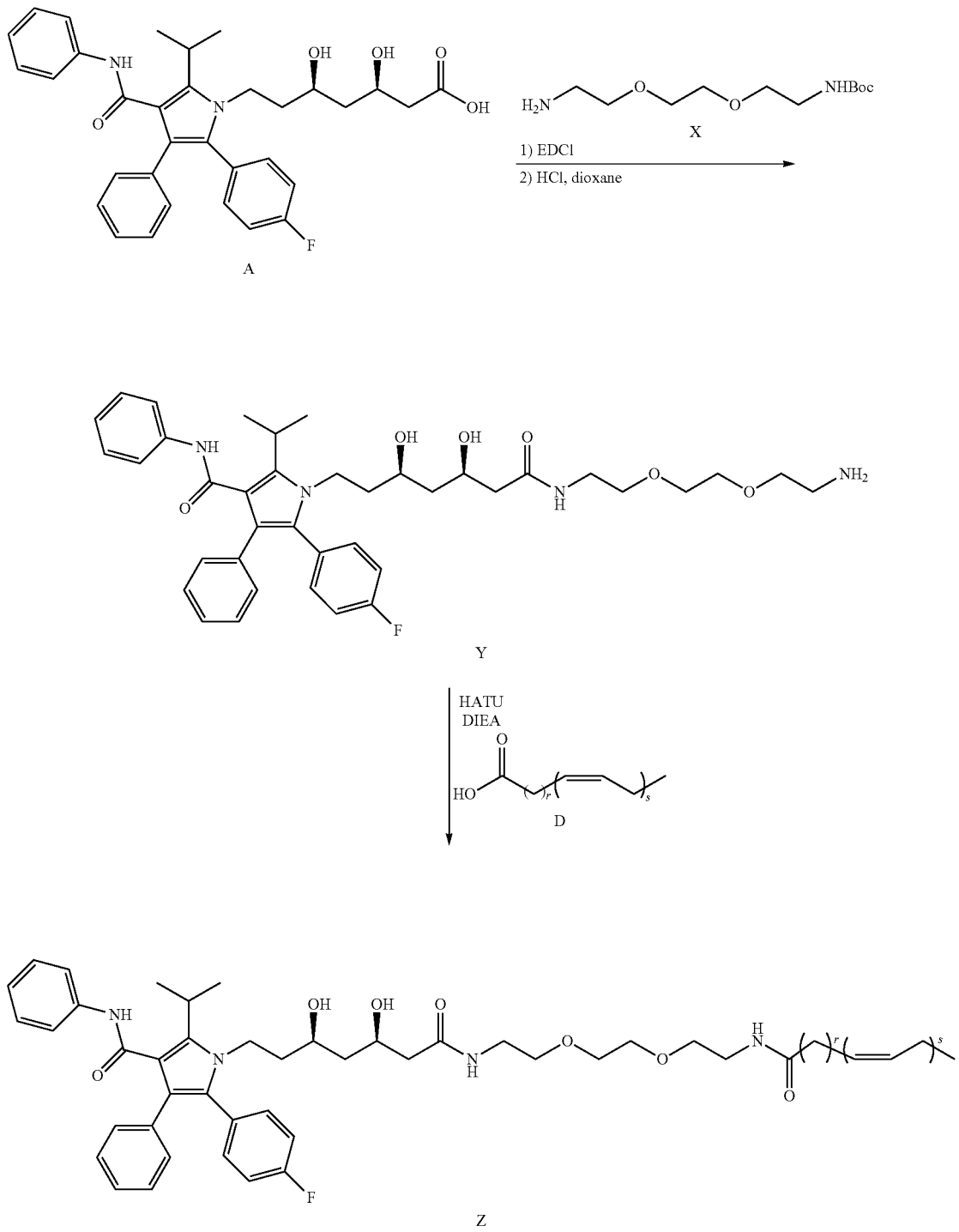

wherein r and s are as defined above.

Compound A can be amidated with the commercially available amine X using a coupling reagent such as DCC, CDI, EDC, optionally with a tertiary amine base and/or catalyst, e.g., DMAP to afford compound Y. The BOC group in compound Y can be removed with acids such as TFA or HCl in a solvent such as $CH_2Cl_2$ or dioxane. The resulting amine can be coupled with a fatty acid of the formula D using a coupling agent such as HATU in the presence of an amine such as DIEA to afford compounds of the formula Z.

Scheme 8

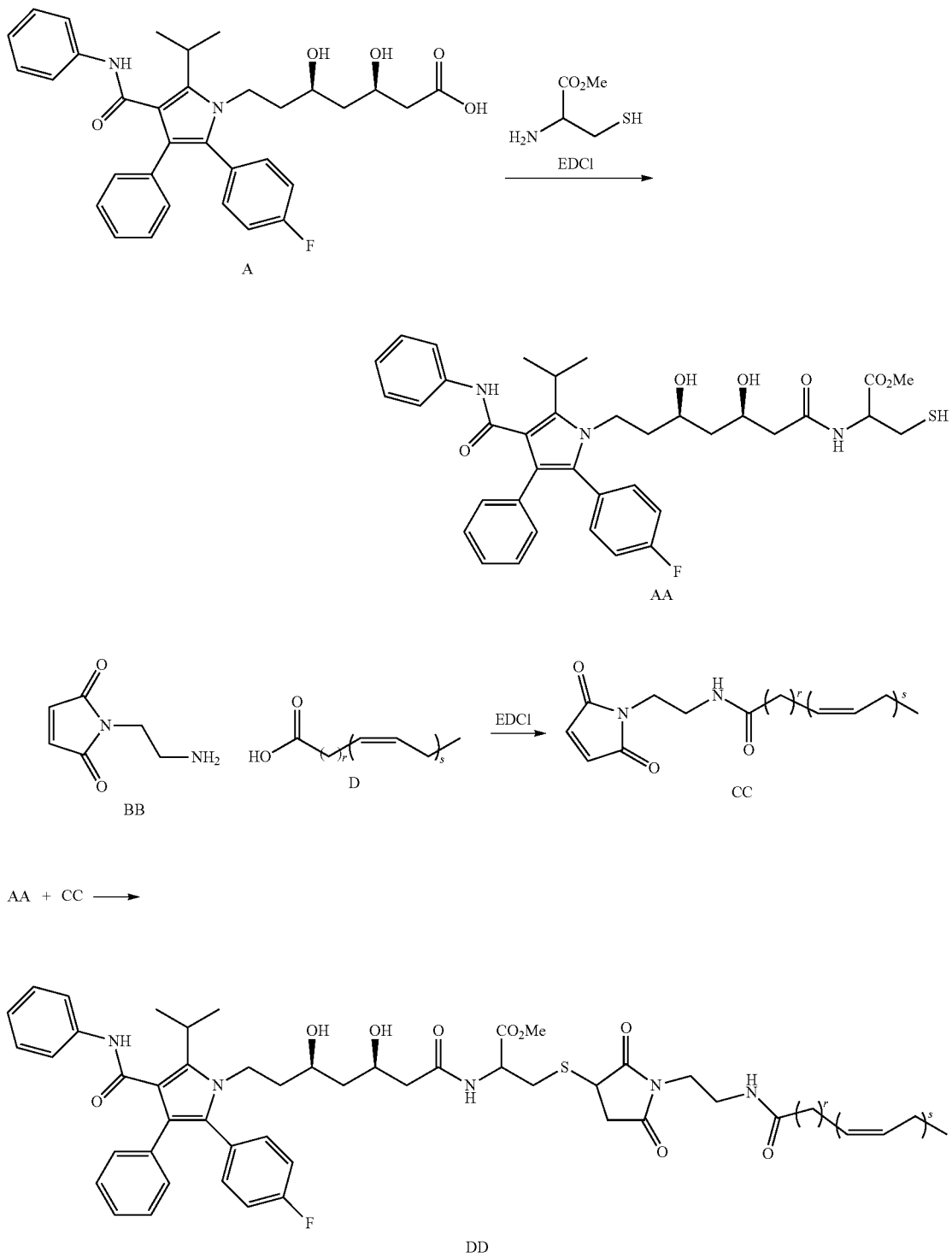

wherein r and s are as defined above.

Compound A can be amidated with the commercially available cysteine methyl ester using a coupling reagent such as DCC, CDI, EDC, or optionally with a tertiary amine base and/or catalyst, e.g., DMAP, to afford compound AA. The commercially available maleimide conjugate BB can be coupled with a fatty acid of the formula D using a coupling agent such as HATU or EDCI to afford compounds of the formula CC. Compound AA can be coupled to compounds of the formula CC in a solvent such as acetonitrile to afford compounds of the formula DD.

Scheme 9

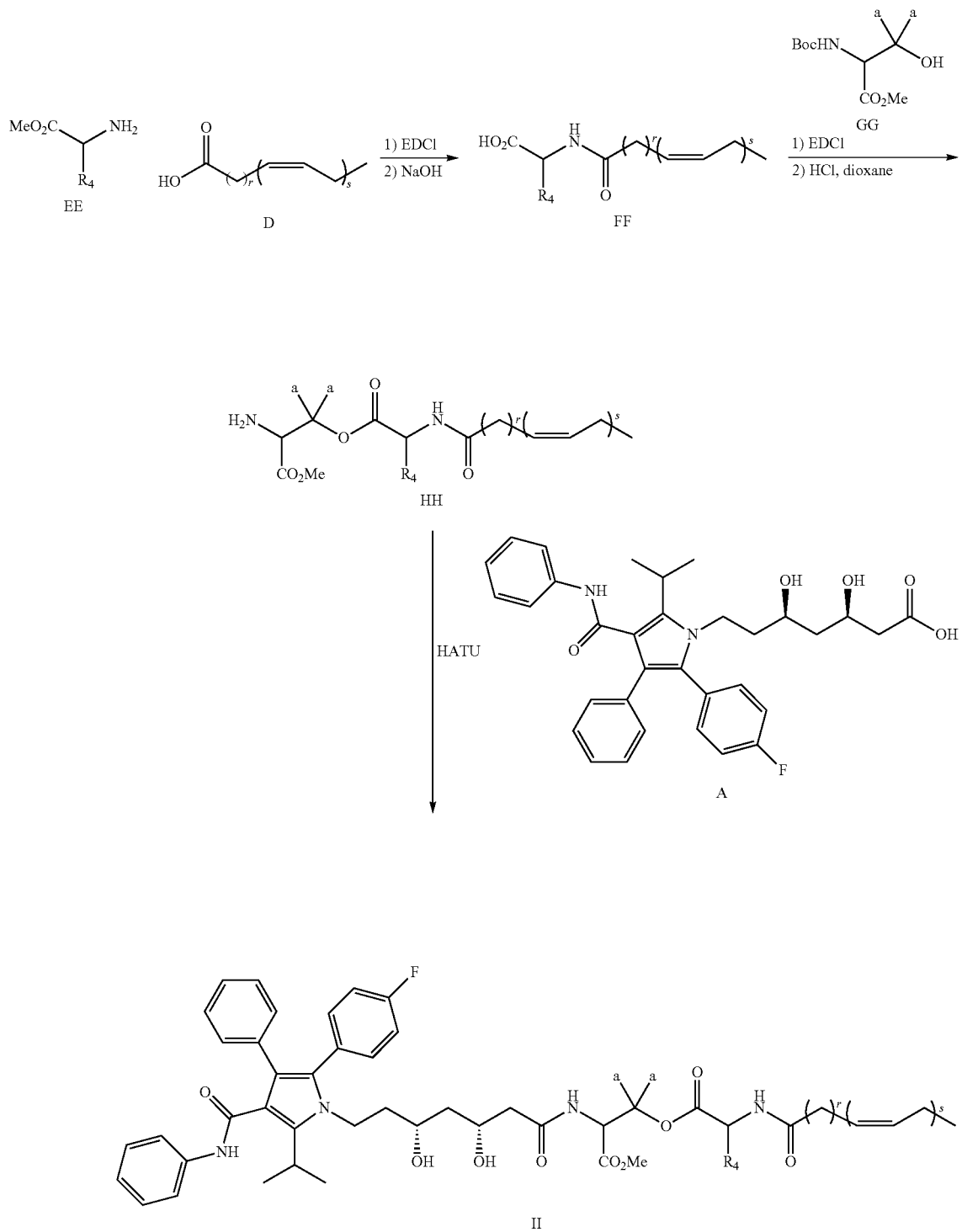

wherein $R_4$, a, r, and s are as defined above.

The commercially available amino acid esters EE can be coupled with a fatty acid of the formula D using a coupling agent such as EDCI or HATU, followed by alkaline hydrolysis of the methyl ester to afford compounds of the formula FF. Compounds of the formula FF can be coupled with the commercially available BOC-amino acid derivatives GG using a coupling agent such as EDCI or HATU. The BOC group can be removed by treatment with acids such as TFA or HCl to afford compounds of the formula HH which can then be coupled with compound A to afford compounds of the formula II.

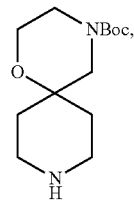

DA1

Scheme 10

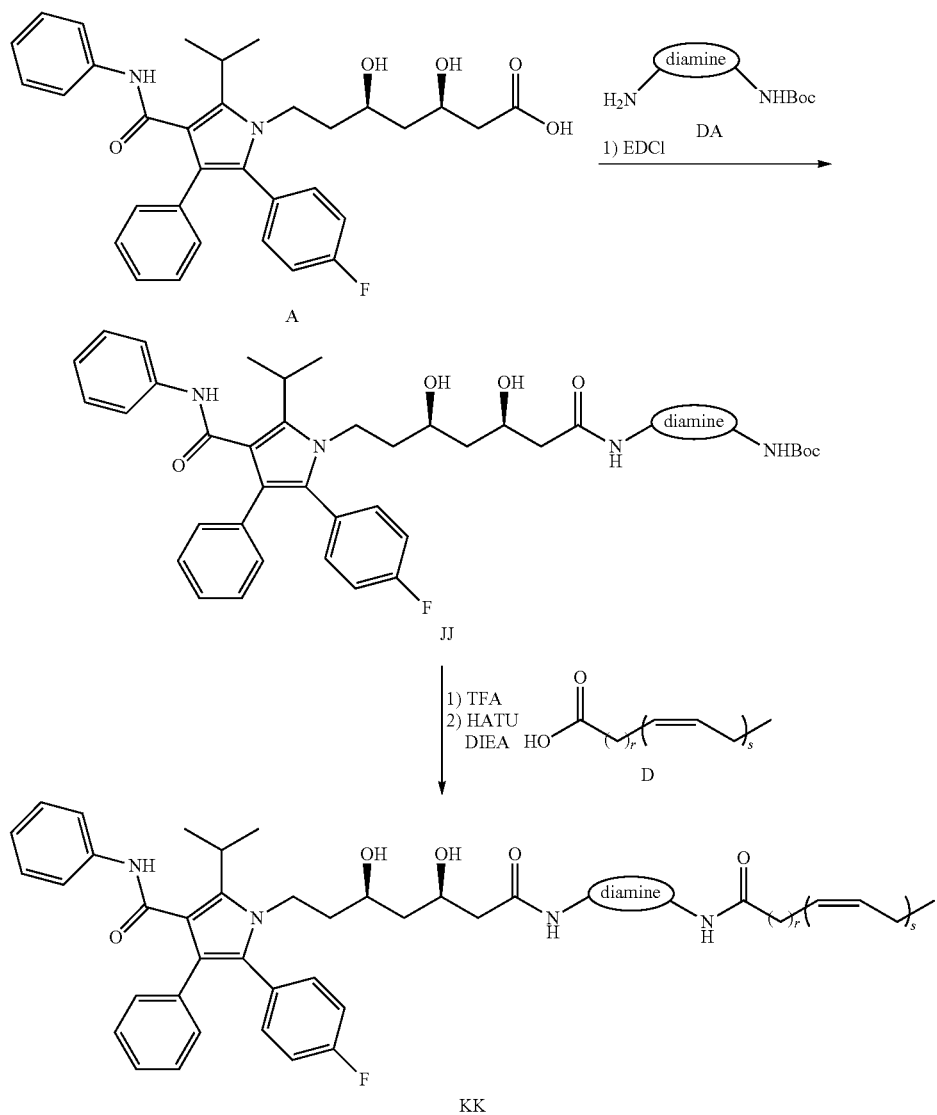

A fatty acid of formula A can be coupled with a BOC-protected diamine of the general formula DA to obtain the BOC-protected amide derivative. After treatment with HCl in dioxane, the resulting amine can be coupled with a fatty acid of the formula D in order to obtain compounds of the formula KK. A variety of BOC-protected diamines are commercially available. The following diamines can be prepared according to the procedures outlined in the corresponding references:

-continued

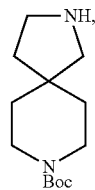

DA2

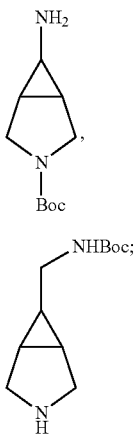

diamine DA1, Stocks et al, *Bioorganic and Medicinal Chemistry Letters* 2010, p. 7458; diamine DA2, Fritch et al, *Bioorganic and Medicinal Chemistry Letters* 2010, p. 6375; diamine DA3 and DA4, Moffat et al, *J. Med. Chem.* 2010, 53, p. 8663-8678). To those familiar in the art, detailed procedures to prepare a variety of mono-protected diamines can also be found in the following references: WO 2004092172, WO 2004092171, and WO 2004092173.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

TNFα Release Assay in RAW 264.7 Macrophages

The purpose of this assay is to measure the ability of small molecules to inhibit the secretion of TNFα in cultured macrophages stimulated with lipopolysaccharide (LPS). Treatment of macrophages with LPS activates inflammatory cytokine pathways primarily through the TLR4-NF-κB signaling axis. Fatty Acid Statin Conjugates inhibit the transcriptional activation of NF-κB and thus decrease the production and release of TNFα. Dexamethasone, a potent agonist of the glucocorticoid receptor is used a positive control for inhibition of TNFα release.

Day 1: Seed RAW 264.7 macrophages into 96 well culture plates. Remove culture media from RAW 264.7 cell growing in a 75 $mm^2$ tissue culture flask (cells should be at ~70% confluence) and add 10 ml of warmed complete growth media (DMEM+10% FBS+1X pen/step). The cells are scraped into suspension using a sterile plate scraper and homogenized by pipetting up and down with a 10 ml serological pipette. The cell concentration is determined using a clinical hematoctyometer. Cells are then diluted to 150,000 cells per ml into growth media. The diluted cells are then transferred to a sterile reagent reservoir and 100 μl of cell suspension is pipetted into each well of a 96 well culture plate using a multichannel pipette (15,000 cells/well). Plates are then incubated at 37° C. under normal tissue culture growth conditions (37° C., humidified $CO_2$ chamber).

Day 2: The test compound sample plate is prepared. Test compounds are prepared in growth media. Compounds are delivered to media from 1000× stocks in 100% DMSO (e.g. for a 10 μM final concentration of test compound, deliver 2 μl of 10 mM test compound to 2 ml of media). At least 150 μl of 1× compound in media is added to 96 well sample plate. Note: the perimeter wells of the 96 well plate are not used to avoid edge effects. Twelve sample wells are prepared with media plus 0.1% DMSO (these samples will serve as the vehicle controls; LPS-stimulated and non-stimulated. 10 μM dexamethasone is used as a positive control). Culture plates are then returned to the growth incubator for 2 hours. Cells are stimulated afterwards by adding 25 μl of 50 ng/ml LPS is added to every well (except the 6 unstimulated vehicle control wells: final concentration of 10 ng/ml LPS. Plates are returned to growth incubator for 3 hours. Afterwards, 100 μl of media supernatant is removed and transferred to a 96 well v-bottom sample plate. The media supernatant plate is centrifuged for 5 minutes at 1000 rpm in a swing-bucket centrifuge, pelleting any cellular debris that may remain in supernatant. 80 μl of supernatant is removed from sample plate and transferred to a fresh v-bottom 96 well plate. Cell viability is measured using Celltiter-glo kit. By measuring cell viability, a given compound's effects on TNFα secretion can show whether such effects are due to cytotoxicity or to inhibition of inflammatory signaling. 100 μl of Celltiter-glo reagent are added to each well of the cell culture plate and afterwards measure the luminescence signal (CPS) of the plate is measured using the Victor 5 plate reader (0.3 second read; 60 second plate shaking prior to read). Cell viability of a given compound at a given concentration is computed as follows:

Cell viability=CPS Sample/(Average CPS unstimulated controls)*100

Mouse TNFα ELISA

Place 20 μl of media supernatant in each well for TNFα ELISA. Follow Invitrogen/Biosource manufacture's protocol for the mouse TNFα ELISA. Chromogen development is typically conducted for 20-30 minutes as described in the manufacturer's protocol. After addition of stop solution, OD 450 nm is measured using the Victor 5 plate reader (0.1 second/well scan). The TNFα secretion percent of control is then determined by using the formula:

100×(OD 450 nm Sample *X*)−(Average OD 450 nm unstimulated vehicle controls)(Average OD 450 nm LPS stimulated vehicle controls)−(Average OD 450 nm unstimulated vehicle controls)

For each test compound, TNFα secretion percent of control is plotted as a function of compound concentration using a four parameter dose-response curve fit equation (XLFIT Model #205):

fit=(*A*+((*B*−*A*)/(1+((*C*/*x*)^*D*))))

inv=(*C*/((((*B*−*A*)/(*y*−*A*))−1)^(1/*D*)))

res=(*y*−fit)

Example 2

Effects of the Fatty Acid Statin Conjugates on NFκB Levels in RAW 264.7 Macrophages RAW 264.7 cells transfected with an NFκB-driven luciferase reporter are plated in 96 well plates. Cells are treated with Vehicle (0.1% ethanol) or test compounds for 2 hours. As a positive control for inhibition of NFκB signaling, 6 wells are treated with 10 μM dexamethasone. Cells are then challenged with 200 ng/mL LPS for 3 hours in the presence of test compounds. A subset of wells treated with vehicle should remain unstimulated with LPS to determine the floor signal of the assay. NFκB driven luciferase activity is developed by addition of BriteLite luciferase kit (Perkin-Elmer) and measured using a Victor V plate reader. NFκB activity (luciferase activity) for each treatment was normalized to Vehicle wells treated with LPS (% NFκB Response). AlamarBlue was used to monitor cell viability to ensure that inhibition of luciferase signal was not a result of compound cytotoxicity.

Example 3

Effects of Compounds of the Invention on the Sterol Biosynthesis in the Rat Hepatocytes Assay A protocol similar to the one outlined in WO 2007/042910 can be used to examine the effects of the fatty acid statin conjugates on the sterol biosynthesis in the rat hepatocytes. Frozen rat hepatocytes can be seeded onto 6-well collagen I coated plates at a density of $10^5$ cells/per well. The cells are grown in Dulbecco's Modified Eagle Medium (DMEM) containing 10% Fetal Bovine Serum (FBS) and 10 mM HEPES (N-2-hydroxyethyl-piperazine-$N^1$-2-ethane sulfonic acid) for 24 hrs. The cells can be pre-incubated with the compounds of the invention for 4 hrs and then labeled by incubating in medium containing 1 uCi/per mL of $^{14}C$ acetic acid for an additional 4 hrs. After labeling, the cells are washed twice with 5 mM MOPS (3-[N-morpholino]propane sulfonic acid) solution containing 150 mM NaCL and 1 mM EDTA and collected in the lysis buffer containing 10% KOH and 80% (vol.) ethanol. The cell lysates are then subjected to saponification at 60° C. for 2 hrs in order to separate labeled cholesterol from labeled non-cholesterol lipids. The lysates are then combined with 0.5 volume of $H_2O$ and 2 volumes of hexane, followed by 30 minutes of vigorous shaking After the separation of the two phases, the upper phase solution is collected and combined with 5 volumes of scintillation cocktail. The amount of $^{14}C$ cholesterol can be quantified by liquid scintillation counting and the appropriate IC50 can be calculated with GraphPad software.

Example 4

Effect of the Compounds of the Invention in the PCSK9 Assay

Cell Culture

HepG2 cells (from ATCC, Catalog no. HB-8065) were maintained in DMEM (Invitrogen) supplemented with 10% fetal bovine serum (Invitrogen). The day prior to the PCSK9 assay, cells were seeded in 96-well collagen coated plates at 25,000 cells/well.

Compound Preparation

The compounds of the invention were stored at −20° C. until used. The test article compound was dissolved in 100% ethanol to a 50 mM stock solution. This was then diluted in FBS to a final concentration of 1 mM. This solution was placed in a sonicating water bath for 30 minutes. Subsequent dilutions were then made in FBS supplemented with an equivalent volume of ethanol and mixed by vortexing.

PCSK9 Secretion Assay

HepG2 cells were seeded onto a collagen coated 96-well plate (Becton Dickinson, Catalog no. 35-4407) the day prior to the assay, as described above. The next day, the cell medium was removed, washed once with 1004 serum free DMEM to remove any residual PCSK9, and replaced with 904 of serum free DMEM. Ten microliters of each compound concentration prepared in FBS was then added. Each concentration of compound was tested in triplicate. The compound was incubated with the cells overnight for 16 hours. Following this incubation, 104 of AlamarBlue was added to each well and cells incubated for another 2 hours. The plates were then removed and AlamarBlue fluorescence was measured (excitation, 550 nm and excitation, 590 nm) to assess cell viability. Cell culture supernatant was then diluted 1:5 in 1:5 in 1× RD5P Calibrator Diluent and PCSK9 ELISA was then performed with 504 of this diluted sample, as per the manufacturer's instructions. The ELISA was measured on a Victor X5 multilabel plate reader (PerkinElmer) at an absorbance of 450 nm with background correction measured at 550 nm (The PCSK9 Elisa kits can be purchased from R&D System, Catalog no. DPC900).

FIG. 1 shows the PCSK9 data in this HepG2 assay when compounds I-1, compound I-22 and atorvastatin were evaluated at the indicated concentrations. Compared to the control, when atorvastatin was evaluated at 1.25, 2.5, 5.0 and 10.0 μM, there was a significant increase in the level of PCSK9 secretion from HepG2 cells. With the fatty acid atorvastatin conjugate 1-22, there was no significant change in the level of PCSK9 that was secreted from HepG2 cells at the two tested concentrations (6.25 and 25 μM). With the fatty acid simvastatin conjugate I-1, there was no significant change in the level of PCSK9 that was secreted from HepG2 cells at the 6.25 μM concentration. With compound I-1, at the high concentration of 25 μM, there was a decrease in the level of PCSK9 that was secreted from HepG2 cells.

Figure 2:
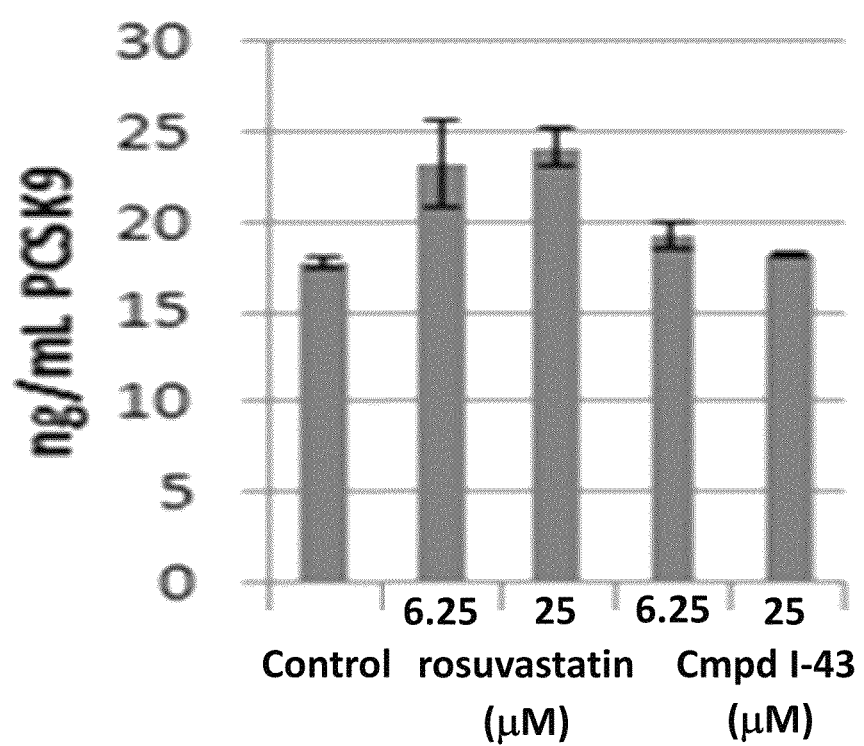
FIG. 2 illustrates PCSK9 secretion levels in HepG2 assay using compound 1-43 and rosuvastatin.

FIG. 2 shows the PCSK9 data in this HepG2 assay when compound 1-43 and rosuvastatin were evaluated at the indicated concentrations. When rosuvastatin was tested at 6.25 and 25 μM in this assay, there was an increase in the level of PCSK9 that was secreted from HepG2 cells. As observed previously with compound 1-22 in FIG. 1, the fatty acid 125612 vl/BN rosuvastatin conjugate 1-43 did not cause an increase in the level of PCSK9 that was secreted from HepG2 cells at the two tested concentrations (6.25 and 25 μM).

Example 5

The Effect of the Compounds of the Invention on Plasma Cholesterol and Other Lipids in ApoE3Leiden Mice The study is conducted using female APOE*3Leiden mice (groups of each n=10) and one untreated reference control group on chow (n=5). To induce dyslipidemia, a high cholesterol Western type diet containing 1% cholesterol, 15% cacao butter, 40.5% sucrose and 1% corn oil (WTD) is fed to the mice for a total experimental period of 20 weeks (of which 4 weeks are a run-in period). To prevent oxidation of the test compound (I-8), 30 mg/kg alpha-tocopherol is added to the high cholesterol diets, i.e. also in the high cholesterol diet control.

In the first 4 weeks (run-in period), a pro-atherogenic state of dyslipidemia characterized by elevated plasma cholesterol levels (about 15-20 mM) is induced in all mice by feeding them an atherogenic diet containing 1% cholesterol. The mice are then separated into a control group (no treatment) and three treatment groups: i) test compound from the invention, ii) atorvastatin and iii) test compound from the invention+ atorvastatin as as described below. The dyslipidemic mice are grouped on the basis of plasma cholesterol at t=0 assayed in 4 h fasting blood. Mice with low cholesterol after the run-in period are excluded so that homogenous experimental groups were obtained. A group of reference mice (n=5) remains on a chow diet during the complete study period (normolipidemic reference mice).

The doses of the test compounds are as follows:
Test compound from the invention: 0.75% w/w in diet.
Atorvastatin: 0.0015% w/w in diet (to achieve about 20% reduction in plasma cholesterol).
Alpha-tocopherol: 0.0030% w/w in diet The test compounds, sufficient for approx. 3 kg of diet (i.e. 25 g of the test compound from the invention), and alpha-tocopherol (>200 mg) are formulated before the start of the treatment period (t=0), by adding the test compounds to melted, hand warm cocoa butter and mixed for 5 min. This mix is then added to the master mix (containing the rest of the ingredients) and mixed thoroughly. The diet is frozen to −20° C. On the subsequent day, the diet is broken into small pellets (approx 5 g per piece) and freeze dried, and stored in vacuum sealed bags (approx 500 g) at −20° C. until use. The diets are refreshed daily and unused diet is discarded.

The following parameters are taken at the indicated time-points (individually unless mentioned otherwise):
1) Body weight at -4, 0, 2, 4 weeks
2) Food intake (g/day/mouse) at 0, 2, 4 weeks (per cage)
3) Plasma total cholesterol at −4, 0, 2, 4 weeks (individually)
4) Plasma triglycerides at −4, 0, 2, 4 weeks (individually)
5) Lipoprotein profiles at 0 (pool of all animals) and 4 weeks (cholesterol distribution over VLDL, LDL and HDL-sized particles, analysis on group level).

EDTA plasma is collected in weeks −4, 0, 2 and 4 weeks. Plasma cholesterol, plasma triglyceride levels and lipoprotein profiles are assayed immediately in fresh plasma using commercially available kits Compounds The following non-limiting compound examples serve to illustrate further embodiments of the fatty acid statin conjugates or fatty acid FXR agonist conjugates. It is to be understood that any embodiments listed in the Examples section are embodiments of the fatty acid statin conjugates or fatty acid FXR agonist conjugates and, as such, are suitable for use in the methods and compositions described above.

Example 6

Preparation of 1-((3R,5R)-7-(2-(4Z,7Z,10Z,13Z,16Z,19Z)-docosa-4,7,10,13,16,19-hexaenamidoethylamino)-3,5-dihydroxy-7-oxoheptyl)-5-(4-fluorophenyl)-2-isopropyl-N,4-diphenyl-1H-pyrrole-3-carboxamide (I-22)

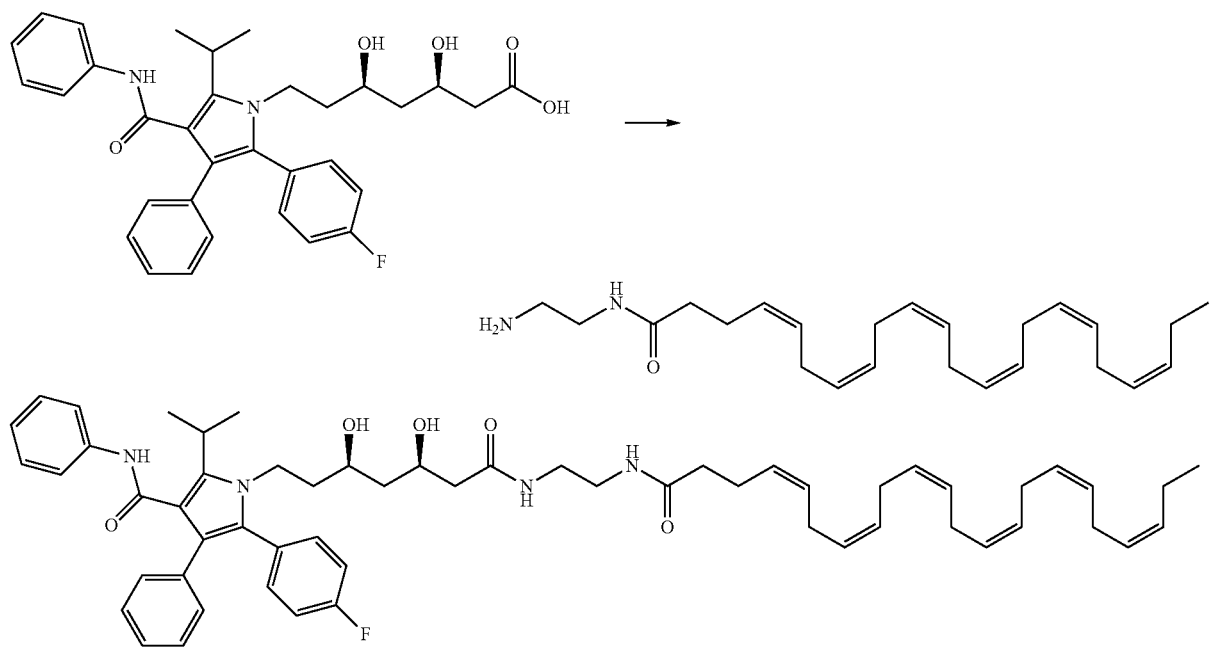

The HCl salt of (4Z,7Z,10Z,13Z,16Z,19Z)—N-(2-aminoethyl)docosa-4,7,10,13,16,19-hexaenamide was prepared according to the procedures outlined in WO 2012115695. This material (2.1 g, 5.17 mmol) was taken up in 100 mL of $CH_2Cl_2$ along with atorvastatin (2.4 g, 4.31 mmol), HATU (2 g, 5.17 mmol) and DIEA (4.5 mL). The resulting reaction mixture was stirred at room temperature for 18 h. It was then diluted with $CH_2Cl_2$ and washed with saturated aqueous $NH_4Cl$ (25 mL) and brine (50 mL). The organic layer was dried ($Na_2SO_4$) and concentrated under reduced pressure. The resulting residue was purified by silica gel chromatography (95% $CH_2Cl_2$, 5% MeOH) to afford 1-((3R,5R)-7-(2-(4Z,7Z,10Z,13Z,16Z,19Z)-docosa-4,7,10,13,16,19-hexaenamidoethylamino)-3,5-dihydroxy-7-oxoheptyl)-5-(4-fluorophenyl)-2-isopropyl-N,4-diphenyl-1H-pyrrole-3-carboxamide. MS calculated for $C_{57}H_{71}FN_4O_5$: 910.54. found: $[M+H]^+$ 911.

Example 7

Preparation of 1-((3R,5R)-3,5-dihydroxy-7-(2-(5Z,8Z,11Z,14Z,17Z)-icosa-5,8,11,14,17-pentaenamido-ethylamino)-7-oxoheptyl)-5-(4-fluorophenyl)-2-isopropyl-N,4-diphenyl-1H-pyrrole-3-carboxamide (I-23)

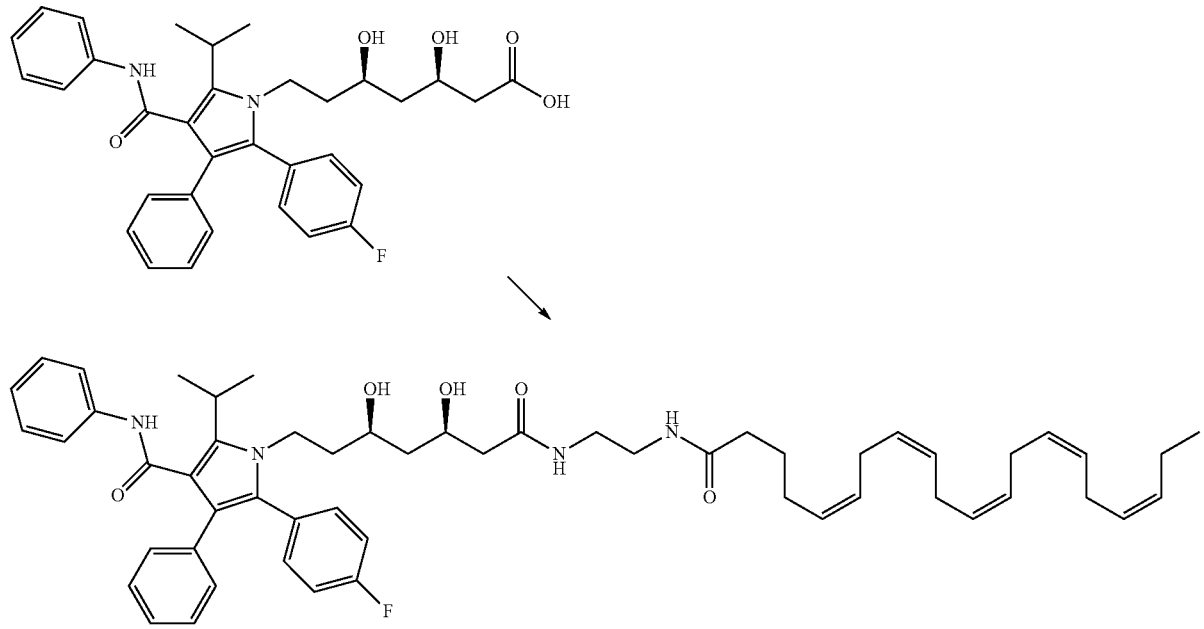

The same procedures outlined in example 6 were employed, substituting (5Z,8Z,11Z,14Z,17Z)—N-(2-aminoethyl)icosa-5,8,11,14,17-pentaenamide as the appropriate amine component during the amide coupling with atorvastatin. (5Z,8Z,11Z,14Z,17Z)—N-(2-aminoethyl)icosa-5,8,11,14,17-pentaenamide, in turn, was prepared according to the procedures outlined in WO 2012115695 using (5Z,8Z,11Z,14Z,17Z)-eicosa-5,8,11,14,17-pentaenoic acid as the starting material. MS calculated for $C_{55}H_{69}FN_4O_5$: 884.53. found: [M+H]$^+$ 885.

Example 8

Preparation of 1-((3R,5R)-3,5-dihydroxy-7-((2-oleamidoethyl)amino)-7-oxoheptyl)-5-(4-fluorophenyl)-2-isopropyl-N,4-diphenyl-1H-pyrrole-3-carboxamide (I-24)

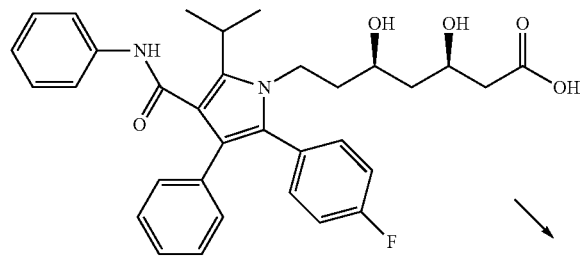

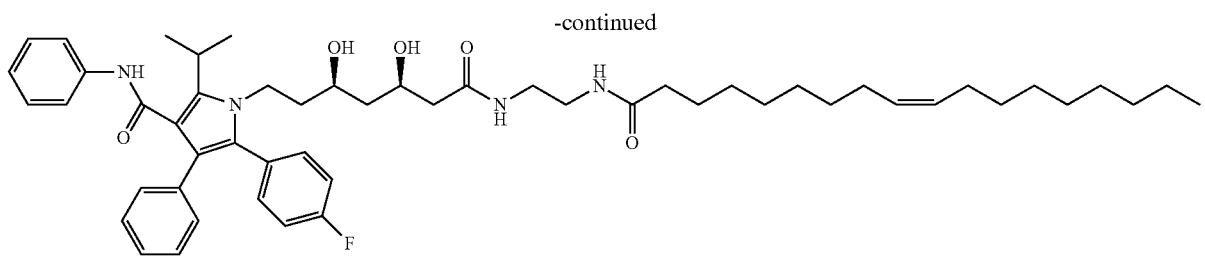

1-((3R,5R)-3,5-dihydroxy-7-((2-oleamidoethyl)amino)-7-oxoheptyl)-5-(4-fluorophenyl)-2-isopropyl-N,4-diphenyl-1H-pyrrole-3-carboxamide was prepared according to the procedures outlined in examples 6 and 7, substituting oleic acid for the fatty acid component. MS calculated for $C_{53}H_{73}FN_4O_5$: 864.56. found: $[M+H]^+$ 865.

Example 9

Preparation of 1-((3R,5R)-7-(2-(2-(4Z,7Z,10Z,13Z,16Z,19Z)-docosa-4,7,10,13,16,19-hexaenamidoethoxy)ethylamino)-3,5-dihydroxy-7-oxoheptyl)-5-(4-fluorophenyl)-2-isopropyl-N,4-diphenyl-1H-pyrrole-3-carboxamide (I-32)

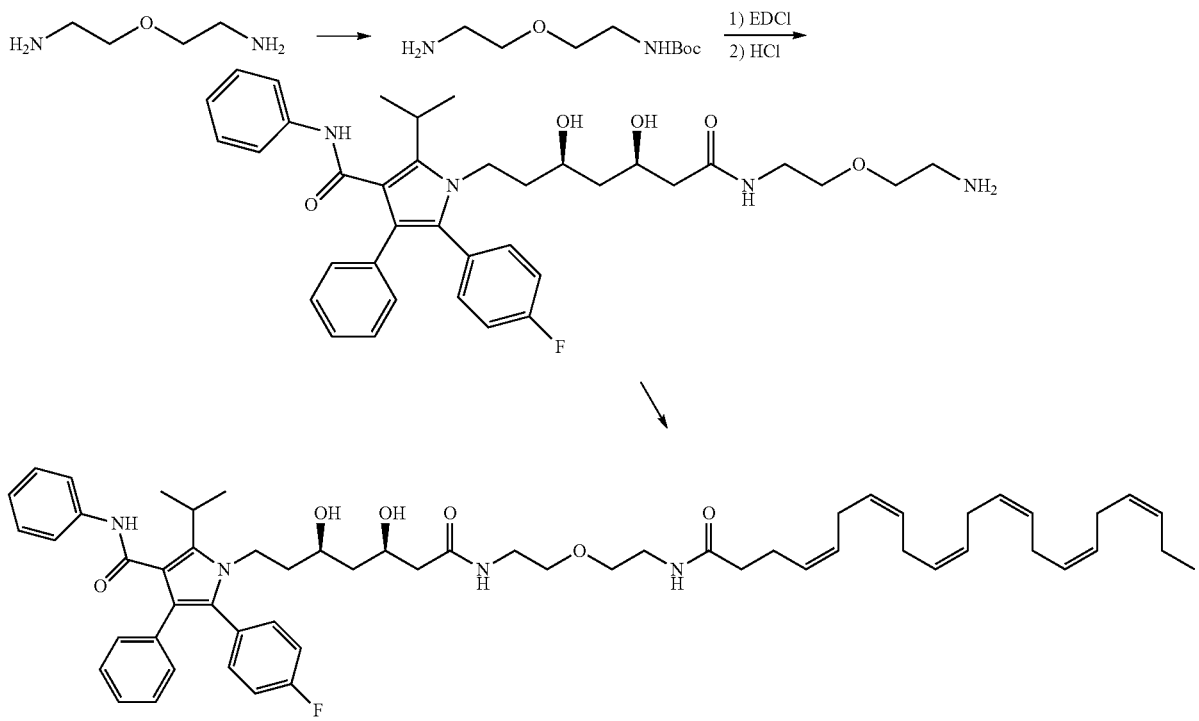

In a typical run, sodium hydroxide (400 mg, 10 mmol) is dissolved in MeOH (70 mL) and 2-(2-aminoethoxyl)ethanamine dihydrochloride (1.0 g, 5.65 mmol) is added. The resulting reaction mixture is stirred at room temperature for 30 min. A solution containing $Boc_2O$ (740 mg, 3.40 mmol) in THF (15 mL) is then added dropwise, at room temperature, over a period of 15 min. The resulting reaction mixture is stirred at room temperature for 18 h and then concentrated under reduced pressure. The resulting residue is taken up in $CH_2Cl_2$ (200 mL) and stirred vigorously at room temperature for 4 h. The mixture is filtered and the filtrate is concentrated under reduced pressure to afford 850 mg of tert-butyl 2-(2-aminoethoxyl)ethylcarbamate (74% yield).

tert-Butyl 2-(2-aminoethoxyl)ethylcarbamate (150 mg, 0.735 mmol) is then taken up in $CH_3CN$ (10 mL) along with the sodium salt of atorvastatin (0.735 mmol) and EDCI (155 mg, 0.81 mmol). The resulting reaction mixture is stirred at room temperature for 18 h. It is then diluted with EtOAc (20 mL), washed with saturated aqueous NaHCO₃, brine, dried over Na₂SO₄, filtered and concentrated under reduced pressure. The resulting residue is purified by silica gel chromatography (9:1 CH₂Cl₂/MeOH) to afford tert-butyl 2-(2-((3R,5R)-7-(2-(4-fluorophenyl)-5-isopropyl-3-phenyl-4-(phenylcarbamoyl)-1H-pyrrol-1-yl)-3,5-dihydroxyheptanamido)ethoxy)ethylcarbamate.

tert-butyl 2-(2-((3R,5R)-7-(2-(4-fluorophenyl)-5-isopropyl-3-phenyl-4-(phenylcarbamoyl)-1H-pyrrol-1-yl)-3,5-dihydroxyheptanamido)ethoxy)ethylcarbamate is taken up in 10 mL of 4 M HCl in dioxane and allowed to stand at room temperature for 2 h. The resulting reaction mixture was concentrated under reduced pressure to afford the HCl salt of 1-((3R,5R)-7-(2-(2-aminoethoxyl)ethylamino)-3,5-dihydroxy-7-oxoheptyl)-5-(4-fluorophenyl)-2-isopropyl-N,4-diphenyl-1H-pyrrole-3-carboxamide. This material is taken up in CH₃CN (10 mL) along with (4Z,7Z,10Z,13Z,16Z,19Z)-docosa-4,7,10,13,16,19-hexaenoic acid (187 mg, 0.57 mmol), HATU (238 mg, 0.63 mmol) and DIEA (300 μL, 1.71 mmol). The resulting reaction mixture is stirred at room temperature for 2 h, diluted with EtOAc and washed successively with saturated aqueous NaHCO₃ and brine. The organic layer is dried over Na₂SO₄, filtered and concentrated under reduced pressure. Purification by silica gel chromatography (5% MeOH—CH₂Cl₂) affords 1-((3R,5R)-7-(2-(2-(4Z,7Z,10Z,13Z,16Z,19Z)-docosa-4,7,10,13,16,19-hexaenamidoethoxy)ethylamino)-3,5-dihydroxy-7-oxoheptyl)-5-(4-fluorophenyl)-2-isopropyl-N,4-diphenyl-1H-pyrrole-3-carboxamide.

Example 10

Preparation of 1-03R,5R)-3,5-dihydroxy-7-((2-((5Z,8Z,11Z,14Z,17Z)—N-methylicosa-5,8,11,14,17-pentaenamido)ethyl)amino)-7-oxoheptyl)-5-(4-fluorophenyl)-2-isopropyl-N,4-diphenyl-1H-pyrrole-3-carboxamide (I-26)

1-((3R,5R)-3,5-Dihydroxy-7-((2-((5Z,8Z,11Z,14Z,17Z)—N-methylicosa-5,8,11,14,17-pentaenamido)ethyl)amino)-7-oxoheptyl)-5-(4-fluorophenyl)-2-isopropyl-N,4-diphenyl-1H-pyrrole-3-carboxamide was prepared according to the procedures outlined in examples 6 and 7 using (5Z,8Z,11Z,14Z,17Z)—N-(2-aminoethyl)-N-methylicosa-5,8,11,14,17-pentaenamide as the appropriate amine component. (5Z,8Z,11Z,14Z,17Z)—N-(2-Aminoethyl)-N-methylicosa-5,8,11,14,17-pentaenamide, in turn, was prepared according to the procedures outlined in WO 2012115695 using tert-butyl (2-(methylamino)ethyl)carbamate and EPA as the appropriate starting materials. MS calculated for C₅₆H₇₁FN₄O₅: 898.54. found: [M+H]⁺ 899.

Example 11

Preparation of 1-((3R,5R)-3,5-dihydroxy-7-((2-(N-methyloleamido)ethyl)amino)-7-oxoheptyl)-5-(4-fluorophenyl)-2-isopropyl-N,4-diphenyl-1H-pyrrole-3-carboxamide (I-27)

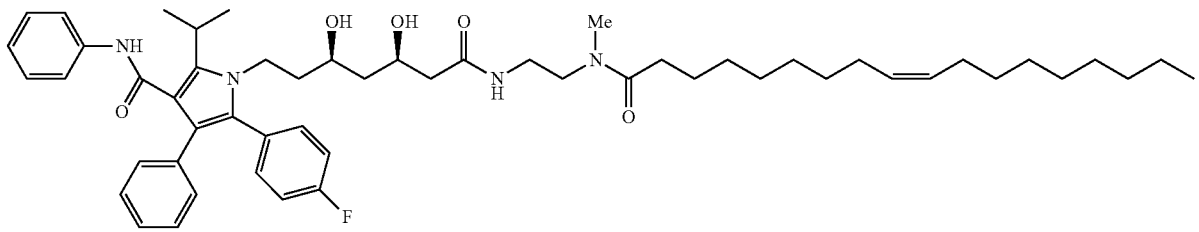

1-((3R,5R)-3,5-Dihydroxy-7-((2-(N-methyloleamido)ethyl)amino)-7-oxoheptyl)-5-(4-fluorophenyl)-2-isopropyl-N,4-diphenyl-1H-pyrrole-3-carboxamide was prepared according to the procedures outlined in examples 6 and 7 using N-(2-aminoethyl)-N-methyloleamide as the appropriate amine component. N-(2-Aminoethyl)-N-methyloleamide, in turn, was prepared according to the procedures outlined in WO 2012115695 using tert-butyl (2-(methylamino)ethyl)carbamate and oleic acid as the appropriate starting materials. MS calculated for C₅₄H₇₅FN₄O₅: 878.57. found: [M+H]⁺ 879.

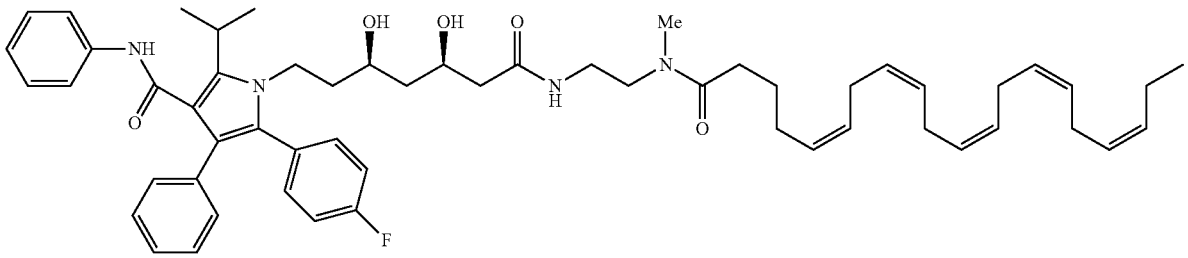 [SMILES: CC/C=C\C/C=C\C/C=C\C/C=C\C/C=C\CCCC(=O)N(C)CCNC(=O)C[C@H](O)C[C@H](O)CCn1c(-c2ccc(F)cc2)c(-c2ccccc2)c(C(=O)Nc2ccccc2)c1C(C)C]

Example 12

Preparation of (5Z,8Z,11Z,14Z,17Z)—N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)icosa-5,8,11,14,17-pentaenamide (I-43)

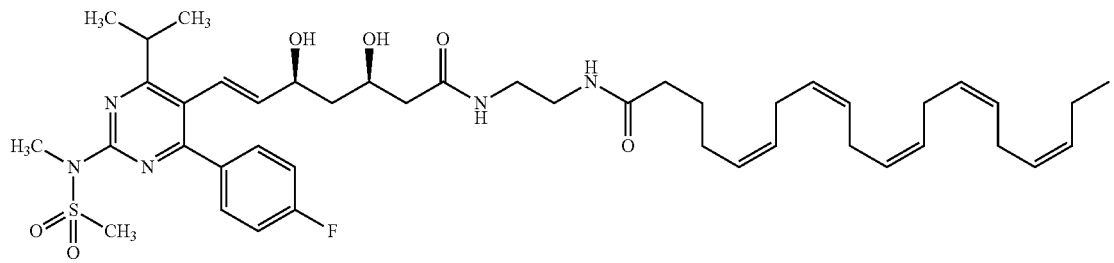 [SMILES: CC/C=C\C/C=C\C/C=C\C/C=C\C/C=C\CCCC(=O)NCCNC(=O)C[C@H](O)C[C@H](O)/C=C/c1c(-c2ccc(F)cc2)nc(N(C)S(C)(=O)=O)nc1C(C)C]

(5Z,8Z,11Z,14Z,17Z)—N-(2-((3R,5S,E)-7-(4-(4-Fluorophenyl)-6-isopropyl-2-(N-methylmethylsulfonamido)pyrimidin-5-yl)-3,5-dihydroxyhept-6-enamido)ethyl)icosa-5,8,11,14,17-pentaenamide was prepared according to the procedures outlined in examples 6 and 7 using rosuvastatin as the appropriate starting material. MS calculated for $C_{44}H_{62}FN_5O_6S$: 807.44. found: $[M+H]^+$ 808.

Example 13

Preparation of (4Z,7Z,10Z,13Z,16Z,19Z)—N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)docosa-4,7,10,13,16,19-hexaenamide (I-44)

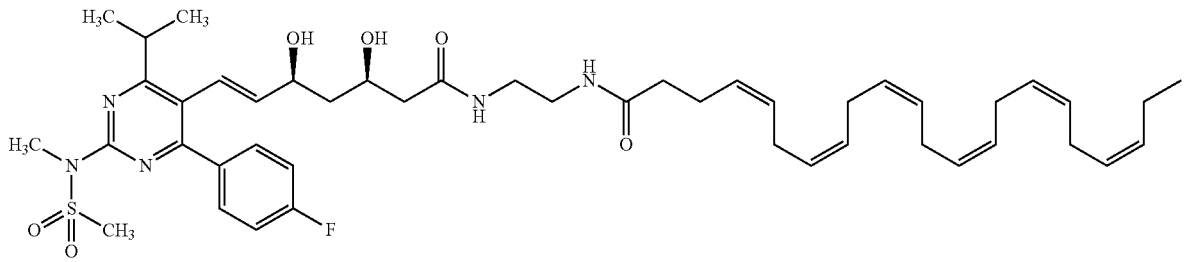 [SMILES: CC/C=C\C/C=C\C/C=C\C/C=C\C/C=C\C/C=C\CCC(=O)NCCNC(=O)C[C@H](O)C[C@H](O)/C=C/c1c(-c2ccc(F)cc2)nc(N(C)S(C)(=O)=O)nc1C(C)C]

(4Z,7Z,10Z,13Z,16Z,19Z)—N-(2-((3R,5S,E)-7-(4-(4-Fluorophenyl)-6-isopropyl-2-(N-methylmethylsulfonamido)pyrimidin-5-yl)-3,5-dihydroxyhept-6-enamido)ethyl)docosa-4,7,10,13,16,19-hexaenamide was prepared according to the procedures outlined in examples 6 and 7 using DHA as the appropriate fatty acid component. MS calculated for $C_{46}H_{64}FN_5O_6S$: 833.46. found: $[M+H]^+$ 834.

Example 14

Preparation of N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)oleamide (I-45)

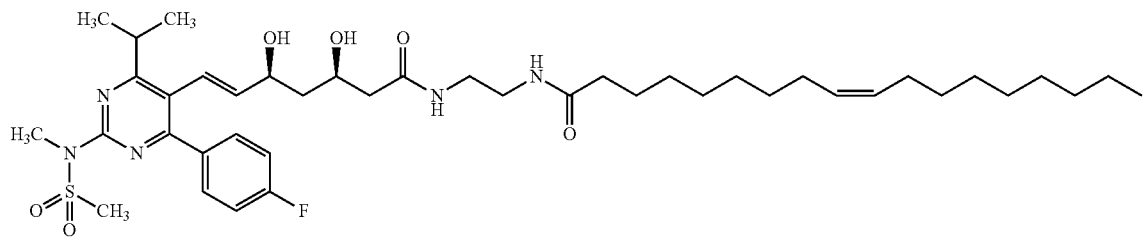 [SMILES: CCCCCCCC/C=C\CCCCCCCC(=O)NCCNC(=O)C[C@H](O)C[C@H](O)/C=C/c1c(-c2ccc(F)cc2)nc(N(C)S(C)(=O)=O)nc1C(C)C]

N-(2-((3R,5S,E)-7-(4-(4-Fluorophenyl)-6-isopropyl-2-(N-methylmethylsulfonamido)pyrimidin-5-yl)-3,5-dihydroxyhept-6-enamido)ethyl)oleamide was prepared according to the procedures outlined in example 13 using oleic acid as the appropriate fatty acid component. MS calculated for $C_{42}H_{66}FN_5O_6S$: 787.47. found: $[M+H]^+$ 788.

Example 15

Preparation of N-(2-((3R,5S,E)-7-(4-(4-fluorophenyl)-6-isopropyl-2-(N-methylmethylsulfonamido)pyrimidin-5-yl)-3,5-dihydroxyhept-6-enamido)ethyl)-N-methyloleamide (I-46)

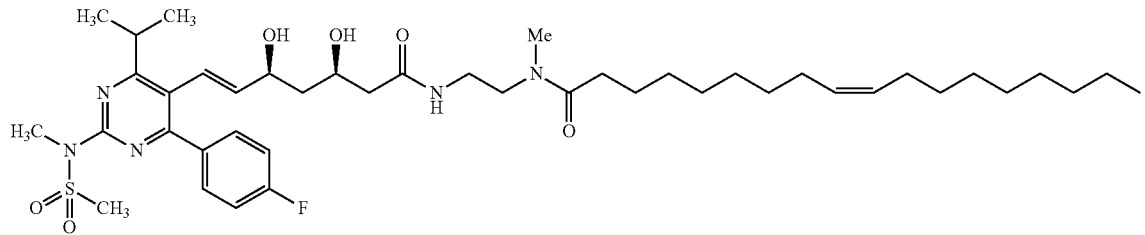 [SMILES: CCCCCCCC/C=C\CCCCCCCC(=O)N(C)CCNC(=O)C[C@H](O)C[C@H](O)/C=C/c1c(-c2ccc(F)cc2)nc(N(C)S(C)(=O)=O)nc1C(C)C]

N-(2-((3R,5S,E)-7-(4-(4-Fluorophenyl)-6-isopropyl-2-(N-methylmethylsulfonamido)pyrimidin-5-yl)-3,5-dihydroxyhept-6-enamido)ethyl)-N-methyloleamide was prepared according to the procedures outlined in example 14 using N-(2-aminoethyl)-N-methyloleamide as the appropriate amine component. MS calculated for $C_{43}H_{68}FN_5O_6S$: 801.49. found: $[M+H]^+$ 802.

Example 16

Preparation of (3R,5S,E)-7-(4-(4-fluorophenyl)-6-isopropyl-2-(N-methylmethylsulfonamido)pyrimidin-5-yl)-3,5-dihydroxy-N-(1-((5Z,8Z,11Z,14Z,17Z)-icosa-5,8,11,14,17-pentaenoyl)piperidin-4-yl)hept-6-enamide (I-59)

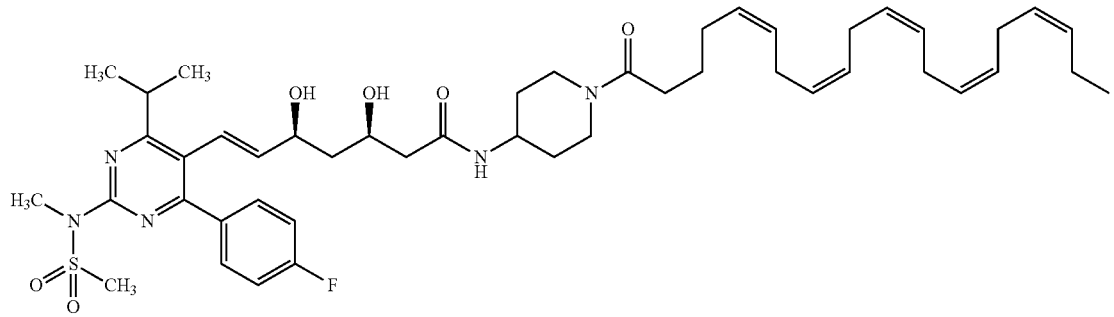 [SMILES: CC/C=C\C/C=C\C/C=C\C/C=C\C/C=C\CCCC(=O)N1CCC(NC(=O)C[C@H](O)C[C@H](O)/C=C/c2c(-c3ccc(F)cc3)nc(N(C)S(C)(=O)=O)nc2C(C)C)CC1]

(3R,5S,E)-7-(4-(4-Fluorophenyl)-6-isopropyl-2-(N-methylmethylsulfonamido)pyrimidin-5-yl)-3,5-dihydroxy-N-(1-((5Z,8Z,11Z,14Z,17Z)-icosa-5,8,11,14,17-pentaenoyl)piperidin-4-yl)hept-6-enamide can be prepared according to the procedures outlined in examples 6 and 7 using (5Z,8Z,11Z,14Z,17Z)-1-(4-aminopiperidin-1-yl)icosa-5,8,11,14,17-pentaen-1-one as the appropriate amine component. (5Z,8Z,11Z,14Z,17Z)-1-(4-Aminopiperidin-1-yl)icosa-5,8,11,14,17-pentaen-1-one can be prepared according to the procedures outlined in WO 2012115695 using tert-butyl piperidin-4-ylcarbamate and EPA as the appropriate starting materials.

Example 17

Preparation of (5Z,8Z,11Z,14Z,17Z)—N-(2-((4R)-4-((3R,5S,7R,8R,9S,10S,13R,14S)-3,7-dihydroxy-10,13-dimethylhexadecahydro-1H-cyclopenta[a]phenanthren-17-yl)pentanamido)ethyl)icosa-5,8,11,14,17-pentaenamide (II-23)

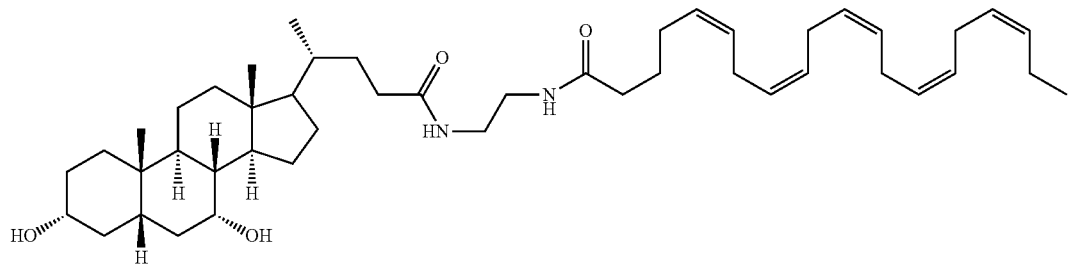

(5Z,8Z,11Z,14Z,17Z)—N-(2-((4R)-4-((3R,5S,7R,8R,9S,10S,13R,14S)-3,7-Dihydroxy-10,13-dimethylhexadecahydro-1H-cyclopenta[a]phenanthren-17-yl)pentanamido)ethyl)icosa-5,8,11,14,17-pentaenamide was prepared according to the procedures outlined in example 6 using (4R)-4-((3R,5S,7R,8R,9S,10S,13R,14S)-3,7-dihydroxy-10,13-dimethylhexadecahydro-1H-cyclopenta[a]phenanthren-17-yl)pentanoic acid as the appropriate starting material. MS calculated for $C_{42}H_{66}FN_5O_6S$: 787.47. found: $[M+H]^+$ 788.

Example 18

Preparation of (5Z,8Z,11Z,14Z,17Z)—N-(2-((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanamido)ethyl)icosa-5,8,11,14,17-pentaenamide (II-2)

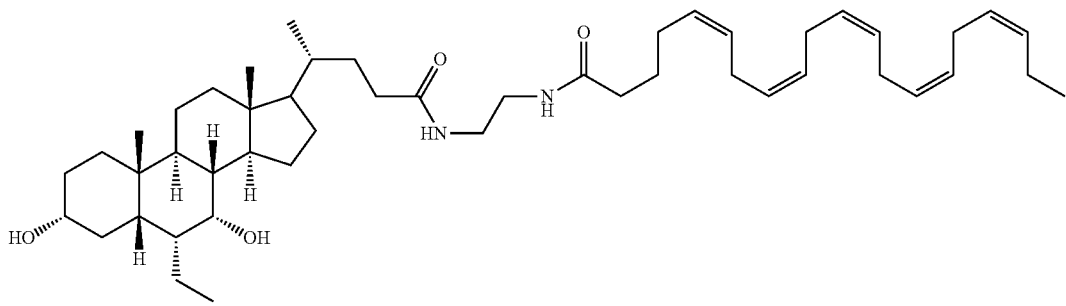

(5Z,8Z,11Z,14Z,17Z)—N-(2((4R)-4-4(3R,5S,6R,7R,8S,9S,10S,13R,14S)-6-Ethyl-3,7-dihydroxy-10,13-dimethylhexadecahydro-1H-cyclopenta[a]phenanthren-17-yl)pentanamido)ethyl)icosa-5,8,11,14,17-pentaenamide can be prepared according to the procedures outlined in example 17 using (4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanoic acid as the appropriate starting material.

Example 19

Preparation of ((4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)-N-(1-((5Z,8Z,11Z,14Z,17Z)-icosa-5,8,11,14,17-pentaenoyl)piperidin-4-yl)pentanamide (II-17)

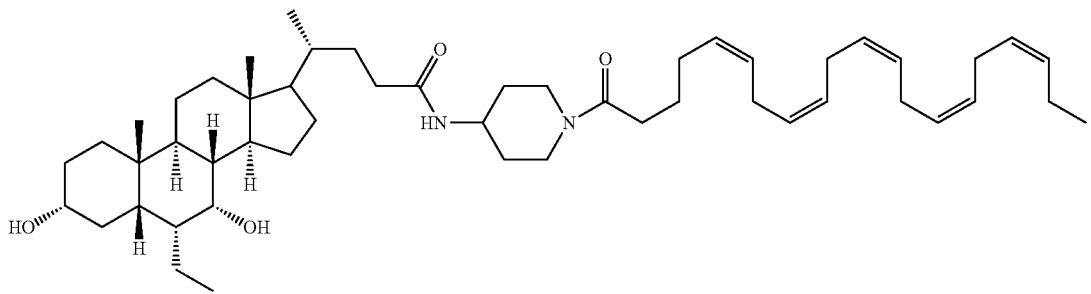

(4R)-4-((3R,5S,6R,7R,8S,9S,10S,13R,14S)-6-Ethyl-3,7-dihydroxy-10,13-dimethylhexadecahydro-1H-cyclopenta[a]phenanthren-17-yl)-N-(1-((5Z,8Z,11Z,14Z,17Z)-icosa-5,8,11,14,17-pentaenoyl)piperidin-4-yl)pentanamide can be prepared according to the procedures outlined in example 16 using (4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)pentanoic acid as the appropriate starting material.

Example 20

Preparation of (4R)-4-((3R,5S,6R,7R,8S,9S,10S,13R,14S)-6-ethyl-3,7-dihydroxy-10,13-dimethyl-hexadecahydro-1H-cyclopenta[a]phenanthren-17-yl)-N-(1-oleoylpiperidin-4-yl)pentanamide (II-18)

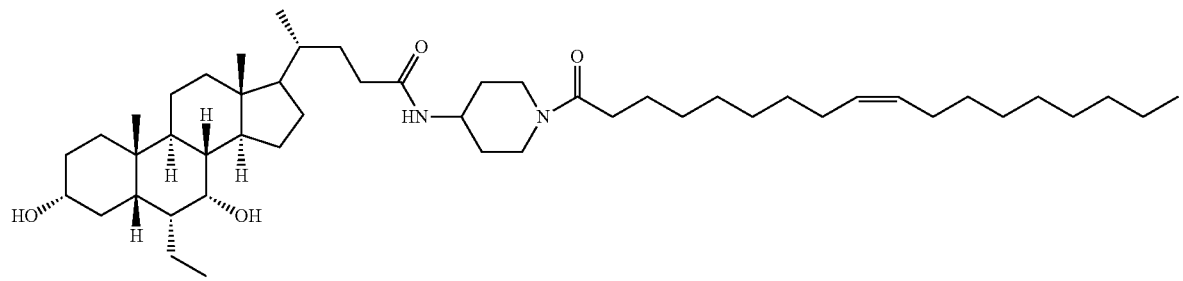

(4R)-4-((3R,5S,6R,7R,8S,9S,10S,13R,14S)-6-ethyl-3,7-dihydroxy-10,13-dimethylhexadecahydro-1H-cyclopenta[a]phenanthren-17-yl)-N-(1-oleoylpiperidin-4-yl)pentanamide can be prepared according to the procedures outlined in example 19 using oleic acid as the appropriate fatty acid component.

Example 21

Preparation of N-(2-((4Z,7Z,10Z,13Z,16Z,19Z)-docosa-4,7,10,13,16,19-hexaenamido)ethyl)-8-fluoro-1,1-dimethyl-3-(4-(3-morpholinopropoxyl)benzoyl)-1,2,3,6-tetrahydroazepino[4,5-b]indole-5-carboxamide (II-58)

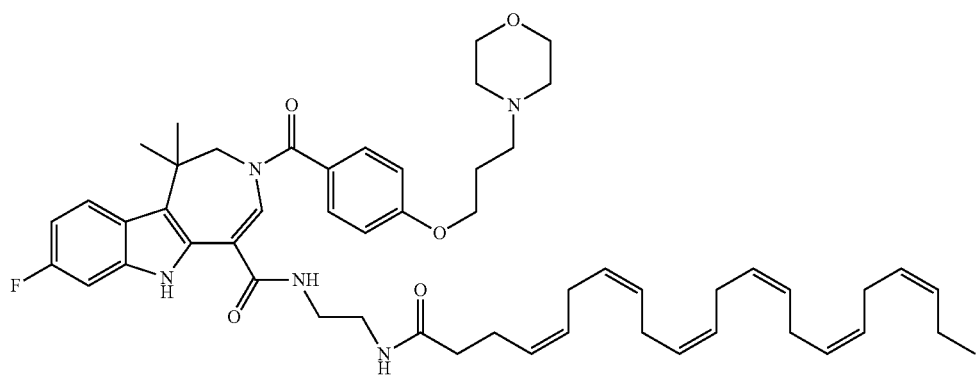 [SMILES: CC/C=C\C/C=C\C/C=C\C/C=C\C/C=C\C/C=C\CCC(=O)NCCNC(=O)C1=CN(C(=O)c2ccc(OCCCN3CCOCC3)cc2)CC(C)(C)c2c1[nH]c1cc(F)ccc21]

N-(2-((4Z,7Z,10Z,13Z,16Z,19Z)-docosa-4,7,10,13,16,19-hexaenamido)ethyl)-8-fluoro-1,1-dimethyl-3-(4-(3-morpholinopropoxyl)benzoyl)-1,2,3,6-tetrahydroazepino[4,5-b]indole-5-carboxamide can be prepared according to the procedures outlined in examples 6 and 7 using 8-fluoro-1,1-dimethyl-3-(4-(3-morpholinopropoxyl)benzoyl)-1,2,3,6-tetrahydroazepino[4,5-b]indole-5-carboxylic acid as the appropriate starting material.

Example 22

Preparation of (Z)-3-(3,4-difluorobenzoyl)-1,1-dimethyl-N-(1-oleoylpiperidin-4-yl)-1,2,3,6-tetrahydroazepino[4,5-b]indole-5-carboxamide (II-72)

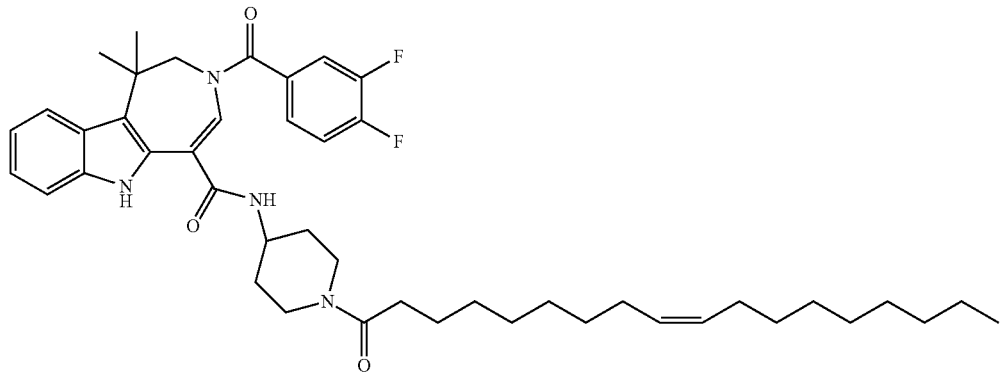 [SMILES: CCCCCCCC/C=C\CCCCCCCC(=O)N1CCC(NC(=O)C2=CN(C(=O)c3ccc(F)c(F)c3)CC(C)(C)c3c2[nH]c2ccccc32)CC1]

(Z)-3-(3,4-difluorobenzoyl)-1,1-dimethyl-N-(1-oleoylpiperidin-4-yl)-1,2,3,6-tetrahydroazepino[4,5-b]indole-5-carboxamide can be prepared according to the procedures outlined in example 16 using using 8-fluoro-1,1-dimethyl-3-(4-(3-morpholinopropoxy)benzoyl)-1,2,3,6-tetrahydroazepino[4,5-b]indole-5-carboxylic acid as the appropriate starting material.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A molecular conjugate comprising a statin selected from the group consisting of atorvastatin, cerivastatin, fluvastatin, lovastatin, mevastatin, pitavasatin, pravastatin, rosuvastatin, and simvastatin covalently linked to a fatty acid, wherein the fatty acid is selected from the group consisting of lipoic acid and omega-3 fatty acids.

2. A compound of Formula I:

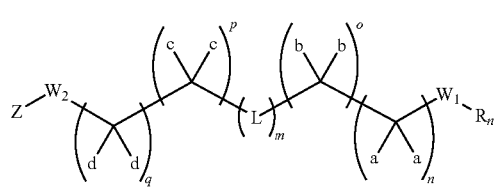

Formula I or a pharmaceutically acceptable salt, hydrate, solvate, enantiomer, or stereoisomer thereof; wherein $R_n$ is

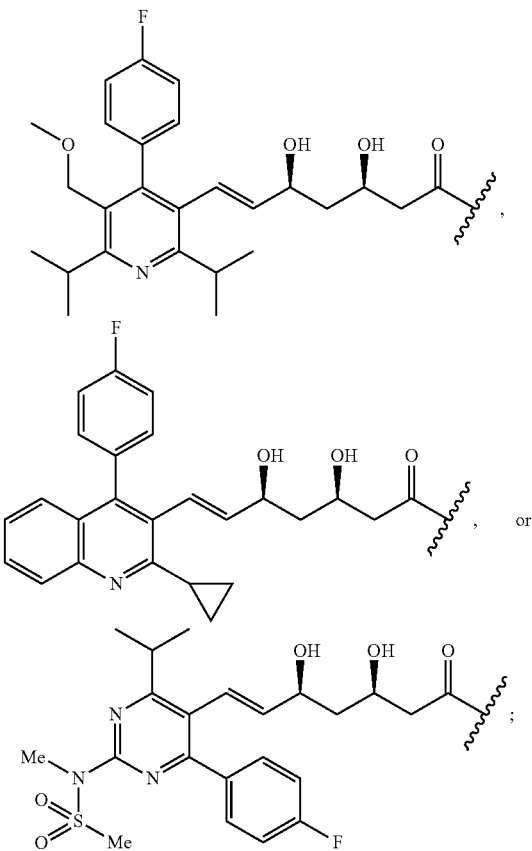

$W_1$ and $W_2$ are each independently S, NH, or NR;

each a, b, c, and d is independently —H, -D, —$CH_3$, —$OCH_3$, —$OCH_2CH_3$, —C(O)OR, —O—Z, or benzyl, or two of a, b, c, and d can be taken together, along with the single carbon to which they are bound, to form a cycloalkyl or heterocycle;
each n, o, p, and q is independently 0, 1, or 2;
each L is independently —O—, —S—, —S(O)—, —S(O)$_2$—, —S—S—, —(C$_1$-C$_6$alkyl)-, —(C$_3$-C$_6$cycloalkyl)-, a heterocycle, a heteroaryl,
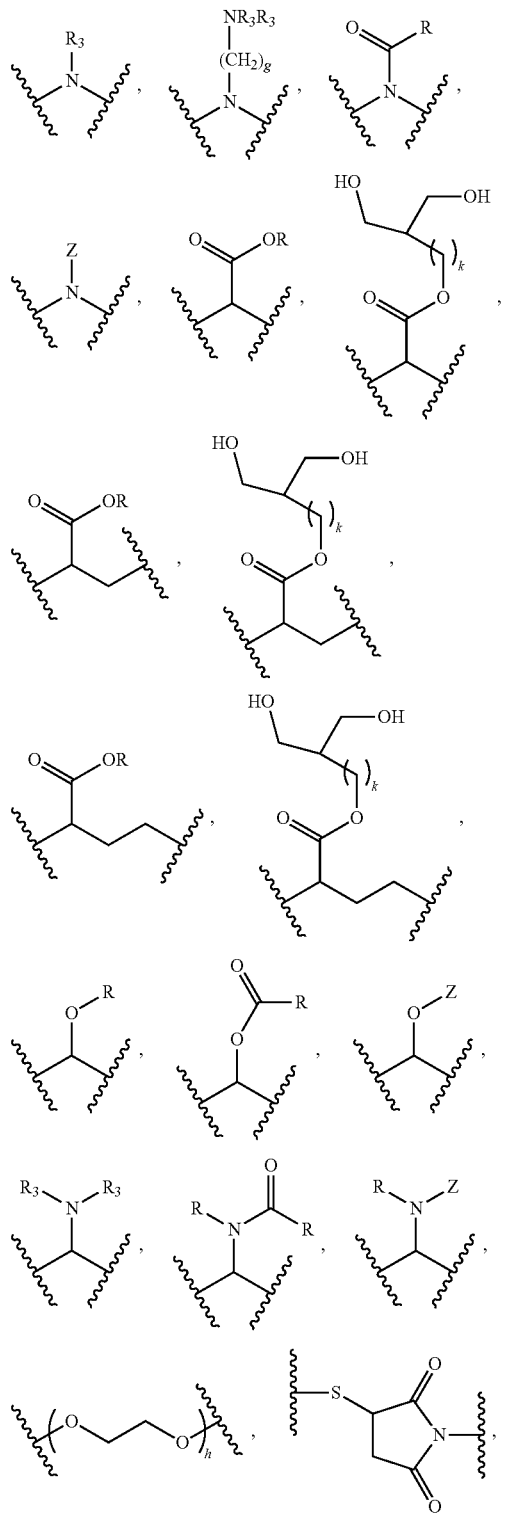
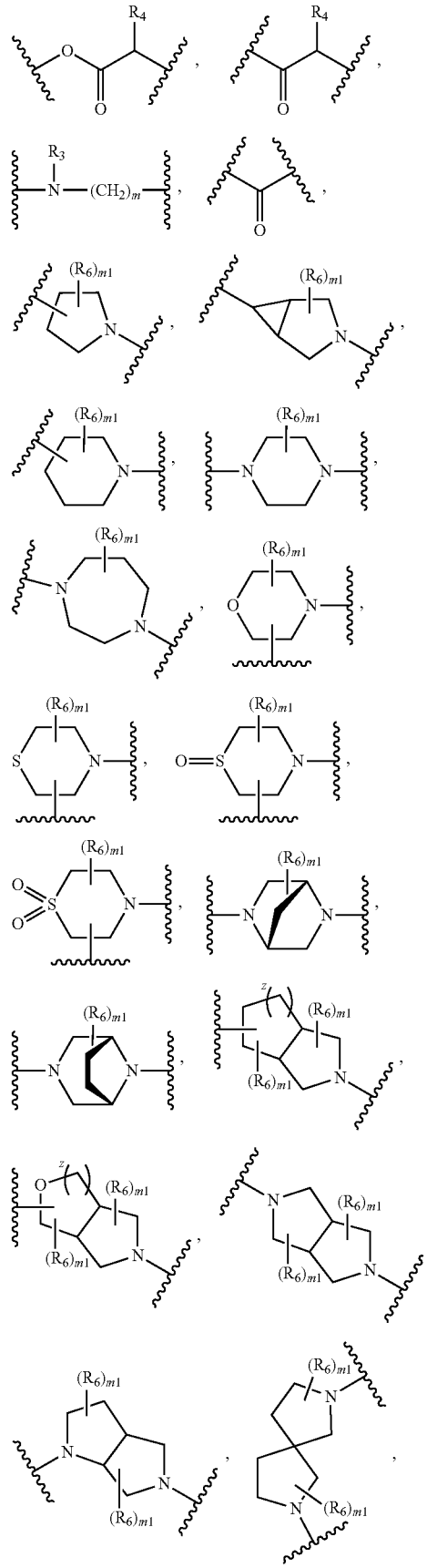

-continued

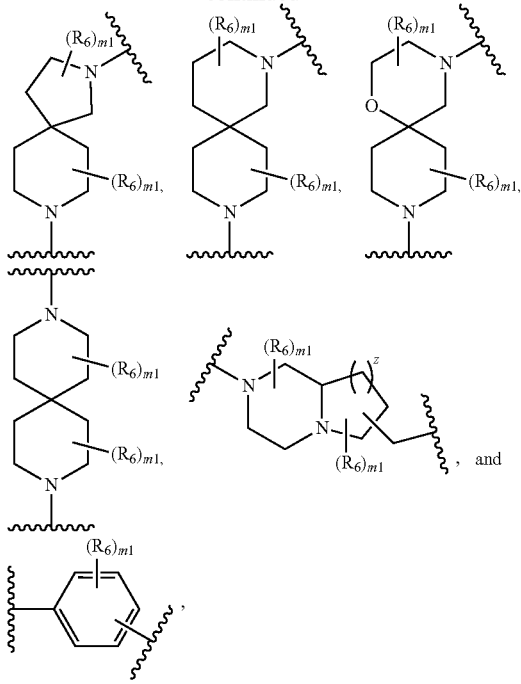

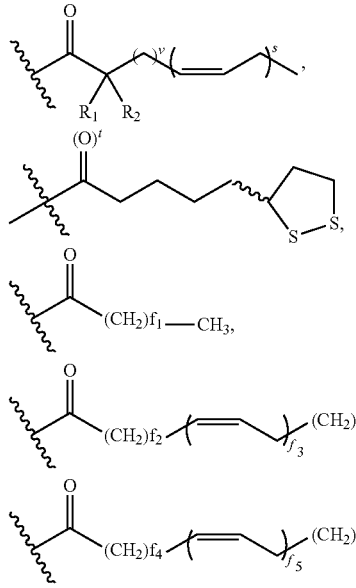

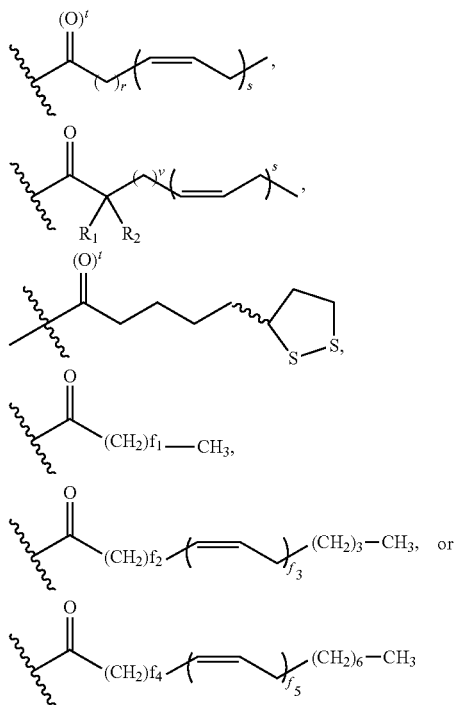

with the proviso that there is at least one wherein the representation of L is not limited directionally left to right as is depicted, rather either the left side or the right side of L can be bound to the $W_1$ side of the compound of Formula I;

$R_6$ is independently —H, -D, —$C_1$-$C_4$ alkyl, -halogen, cyano, oxo, thiooxo, —OH, —C(O)$C_1$-$C_4$ alkyl, —O-aryl, —O-benzyl, —OC(O)$C_1$-$C_4$ alkyl, —$C_2$-$C_3$ alkene, —$C_2$-$C_3$ alkyne, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2C_1$-$C_3$ alkyl;

each g is independently 2, 3, or 4;

each h is independently 1, 2, 3, or 4;

m is 0, 1, 2, or 3; if m is more than 1, then L can be the same or different;

ml is 0, 1, 2 or 3;

k is 0, 1, 2, or 3;

z is 1, 2, or 3;

each $R_3$ is independently —H or —$C_1$-$C_6$ alkyl, or both $R_3$ groups, when taken together with the nitrogen to which they are attached, can form a heterocycle;

each $R_4$ is independently e, —H, or straight or branched —$C_1$-$C_{10}$ alkyl which can be optionally substituted with —OH, —$NH_2$, —$CO_2R$, —$CONH_2$, phenyl, —$C_6H_4OH$, imidazole, or arginine;

each e is independently —H or any one of the side chains of the naturally occurring amino acids;

each Z is independently —H,

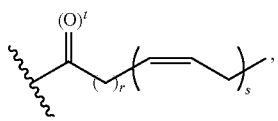

in the compound;

each r is independently 2, 3, or 7;

each s is independently 3, 5, or 6;

each t is independently 0 or 1;

each v is independently 1, 2, or 6;

each $f_1$ is independently 4, 5, 6, 7, 8, 9, 10, 11, 12, 13, 14, 15, 16, 17, 18, 19, 20, 21, 22, 23, 24, 25, or 26;

each $f_2$ is independently 3, 4, 5, 6, 7, 8, 9, 10, or 11;

each $f_3$ is independently 2, 3, 4, or 5;

each $f_4$ is independently 3, 7, 8, 9, 11, or 13;

each $f_5$ is independently 1 or 3;

$R_1$ and $R_2$ are each independently —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_2$-$C_3$ alkene, —$C_2$-$C_3$ alkyne, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, or —S(O)$_2$$C_1$-$C_3$ alkyl; and each R is independently —H, or straight or branched $C_1$-$C_4$ alkyl optionally substituted with OH or halogen.

3. A pharmaceutical composition comprising the molecular conjugate of claim 1 and a pharmaceutically acceptable carrier.

4. A pharmaceutical composition comprising the compound of claim 2 and a pharmaceutically acceptable carrier.

5. A method of treating a metabolic disease comprising administering to a patient in need thereof an effective amount of the molecular conjugate of claim 1.

6. The method of claim 5, wherein the metabolic disease is selected from the group consisting of hypertriglyceridemia, severe hypertriglyceridemia, hypercholesterolemia, familial hypercholesterolemia, elevated cholesterol caused by a genetic condition, fatty liver disease, nonalcoholic fatty liver disease (NFLD), nonalcoholic steatohepatitis (NASH), dyslipidemia, mixed dyslipidemia, Type I hyperlipoproteinemia, Type V hyperlipoproteinemia, atherosclerosis, coronary heart disease, Type 2 diabetes, diabetic nephropathy, diabetic neuropathy, diabetic retinopathy, metabolic syndrome, abdominal aortic aneurysm, and cardiovascular disease.

7. A method for treating atherosclerosis, coronary heart disease, hypercholesterolemia, familial hypercholesterolemia, or abdominal aortic aneurysm comprising administering to a patient in need thereof an effective amount of the molecular conjugate of claim 1.

8. A method of treating a metabolic disease comprising administering to a patient in need thereof an effective amount of the compound of claim 2.

9. The method of claim 8, wherein the metabolic disease is selected from the group consisting of hypertriglyceridemia, severe hypertriglyceridemia, hypercholesterolemia, familial hypercholesterolemia, elevated cholesterol caused by a genetic condition, fatty liver disease, nonalcoholic fatty liver disease (NFLD), nonalcoholic steatohepatitis (NASH), dyslipidemia, mixed dyslipidemia, Type I hyperlipoproteinemia, Type V hyperlipoproteinemia, atherosclerosis, coronary heart disease, Type 2 diabetes, diabetic nephropathy, diabetic neuropathy, diabetic retinopathy, metabolic syndrome, abdominal aortic aneurysm, and cardiovascular disease.

10. A method for treating atherosclerosis, coronary heart disease, hypercholesterolemia, familial hypercholesterolemia, or abdominal aortic aneurysm comprising administering to a patient in need thereof an effective amount of the compound of claim 2.

11. The compound of claim 2, wherein Z is

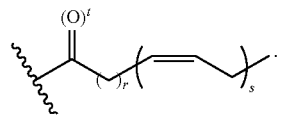

12. The compound of claim 11, wherein r is 2 and s is 6.
13. The compound of claim 11, wherein r is 3 and s is 5.
14. The compound of claim 2, wherein Z is

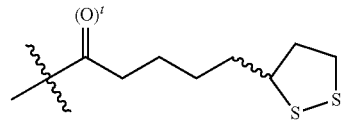

and t is 1.

15. The compound of claim 2, wherein m is 0.

* * * * *